United States Patent
Magolan et al.

(10) Patent No.: US 11,795,127 B2
(45) Date of Patent: Oct. 24, 2023

(54) PROCESSES FOR THE PREPARATION OF ORTHO-ALLYLATED HYDROXY ARYL COMPOUNDS

(71) Applicant: McMaster University, Hamilton (CA)

(72) Inventors: Jakob Magolan, Grimsby (CA); Nicholas Jentsch, Fenton, MO (US); Xiong Zhang, Tianjin (CN); Mathew Piotrowski, Woodstock (CA); Patrick Darveau, Lévis (CA); Meghan Fragis, Ajax (CA); Jarrod Johnson, St. George (CA); Nicole Ritchie, Harrow (CA); Arnav Kaul, Scarborough (CA)

(73) Assignee: McMaster University, Hamilton (CA)

( * ) Notice: Subject to any disclaimer, the term of this patent is extended or adjusted under 35 U.S.C. 154(b) by 0 days.

(21) Appl. No.: 17/964,347

(22) Filed: Oct. 12, 2022

(65) Prior Publication Data
US 2023/0113567 A1    Apr. 13, 2023

Related U.S. Application Data

(62) Division of application No. 17/303,462, filed on May 28, 2021, now Pat. No. 11,512,034.

(60) Provisional application No. 63/031,997, filed on May 29, 2020.

(51) Int. Cl.
| | |
|---|---|
| *C07C 37/14* | (2006.01) |
| *C07J 7/00* | (2006.01) |
| *B01J 21/04* | (2006.01) |
| *C07D 209/08* | (2006.01) |
| *C07C 41/26* | (2006.01) |
| *C07D 307/80* | (2006.01) |
| *C07C 201/12* | (2006.01) |
| *C07J 1/00* | (2006.01) |
| *C07D 311/30* | (2006.01) |
| *C07D 311/32* | (2006.01) |
| *C07C 253/30* | (2006.01) |

(52) U.S. Cl.
CPC .............. *C07C 37/14* (2013.01); *B01J 21/04* (2013.01); *C07C 41/26* (2013.01); *C07C 201/12* (2013.01); *C07C 253/30* (2013.01); *C07D 209/08* (2013.01); *C07D 307/80* (2013.01); *C07D 311/30* (2013.01); *C07D 311/32* (2013.01); *C07J 1/0059* (2013.01); *C07J 7/0005* (2013.01)

(58) Field of Classification Search
CPC .................................................... C07C 37/14
See application file for complete search history.

(56) References Cited

U.S. PATENT DOCUMENTS

| | | | |
|---|---|---|---|
| 11,512,034 B2 * | 11/2022 | Magolan | ............. C07D 307/79 |
| 2017/0283837 A1 | 10/2017 | Kavarana et al. | |
| 2020/0115306 A1 | 4/2020 | Smeltzer et al. | |
| 2021/0276936 A1 | 9/2021 | Smeltzer et al. | |
| 2022/0024843 A1 | 1/2022 | Brumar et al. | |

FOREIGN PATENT DOCUMENTS

EP          0143952 A1      6/1985

OTHER PUBLICATIONS

Jentsch et al., "Synthesis of Cannabigerol derivatives via direct ortho-allylation of phenols" Abstracts of Papers, 258th ACS National Meeting & Exposition, San Diego, CA, United States, Aug. 25-29, 2019, pp. ORGN-0551 https://www.morressier.com/o/event/5fc6445603137aa5258c485b/article/5fc645232d78d1fec4675567.

Jakob Magolan, "Chemical Synthesis of Cannabinoids", Conference Hosted by McMaster's Centre for Medicinal Cannabis Research, Jun. 1, 2019. No abstract available. Disclosed synthesis of cannabigerol from olivetol and geraniol in the presence of alumina and compared known methods.

Jentsch et al. "Efficient Synthesis of Cannabigerol, Grifolin, and Piperogalin via Alumina-Promoted Allylation", J. Nat. Prod. 2020, 83, 2587-2591.

Kiong Zhang, (2020) "Alumina directed ortho allylation of phenols", PhD Thesis, McMaster University, Hamilton.

International Search Report and Written Opinion of corresponding International Patent Application No. PCT/CA2021/050733 dated Aug. 23, 2021, 14 pages.

Chukicheva et al., "Alkylation of phenol and hydroquinone by prenyl in the presence of organoaluminum catalysts", Chem. Nat. Compounds, 2018, 54(1), pp. 1-6.

(Continued)

*Primary Examiner* — Golam M Shameem
(74) *Attorney, Agent, or Firm* — Bereskin & Parr LLP/S.E.N.C.R.L., s.r.l.; Patricia Folkins

(57) ABSTRACT

The present application describes process for preparing an ortho-allylated hydroxy aryl compounds such as compounds of Formula (I) by reacting an allylic alcohol with a hydroxy aryl compound in the presence of aluminum compound selected from alumina and aluminum alkoxides and in a non-protic solvent wherein at least one carbon atom ortho to the hydroxy group in the hydroxy aryl compound is unsubstituted. The present application also includes compounds of Formula (I).

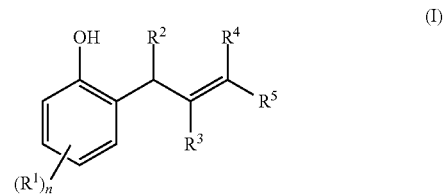

20 Claims, No Drawings

(56) References Cited

OTHER PUBLICATIONS

Chukicheva et al., "Synthesis and biological activity of prenylated phenols", Chem. Nat. Compunds, 2018, 54(5), pp. 875-882.

Zhang et al., "Alkylation of indoles with α, β-unsaturated ketones using alumina in hexanes", Adv. Synth. Catal., 2019, 361, pp. 5548-5551.

Glusenkamp et al., "C-prenylation of phenols promoted by aluminum oxide surfaces", J. Org. Chem., 1986, 51, pp. 4481-4483.

Baek, Seung-Hwa et al. "Boron Trifloride etherate on alimina—a modified Lewis Acid reagent. An improved synthesis of cannabidiol" Tetrahedron Letters, vol. 26 (8), p. 1083-6, 1985.

Baek, Seung-Hwa et al. "Boron Trifloride etherate on alimina—a modified Lewis Acid reagent (V). A conveneint single step synthesis of cannabinoids" Bull. Korean Chem. Soc. 1995 vol. 16 (3), pp. 293-296.

Taura, Futoshi et al., "Cannabinerolic Acid, a Cannabinoid From Cannabis Sativa*", Phytochemistry, vol. 39, No. 2, pp. 457-458, 1995.

Gaoni, Y. , and R. Mechoulam . "The structure and synthesis of cannabigerol, a new hashish constituent." Proceedings of the Chemical Society, London, 1964, March, p. 82.

Jentsch et al., "Synthesis of Cannabigerol derivatives via direct ortho-allylation of phenols", 258th ACS National Meeting & Exposition, San Diego, CA, United States, Aug. 25-29, 2019, Copy of slides.

Third Party Prior Art Submission and Protest made on Canadian Patent Application No. 3,132,439, Mar. 29, 2022.

Citti, C. et al., A novel phytocannabinoid isolated from *Cannabis sativa* L. with an in vivo cannabimimetic activity higher than delta9-tetrahydrocannabinol: delta9-Tetrahydrocannabiphorol.

\* cited by examiner

PROCESSES FOR THE PREPARATION OF ORTHO-ALLYLATED HYDROXY ARYL COMPOUNDS

RELATED APPLICATIONS

The present application is a divisional of co-pending U.S. patent application Ser. No. 17/303,462 filed on May 28, 2021 which claims the benefit of priority of U.S. provisional patent application No. 63/031,997 filed on May 29, 2020 the contents of both of which are incorporated herein by reference in their entirety.

FIELD

The present application is related to process for preparing ortho-allylated hydroxy aryl compounds, in particular using alumina or aluminum alkoxides and a non-protic solvent.

BACKGROUND

The phenol (or hydroxy aryl) moiety is ubiquitous in natural products and present in many synthetic compounds of value in medicinal chemistry and materials sciences.[1-3] Regiospecific ortho allylation of phenols presents a significant synthetic challenge.[4-6] More broadly, any form of ortho-regiospecific functionalization of phenols is a synthetic challenge that has previously been addressed with creative synthetic methodology solutions.[7-17]

Phenols undergo electrophilic aromatic substitution (EAS) reactions with generally poor regioselectivity between ortho- and para-positions, although enhancement of ortho-selectivity has been achieved for some substrates with a variety of additives including amines[45-47] ammonium salts,[48] thioureas,[49-51] and Lewis acids.[52-55] Similarly, oxidative methods of phenol substitution also typically yield mixtures of ortho- and para-substituted products,[56] with ortho-enhancement reported in rare cases.[57-61] Ball and co-workers recently developed an ortho-specific arylation of unprotected phenols with boronic acids using a stoichiometric bismuth reagent.[62] Therefore, the efficient one-step ortho-selective substitution unprotected phenols remains a synthetic challenge.

SUMMARY

The Applicants have developed an efficient one step process of preparing ortho-allylated hydroxy aryl compounds (e.g. ortho-allylated phenolics). More specifically, the Applicants have discovered a general new approach to the ortho-allylation of unprotected hydroxy aryl compounds (e.g. phenolics) using allylic alcohols through alumina promoted allylation in non-protic, for example hydrophobic, solvents. Using various allylic alcohols and phenolics, the Applicants have shown that when using this process, the allylation occurs regiospecifically with the allylation occurring preferentially at a position ortho to the hydroxy of the hydroxy aryl compound.

The Applicants have also discovered that the ortho-allylation of unprotected hydroxy aryl compounds with allylic alcohols can be effected using alumina in combination with further additives including dehydrating agents such as magnesium sulfate. The Applicants have further surprisingly discovered that the ortho-allylation of unprotected hydroxy aryl compounds with allylic alcohols can also be effected using aluminum alkoxides such as aluminum isopropoxide, Accordingly, the application includes a process for preparing an ortho-allylated hydroxy aryl compound comprising reacting an allylic alcohol with a hydroxy aryl compound in the presence of an aluminum compound selected from alumina and aluminum alkoxides and in a non-protic solvent to form the ortho-allylated hydroxy aryl compound, wherein at least one carbon atom ortho to the hydroxy group in the hydroxy aryl compound is unsubstituted.

In an embodiment, the application further includes a process for preparing a compound of Formula (I) comprising:

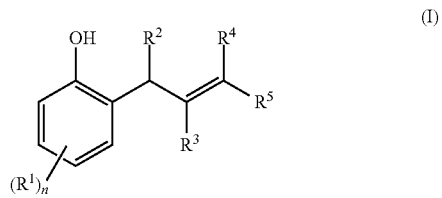

reacting a compound of Formula (II)

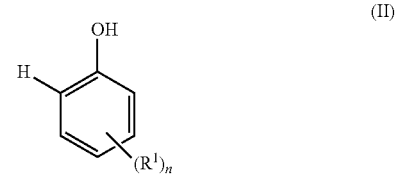

with a compound of Formula (III)

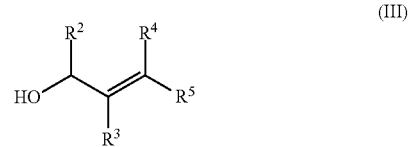

in presence of aluminum compound selected from alumina and aluminum alkoxides and in a non-protic solvent to form the compound of Formula (I), wherein:
  each $R^1$ is independently OH, halo, CN, $NO_2$ or COOH, or independently selected from any suitable unsubstituted or substituted alkyl, alkenyl, alkynyl, cycloalkyl, heterocycloalkyl, aryl, heteroaryl, Z-alkyl, Z-alkenyl, Z-alkynyl, Z-cycloalkyl, Z-heterocycloalkyl, Z-aryl, Z and Z-heteroaryl, wherein the substituents are selected from OH, halo, alkyl, O-alkyl, aryl, cycloalkyl, heteroaryl and heterocycloalkyl groups, or
  when n is greater than 1, two $R^1$ groups are linked together to form an unsubstituted or substituted polycyclic ring system having 8 or more atoms together with the phenyl ring to which said $R^1$ groups are bonded, and in which one or more carbon atoms in said polycyclic ring system is optionally replaced with a heteromoiety selected from $NR^6$, O and S; wherein the polycyclic ring system is optionally substituted with one or more substituents selected from =O, OH, halo, alkyl, alkenyl, alkynyl, O-alkyl, O-alkenyl, O-alkynyl, aryl, heteroaryl, cycloalkyl, and heterocycloalkyl, the latter 10 groups being optionally substituted with one or more substituents selected from OH, alkyl, alkenyl, and O-alkyl;

Z is selected from O, C(O), CO$_2$, S, SO$_2$, SO, and NR$^7$;

R$^2$ is H;

R$^3$ is selected from H and any suitable unsubstituted or substituted alkyl; R$^4$ is H, or selected from any suitable unsubstituted or substituted alkyl; aryl, alkylenearyl, heteroaryl, and alkyleneheteroaryl;

R$^5$ is H, or selected from any suitable unsubstituted or substituted alkyl, alkenyl, alkynyl, cycloalkyl, heterocycloalkyl, aryl and heteroaryl, wherein the substituents are selected from OH, halo, alkyl, O-alkyl, aryl, cycloalkyl, heteroaryl and heterocycloalkyl groups; or any two of R$^2$, R$^3$, R$^4$ and R$^5$ are linked together to form an unsubstituted or substituted monocyclic or polycyclic ring system having 4 or more atoms together with the carbon atoms to which said any two of R$^2$, R$^3$, R$^4$ and R$^5$ are bonded, wherein the monocyclic or polycyclic ring system is optionally substituted with one or more substituents selected from =O, OH, halo, alkyl, alkenyl, alkynyl, O-alkyl, O-alkenyl, O-alkynyl, aryl, heteroaryl, cycloalkyl, and heterocycloalkyl, the latter 10 groups being optionally substituted with OH, alkyl, alkenyl and O-alkyl;

R$^6$ and R$^7$ are independently selected from H and unsubstituted or substituted alkyl;

n is an integer selected from 0 to 4, and all alkyl, alkenyl, alkynyl, alkylene, alkenylene, alkynylene, cycloalkyl, and heterocycloalkyl groups are optionally fluoro-substituted.

In an embodiment, the application further includes a process for preparing a compound of Formula (I) comprising:

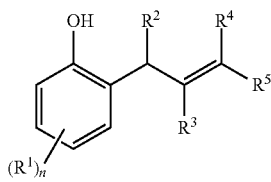
(I)

reacting a compound of Formula (II)

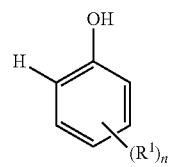
(II)

with a compound of Formula (III)

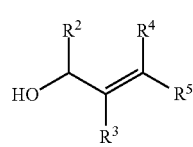
(III)

in presence of an aluminum compound selected from alumina and aluminum alkoxides and in a hydrophobic solvent under forming of the compound of Formula (I), wherein:

each R$^1$ is independently selected from OH, halo, CN, NO$_2$, COOH, C$_{1-16}$alkyl, C$_{2-16}$alkenyl, C$_{2-16}$alkynyl, C$_{3-18}$ cycloalkyl, C$_{1-16}$alkyleneC$_{3-18}$ cycloalkyl, C$_{2-16}$alkenyleneC$_{3-18}$ cycloalkyl, C$_{2-16}$alkynyleneC$_{3-18}$ cycloalkyl, C$_{3-18}$heterocycloalkyl, C$_{1-16}$alkylene C$_{3-18}$heterocycloalkyl, C$_{1-10}$alkenyleneC$_{3-18}$ heterocycloalkyl, C$_{2-16}$alkynyleneC$_{3-18}$heterocycloalkyl, C$_{6-18}$aryl, C$_{1-16}$alkyleneC$_{6-18}$ aryl, C$_{2-16}$alkenylene C$_{6-18}$ aryl, C$_{2-16}$alkynyleneC$_{6-18}$ aryl, C$_{5-18}$heteroaryl, C$_{2-16}$alkyleneC$_{5-18}$heteroaryl, C$_{2-16}$alkenylene C$_{5-18}$heteroaryl, C$_{2-16}$alkynyleneC$_{5-18}$heteroaryl, Z—C$_{1-16}$alkyl, Z—C$_{2-16}$alkenyl, Z—C$_{2-16}$alkynyl, Z—C$_{3-18}$ cycloalkyl, Z—C$_{1-16}$alkyleneC$_{3-18}$cycloalkyl, Z—C$_{2-16}$alkenyleneC$_{3-18}$ cycloalkyl, Z—C$_{2-16}$alkynyleneC$_{3-18}$ cycloalkyl, Z—C$_{3-18}$heterocycloalkyl, Z—C$_{1-16}$alkyleneC$_{3-18}$ heterocycloalkyl, Z—C$_{2-16}$alkenyleneC$_{3-18}$heterocycloalkyl, Z—C$_{2-16}$ alkynyleneC$_{3-18}$heterocycloalkyl, Z—C$_{6-18}$ aryl, Z—C$_{1-16}$alkyleneC$_{6-18}$ aryl, Z—C$_{2-16}$alkenyleneC$_{6-18}$ aryl, Z—C$_{2-16}$alkynyleneC$_{6-18}$ aryl, Z—C$_{5-18}$heteroaryl, Z—C$_{1-16}$alkyleneC$_{5-18}$heteroaryl, Z—C$_{2-16}$alkenyleneC$_{5-18}$heteroaryl, and Z—C$_{2-16}$alkyleneC$_{5-18}$heteroaryl, wherein all alkyl, alkenyl, alkynyl, alkylene, alkenylene, alkynylene, cycloalkyl, heterocycloalkyl, aryl, and heteroaryl groups are optionally substituted with one or more substituents selected from OH, halo, C$_{1-16}$alkyl, C$_{2-16}$alkenyl, C$_{2-6}$alkynyl, OC$_{1-16}$alkyl, OC$_{2-16}$alkenyl, and OC$_{2-16}$alkynyl; or when n is greater than 1, two R$^1$ groups are linked together to form a polycyclic ring system having 8 or more atoms together with the phenyl ring to which said groups are bonded, and in which one or more carbon atoms in said polycyclic ring system is optionally replaced with a heteromoiety selected from NR$^6$, O and S, wherein the polycyclic ring system is optionally substituted with one or more substituents selected from =O, OH, halo, C$_{1-16}$alkyl, C$_{2-16}$alkenyl, C$_{2-16}$alkynyl, OC$_{2-16}$alkenyl, OC$_{2-16}$alkynyl; C$_{1-16}$alkyleneOR$^8$, C$_{2-16}$alkenyleneOR$^8$, C$_{2-16}$alkynyleneOR$^8$, C$_{6-18}$aryl, C$_{3-18}$ cycloalkyl, C$_{3-18}$ heterocycloalkyl, and C$_{5-18}$heteroaryl, the latter 4 groups being optionally substituted with one or more substituents selected from OH, halo, C$_{1-16}$alkyl, OC$_{1-16}$alkyl, and C$_{2-16}$alkenyl;

Z is selected from O, C(O), CO$_2$, S, SO$_2$, SO, and NR$^7$;

R$^2$ is selected from H,

R$^3$ is selected from H and C$_{1-6}$alkyl,

R$^4$ is selected from H, C$_{1-6}$alkyl, C$_{6-18}$aryl, C$_{1-16}$alkyleneC$_{6-18}$aryl, C$_{5-18}$ heteroaryl, and C$_{2-16}$alkylene C$_{5-18}$heteroaryl;

R$^5$ is selected from H, C$_{1-26}$alkyl, C$_{2-26}$alkenyl, C$_{2-26}$alkynyl, C$_{3-18}$ cycloalkyl, C$_{1-16}$alkyleneC$_{3-18}$ cycloalkyl, C$_{2-16}$alkenyleneC$_{3-18}$ cycloalkyl, C$_{2-16}$alkynylene C$_{3-18}$cycloalkyl, C$_{3-18}$ heterocycloalkyl, C$_{1-16}$alkyleneC$_{3-18}$ heterocycloalkyl, C$_{1-16}$alkenyleneC$_{3-18}$ heterocycloalkyl, C$_{2-16}$alkynyleneC$_{3-18}$ heterocycloalkyl, C$_{6-18}$aryl, C$_{1-16}$alkyleneC$_{6-18}$ aryl, C$_{2-16}$alkenylene C$_{6-18}$aryl, C$_{2-16}$alkynyleneC$_{6-18}$aryl, C$_{5-18}$heteroaryl, C$_{2-16}$alkyleneC$_{5-18}$heteroaryl, C$_{2-16}$alkenyleneC$_{5-18}$ heteroaryl, C$_{2-16}$alkynyleneC$_{5-18}$heteroaryl, wherein all cycloalkyl, heterocycloalkyl, aryl and heteroaryl are optionally substituted with one or more substituents selected from OH, NO$_2$, CN, halo, C$_{1-16}$alkyl, C$_{2-16}$alkenyl, $C_{2-16}$alkynyl, $OC_{2-16}$alkenyl, $OC_{2-16}$alkynyl, $C_{1-16}$alkyleneOR$^9$ $C_{2-16}$alkenyleneOR$^9$, $C_{2-16}$alkynyleneOR$^9$, $SO_3C_{1-16}$alkyl, $SO_3C_{6-16}$aryl, and $SO_3C_{5-18}$heteroaryl substituted with $C_{1-16}$alkyl; or any two of R$^2$, R$^3$, R$^4$ and R$^5$ are linked together to form an unsubstituted or substituted monocyclic or polycyclic ring system having 4 or more atoms together with the carbon atoms to which said any two of R$^2$, R$^3$, R$^4$ and R$^5$ are bonded, wherein the monocyclic or polycyclic ring system is optionally substituted with one or more substituents selected =O, OH, halo, $C_{1-16}$alkyl, $C_{2-16}$alkenyl, $C_{2-16}$alkynyl, $OC_{1-16}$alkyl, $OC_{2-16}$alkenyl, $OC_{2-16}$alkynyl; $C_{1-16}$alkyleneOR$^8$, $C_{2-16}$alkenyleneOR$^8$, $C_{2-16}$alkynyleneOR$^8$, $C_{6-18}$aryl, $C_{3-18}$cycloalkyl, $C_{3-18}$heterocycloalkyl, and $C_{5-18}$heteroaryl, the latter 4 groups being optionally substituted with one or more substituents selected from OH, halo, $C_{1-16}$alkyl, $OC_{1-16}$alkyl, and $C_{2-16}$alkenyl;

R$^6$, R$^7$, R$^8$ and R$^9$ are independently selected from H and $C_{1-6}$alkyl;

n is an integer selected from 0 to 4, and all alkyl, alkenyl, alkynyl, alkylene, alkenylene, alkynylene, cycloalkyl, and heterocycloalkyl groups are optionally fluoro-substituted.

The present application also includes novel compounds of Formula (I).

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

DETAILED DESCRIPTION

I. Definitions

Unless otherwise indicated, the definitions and embodiments described in this and other sections are intended to be applicable to all embodiments and aspects of the present application herein described for which they are suitable as would be understood by a person skilled in the art.

All features disclosed in the specification, including the claims, abstract, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent, or similar purpose, unless expressly stated otherwise.

The term "process of the application" and the like as used herein refers to a process of preparing ortho-allylated hydroxy aryl compounds including compounds of Formula (I) and (I-A) as described herein.

The term "and/or" as used herein means that the listed items are present, or used, individually or in combination. In effect, this term means that "at least one of" or "one or more" of the listed items is used or present. The term "and/or" with respect to pharmaceutically acceptable salts and/or solvates thereof means that the compounds of the application exist as individual salts and hydrates, as well as a combination of, for example, a solvate of a salt of a compound of the application.

As used in the present application, the singular forms "a", "an" and "the" include plural references unless the content clearly dictates otherwise. For example, an embodiment including "a solvent" should be understood to present certain aspects with one solvent, or two or more additional solvents.

In embodiments comprising an "additional" or "second" component, such as an additional or second solvent, the second component as used herein is chemically different from the other components or first component. A "third" component is different from the other, first, and second components, and further enumerated or "additional" components are similarly different.

As used in this application and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "consisting" and its derivatives as used herein are intended to be closed terms that specify the presence of the stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

The term "suitable" as used herein means that the selection of the particular compound or conditions would depend on the specific synthetic manipulation to be performed, the identity of the molecule(s) to be transformed and/or the specific use for the compound, but the selection would be well within the skill of a person trained in the art. All process/method steps described herein are to be conducted under conditions sufficient to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

The terms "about", "substantially" and "approximately" as used herein mean a reasonable amount of deviation of the modified term such that the end result is not significantly changed. These terms of degree should be construed as including a deviation of at least ±5% of the modified term if this deviation would not negate the meaning of the word.

The present description refers to a number of chemical terms and abbreviations used by those skilled in the art. Nevertheless, definitions of selected terms are provided for clarity and consistency.

The term "alkyl" as used herein, whether it is used alone or as part of another group, means straight or branched chain, saturated alkyl groups. The number of carbon atoms that are possible in the referenced alkyl group are indicated by the prefix "$C_{n1-n2}$". For example, the term ° alkyl means an alkyl group having 1, 2, 3, 4, 5, 6, 7, 8, 9 or 10 carbon atoms. All alkyl groups are optionally fluoro-substituted.

The term "alkenyl" as used herein, whether it is used alone or as part of another group, means straight or branched chain, unsaturated alkyl groups containing at least one double bond. The number of carbon atoms that are possible in the referenced alkyl group are indicated by the prefix "$C_{n1-n2}$". For example, the term $C_{2-6}$alkenyl means an alkenyl group having 2, 3, 4, 5 or 6 carbon atoms. All alkenyl groups are optionally fluoro-substituted.

The term "alkynyl" as used herein, whether it is used alone or as part of another group, means straight or branched chain, unsaturated alkynyl groups containing at least one triple bond. The number of carbon atoms that are possible in the referenced alkyl group are indicated by the prefix "$C_{n1-n2}$". For example, the term $C_{2-6}$alkynyl means an alkynyl group having 2, 3, 4, 5 or 6 carbon atoms. All alkynyl groups are optionally fluoro-substituted.

The term "alkylene", whether it is used alone or as part of another group, means straight or branched chain, saturated alkylene group, that is, a saturated carbon chain that contains substituents on two of its ends. The number of carbon atoms that are possible in the referenced alkylene group are indicated by the prefix "$C_{n1-n2}$". For example, the term $C_{2-6}$alkylene means an alkylene group having 2, 3, 4, 5 or 6 carbon atoms. All alkylene groups are optionally fluoro-substituted.

The term "alkenylene" as used herein, whether it is used alone or as part of another group, means a straight or branched chain, unsaturated alkylene group, that is, an unsaturated carbon chain that contains substituents on two of its ends and at least one double bond. The number of carbon atoms that are possible in the referenced alkenylene group are indicated by the prefix "$C_{n1-n2}$". For example, the term $C_{2-6}$alkenylene means an alkenylene group having 2, 3, 4, 5 or 6 carbon atoms. All alkenylene groups are optionally fluorosubstitutes.

The term "alkynylene" as used herein, whether it is used alone or as part of another group, means a straight or branched chain, unsaturated alkylene group, that is, an unsaturated carbon chain that contains substituents on two of its ends and at least one triple bond. The number of carbon atoms that are possible in the referenced alkynylene group are indicated by the prefix "$C_{n1-n2}$". For example, the term $C_{2-6}$alkynylene means an alkynylene group having 2, 3, 4, 5 or 6 carbon atoms. All alkynylene groups are optionally fluorosubstituted.

The term "aryl" as used herein, whether it is used alone or as part of another group, refers to cyclic groups containing from 6 to 20 atoms and at least one carbocyclic aromatic ring. All aryl groups are optionally fluorosubstituted.

The term "cycloalkyl," as used herein, whether it is used alone or as part of another group, refers to cyclic groups containing from 3 to 20 atoms and at least one carbocyclic non aromatic ring. The number of carbon atoms that are possible in the referenced cycloalkyl group are indicated by the numerical prefix "$C_{n1-n2}$". For example, the term $C_{3-10}$ cycloalkyl means a cycloalkyl group having 3, 4, 5, 6, 7, 8, 9 or 10 carbon atoms. All cycloalkyl groups are optionally fluoro-substituted.

The term "heterocycloalkyl" as used herein, whether it is used alone or as part of another group, refers to cyclic groups containing at least one non-aromatic ring containing from 3 to 20 atoms in which one or more of the atoms are a heteroatom selected from O, S and N and the remaining atoms are C. Heterocycloalkyl groups are either saturated or unsaturated (i.e. contain one or more double bonds). When a heterocycloalkyl group contains the prefix $C_{n1-n2}$ this prefix indicates the number of carbon atoms in the corresponding carbocyclic group, in which one or more, suitably 1 to 5, of the ring atoms is replaced with a heteroatom as selected from O, S and N and the remaining atoms are C. All heterocycloalkyl groups are optionally fluoro-substituted. The heteroatom in heterocycloalkyl groups is optionally substituted or oxidized where valency allows.

The term "heteroaryl" as used herein, whether it is used alone or as part of another group, refers to cyclic groups containing at least one heteroaromatic ring containing 5-20 atoms in which one or more of the atoms are a heteroatom selected from O, S and N and the remaining atoms are C. When a heteroaryl group contains the prefix $C_{n1-n2}$ this prefix indicates the number of carbon atoms in the corresponding carbocyclic group, in which one or more, suitably 1 to 5, of the ring atoms is replaced with a heteroatom as defined above. All heteroaryl groups are optionally fluoro-substituted. The heteroatom in heteroaryl groups is optionally substituted or oxidized where valency allows.

All cyclic groups, including aryl, heteroaryl, heterocycloalkyl and cycloalkyl groups, contain one or more than one ring (i.e. are polycyclic). When a cyclic group contains more than one ring, the rings may be fused, bridged, spirofused or linked by a bond. All cyclic groups are optionally fluoro-substituted.

The term "ring system" as used herein refers to a carbon- or heteroatom-containing ring system, that includes monocycles, fused bicyclic and polycyclic rings, and bridged rings.

The term "polycyclic" as used herein means cyclic groups that contain more than one ring linked together and includes, for example, groups that contain two (bicyclic), three (tricyclic) or four (quadracyclic) rings. The rings may be linked through a single bond, a single atom (spirocyclic) or through two atoms (fused and bridged). All polycyclic groups are optionally fluoro-substituted.

The term "benzofused" as used herein refers to a polycyclic group in which a benzene ring is fused with another ring.

A first ring being "fused" with a second ring means the first ring and the second ring share two adjacent atoms there between.

A first ring being "bridged" with a second ring means the first ring and the second ring share two non-adjacent atoms there between.

A first ring being "spirofused" with a second ring means the first ring and the second ring share one atom there between.

The term "fluoro-substituted" refers to the substitution of one or more, including all, available hydrogens in a referenced group with fluoro.

The terms "halo" or "halogen" as used herein, whether it is used alone or as part of another group, refers to a halogen atom and includes fluoro, chloro, bromo and iodo.

The term "available", as in "available hydrogen atoms" or "available atoms" refers to atoms that would be known to a person skilled in the art to be capable of replacement by a substituent.

The term "protecting group" or "PG" and the like as used herein refers to a chemical moiety which protects or masks a reactive portion of a molecule to prevent side reactions in those reactive portions of the molecule, while manipulating or reacting a different portion of the molecule. After the manipulation or reaction is complete, the protecting group is removed under conditions that do not degrade or decompose the remaining portions of the molecule. The selection of a suitable protecting group can be made by a person skilled in the art. Many conventional protecting groups are known in the art, for example as described in "Protective Groups in Organic Chemistry" McOmie, J. F. W. Ed., Plenum Press, 1973, in Greene, T. W. and Wuts, P. G. M., "Protective Groups in Organic Synthesis", John Wiley & Sons, $3^{rd}$ Edition, 1999 and in Kocienski, P. Protecting Groups, 3rd Edition, 2003, Georg Thieme Verlag (The Americas).

The term "deuterated" as used herein means that one or more, including all, of the hydrogens on a group are replaced with deuterium (I.e. [²H]).

The term "allylic alcohol" as used herein refers to a compound comprising a hydroxy substituent (—OH) attached to a spa hybridized carbon which is adjacent to a double bond.

The term "hydroxy aryl compound(s)" or "phenolics" as used herein refers to a compound comprising at least one hydroxy substituent on an aryl ring. In the case of phenolics, the aryl group is phenyl.

The term "ortho-allylated hydroxy aryl compound(s)" or "ortho-allylated hydroxy phenolics" as used herein refers to a compound comprising an allylic group in a position ortho to a hydroxy group on an aryl ring. In the case of ortho-allylated hydroxy phenolics, the aryl group is phenyl.

The term "allylic group" as used herein refer to a substituent comprising a double bond adjacent to a methylene which is covalently attached to the rest of the molecule.

The term "alumina" as used herein refers to aluminium oxide having the chemical formula: $Al_2O_3$ $(H_2O)n$ where n is in the range of 0 to 1.

The term "acidic alumina" as used herein refers to activated alumina that has been treated so that a 5% aqueous suspension of the alumina has a pH less than 7.

The term "basic alumina" as used herein refers to activated alumina that has been treated so that a 5% aqueous suspension of the alumina has a pH of greater than 7.

The term "neutral alumina" as used herein refers to activated alumina wherein a 5% aqueous suspension of the alumina has a neutral pH.

The term "activated alumina" as used herein refers to alumina that has been treated under dehydroxylation conditions to provide a highly porous material with a low water content.

The term "aluminum alkoxide" as used herein refers to a compound having having one to three reactive alkoxy (—O-alkyl) groups per atom of aluminum.

The term "aluminum isopropoxide" as used herein refers to a compound having one to three reactive isopropoxy groups per atom of aluminum.

The term "non-protic solvent" as used herein includes both non polar solvent and polar aprotic solvents.

The term "non-polar solvent" as used herein refers to a solvent that has little or no polarity and includes hydrophobic solvents.

The term "polar aprotic solvent" as used herein refers to a solvent a solvent that does not have an acidic proton and is polar.

The term "together with the phenyl ring to which said groups are bonded" as used herein means that the specified number of atoms in the polycyclic ring system includes the 6 carbon atoms in the phenyl ring.

The term "unsubstituted", as used herein means that the referenced atom does not contain a substituent group other than a hydrogen atom.

The term "substituted" as used herein means that the referenced atom contains at least one substituent group other that a hydrogen atom.

The term "substituent group" as used herein refers to any chemical grouping, including groups comprising carbon atoms and/or heteroatoms that is compatible with the reaction conditions of the processes of the application.

The term "major isomer" as used herein refers to a stereochemical isomer, including a regional isomer, that is the most abundant isomer in a mixture of isomers of the same compound. Conversely, the term "minor isomer" as used herein refers to a stereochemical isomer, including a regional isomer, that is not the most abundant isomer in a mixture of isomers of the same compound.

In the processes of the application, it is typical for the compounds, including starting materials and products to be present as a mixture of isomers. For example, when it is shown that the R- or S-isomer is a product or starting material of a reaction, this means that that isomer is present in greater than 80%, 85%, 90%, 95%, 98% or 99% by weight based on the total amount of R- and S-isomers.

The products of the processes of the application may be isolated according to known methods, for example, the compounds may be isolated by evaporation of the solvent, by filtration, centrifugation, chromatography or other suitable method.

II. Processes of the Application

The Applicants have developed an efficient one step process of preparing ortho-allylated hydroxy aryl compounds (e.g. ortho-allylated phenolics). More specifically, the Applicants have discovered a general new approach to the ortho-allylation of unprotected hydroxy aryl compounds (e.g. phenolics) using allylic alcohols through alumina promoted allylation in non-protic, for example hydrophobic, solvents. Using various allylic alcohols and phenolics, the Applicants have shown that when using this process, the allylation occurs regiospecifically with the allylation occurring preferentially at a position ortho to the hydroxy of the hydroxy aryl compound. Further, the process generally occurs with little or no formation of the para-substituted and/or disubstituted product.

The Applicants have also discovered that the ortho-allylation of unprotected hydroxy aryl compounds with allylic alcohols can be effected using alumina in combination with further additives including dehydrating agents such as magnesium sulfate and various acids. Similarly, the ortho-allylation reaction with, for example, alumina and a dehydrating agents such as magnesium sulfate, was found to occur regiospecifically with the allylation occurring preferentially at a position ortho to the hydroxy of the hydroxy aryl compound.

The Applicants have further surprisingly discovered that the ortho-allylation of unprotected hydroxy aryl compounds with allylic alcohols can also be effected using aluminum alkoxides such as aluminum isopropoxide. Similarly, the ortho-allylation reaction with aluminum alkoxide such as aluminum isopropoxide was found to occur regiospecifically with the allylation occurring preferentially at a position ortho to the hydroxy of the hydroxy aryl compound.

Accordingly, the application includes a process for preparing an ortho-allylated hydroxy aryl compound comprising reacting an allylic alcohol with a hydroxy aryl compound in the presence of an aluminum compound selected from alumina and aluminum alkoxides and in a non-protic solvent to form the ortho-allylated hydroxy aryl compound, wherein at least one carbon atom ortho to the hydroxy group in the hydroxy aryl compound is unsubstituted.

In an embodiment, the aluminum compound is alumina. Accordingly, the application also includes a process for preparing an ortho-allylated hydroxy aryl compound comprising reacting an allylic alcohol with a hydroxy aryl compound in the presence of alumina and in a non-protic solvent to form the ortho-allylated hydroxy aryl compound, wherein at least one carbon atom ortho to the hydroxy group in the hydroxy aryl compound is unsubstituted.

In an embodiment, the process provides the ortho isomer as the major isomer. Accordingly, in an embodiment, the present application also includes a process for selectively preparing an ortho-allylated hydroxy aryl compound comprising reacting an allylic alcohol with a hydroxy aryl compound in the presence of alumina and in a hydrophobic solvent to form the ortho-allylated hydroxy aryl compound, wherein at least one carbon atom ortho to the hydroxy group in the hydroxy aryl compound is unsubstituted.

In an embodiment, the alumina is neutral, basic or acidic alumina. In an embodiment, the alumina is neutral alumina. In an embodiment, the alumina is basic alumina. In an embodiment, the alumina is acidic alumina.

In an embodiment, the non-protic solvent is a mixture of one or more non-protic solvents. In an embodiment, the non-protic solvent, suitably non-protic organic solvent, is a non-polar solvent or a polar aprotic solvent. In an embodiment, the non-polar solvent comprises hydrophobic solvents. In an embodiment, the non-protic solvent is selected from hexane, hexanes, heptane, heptanes, cyclohexane, petroleum ether, octane, diglyme, toluene, xylenes, benzene, chloroform, fluorinated alkanes, dichloromethane (DCM), 1,2-dichloroethane (DCE), ethyl acetate, carbon tetrachloride, tetrahydrofuran (THF), diethyl ether, diisopropyl ether, isooctane, methyl ethyl ketone, acetone, dimethyl sulfoxide, dimethylformamide, methyl tert-butyl ether, trichloroethane, n-butyl acetate, chlorobenzene acetonitrile, and trifluorotoluene, and mixtures thereof. In an embodiment, the non-protic solvent is selected from hexane, hexanes, heptane, heptanes, cyclohexane, petroleum ether, octane, diglyme, toluene, xylenes, benzene, chloroform, fluorinated alkanes, dichloromethane (DCM), 1,2-dichloroethane (DCE), ethyl acetate, carbon tetrachloride, tetrahydrofuran (THF), diethyl ether, diisopropyl ether, isooctane, methyl ethyl ketone, methyl tert-butyl ether, trichloroethane, n-butyl acetate, chlorobenzene acetonitrile, and trifluorotoluene, and mixtures thereof. In an embodiment, the non-protic solvent is a hydrophobic solvent selected from hexane, hexanes, heptane, heptanes, cyclohexane, toluene, xylene, dichloromethane and 1,2-dichloroethane. In an embodiment, the hydrophobic solvent is selected from hexane, hexanes, toluene, dichloromethane and 1,2-dichloroethane. In an embodiment, the hydrophobic solvent is hexanes. In an embodiment, the hydrophobic solvent is 1,2-dichloroethane.

In an embodiment, the allylic alcohol is any compound that comprises a hydroxy group attached to an sp$^3$ hybridized carbon that is adjacent to double bond.

In an embodiment, the allylic alcohol is a naturally occurring allylic alcohol. In an embodiment, the allylic alcohol is a terpene alcohol, a vitamin, or a cinnamyl alcohol.

In an embodiment, the allylic alcohol is a terpene alcohol. In an embodiment, the terpene alcohol is a monoterpene alcohol, diterpene alcohol or sequiterpene alcohol.

In an embodiment, the terpene alcohol comprises a prenyl (e.g., 3,3-dimethylallyl) functional,

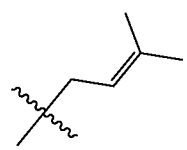 [SMILES: *CC=C(C)C]

or repeating prenyl functional groups. Therefore, in an embodiment, the terpene alcohol is prenol, geraniol, phytol, farnesol, or nerol.

In an embodiment, the monoterpene alcohol is isopiperitenol.

In an embodiment, the vitamin or derivative thereof is retinol.

In an embodiment, the allylic alcohol is cinnamyl alcohol. In an embodiment, the allylic alcohol is a substituted cinnamyl alcohol. In an embodiment, the substituted cinnamyl alcohol is substituted on the aryl ring.

In an embodiment, the hydroxy aryl compound or phenolic is phenol or a substituted phenol. In an embodiment, the hydroxy aryl compound is resorcinol or a substituted resorcinol. In an embodiment, the hydroxyl aryl compound is a phloroglucinol or a substituted phloroglucinol. In an embodiment, the hydroxy aryl compound is a hydroxy chalconoid or a meta-dihydroxychalconoid. In an embodiment, the hydroxyl aryl compound is a moracin or a substituted moracin. In an embodiment, the hydroxyl aryl compound is a stilbenoid. In an embodiment, the stilbenoid is resveratrol. In an embodiment, the hydroxy aryl compound is a polycyclic hydroxy aryl compound (e.g. polyhydroxyphenolic compound).

In an embodiment, the hydroxy aryl compound is a hydroxy substituted monocyclic heteroaryl.

In an embodiment, the hydroxy aryl compound is a polycyclic hydroxy aryl compound. In an embodiment, the polycyclic hydroxy aryl compound is a hydroxy polyaromatic compound, steroid alcohol, a hydroxy benzofused compound, hydroxy polycyclic heterocycle or a hydroxy polycyclic heteroaryl.

In an embodiment, the polycyclic hydroxy aryl compound is a hydroxy polyaromatic compound. In an embodiment, the polyaromatic compound in the hydroxy polyaromatic compound is a naphthalene, anthracene, phenanthrene, tetracene, chrysene, triphenylene, pyrene, pentacene, benzo[a]pyrene, corannulene, benzo[ghi]perylene, coronene, ovalene or benzo[c]fluorine. In an embodiment, the polyaromatic compound in the hydroxy polyaromatic compound is a naphthalene. In an embodiment, the polycyclic hydroxy aryl compound is a polyhydroxy polyaromatic compound.

In an embodiment, the polycyclic hydroxy aryl compound is a steroid alcohol. In an embodiment, the steroid alcohol is an estrogen. In an embodiment, the estrogen is estrone, estradiol, estriol, or estetrol. In an embodiment, the steroid alcohol is an estrogen derivative. In an embodiment, the estrogen derivative is ethinyl estradiol.

In an embodiment, the polycyclic hydroxy aryl compound is a hydroxy benzofused compound. In an embodiment, the hydroxy benzofused compound is a hydroxy chromone, or a meta-dihydroxy chromone. In an embodiment, the benzofused compound is a flavonol, isoflavonol, flavavonol or isoflavavonol. In an embodiment, the benzofused compound is a hydroxy coumarin. In an embodiment, the benzofused compound is a hydroxy xanthone. In an embodiment, the benzofused compound is a benzofurochromenone.

In an embodiment, the polycyclic hydroxy aryl compound is a hydroxy substituted polycyclic heterocycle or heteroaryl. In an embodiment, hydroxy substituted polycyclic heteroaryl is hydroxy substituted indolyl, isoindolyl or benzofuranyl.

In an embodiment, the ortho-allylated hydroxy aryl compound is a naturally occurring compound. In an embodiment, the ortho-allylated hydroxy aryl compound is an ortho-allylated resorcinol, an ortho-allylated phloroglucinol, an ortho-allylated chalcone, and ortho-allylated cannabinoid, an ortho-allylated meta-dihydroxy chalconoid, an ortho-allylated hydroxy chalconoid, an ortho-allylated meta-dihydroxychalconoid, an ortho-allylated moracin, an ortho-allylated stilbenoid, an ortho-allylated hydroxy naphthalene, an ortho-allylated hydroxy anthracene, an ortho-allylated hydroxy phenanthrene, an ortho-allylated hydroxy tetracene, an ortho-allylated hydroxy chrysene, an ortho-allylated hydroxy triphenylene, an ortho-allylated hydroxy pyrene, an ortho-allylated hydroxy pentacene, an ortho-allylated hydroxy benzo[a]pyrene, an ortho-allylated hydroxy corannulene, an ortho-allylated hydroxy benzo[ghi]perylene, an ortho-allylated hydroxy coronene, an ortho-allylated hydroxy ovalene, an ortho-allylated hydroxy benzo[c]fluorine, an ortho-allylated steroid alcohol, an ortho-allylated flavanonol, an ortho-allylated isoflavanonol, an ortho-allylated flavonols, an ortho-allylated isoflavonol, an ortho-allylated steroid, an ortho-allylated hydroxy chromone, ortho-allylated meta-dihydroxy chromone, an ortho-allylated hydroxy xanthone or an ortho-allylated coumarin.

In an embodiment, the ortho-allylated hydroxy aryl compound comprises a prenyl (e.g. 3,3-dimethylallyl) functional group or repeating prenyl functional groups such as prenyl, geranyl, phytyl, farnesyl, or neryl. Therefore, in an embodiment, the ortho-allylated hydroxy aryl compound is an ortho-prenylated hydroxy aryl compound or an ortho-prenylated phenolic.

In an embodiment, the ortho-allylated cannabinoid is selected from cannabidiol, cannabidivarin, cannabigerol, cannabigerorcin and cannabigerivarin. In an embodiment, the ortho-allylated cannabinoid is selected from cannabidivarin, cannabigerol, cannabigerorcin and cannabigerivarin. In an embodiment, the ortho-allylated cannabinoid is cannabidiol.

In an embodiment, the ortho-allylated hydroxy aryl compound is selected from an ortho-allylated flavanonol, an ortho-allylated flavonol, an ortho-allylated isoflavanonol, an ortho-allylated isoflavonol, isoflavonol or an ortho-allylated hydroxy chromone.

In an embodiment, the ortho-allylated hydroxy aryl compound is an ortho-allylated coumarin.

In an embodiment, the forming of the ortho-allylated hydroxy aryl compound comprises mixing the allylic alcohol, hydroxy aryl compound and the aluminum compound in the non-protic solvent under continuous flow reaction conditions using for example continuous processors. Continuous flow processors comprise a combination of mixing and conveying means that allow the reactants to flow into or through a mixing means, react to form products and allow the products to flow out of the mixing means for isolation and purification on a continuous basis. In the mixing and conveying means, the reaction conditions (such as temperature and pressure) can be controlled. Such continuous flow processors are well known in the art. In an embodiment, the flow reaction conditions comprise a heterogeneous reactor comprising for example a fixed bed reactor, a trickle bed reactor, a moving bed reactor or a rotation bed reactor. In some embodiments, the aluminum compound is comprised in the bed reactor and the other reagents, including the compounds of Formula II and III and optional additives flow through the bed to be converted into compound of Formula I.

In an embodiment, the forming of the ortho-allylated hydroxy aryl compound comprises mixing the allylic alcohol, hydroxy aryl compound and the aluminum compound in the non-protic solvent under batch reaction conditions.

In an embodiment, when forming a mono ortho-allylated hydroxy aryl compound, the forming of the ortho-allylated hydroxy aryl compound further comprises mixing the allylic alcohol, the hydroxy aryl compound and the aluminum compound in the non-protic solvent with the addition of excess amounts of the hydroxy aryl compound. In an embodiment, the forming of the ortho-allylated hydroxy aryl compound comprises mixing the allylic alcohol, hydroxy aryl compound and aluminum compound in the non-protic solvent with the addition of, for example, about 1.1 to about 5, about 1.1 to about 4, about 1.1 to about 3, about 2 to about 5, about 2 to about 4, about 3 to about 4, or about 1.5 to about 3 molar equivalents of the hydroxy aryl compound relative to the amount of the allylic alcohol. In an embodiment, the forming of the ortho-allylated hydroxy aryl compound comprises mixing the allylic alcohol, hydroxy aryl compound and aluminum compound in the non-protic solvent with the addition of, for example, about 1 to about 5, about 1 to about 4, about 1 to about 3, or about 1.5 to about 3 molar equivalents of the hydroxy aryl compound relative to the amount of the allylic alcohol. In an embodiment, the conditions forming of the ortho-allylated hydroxy aryl compound comprises mixing the allylic alcohol, hydroxy aryl compound and aluminum compound in the non-protic solvent with about 1.5 molar equivalents of the hydroxy aryl compound relative to the amount of the allylic alcohol.

In an embodiment, when forming an mono ortho-allylated hydroxy aryl compound the forming of the ortho-allylated hydroxy aryl compound further comprises mixing the allylic alcohol, the hydroxy aryl compound and the aluminum compound in the non-protic solvent with about 1.5 to about 4 molar equivalents, about 1.5 to about 5 molar, about 2 to about 5, about 2 to about 4, or about 3 to about 4 molar equivalents of the compound of Formula (II) relative to the amount of the compound of Formula (III). In an embodiment, the forming of the ortho-allylated hydroxy aryl compound further comprises mixing the allylic alcohol, the hydroxy aryl compound and the aluminum compound in the non-protic solvent with about 3 to about 4 molar equivalents of the compound of Formula (II) relative to the amount of the compound of Formula (III).

In an embodiment, when it is desired to add additional allyl groups, beyond the ortho-allyl group (i.e. a polyallylated hydroxy aryl compound such as a di-, tri- and tetra-allylated hydroxy aryl compound), the forming of the polyallylated hydroxy aryl compound further comprises mixing the allylic alcohol, the hydroxy aryl compound and the aluminum compound in the non-protic solvent with the addition of excess amounts of the allylic alcohol. In an embodiment, the forming of the polyallylated hydroxy aryl compound comprises mixing the allylic alcohol, hydroxy aryl compound and aluminum compound in the non-protic solvent with the addition of, for example, about 1.1 to about 5, about 1.1 to about 4, about 1.1 to about 3, about 2 to about 5, 1.5 to about 4, about 2 to about 4, about 3 to about 4, about 3 to about 5, about 4 to about 5, or about 1.5 to about 3 molar equivalents of the allylic alcohol relative to the amount of the hydroxy aryl compound. In an embodiment, the conditions forming of the polyallylated hydroxy aryl compound comprises mixing the allylic alcohol, hydroxy aryl compound and aluminum compound in the non-protic solvent with about 3 to about 4, about 3 to about 5, or about 4 to about 5 molar equivalents of the allylic alcohol relative to the amount of the hydroxy aryl compound.

In an embodiment, the forming of the ortho-allylated hydroxy aryl compound further comprises mixing the allylic alcohol, the hydroxy aryl compound and the aluminum compound in the non-protic solvent with the addition of the aluminum compound in the amount of about 1 g to about 3 g, about 1.5 g to about 3 g, or about 1.5 g to about 2 g per 1 mmol of the allylic alcohol. In an embodiment, the forming of the ortho-allylated hydroxy aryl compound comprises mixing the allylic alcohol, the hydroxy aryl compound and the aluminum compound in the non-protic solvent with the addition of the aluminum compound in the amount of about 2 g per 1 mmol of the allylic alcohol. In an embodiment, the aluminum compound is alumina. In an embodiment, the alumina is acidic alumina. In an embodiment, the acidic alumina, has a pH of less than about 6.5, about 6, about 5.5, about 5.0, about 4.5 or about 4.0. In an embodiment, the acidic alumina has a pH of less than about 5.5, about 5.0, about 4.5 or about 4.0. In an embodiment, the acidic alumina, has a pH of about 4.5.

In an embodiment, the alumina is basic alumina. In an embodiment, the basic alumina, has a pH of greater than about 7.5, about 8, about 8.5, about 9.0, about 9.5, about 10 or about 10.5. In an embodiment, the basic alumina has a pH of greater than about 9.0, about 9.5, about 10 or about 10.5. In an embodiment, the basic alumina has a pH of about 10.

In an embodiment, the alumina is neutral alumina. In an embodiment, the neutral alumina has a pH of about 7.

In an embodiment, the forming of the ortho-allylated hydroxy aryl compound further comprises mixing the allylic alcohol, the hydroxy aryl compound and the aluminum compound in the non-protic solvent to form a reaction mixture and heating the reaction mixture.

In an embodiment, the forming of the ortho-allylated hydroxy aryl compound further comprises mixing the allylic alcohol, the hydroxy aryl compound and the aluminum compound in the non-protic solvent to form a reaction mixture and heating the reaction mixture to the boiling point (refluxing temperature) of the solvent. In an embodiment, the forming of the ortho-allylated hydroxy aryl compound further comprises mixing the allylic alcohol, the hydroxy aryl compound and the alumina in DCE to form a reaction mixture and heating the reaction mixture to about 40° C. to about 83° C., about 60° C. to about 83° C., about 70° C. to about 83° C., or about 83° C.

In an embodiment, the forming of the ortho-allylated hydroxy aryl compound further comprises mixing the allylic alcohol, the hydroxy aryl compound and the aluminum compound in the non-protic solvent to form a reaction mixture, and heating the reaction mixture for about 4 hours to about 24 hours, about 6 hours to about 24 hours, or about 12 hours to 24 hours. In an embodiment, the forming of the ortho-allylated hydroxy aryl compound further comprises mixing the allylic alcohol, the hydroxy aryl compound and the aluminum compound in the non-protic solvent to form a reaction mixture, and heating the reaction mixture at the refluxing temperature of the solvent for about 24 hours.

In an embodiment, the forming of the ortho-allylated hydroxy aryl compound comprises mixing the allylic alcohol, the hydroxy aryl compound and the aluminum compound in the non-protic solvent to form a reaction mixture and heating the reaction mixture under microwave synthesis conditions. Therefore, in an embodiment, the forming of the ortho-allylated hydroxy aryl compound comprises mixing the allylic alcohol, the hydroxy aryl compound and the aluminum compound in the non-protic solvent to form a reaction mixture and heating the reaction mixture using microwave radiation. In an embodiment, the microwave synthesis conditions comprise heating the reaction mixture in a microwave reactor. In an embodiment, the microwave synthesis conditions comprise heating the reaction mixture in a microwave reactor to about 100° C. to about 175° C., about 125° C. to about 175° C., or about 150° C.

In an embodiment, after heating, the reaction mixture is cooled and filtered through a filter agent, such as Celite® or silica, and the filtrate is concentrated for example, by evaporation such as rotoevaporation, to provide a crude product that comprises the ortho-allylated hydroxy aryl compound. In an embodiment, the crude product is then purified using chromatography such as column chromatography using a suitable solvent or mixture of solvents, or any other known purification method.

In an embodiment, the column chromatography is flash column chromatography. In an embodiment, the suitable mixture of solvents for column chromatography is ethyl acetate and hexane.

In an embodiment, the crude product is purified by crystallization. In an embodiment, the crude product is purified by crystallization without the use of chromatography. In an embodiment, the crude product is crystallized using hexane, hexanes, heptane, heptanes, cyclohexane, toluene, xylene and the like. In an embodiment, the crude product is a crude ortho-allylated cannabinoid and the crude product is crystallized using hexane, hexanes, heptane, heptanes, or cyclohexane. In an embodiment, the crude product is a crude ortho-allylated cannabinoid and the crude product is crystallized with heptane.

In an embodiment, the crude product is purified by distillation. In an embodiment, the crude product is purified by distillation without the use of chromatography. In an embodiment, the crude product is a crude ortho-allylated cannabinoid and the crude product is purified by distillation.

In an embodiment, the process of the application can be performed consecutively such that the ortho-allylated hydroxy aryl compound formed from a first process of the application is used as the hydroxy aryl compound in a subsequent process of the application. Accordingly, in the embodiment, the hydroxy aryl compound is the ortho-allylated hydroxy aryl formed by a process of the application described above.

In an embodiment, the process provides the ortho-allylated hydroxy aryl compound as the major product of the process. In an embodiment, the process provides the ortho-allylated hydroxy aryl compound in a yield of greater than about 15%, about 20%, about 25%, about 30%, about 35%, about 40%, about 45%, about 50%, about 55%, about 60%, about 65%, about 70%, about 75%, about 80%, about 85%, about 90% or about 95%.

In an embodiment, the process provides the ortho-allylated hydroxy aryl compound in a yield of greater an about 55%, about 60%, about 65%, about 70%, about 75%, about 80%, about 85%, about 90% or about 95%. In an embodiment, the process provides the ortho-allylated hydroxy aryl compound in a yield of greater an about 70%, about 75%, about 80%, about 85%, about 90% or about 95%.

The Applicants have also shown that an ortho-allylated hydroxy aryl compound can be formed by reacting an allylic alcohol with a hydroxy aryl compound in the presence of alumina and further additives including dehydrating reagents such as magnesium sulfate and/or various acids. Therefore, the process of the application further comprises the use of a dehydrating reagent and/or an acid in combination with the aluminum compound. Therefore, the application also includes a process for preparing an ortho-allylated hydroxy aryl compound comprising reacting an allylic alcohol with a hydroxy aryl compound in the presence of alumina and a dehydrating agent in a non-protic solvent to form the ortho-allylated hydroxy aryl compound, wherein at least one carbon atom ortho to the hydroxy group in the hydroxy aryl compound is unsubstituted.

In an embodiment, the dehydrating agent is selected from magnesium sulfate, sodium sulfate, aluminum phosphate, calcium oxide, cyanuric chloride, orthoformic acid, phosphorus pentoxide, sulfuric acid and molecular sieves, and combinations thereof. In an embodiment, the dehydrating agent is selected from magnesium sulfate, sodium sulfate, aluminum phosphate, calcium oxide, cyanuric chloride, orthoformic acid, phosphorus pentoxide, and molecular sieves, and combinations thereof. In an embodiment, the dehydrating agent is magnesium sulfate.

The Applicants have found that the alumina can be acidic alumina. It would be appreciated by a person skilled in the art that acid can be added to the alumina in process of the application. Therefore, in an embodiment, the application also includes a process for preparing an ortho-allylated hydroxy aryl compound comprising reacting an allylic alcohol with a hydroxy aryl compound in the presence of alumina and an acid in a non-protic solvent to form the ortho-allylated hydroxy aryl compound, wherein at least one carbon atom ortho to the hydroxy group in the hydroxy aryl compound is unsubstituted.

In an embodiment the acid is selected from a Lewis acid and a Bronsted acid, and a combination thereof. In an embodiment, the Lewis acid is selected from boron trichloride, boron trifluoride, boron trifluoride diethyl etherate, iron (III) bromide, iron (III) chloride, aluminum chloride, aluminum bromide, tin (IV) chloride, titanium (IV) chloride, and titanium (IV) isopropoxide and a combination thereof. In an embodiment, the Bronsted acid is selected from hydrochloric acid, sulfuric acid, nitric acid, phosphoric acid, acetic acid, trifluoroacetic acid, toluene sulfonic acid, trichloroacetic acid, boric acid, oleic acid, palmitic acid, and camphor sulfonic acid and a combination thereof.

In an embodiment, the allylic alcohol, hydroxy aryl compound and ortho-allylated hydroxy aryl compound are as described above.

In an embodiment, the forming of the ortho-allylated hydroxy aryl compound in the presence of alumina and a further additive such as a dehydrating agent and/or an acid in a non-protic solvent are under conditions as described above for the forming of the ortho-allylated hydroxy aryl compound in the presence of aluminum compound such as alumina alone in a non-protic solvent.

The Applicants have further shown that an ortho-allylated hydroxy aryl compound can be formed by reacting an allylic alcohol with a hydroxy aryl compound in the presence of an aluminum alkoxide such as aluminum isopropoxide. Therefore, in an embodiment, the aluminum compound is aluminum alkoxide.

Accordingly, the application also includes a process for preparing an ortho-allylated hydroxy aryl compound comprising reacting an allylic alcohol with a hydroxy aryl compound in the presence of an aluminum alkoxide and in a non-protic solvent to form the ortho-allylated hydroxy aryl compound, wherein at least one carbon atom ortho to the hydroxy group in the hydroxy aryl compound is unsubstituted.

In an embodiment, the aluminum alkoxide dissolves in the non-protic solvent. Therefore, the reacting an allylic alcohol with a hydroxy aryl compound in the presence of an aluminum alkoxide and in a non-protic solvent to form the ortho-allylated hydroxy aryl compound, wherein at least one carbon atom ortho to the hydroxy group in the hydroxy aryl compound is unsubstituted is a homogenous reaction.

In an embodiment, the allylic alcohol, hydroxy aryl compound and ortho-allylated hydroxy aryl compound are as described above.

In an embodiment, the forming of the ortho-allylated hydroxy aryl compound in the presence of aluminum alkoxide in a non-protic solvent are under conditions as described above for the forming of the ortho-allylated hydroxy aryl compound in the presence of alumina in a non-protic solvent.

In an embodiment, the aluminum alkoxide is an aluminum $C_{1-10}$alkoxide. In an embodiment, the aluminum alkoxide is an aluminum $C_{1-6}$alkoxide. In an embodiment, the aluminum alkoxide is an aluminum $C_{1-6}$alkoxide. In an embodiment, the aluminum alkoxide is selected from aluminum methoxide, aluminum ethoxide, aluminum-n-propoxide, aluminum isopropoxide, aluminum-n-butoxide, aluminum-sec-butoxide, aluminum-iso-propoxide and aluminum tert-butoxide. In an embodiment, the aluminum alkoxide is aluminum isopropoxide. In an embodiment, the allylic alcohols and the hydroxy aryl compounds are both available from commercial sources or can be prepared using methods known in the art.

In an embodiment, the alumina (e.g., neutral, basic and acidic alumina) is available from commercial sources.

In an embodiment, the aluminum alkoxide (e.g. aluminum isopropoxide) is available from commercial sources.

In an embodiment, the application further includes a process for preparing a compound of Formula (I) comprising:

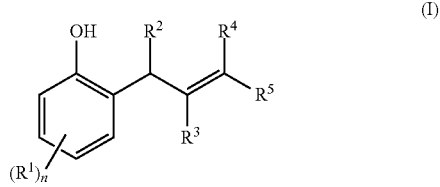

reacting a compound of Formula (II)

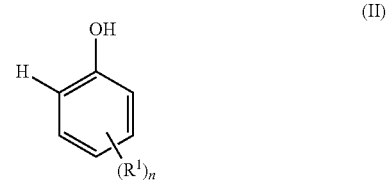

with a compound of Formula (III)

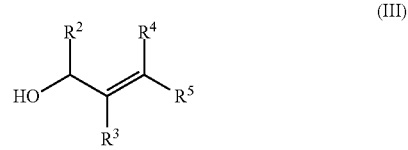

in the presence of an aluminum compound selected from alumina and aluminum alkoxides and in a non-protic solvent to form the compound of Formula (I), wherein:
each $R^1$ is independently OH, halo, CN, $NO_2$ or COOH, or independently selected from any suitable unsubstituted or substituted alkyl, alkenyl, alkynyl, cycloalkyl, heterocycloalkyl, aryl, heteroaryl, Z-alkyl, Z-alkenyl, Z-alkynyl, Z-cycloalkyl, Z-heterocycloalkyl, Z-aryl, Z and Z-heteroaryl, wherein the substituents are selected from OH, halo, alkyl, O-alkyl, aryl, cycloalkyl, heteroaryl and heterocycloalkyl groups, the latter 4 groups being optionally substituted with one or more substituents selected from OH, alkyl, alkenyl, and O-alkyl; or when n is greater than 1, two $R^1$ groups are linked together to form an unsubstituted or substituted polycyclic ring system having 8 or more atoms together with the phenyl ring to which said $R^1$ groups are bonded, and in which one or more carbon atoms in said polycyclic ring system is optionally replaced with a heteromoiety selected from $NR^6$, O and S; wherein the polycyclic ring system is optionally substituted with one or more substituents selected from =O, OH, halo, alkyl, alkenyl, alkynyl, O-alkyl, O-alkenyl, O-alkynyl, aryl, heteroaryl, cycloalkyl, and heterocycloalkyl the latter 10 groups being optionally substituted with one or more substituents selected from OH, alkyl, alkenyl, and O-alkyl;

Z is selected from O, C(O), $CO_2$, S, $SO_2$, SO, and $NR^7$;
$R^2$ is H;
$R^3$ is selected from H and any suitable unsubstituted or substituted alkyl;
$R^4$ is H, or selected from any suitable unsubstituted or substituted alkyl; aryl, alkylenearyl, heteroaryl, and alkyleneheteroaryl;
$R^5$ is H, or selected from any suitable unsubstituted or substituted alkyl, alkenyl, alkynyl, cycloalkyl, heterocycloalkyl, aryl and heteroaryl, wherein the substituents are selected from OH, halo, alkyl, O-alkyl, aryl, cycloalkyl, heteroaryl and heterocycloalkyl groups; or
any two of $R^2$, $R^3$, $R^4$ and $R^5$ are linked together to form an unsubstituted or substituted monocyclic or polycyclic ring system having 4 or more atoms together with the carbon atoms to which said any two of $R^2$, $R^3$, $R^4$ and $R^5$ are bonded, wherein the monocyclic or polycyclic ring system is optionally substituted with one or more substituents selected from =O, OH, halo, alkyl, alkenyl, alkynyl, O-alkyl, O-alkenyl, O-alkynyl, aryl, heteroaryl, cycloalkyl, and heterocycloalkyl, the latter 10 groups being optionally substituted with OH, alkyl, alkenyl, and O-alkyl;
$R^6$ and $R^7$ are independently selected from H and unsubstituted or substituted alkyl;
n is an integer selected from 0 to 4, and
all alkyl, alkenyl, alkynyl, alkylene, alkenylene, alkynylene, cycloalkyl, and heterocycloalkyl groups are optionally fluoro-substituted.

In an embodiment, the aluminum compound is alumina.
Therefore, in an embodiment, the application further includes a process for preparing a compound of Formula (I) comprising:

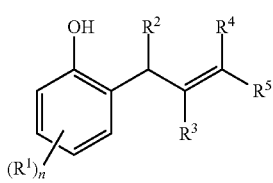
(I)

reacting a compound of Formula (II)

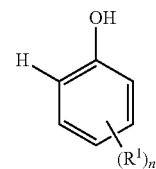
(II)

with a compound of Formula (III)

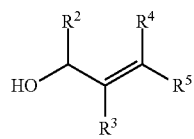
(III)

in presence of alumina and in a hydrophobic solvent under conditions to form the compound of Formula (I),
wherein:
each $R^1$ is independently OH, halo, CN, $NO_2$ or COOH, or independently selected from any suitable unsubstituted or substituted alkyl, alkenyl, alkynyl, cycloalkyl, heterocycloalkyl, aryl, heteroaryl, Z-alkyl, Z-alkenyl, Z-alkynyl, Z-cycloalkyl, Z-heterocycloalkyl, Z-aryl, Z and Z-heteroaryl, wherein the substituents are selected from OH, halo, alkyl, O-alkyl, aryl, cycloalkyl, heteroaryl and heterocycloalkyl groups, the latter 4 groups being optionally substituted with one or more substituents selected from OH, alkyl, alkenyl, alkynyl, O-alkyl, or O-alkenyl; or when n is greater than 1, two $R^1$ groups are linked together to form an unsubstituted or substituted polycyclic ring system having 8 or more atoms together with the phenyl ring to which said $R^1$ groups are bonded, and in which one or more carbon atoms in said polycyclic ring system is optionally replaced with a heteromoiety selected from $NR^6$, O and S; wherein the polycyclic ring system is optionally substituted with one or more substituents selected from =O, OH, halo, alkyl, alkenyl, alkynyl, O-alkyl, O-alkenyl, O-alkynyl, aryl, heteroaryl, cycloalkyl, and heterocycloalkyl the latter 10 groups being optionally substituted with one or more substituents selected from OH, alkyl, alkenyl, and O-alkyl;

Z is selected from O, C(O), $CO_2$, S, $SO_2$, SO, and $NR^7$;
$R^2$ is selected from H and any suitable unsubstituted or substituted alkyl;
$R^3$ is selected from H and any suitable unsubstituted or substituted alkyl;
$R^4$ is H, or selected from any suitable unsubstituted or substituted alkyl; aryl, alkylenearyl, heteroaryl, and alkyleneheteroaryl;
$R^5$ is H, or selected from any suitable unsubstituted or substituted alkyl, alkenyl, alkynyl, cycloalkyl, heterocycloalkyl, aryl and heteroaryl, wherein the substituents are selected from OH, halo, alkyl, O-alkyl, aryl, cycloalkyl, heteroaryl and heterocycloalkyl groups; or
any two of $R^2$, $R^3$, $R^4$ and $R^5$ are linked together to form an unsubstituted or substituted monocyclic or polycyclic ring system having 4 or more atoms together with the carbon atoms to which said any two of $R^2$, $R^3$, $R^4$ and R⁵ are bonded, wherein the monocyclic or polycyclic ring system is optionally substituted with one or more substituents selected from =O, OH, halo, alkyl, alkenyl, alkynyl, O-alkyl, O-alkenyl, O-alkynyl, aryl, heteroaryl, cycloalkyl, and heterocycloalkyl, the latter 10 groups being optionally substituted with OH, alkyl, alkenyl, and O-alkyl;

$R^6$ and $R^7$ are independently selected from H and unsubstituted or substituted alkyl;

n is an integer selected from 0 to 4, and all alkyl, alkenyl, alkynyl, alkylene, alkenylene, alkynylene, cycloalkyl, and heterocycloalkyl groups are optionally fluoro-substituted.

In an embodiment, the application further includes a process for preparing a compound of Formula (I) comprising:

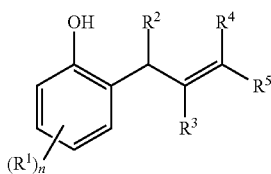
(I)

reacting a compound of Formula (II)

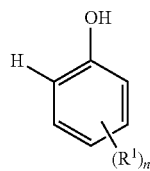
(II)

with a compound of Formula (III)

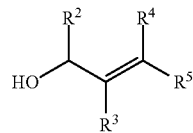
(III)

in the presence of an aluminum compound selected from alumina and aluminum alkoxides and in a non-protic solvent to form the compound of Formula (I), wherein:

each $R^1$ is independently selected from OH, halo, CN, NO$_2$, COOH, C$_{2-16}$alkenyl, C$_{2-16}$alkynyl, C$_{3-18}$cycloalkyl, C$_{1-16}$alkyleneC$_{3-18}$ cycloalkyl, C$_{2-16}$alkenyleneC$_{3-18}$cycloalkyl, C$_{2-16}$alkynyleneC$_{3-18}$ cycloalkyl, C$_{3-18}$heterocycloalkyl, C$_{1-16}$alkyleneC$_{3-18}$heterocycloalkyl, C$_{1-10}$alkenyleneC$_{3-18}$heterocycloalkyl, C$_{2-16}$alkynyleneC$_{3-18}$heterocycloalkyl, C$_{6-18}$aryl, C$_{1-16}$alkyleneC$_{6-18}$aryl, C$_{2-16}$alkenyleneC$_{6-18}$aryl, C$_{2-16}$alkynyleneC$_{6-18}$ aryl, C$_{5-18}$heteroaryl, C$_{2-16}$alkyleneC$_{5-18}$heteroaryl, C$_{2-16}$alkenyleneC$_{5-18}$heteroaryl, C$_{2-16}$alkynyleneC$_{5-18}$heteroaryl, Z—C$_{1-16}$alkyl, Z—C$_{2-16}$alkenyl, Z—C$_{2-16}$alkynyl, Z—C$_{3-18}$ cycloalkyl, Z—C$_{1-16}$alkyleneC$_{3-18}$cycloalkyl, Z—C$_{2-16}$alkenyleneC$_{3-18}$ cycloalkyl, Z—C$_{2-16}$alkynyleneC$_{3-18}$ cycloalkyl, Z—C$_{3-18}$heterocycloalkyl, Z—C$_{1-16}$alkyleneC$_{3-18}$ heterocycloalkyl, Z—C$_{2-16}$alkenyleneC$_{3-18}$heterocycloalkyl, Z—C$_{2-16}$alkynyleneC$_{3-18}$ heterocycloalkyl, Z—C$_{6-18}$aryl, Z—C$_{1-16}$alkyleneC$_{6-18}$aryl, Z—C$_{2-16}$alkenyleneC$_{6-18}$aryl, Z—C$_{2-16}$alkynyleneC$_{6-18}$aryl, Z—C$_{5-18}$heteroaryl, Z—C$_{1-16}$alkyleneC$_{5-18}$heteroaryl, Z—C$_{2-16}$alkenyleneC$_{5-18}$ heteroaryl, and Z—C$_{2-16}$alkynyleneC$_{5-18}$heteroaryl, wherein all alkyl, alkenyl, alkynyl, alkylene, alkenylene, alkynylene, cycloalkyl heterocycloalkyl, aryl, and heteroaryl groups are optionally substituted with one or more substituents selected from OH, halo, C$_{1-16}$alkyl, C$_{2-16}$alkenyl, C$_{2-6}$alkynyl, OC$_{1-16}$alkyl, OC$_{2-16}$alkenyl, and OC$_{2-16}$alkynyl; or when n is greater than 1, two $R^1$ groups are linked together to form a polycyclic ring system having 8 or more atoms together with the phenyl ring to which said groups are bonded, and in which one or more carbon atoms in said polycyclic ring system is optionally replaced with a heteromoiety selected from NR⁶, O and S, wherein the polycyclic ring system is optionally substituted with one or more substituents selected from =O, OH, halo, C$_{1-16}$alkyl, C$_{2-16}$alkenyl, C$_{2-16}$alkynyl, OC$_{2-16}$alkenyl, OC$_{2-16}$alkynyl, C(O)C$_{1-16}$alkyl, C(O) C$_{2-16}$alkenyl, C(O)C$_{2-16}$alkynyl, C$_{1-16}$alkyleneOR⁸, C$_{2-16}$alkenyleneOR⁸, C$_{2-16}$alkynyleneOR⁸, C$_{6-18}$aryl, C$_{3-18}$cycloalkyl, C$_{3-18}$heterocycloalkyl, and C$_{3-18}$heteroaryl, the latter 4 groups being optionally substituted with one or more substituents selected from OH, halo, C$_{1-16}$alkyl, OC$_{1-16}$alkyl, and C$_{2-16}$alkenyl;

Z is selected from O, C(O), CO$_2$, S, SO$_2$, SO, and NR⁷;

$R^2$ is H, $R^3$ is selected from H and C$_{1-6}$alkyl, $R^4$ is selected from H, C$_{1-6}$alkyl, C$_{6-18}$aryl, C$_{1-16}$alkyleneC$_{6-18}$aryl, C$_{5-18}$ heteroaryl, and C$_{2-16}$alkylene C$_{5-18}$heteroaryl;

$R^5$ is selected from H, C$_{1-26}$alkyl, C$_{2-26}$alkenyl, C$_{2-26}$alkynyl, C$_{3-18}$ cycloalkyl, C$_{1-16}$alkyleneC$_{3-18}$ cycloalkyl, C$_{2-16}$alkenyleneC$_{3-18}$ cycloalkyl, C$_{2-16}$alkynylene C$_{3-18}$cycloalkyl, C$_{3-18}$ heterocycloalkyl, C$_{1-16}$alkyleneC$_{3-18}$ heterocycloalkyl, C$_{1-16}$alkenyleneC$_{3-18}$ heterocycloalkyl, C$_{2-16}$alkynyleneC$_{3-18}$ heterocycloalkyl, C$_{6-18}$ aryl, C$_{1-16}$alkyleneC$_{6-18}$ aryl, C$_{2-16}$alkenylene C$_{6-18}$ aryl, C$_{2-16}$alkynyleneC$_{6-18}$ aryl, C$_{5-18}$heteroaryl, C$_{2-16}$alkyleneC$_{5-18}$heteroaryl, C$_{2-16}$alkenyleneC$_{5-18}$ heteroaryl, C$_{2-16}$alkynyleneC$_{5-18}$heteroaryl, wherein all cycloalkyl, heterocycloalkyl, aryl and heteroaryl are optionally substituted with one or more substituents selected from OH, NO$_2$, CN, halo, C$_{1-16}$alkyl, C$_{2-16}$alkenyl, C$_{2-16}$alkynyl, OC$_{1-16}$alkyl, OC$_{2-16}$alkenyl, OC$_{2-16}$alkynyl, C$_{1-16}$alkyleneOR⁹ C$_{2-16}$alkenyleneOR⁹, C$_{2-16}$alkynyleneOR⁹, SO$_3$C$_{1-16}$alkyl, SO$_3$C$_{6-16}$ aryl, and SO$_3$C$_{5-18}$ heteroaryl substituted with C$_{1-16}$alkyl; or any two of $R^2$, $R^3$, $R^4$ and $R^5$ are linked together to form an unsubstituted or substituted monocyclic or polycyclic ring system having 4 or more atoms together with the carbon atoms to which said any two of $R^2$, $R^3$, $R^4$ and $R^5$ are bonded, wherein the monocyclic or polycyclic ring system is optionally substituted with one or more substituents selected =O, OH, halo, C$_{1-16}$alkyl, C$_{2-16}$alkenyl, C$_{2-16}$alkynyl, OC$_{1-16}$alkyl, OC$_{2-16}$alkenyl, OC$_{2-16}$alkynyl; C$_{1-16}$alkyleneOR⁸, C$_{2-16}$alkenyleneOR⁸, C$_{2-16}$alkynyleneOR⁸, C$_{6-18}$ aryl, C$_{3-18}$cycloalkyl, C$_{3-18}$heterocycloalkyl, and C$_{5-18}$heteroaryl, the latter 4 groups being optionally substituted with one or more substituents selected from OH, halo, C$_{1-16}$alkyl, OC$_{1-16}$alkyl, and C$_{2-16}$alkenyl;

$R^6$, $R^7$, $R^8$ and $R^9$ are independently selected from H and $C_{1-6}$alkyl;

n is an integer selected from 0 to 4, and all alkyl, alkenyl, alkynyl, alkylene, alkenylene, alkynylene, cycloalkyl, and heterocycloalkyl groups are optionally fluoro-substituted.

In an embodiment, the aluminum compound is alumina. Therefore, in an embodiment, the process of the application comprises reacting the compound of Formula (II) as defined above with a compound of Formula (III) as defined above in the presence of alumina and in a non-protic solvent to form the compound of Formula (I) as defined above.

Therefore, in an embodiment, the application further includes a process for preparing a compound of Formula (I) comprising:

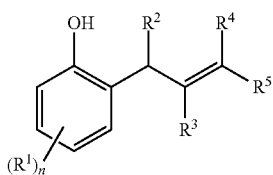
(I)

reacting a compound of Formula (II)

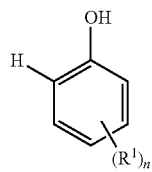
(II)

with a compound of Formula (III)

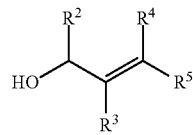
(III)

in presence of alumina and in a hydrophobic solvent under conditions to form the compound of Formula (I), wherein:

each $R^1$ is independently selected from OH, halo, CN, $NO_2$, COOH, $C_{2-16}$alkenyl, $C_{2-16}$alkynyl, $C_{3-18}$ cycloalkyl, $C_{1-16}$alkylene$C_{3-18}$ cycloalkyl, $C_{2-16}$alkenylene$C_{3-18}$cycloalkyl, $C_{2-16}$alkynylene$C_{3-18}$ cycloalkyl, $C_{3-18}$heterocycloalkyl, $C_{1-16}$alkylene$C_{3-18}$heterocycloalkyl, $C_{1-10}$alkenylene$C_{3-18}$heterocycloalkyl, $C_{2-16}$alkynylene$C_{3-18}$heterocycloalkyl, $C_{6-18}$aryl, $C_{1-16}$alkylene$C_{6-18}$aryl, $C_{2-16}$alkenylene$C_{6-18}$aryl, $C_{2-16}$alkynylene$C_{6-18}$ aryl, $C_{5-18}$heteroaryl, $C_{2-16}$alkylene$C_{5-18}$heteroaryl, $C_{2-16}$alkenylene$C_{5-18}$heteroaryl, $C_{2-16}$alkynylene$C_{5-18}$heteroaryl, 16alkyl, Z—$C_{2-16}$alkenyl, Z—$C_{2-16}$alkynyl, Z—$C_{3-18}$ cycloalkyl, Z—$C_{1-16}$alkylene$C_{3-18}$cycloalkyl, Z—$C_{2-16}$alkenylene$C_{3-18}$ cycloalkyl, Z—$C_{2-16}$alkynylene$C_{3-18}$ cycloalkyl, Z—$C_{3-18}$heterocycloalkyl, Z—$C_{1-16}$alkylene$C_{3-18}$ heterocycloalkyl, Z—$C_{2-16}$alkenylene$C_{3-18}$heterocycloalkyl, Z—$C_{2-16}$alkynylene$C_{3-18}$ heterocycloalkyl, Z—$C_{6-18}$aryl, Z—$C_{1-16}$alkylene$C_{6-18}$aryl, Z—$C_{2-16}$alkenylene$C_{6-18}$aryl, Z—$C_{2-16}$alkynylene $C_{6-18}$aryl, Z—$C_{5-18}$heteroaryl, Z—$C_{1-16}$alkylene $C_{5-18}$heteroaryl, Z—$C_{2-16}$alkenylene$C_{5-18}$ heteroaryl, and Z—$C_{2-16}$alkynylene$C_{5-18}$heteroaryl, wherein all alkyl, alkenyl, alkynyl, alkylene, alkenylene, alkynylene, cycloalkyl heterocycloalkyl, aryl, and heteroaryl groups are optionally substituted with one or more substituents selected from OH, halo, $C_{1-16}$alkyl, $C_{2-16}$alkenyl, $C_{2-6}$alkynyl, $OC_{1-16}$alkyl, $OC_{2-16}$alkenyl, and $OC_{2-16}$alkynyl; or when n is greater than 1, two $R^1$ groups are linked together to form a polycyclic ring system having 8 or more atoms together with the phenyl ring to which said groups are bonded, and in which one or more carbon atoms in said polycyclic ring system is optionally replaced with a heteromoiety selected from $NR^6$, O and S, wherein the polycyclic ring system is optionally substituted with one or more substituents selected from =O, OH, halo, $C_{1-16}$alkyl, $C_{2-16}$alkenyl, $C_{2-16}$alkynyl, $OC_{2-16}$alkenyl, $OC_{2-16}$alkynyl; $C_{1-16}$alkyleneOR$^8$, $C_{2-16}$alkenyleneOR$^8$, $C_{2-16}$alkynyleneOR$^8$, $C_{6-18}$aryl, $C_{3-18}$ cycloalkyl, $C_{3-18}$ heterocycloalkyl, and $C_{5-18}$heteroaryl, the latter 4 groups being optionally substituted with one or more substituents selected from OH, halo, $C_{1-16}$alkyl, $OC_{1-16}$alkyl, and $C_{2-16}$alkenyl;

Z is selected from O, C(O), $CO_2$, S, $SO_2$, SO, and $NR^7$;

$R^2$ is selected from H and $C_{1-6}$alkyl, $R^3$ is selected from H and $C_{1-6}$alkyl, $R^4$ is selected from H, $C_{1-6}$alkyl, $C_{6-18}$aryl, $C_{1-16}$alkylene$C_{6-18}$aryl, $C_{5-18}$ heteroaryl, and $C_{2-16}$alkylene $C_{5-18}$heteroaryl;

$R^5$ is selected from H, $C_{1-26}$alkyl, $C_{2-26}$alkenyl, $C_{2-26}$alkynyl, $C_{3-18}$ cycloalkyl, $C_{1-16}$alkylene$C_{3-18}$ cycloalkyl, $C_{2-16}$alkenylene$C_{3-18}$ cycloalkyl, $C_{2-16}$alkynylene $C_{3-18}$cycloalkyl, $C_{3-18}$ heterocycloalkyl, $C_{1-16}$alkylene$C_{3-18}$ heterocycloalkyl, $C_{1-16}$alkenylene$C_{3-18}$ heterocycloalkyl, $C_{2-16}$alkynylene$C_{3-18}$ heterocycloalkyl, $C_{6-18}$aryl, $C_{1-16}$alkylene$C_{6-18}$ aryl, $C_{2-16}$alkenylene $C_{6-18}$aryl, $C_{2-16}$alkynylene$C_{6-18}$aryl, $C_{5-18}$heteroaryl, $C_{2-16}$alkylene$C_{5-18}$heteroaryl, $C_{2-16}$alkenylene$C_{5-18}$ heteroaryl, $C_{2-16}$alkynylene$C_{5-18}$heteroaryl, wherein all cycloalkyl, heterocycloalkyl, aryl and heteroaryl are optionally substituted with one or more substituents selected from OH, $NO_2$, CN, halo, $C_{1-16}$alkyl, $C_{2-16}$alkenyl, $C_{2-16}$alkynyl, $OC_{2-16}$alkenyl, $OC_{2-16}$alkynyl, $C_{1-16}$alkyleneOR$^9$ $C_{2-16}$alkenyleneOR$^9$, $C_{2-16}$alkynyleneOR$^9$, $SO_3C_{1-16}$alkyl, $SO_3C_{6-16}$aryl, and $SO_3C_{5-18}$heteroaryl substituted with $C_{1-16}$alkyl; or any two of $R^2$, $R^3$, $R^4$ and $R^5$ are linked together to form an unsubstituted or substituted monocyclic or polycyclic ring system having 4 or more atoms together with the carbon atoms to which said any two of $R^2$, $R^3$, $R^4$ and $R^5$ are bonded, wherein the monocyclic or polycyclic ring system is optionally substituted with one or more substituents selected =O, OH, halo, $C_{1-16}$alkyl, $C_{2-16}$alkenyl, $C_{2-16}$alkynyl, $OC_{1-16}$alkyl, $OC_{2-16}$alkenyl, $OC_{2-16}$alkynyl; $C_{1-16}$alkyleneOR$^8$, $C_{2-16}$alkenyleneOR$^8$, $C_{2-16}$alkynyleneOR$^8$, $C_{6-18}$ aryl, $C_{3-18}$ cycloalkyl, $C_{3-18}$ heterocycloalkyl, and $C_{5-18}$heteroaryl, the latter 4 groups being optionally substituted with one or more substituents selected from OH, halo, $C_{1-16}$alkyl, $OC_{1-16}$alkyl, and $C_{2-16}$alkenyl;

$R^6$, $R^7$, $R^8$ and $R^9$ are independently selected from H and $C_{1-6}$alkyl;

n is an integer selected from 0 to 4, and all alkyl, alkenyl, alkynyl, alkylene, alkenylene, alkynylene, cycloalkyl, and heterocycloalkyl groups are optionally fluoro-substituted.

In an embodiment, the process selectively forms the compound of Formula (I) as the major isomer. Accordingly, in an embodiment, the present application also includes a process for selectively preparing a compound of Formula (I) comprising reacting a compound of Formula (II) with a compound of Formula (III) in presence of an aluminum compound and in a non-protic solvent under forming of the compound of Formula (I), wherein the compounds of Formulae (I) to (III) are as defined above.

In an embodiment, the aluminum compound is alumina. In an embodiment, the alumina is neutral, basic or acidic alumina. In an embodiment, the alumina is neutral alumina. In an embodiment, the alumina is basic alumina. In an embodiment, the alumina is acidic alumina.

In an embodiment, the non-protic solvent is a mixture of one or more non-protic solvents. In an embodiment, the non-protic solvent, suitably non-protic organic solvent, is a non-polar solvent or a polar aprotic solvent. In an embodiment, the non-polar solvent comprises hydrophobic solvents. In an embodiment, the non-protic solvent is selected from hexane, hexanes, heptane, heptanes, cyclohexane, petroleum ether, octane, diglyme, toluene, xylenes, benzene, chloroform, fluorinated alkanes, dichloromethane (DCM), 1,2-dichloroethane (DCE), ethyl acetate, carbon tetrachloride, tetrahydrofuran (THF), diethyl ether, diisopropyl ether, isooctane, methyl ethyl ketone, acetone, dimethyl sulfoxide, dimethylformamide methyl tert-butyl ether, trichloroethane, n-butyl acetate, chlorobenzene acetonitrile, and trifluorotoluene, and mixtures thereof. In an embodiment, the non-protic solvent is selected from hexane, hexanes, heptane, heptanes, cyclohexane, petroleum ether, octane, diglyme, toluene, xylenes, benzene, chloroform, fluorinated alkanes, dichloromethane (DCM), 1,2-dichloroethane (DCE), ethyl acetate, carbon tetrachloride, tetrahydrofuran (THF), diethyl ether, diisopropyl ether, isooctane, methyl ethyl ketone, methyl tert-butyl ether, trichloroethane, n-butyl acetate, chlorobenzene acetonitrile, and trifluorotoluene, and mixtures thereof. In an embodiment, the non-protic solvent is a hydrophobic solvent selected from hexane, hexanes, heptane, heptanes, cyclohexane, toluene, xylene, dichloromethane and 1,2-dichloroethane. In an embodiment, the hydrophobic solvent is selected from hexane, hexanes, toluene, dichloromethane and 1,2-dichloroethane. In an embodiment, the hydrophobic solvent is hexanes. In an embodiment, the hydrophobic solvent is 1,2-dichloroethane.

In an embodiment, Z is selected from O, C(O), and $CO_2$. In an embodiment, Z is selected from O and C(O). In an embodiment, Z is O. In an embodiment, Z is C(O).

In an embodiment, each $R^1$ is independently selected from OH, halo, CN, $NO_2$, COOH, $C_{1-16}$alkyl, $C_{2-16}$alkenyl, $C_{2-16}$alkynyl, $C_{3-18}$ cycloalkyl, $C_{1-12}$alkylene$C_{3-18}$cycloalkyl, $C_{2-16}$alkenylene$C_{3-18}$ cycloalkyl, $C_{3-18}$heterocycloalkyl, $C_{1-12}$alkylene$C_{3-18}$heterocycloalkyl, $C_{1-16}$alkenylene$C_{3-18}$ heterocycloalkyl, $C_{6-18}$aryl, $C_{1-16}$alkylene$C_{6-18}$aryl, $C_{2-16}$alkenylene$C_{6-18}$aryl, $C_{5-18}$heteroaryl, $C_{2-16}$alkylene$C_{5-18}$heteroaryl, $C_{2-16}$alkenylene$C_{5-18}$heteroaryl, Z—$C_{1-16}$alkyl, Z—$C_{2-16}$alkenyl, Z—$C_{2-16}$alkynyl, Z—$C_{5-18}$ cycloalkyl, Z—$C_{1-12}$alkylene$C_{3-18}$ cycloalkyl, Z—$C_{2-16}$alkenylene$C_{3-18}$ cycloalkyl, Z—$C_{5-18}$ heterocycloalkyl, Z—$C_{1-16}$alkylene$C_{3-18}$ heterocycloalkyl, Z—$C_{1-16}$alkenylene$C_{3-18}$ heterocycloalkyl, Z—$C_{6-18}$ aryl, Z—$C_{1-12}$alkylene$C_{6-18}$aryl, Z—$C_{2-16}$alkenylene$C_{6-18}$aryl, Z—$C_{5-18}$ heteroaryl, Z—$C_{1-12}$alkylene$C_{5-18}$heteroaryl, and Z—$C_{2-16}$alkenylene$C_{5-18}$heteroaryl, wherein all alkyl, alkenyl, alkynyl, alkylene, alkenylene alkynylene cycloalkyl heterocycloalkyl, aryl and heteroaryl groups are optionally substituted with one or more substituents selected from OH, halo, $C_{1-12}$alkyl, $C_{2-16}$alkenyl, $C_{2-6}$alkynyl, $OC_{1-12}$alkyl, $OC_{2-16}$alkenyl, and $OC_{2-16}$alkynyl.

In an embodiment, each $R^1$ is independently selected from OH, halo, CN, $NO_2$, $C_{2-16}$alkenyl, $C_{2-16}$alkynyl, $C_{3-18}$ cycloalkyl, $C_{1-12}$alkylene$C_{3-18}$ cycloalkyl, $C_{2-16}$alkenylene$C_{3-18}$cycloalkyl, $C_{3-18}$heterocycloalkyl, $C_{1-12}$alkylene $C_{3-18}$ heterocycloalkyl, $C_{1-12}$alkenylene$C_{3-18}$ heterocycloalkyl, $C_{6-18}$aryl, $C_{1-12}$alkylene$C_{6-18}$aryl, $C_{2-16}$alkenylene$C_{6-18}$ aryl, $C_{5-18}$heteroaryl, $C_{2-16}$alkylene$C_{5-18}$heteroaryl, $C_{2-16}$alkenylene$C_{5-18}$heteroaryl, Z—$O_{1-12}$alkyl, Z—$C_{2-16}$alkenyl, Z—$C_{5-18}$ cycloalkyl, Z—$C_{1-12}$alkylene$C_{3-18}$ cycloalkyl, Z—$C_{2-16}$alkenylene$C_{3-18}$cycloalkyl, Z—$C_{5-18}$ heterocycloalkyl, Z—$C_{1-12}$alkylene$C_{3-18}$ heterocycloalkyl, Z—$C_{1-12}$alkenylene$C_{3-18}$heterocycloalkyl, Z—$O_{6-18}$aryl, Z—$C_{1-12}$alkylene$C_{6-18}$aryl, Z—$C_{2-16}$alkenylene$C_{6-18}$aryl, Z—$C_{5-18}$heteroaryl, Z—$C_{1-12}$alkylene$C_{5-18}$heteroaryl, and Z—$C_{2-16}$alkenylene$C_{5-18}$heteroaryl, wherein all alkyl, alkenyl, alkynyl, alkylene, alkenylene, alkynylene cycloalkyl heterocycloalkyl, aryl and heteroaryl groups are optionally substituted with one or more substituents selected from OH, halo, $C_{1-12}$alkyl, $C_{2-16}$alkenyl, $C_{2-6}$alkynyl, $OC_{1-12}$alkyl, $OC_{2-16}$alkenyl, and $OC_{2-16}$alkynyl.

In an embodiment, each $R^1$ is independently selected from OH, Br, Cl, F, $NO_2$, CN, $C_{2-16}$alkenyl, $C_{2-16}$alkynyl and Z—$C_{1-12}$alkyl wherein each alkyl, alkenyl and alkynyl, groups are optionally substituted with one or more substituents selected from OH, F, and $OC_{1-12}$alkyl.

In an embodiment, Z is O and each $R^1$ is independently selected from OH, Br, Cl, F, $NO_2$, CN, $C_{1-12}$alkyl, $C_{2-16}$alkenyl, $C_{2-16}$alkynyl and O—$C_{1-12}$alkyl wherein each alkyl, alkenyl, and alkynyl groups are optionally substituted with one or more substituents selected from OH, F, and $OC_{1-12}$alkyl.

In an embodiment, each $R^1$ is independently selected from OH, Br, Cl, F, $NO_2$, CN, $C_{2-16}$alkenyl, $C_{2-16}$alkynyl, O—$C_{1-12}$alkyl and $C_{1-16}$alkyleneOH. In an embodiment, each $R^1$ is independently selected from OH, Br, Cl, F, $NO_2$, CN, $C_{2-16}$alkenyl, O—$C_{1-6}$alkyl and $C_{1-6}$alkyleneOH.

In an embodiment, Z is O or C(O) and each $R^1$ is independently selected from OH, Br, Cl, F, $C_{2-16}$alkenyl, $C_{2-16}$alkynyl, O—$C_{1-12}$alkyl and $C_{1-16}$alkyleneOH, $C(O)C_{1-12}$alkyl, $C(O)C_{2-16}$alkenyl, $C(O)C_{3-18}$ cycloalkyl, $C(O)C_{1-12}$alkylene$C_{3-18}$cycloalkyl, $C(O)C_{2-16}$alkenylene$C_{3-18}$ cycloalkyl, $C(O)C_{3-18}$ heterocycloalkyl, $C(O)C_{1-12}$alkylene$C_{3-18}$heterocycloalkyl, $C(O)C_{1-12}$alkenylene$C_{3-18}$ heterocycloalkyl, $C(O)C_{6-18}$ aryl, $C(O)C_{1-12}$alkylene$C_{6-18}$ aryl, $C(O)C_{2-16}$alkenylene$C_{6-18}$ aryl, $C(O)C_{5-18}$heteroaryl, $C(O)C_{1-12}$alkylene$C_{5-18}$heteroaryl and $C(O)C_{2-16}$alkenylene$C_{5-18}$heteroaryl wherein all alkyl, alkenyl, alkynyl, alkylene, alkenylene, alkynylene, cycloalkyl, heterocycloalkyl, aryl, and heteroaryl groups are optionally substituted with one or more substituents selected from OH, halo, $C_{1-16}$alkyl, $C_{2-16}$alkenyl, $C_{2-6}$alkynyl, $OC_{1-16}$alkyl, $OC_{2-16}$alkenyl, and $OC_{2-16}$alkynyl. In an embodiment, $R^1$ is selected from OH, Br, Cl, F, $C_{2-16}$alkenyl, $C_{2-16}$alkynyl, O—$C_{1-12}$alkyl, $C_{1-16}$alkyleneOH, $C(O)C_{1-12}$alkyl, $C(O)C_{2-16}$alkenyl, $C(O)C_{1-12}$alkenylene$C_{3-18}$heterocycloalkyl, $C(O)C_{1-12}$alkylene$C_{6-18}$ heterocycloalkyl, $C(O)C_{6-18}$ aryl, $C(O)C_{1-12}$alkylene$C_{6-18}$ aryl and $C(O)C_{2-16}$alkenylene$C_{6-18}$ aryl wherein all alkyl, alkenyl, alkynyl, alkylene, alkenylene, alkylene, heterocycloalkyl, and aryl groups are optionally substituted with one or more substituents selected from OH, halo, $C_{1-16}$alkyl, $C_{2-16}$alkenyl, $C_{2-6}$alkynyl, $OC_{1-16}$alkyl, $OC_{2-16}$alkenyl, and $OC_{2-16}$alkynyl.

In an embodiment, each $R^1$ is independently selected from OH, Br, Cl, F, $C_{1-12}$alkyl, $C_{2-16}$alkenyl, $C_{2-16}$alkynyl, O—$C_{1-12}$alkyl, $C_{1-16}$alkyleneOH, $C(O)C_{1-12}$alkylene $C_{6-18}$heterocycloalkyl, $C(O)C_{1-12}$alkenylene$C_{3-18}$ heterocycloalkyl, $C(O)C_{1-12}$alkyl, $C(O)C_{1-12}$alkylene$C_{6-18}$ aryl, $C(O)C_{2-16}$alkenylene$C_{6-18}$ aryl, and $C(O)C_{6-18}$ aryl wherein all alkyl, alkenyl, alkylene, alkenylene, alkynyl, heterocycloalkyl, and aryl groups are optionally substituted with one or more substituents selected from OH, halo, $C_{1-16}$alkyl, $C_{2-16}$alkenyl and $OC_{1-16}$alkyl.

In an embodiment, one $R^1$ is selected from $C(O)C_{1-12}$alkylene$C_{6-18}$aryl and $C(O)C_{2-16}$alkenylene$C_{6-18}$ aryl, wherein alkylene, alkenylene and aryl groups are optionally substituted with one or more substituents selected from OH, halo, $C_{1-16}$alkyl, $C_{2-16}$alkenyl and $OC_{1-6}$alkyl.

In an embodiment, one $R^1$ is selected from $C(O)C_{1-12}$alkyl wherein all alkyl groups are optionally substituted with one or more substituents selected from OH, halo, $C_{1-16}$alkyl, $C_{2-16}$alkenyl and $OC_{1-6}$alkyl.

In an embodiment, one $R^1$ is selected from $C(O)C_{1-12}$alkylene$C_{6-18}$heterocycloalkyl and $C(O)C_{1-12}$alkenylene$C_{6-18}$ heterocycloalkyl wherein all alkylene, alkenylene, and heterocycloalkyl groups are optionally substituted with one or more substituents selected from OH, halo, $C_{1-16}$alkyl, $C_{2-16}$alkenyl and $OC_{1-6}$alkyl.

In an embodiment, one $R^1$ is selected from $C(O)C_{6-18}$aryl optionally substituted with one or more substituents selected from OH, halo, $C_{1-16}$alkyl, $C_{2-16}$alkenyl and $OC_{1-6}$alkyl.

In an embodiment, the $C_3$-$C_{18}$cycloalkyl in $R^1$ is independently selected from cyclopropyl, cyclobutyl, cyclopentyl, cyclohexyl, cycloheptyl, cyclooctyl, cyclononyl and cyclodecanyl.

In an embodiment, the heterocycloalkyl in $R^1$ is selected dihydrobenzofuranyl, benzodioxolyl aziridinyl, oxiranyl, chromanyl, isochromanyl, thiiranyl, oxaxiridinyl, 1,3-dioxolanyl, dihydrobenzothiopyranyl, dihydrobenzothiopyranyl sulfone, dioxiranyl, azetidinyl, oxetanyl, theitanyl, diazetidinyl, dioxetanyl, dihydropyranochromenyl, chromenyl, dihydrochromenonyl chromenonyl, chromanonyl, dithietanyl, tetrahydrofuranyl, tetrahydrothiophenyl, pyrrolidinyl, imidazolidinyl, 2-oxopiperdinyl, pyrazolidinyl, 2-oxoazepinyl, isoxthiolidinyl, thiazolidinyl, isothiazolidinyl, dioxolanyl, dithiolanyl, piperidinyl, triazolyl, furazanyl, oxadiazolyl, thiadiazolyl, dioxazolyl, dithiazolyl, tetrazolyl, oxatetrazolyl, tetrahydropyranyl, diazinanyl (e.g., piperazinyl), piperidyl morpholinyl, thiomorpholinyl, dioxanyl, dithianyl, azepanyl, oxepanyl, thiepanyl and diazepanyl.

In an embodiment, the heteroaryl in $R^1$ is selected from azepinyl, benzisoxazolyl, benzofurazanyl, benzopyranyl, benzothiopyranyl, benzofuryl, benzothiazolyl, benzothienyl, benzoxazolyl, cinnolinyl, dihydrobenzofuryl, dihydrobenzothienyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, oxazolyl, 2-oxopiperazinyl, 2-oxopyrrolidinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, triazolyl and thienyl.

In an embodiment, each $R^1$ independently selected from OH, Br, Cl, F, $C_{1-12}$alkyl, $C_{2-16}$alkenyl, $C_{2-16}$alkynyl, O—$C_{1-12}$alkyl and $C_{1-16}$alkyleneOH, $C(O)C_{1-12}$alkyl, $C_{3-18}$cycloalkyl, $C_{1-12}$alkylene$C_{3-18}$ cycloalkyl, $C_{2-16}$alkenylene$C_{3-18}$ cycloalkyl, $C_{3-18}$heterocycloalkyl, $C_{1-12}$alkylene$C_{3-18}$ heterocycloalkyl, $C_{1-16}$alkenylene$C_{3-18}$hetero cycloalkyl, $C_{6-18}$ aryl, $C_{1-16}$alkylene$C_{6-18}$ aryl, $C_{2-16}$alkenylene$C_{6-18}$ aryl, $C_{5-18}$heteroaryl, $C_{2-16}$alkylene$C_{5-18}$heteroaryl, and $C_{2-16}$alkenylene$C_{5-18}$heteroaryl wherein all alkyl, alkenyl, alkynyl, alkylene, alkenylene, aryl, cycloalkyl, heteroaryl and heterocycloalkyl groups are optionally substituted with one or more substituents selected from OH, halo, $C_{1-12}$alkyl, $C_{2-16}$alkenyl, $C_{2-6}$alkynyl, $OC_{1-12}$alkyl, $OC_{2-16}$alkenyl, and $OC_{2-16}$alkynyl.

In an embodiment, one $R^1$ is selected from $C_{3-18}$ cycloalkyl, $C_{1-12}$alkylene$C_{3-18}$cycloalkyl, $C_{2-16}$alkenylene$C_{3-18}$ cycloalkyl, $C_{3-18}$heterocycloalkyl, $C_{1-12}$alkylene$C_{3-18}$heterocycloalkyl, and $C_{1-16}$alkenylene$C_{3-18}$ heterocycloalkyl wherein all alkyl, alkenyl, alkynyl, alkylene, cycloalkyl and heterocycloalkyl groups are optionally substituted with one or more substituents selected from OH, halo, $C_{1-12}$alkyl, $C_{2-16}$alkenyl, $C_{2-6}$alkynyl, $OC_{1-12}$alkyl, $OC_{2-16}$alkenyl, and $OC_{2-16}$alkynyl. In an embodiment, one $R^1$ is selected from $C_{3-18}$cycloalkyl, $C_{1-6}$alkylene$C_{3-18}$ cycloalkyl, $C_{2-6}$alkenylene$C_{3-18}$cycloalkyl, $C_{3-18}$heterocycloalkyl, $C_{1-6}$alkylene$C_{3-18}$heterocycloalkyl, or $C_{2-6}$alkenylene$C_{3-18}$heterocycloalkyl wherein all alkyl, alkenyl, alkylene, cycloalkyl and heterocycloalkyl groups are optionally substituted with one or more substituents selected from OH, halo, $C_{1-12}$alkyl, $C_{2-16}$alkenyl, $C_{2-6}$alkynyl, $OC_{1-12}$alkyl, $OC_{2-16}$alkenyl, and $OC_{2-16}$alkynyl. In an embodiment, the heterocycloalkyl in $R^1$ is benzofurochromenone, dihydropyranochromenyl, chromenyl, dihydrochromenonyl, chromenonyl, chromanonyl dihydrobenzofuranyl, benzodioxolyl, or dithianyl optionally substituted with one or more substituents selected from OH, halo, $C_{1-12}$alkyl, $C_{2-16}$alkenyl, $C_{2-6}$alkynyl, $OC_{1-12}$alkyl, $OC_{2-16}$alkenyl, and $OC_{2-16}$alkynyl. In an embodiment, one $R^1$ is benzofurochromenone, dihydropyranochromenyl, chromenyl, dihydrochromenonyl, chromenonyl, chromanonyl dihydrobenzofuranyl, $C_{1-6}$alkylenedihydrobenzofuranyl, $C_{2-6}$alkenylenedihydrobenzofuranyl, benzodioxolyl, $C_{1-6}$alkylenebenzodioxolyl, $C_{2-6}$alkenylenebenzodioxolyl, dithianyl $C_{1-6}$alkylenedithianyl, or $C_{1-6}$alkenylenedithianyl optionally substituted with one or more substituents selected from OH, halo, $C_{1-12}$alkyl, $C_{2-16}$alkenyl, $C_{2-6}$alkynyl, $OC_{1-12}$alkyl, $OC_{2-16}$alkenyl, and $OC_{2-16}$alkynyl. In an embodiment, one $R^1$ is benzofurochromenone, dihydropyranochromenyl, chromenyl, dihydrochromenonyl, chromenonyl, chromanonyl, dihydrobenzofuranyl, $C_{2-6}$alkenylenedihydrobenzofuranyl, benzodioxolyl, or dithianyl optionally substituted with one or more substituents selected from OH, halo, $C_{1-12}$alkyl, $C_{2-16}$alkenyl, $C_{2-6}$alkynyl, $OC_{2-16}$alkenyl, and $OC_{2-16}$alkynyl.

In an embodiment, one $R^1$ is selected from $C_{6-18}$aryl, $C_{1-16}$alkylene$C_{6-18}$aryl, $C_{2-16}$alkenylene$C_{6-18}$ aryl, $C_{6-18}$heteroaryl, $C_{2-16}$alkylene$C_{5-18}$heteroaryl, and $C_{2-16}$alkenylene$C_{5-18}$heteroaryl wherein all alkyl, alkenyl, alkynyl, alkylene, aryl, cycloalkyl, heteroaryl and heterocycloalkyl groups are optionally substituted with one or more substituents selected from OH, halo, $C_{1-12}$alkyl, $C_{2-16}$alkenyl, $C_{2-6}$alkynyl, $OC_{2-16}$alkenyl, and $OC_{2-16}$ alkynyl. In an embodiment, one $R^1$ is selected from $C_{6-18}$aryl, $C_{2-6}$alkylene$C_{5-18}$heteroaryl, $C_{2-6}$alkenylene$C_{5-18}$heteroaryl, $C_{1-6}$alkylene$C_{6-18}$aryl and $C_{1-6}$alkenylene$C_{6-18}$aryl, wherein all alkyl, alkenyl, alkynyl, alkylene, heteroaryl aryl, groups are optionally substituted with one or more substituents selected from OH, halo, $C_{1-12}$alkyl, $C_{2-16}$alkenyl and $OC_{1-12}$alkyl. In an embodiment, one $R^1$ is selected from phenyl, $C_2$alkylenephenyl and $C_2$alkenylenephenyl, wherein all alkyl, alkenyl, alkynyl, alkylene and phenyl groups are optionally substituted with one or more substituents selected from OH, halo, $C_{1-12}$alkyl, $C_{2-16}$alkenyl and $OC_{1-12}$alkyl.

In an embodiment, one $R^1$ is selected from OH, $O_{6-18}$aryl, and $C_{5-18}$heteroaryl, wherein all alkyl, alkenyl, alkynyl, aryl, and, heteroaryl groups are optionally substituted with one or more substituents selected from OH, $C_{1-12}$alkyl, $C_{2-16}$alkenyl, $OC_{1-12}$alkyl, $OC_{2-16}$alkenyl. In an embodiment, when n is greater than 1, specifically when n is 2, two $R^1$ groups are linked together to form a polycyclic ring system having 8 or more atoms together with the phenyl ring to which said groups are bonded, and in which one or more carbon atoms in said polycyclic ring system is optionally replaced with a heteromoiety selected from $NR^6$, O and S, wherein the polycyclic ring system is optionally substituted with one or more substituents selected from OH, $=$O, halo, $C_{1-16}$alkyl, $C_{2-16}$alkenyl, $C_{2-16}$alkynyl, $OC_{2-16}$alkenyl, $OC_{2-16}$alkynyl; $C_{1-16}$alkyleneOR$^8$, $C_{2-16}$alkenyleneOR$^8$, $C_{2-16}$alkynyleneOR$^8$, $C_{6-18}$aryl, $C_{3-18}$cycloalkyl, $C_{3-18}$heterocycloalkyl, and $C_{5-18}$heteroaryl, the latter 4 groups being optionally substituted with one or more substituents selected from OH, halo, $C_{1-16}$alkyl, $OC_{1-16}$alkyl, and $C_{2-16}$alkenyl.

In an embodiment, the polycyclic ring system is a bridged polycyclic ring system, which is optionally substituted with one or more substituents selected from OH, $=$O, halo, $C_{1-16}$alkyl, $C_{2-16}$alkenyl, $C_{2-16}$alkynyl, $OC_{1-16}$alkyl, $OC_{2-16}$alkenyl, and $OC_{2-16}$alkynyl. In an embodiment, the polycyclic ring system is a spirofused polycyclic ring system, which is optionally substituted with one or more substituents selected from OH, $=$O, halo, $C_{1-16}$alkyl, $C_{2-16}$alkenyl, $C_{2-16}$alkynyl, $OC_{2-16}$alkenyl, and $OC_{2-16}$alkynyl. In an embodiment, the polycyclic ring system is a fused polycyclic ring system, which is optionally substituted with one or more substituents selected from OH, $=$O, halo, $C_{1-16}$alkyl, $C_{2-16}$alkenyl, $C_{2-16}$alkynyl, $OC_{1-16}$alkyl, $OC_{2-16}$alkenyl, and $OC_{2-16}$alkynyl.

In an embodiment, the polycyclic ring system is selected from a polycyclic cycloalkyl ring system, polycyclic heterocyclyl ring system, a polycyclic heteroaryl ring system and a polycyclic aryl ring system, which are optionally substituted with one or more substituents selected from OH, $=$O, halo, $C_{1-16}$alkyl, $C_{2-16}$alkenyl, $C_{2-16}$alkynyl, $OC_{1-16}$alkyl, $OC_{2-16}$alkenyl, $OC_{2-16}$alkynyl, $C(O)C_{1-16}$alkyl, $C(O)C_{2-16}$alkenyl, $C(O)C_{2-16}$alkynyl, $C_{1-16}$alkyleneOR$^8$, $C_{2-16}$alkenyleneOR$^8$, $C_{2-16}$alkynyleneOR$^8$, $C_{6-18}$ aryl, $C_{3-18}$cycloalkyl, $C_{3-18}$heterocycloalkyl, and $C_{5-18}$heteroaryl, the latter 4 groups being optionally substituted with one or more substituents selected from OH, halo, $C_{1-16}$alkyl, $OC_{1-16}$alkyl, and $C_{2-16}$alkenyl. In an embodiment, the polycyclic ring system is selected from a polycyclic cycloalkyl ring system, polycyclic heterocyclyl ring system, a polycyclic heteroaryl ring system and a polycyclic aryl ring system, which are optionally substituted with one or more substituents selected from OH, $=$O, halo, $C_{1-16}$alkyl, $C_{2-16}$alkenyl, $C_{2-16}$alkynyl, $OC_{1-16}$alkyl, $OC_{2-16}$alkenyl and $OC_{2-16}$alkynyl.

In an embodiment, the polycyclic ring system is selected from a bicyclic, tricyclic and a quadracyclic ring system, which are optionally substituted with one or more substituents selected from OH, $=$O, halo, $C_{1-16}$alkyl, $C_{2-16}$alkenyl, $C_{2-16}$alkynyl, $OC_{1-16}$alkyl, $OC_{2-16}$alkenyl, $OC_{2-16}$alkynyl, $C(O)C_{1-16}$alkyl, $C(O)C_{2-16}$alkenyl, $C(O)C_{2-16}$alkynyl, $C_{1-16}$alkyleneOR$^8$, $C_{2-16}$alkenyleneOR$^8$, $C_{2-16}$alkynyleneOR$^8$, $C_{6-18}$ aryl, $C_{3-18}$ cycloalkyl, $C_{3-18}$heterocycloalkyl, and $C_{5-18}$heteroaryl, the latter 4 groups being optionally substituted with one or more substituents selected from OH, halo, $C_{1-16}$alkyl, $OC_{1-16}$alkyl, and $C_{2-16}$alkenyl. In an embodiment, the polycyclic ring system is selected from a bicyclic, tricyclic and a quadracyclic ring system, which are optionally substituted with one or more substituents selected from OH, halo, $C_{1-12}$alkyl, $C_{2-16}$alkenyl, $C_{2-16}$alkynyl, $OC_{1-16}$alkyl, $OC_{2-16}$alkenyl.

In an embodiment, the polycyclic ring system is a gonanyl (steroid nucleus) which is optionally substituted with one or more substituents selected from OH, $=$O, halo, $C_{1-16}$alkyl, $C_{2-16}$alkenyl, $C_{2-16}$alkynyl, $OC_{1-16}$alkyl, $OC_{2-16}$alkenyl, $OC_{2-16}$alkynyl, $C_{1-16}$alkyleneOR$^8$, $C(O)C_{1-16}$alkyl, $C(O)C_{2-16}$alkenyl, $C(O)C_{2-16}$alkynyl, $C_{2-16}$alkenyleneOR$^8$, $C_{2-16}$alkynyleneOR$^8$, $C_{6-18}$ aryl, $C_{3-18}$ cycloalkyl, $C_{3-18}$heterocycloalkyl, and $C_{5-18}$heteroaryl, the latter 4 groups being optionally substituted with one or more substituents selected from OH, halo, $C_{1-16}$alkyl, $OC_{1-16}$alkyl, and $C_{2-16}$alkenyl. In an embodiment, the polycyclic ring system is a gonanyl (steroid nucleus) wherein the gonanyl ring system is optionally substituted with one or more substituents selected from OH, $=$O, $C_{1-6}$alkyl, $C_{2-16}$alkenyl, $C_{2-6}$alkynyl, and $OC_{1-6}$alkyl. In an embodiment, two adjacent $R^1$ groups are linked together to form a gonanyl ring system, wherein the gonanyl ring system is optionally substituted with one or more substituents selected from OH, $=$O, $C_{1-6}$alkyl, $C_{2-16}$alkenyl, $C_{2-6}$alkynyl, and $OC_{1-6}$alkyl.

In an embodiment, the polycyclic heteroaryl ring system is selected from benzofuranyl, isobenzofuranyl, indolyl, isoindolyl, quinolinyl, isoquinolinyl, benzepinyl, carbazolyl, and acridinyl which are optionally substituted with one or more substituents selected from OH, $=$O, halo, $C_{1-16}$alkyl, $C_{2-16}$alkenyl, $C_{2-16}$alkynyl, $OC_{1-16}$alkyl, $OC_{2-16}$alkenyl, $OC_{2-16}$alkynyl, $C(O)C_{1-16}$alkyl, $C(O)C_{2-16}$alkenyl, $C(O)C_{2-16}$alkynyl, $C_{1-16}$alkyleneOR$^8$, $C_{2-16}$alkenyleneOR$^8$, $C_{2-16}$alkynyleneOR$^8$, $C_{6-18}$aryl, $C_{3-18}$cycloalkyl, $C_{3-18}$heterocycloalkyl, and $C_{5-18}$heteroaryl, the latter 4 groups being optionally substituted with one or more substituents selected from OH, halo, $C_{1-16}$alkyl, $OC_{1-16}$alkyl, and $C_{2-16}$alkenyl. In an embodiment, the polycyclic heteroaryl ring system is selected from benzofuranyl, isobenzofuranyl, indolyl, isoindolyl, quinolinyl, and isoquinolinyl which are optionally substituted with one or more substituents selected from OH, $=$O, halo, $C_{1-16}$alkyl, $C_{2-16}$alkenyl, $C_{2-16}$alkynyl, $OC_{1-16}$alkyl, $OC_{2-16}$alkenyl, $OC_{2-16}$alkynyl, $C(O)C_{1-16}$alkyl, $C(O)C_{2-16}$alkenyl, $C(O)C_{2-16}$alkynyl, $C_{1-16}$alkyleneOR$^8$, $C_{2-16}$alkenyleneOR$^8$, $C_{2-16}$alkynyleneOR$^8$, $C_{6-18}$aryl, $C_{3-18}$cycloalkyl, $C_{3-18}$heterocycloalkyl, and $C_{5-18}$heteroaryl, the latter 4 groups being optionally substituted with one or more substituents selected from OH, halo, $C_{1-16}$alkyl, $OC_{1-16}$alkyl, and $C_{2-16}$alkenyl.

In an embodiment, the polycyclic heterocyclyl system is a benzofused ring system which is optionally substituted with one or more substituents selected from OH, $=$O, halo, $C_{1-16}$alkyl, $C_{2-16}$alkenyl, $C_{2-16}$alkynyl, $OC_{1-16}$alkyl, $OC_{2-16}$alkenyl, $OC_{2-16}$alkynyl, $C(O)C_{1-16}$alkyl, $C(O)C_{2-16}$alkenyl, $C(O)C_{2-16}$alkynyl, $C_{1-16}$alkyleneOR$^8$, $C_{2-16}$alkenyleneOR$^8$, $C_{2-16}$alkynyleneOR$^8$, $C_{6-18}$aryl, $C_{3-18}$cycloalkyl, $C_{3-18}$heterocycloalkyl, and $C_{5-18}$heteroaryl the latter 4 groups being optionally substituted with one or more substituents selected from OH, halo, $C_{1-16}$alkyl, $OC_{1-16}$alkyl, and $C_{2-16}$alkenyl. In an embodiment, the benzofused ring system is selected from benzofurochromenone, benzodiozinyl, benzodiozolyl, indenyl, indolinyl, chromenyl, dihydrochromenonyl, chromenonyl, chromanonyl, benzoxazinyl, quinolinonyl, isoquinolinonyl and coumarinyl which are optionally substituted with one or more substituents selected from OH, $=$O, halo, $C_{1-16}$alkyl, $C_{2-16}$alkenyl, $C_{2-16}$alkynyl, $OC_{1-16}$alkyl, $OC_{2-16}$alkenyl, $OC_{2-16}$alkynyl, $C_{1-16}$alkyleneOR$^8$, $C_{2-16}$alkenyleneOR$^8$, $C_{2-16}$alkynyleneOR$^8$, $C_{6-18}$ aryl, $C_{3-18}$ cycloalkyl, $C_{3-18}$ heterocycloalkyl, and $C_{5-18}$heteroaryl, the latter 4 groups being optionally substituted with one or more substituents selected from OH, halo, $C_{1-16}$alkyl, $OC_{1-16}$alkyl, and $C_{2-16}$alkenyl. In an embodiment, the benzofused ring system is selected from benzofurochromenone, benzodiozinyl, benzodiozolyl, indenyl, indolinyl, chromenyl, dihydrochromenonyl chromenonyl, chromanonyl, benzoxazinyl, quinolinonyl and isoquinolinonyl which are optionally substituted with one or more substituents selected from OH, =O, halo, $C_{1-16}$alkyl, $C_{2-16}$alkenyl, $C_{2-16}$alkynyl, $OC_{1-16}$alkyl, $OC_{2-16}$alkenyl, $OC_{2-16}$alkynyl, $C_{1-16}$alkyleneOR$^8$, $C(O)C_{1-16}$alkyl, $C(O)C_{2-16}$alkenyl, $C(O)C_{2-16}$alkynyl, $C_{2-16}$alkenyleneOR$^8$, $C_{2-16}$alkynyleneOR$^8$, $C_{6-18}$ aryl, $C_{3-18}$ cycloalkyl, $C_{3-18}$heterocycloalkyl, and $C_{5-18}$heteroaryl, the latter 4 groups being optionally substituted with one or more substituents selected from OH, halo, $C_{1-16}$alkyl, $OC_{1-16}$alkyl, and $C_{2-16}$alkenyl.

In an embodiment, the benzofused ring system is selected from chromenyl, chromenonyl (chromonyl) and chromanonyl (dihydrochromenonyl) which are optionally substituted with one or more substituents selected from OH, =O, halo, $C_{1-16}$alkyl, $C_{2-16}$alkenyl, $C_{2-16}$alkynyl, $OC_{1-16}$alkyl, $OC_{2-16}$alkenyl, $OC_{2-16}$alkynyl, $C_{1-16}$alkyleneOR$^8$, $C(O)C_{1-16}$alkyl, $C(O)C_{2-16}$alkenyl, $C(O)C_{2-16}$alkynyl, $C_{2-16}$alkenyleneOR$^8$, $C_{2-16}$alkynyleneOR$^8$, $C_{6-18}$aryl, $C_{3-18}$cycloalkyl, $C_{3-18}$heterocycloalkyl, and $C_{5-18}$heteroaryl, the latter 4 groups being optionally substituted with one or more substituents selected from OH, halo, $C_{1-16}$alkyl, $OC_{1-16}$alkyl, and $C_{2-16}$alkenyl. In an embodiment, the benzofused ring system is selected from chromenyl, chromenonyl (chromonyl) and chromanonyl (dihydrochromenonyl) which are optionally substituted with one or more substituents selected from OH, $C_{1-16}$alkyl, $OC_{1-16}$alkyl, $C_{6-18}$aryl, $C_{3-18}$ cycloalkyl, $C_{3-18}$heterocycloalkyl, and $C_{5-18}$heteroaryl, the latter 4 groups being optionally substituted with one or more substituents selected from OH, halo, $C_{1-16}$alkyl, $OC_{1-16}$alkyl, and $C_{2-16}$alkenyl. In an embodiment, the benzofused ring system is selected from chromenyl, chromenonyl (chromonyl) and chromanonyl (dihydrochromenonyl) which are optionally substituted with one or more substituents selected from OH, $C_{1-16}$alkyl, $OC_{1-16}$alkyl, $C_{6-18}$aryl, $C_{3-18}$cycloalkyl, $C_{3-18}$heterocycloalkyl, and $C_{5-18}$heteroaryl, the latter 4 groups being optionally substituted with one or more substituents selected from OH, halo, $C_{1-16}$alkyl, $OC_{1-16}$alkyl, and $C_{2-16}$alkenyl. In an embodiment, the benzofused ring system is selected from chromenonyl (chromonyl) and chromanonyl (dihydrochromenonyl) which are optionally substituted with one or more substituents selected from OH, $C_{1-16}$alkyl, $OC_{1-16}$alkyl, $C_{3-18}$heterocycloalkyl, and $C_{6-18}$aryl, the latter two groups being optionally substituted with one or more substituents selected from OH, halo, $C_{1-16}$alkyl, $OC_{1-16}$alkyl, and $C_{2-16}$alkenyl.

In an embodiment, the benzofused ring system is selected from

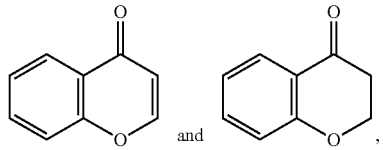 [SMILES: O=c1ccoc2ccccc12 ; O=C1CCOc2ccccc21]

which are optionally substituted with one or more substituents selected from OH, $C_{1-16}$alkyl, $OC_{1-16}$alkyl, $C_{3-18}$heterocycloalkyl, and $C_{6-18}$aryl the latter two groups being optionally substituted with one or more substituents selected from OH, halo, $C_{1-16}$alkyl, $OC_{1-16}$alkyl, and $C_{2-16}$alkenyl. In an embodiment, the $C_{3-18}$heterocycloalkyl is benzodioxolyl or naphthalenone. In an embodiment, the $C_{6-18}$aryl is phenyl.

Therefore, in an embodiment, the benzofused ring system is a flavonyl, isoflavonyl, flavavonyl or isoflavavonyl, which are optionally substituted with one or more substituents selected from OH, halo, $C_{1-16}$alkyl, $OC_{1-16}$alkyl, and $C_{2-16}$alkenyl. In an embodiment, the benzofused ring system is selected from

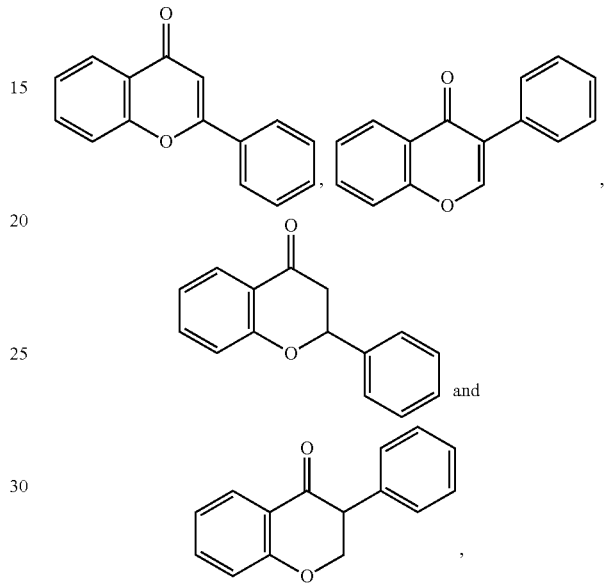

which are optionally substituted with one or more substituents selected from OH, halo, $C_{1-16}$alkyl, $OC_{1-16}$alkyl, and $C_{2-16}$alkenyl.

In an embodiment, the benzofused ring system is coumarinyl which is optionally substituted with one or more substituents selected from OH, =O, halo, $C_{1-16}$alkyl, $C_{2-16}$alkenyl, $C_{2-16}$alkynyl, $OC_{1-16}$alkyl, $OC_{2-16}$alkenyl, $OC_{2-16}$alkynyl, $C_{1-16}$alkyleneOR$^8$, $C_{2-16}$alkenyleneOR$^8$, $C_{2-16}$alkynyleneOR$^8$, $C_{6-18}$ aryl, $C_{3-18}$ cycloalkyl, $C_{3-18}$heterocycloalkyl, and $C_{5-18}$heteroaryl, the latter 4 groups being optionally substituted with one or more substituents selected from OH, halo, $C_{1-16}$alkyl, $OC_{1-16}$alkyl, and $C_{2-16}$alkenyl. In an embodiment, the benzofused ring system is coumarinyl which is optionally substituted with one or more substituents selected from OH, =O, $C_{1-16}$alkyl, $C_{2-16}$alkenyl, $C_{2-16}$alkynyl, $OC_{1-16}$alkyl, $OC_{2-16}$alkenyl, and $OC_{2-16}$alkynyl. In an embodiment, the benzofused ring system is coumarinyl which is optionally substituted with one or more substituents selected from OH, $C_{1-16}$alkyl, $C_{2-16}$alkenyl, and $OC_{1-16}$alkyl.

In an embodiment, the polycyclic heterocyclyl ring system is a tricyclic heterocyclyl ring system which is optionally substituted with one or more substituents selected from OH, =O, halo, $C_{1-16}$alkyl, $C_{2-16}$alkenyl, $C_{2-16}$alkynyl, $OC_{1-16}$alkyl, $OC_{2-16}$alkenyl, $OC_{2-16}$alkynyl, $C_{1-16}$alkyleneOR$^8$, $C(O)C_{1-16}$alkyl, $C(O)C_{2-16}$alkenyl, $C(O)C_{2-16}$alkynyl, $C_{2-16}$alkenyleneOR$^8$, $C_{2-16}$alkynyleneOR$^8$, $C_{6-18}$ aryl, $C_{3-18}$ cycloalkyl, $C_{3-18}$heterocycloalkyl, and $C_{3-18}$heterocycloalkyl, the latter 4 groups being optionally substituted with one or more substituents selected from OH, halo, $C_{1-16}$alkyl, $OC_{1-16}$alkyl, and $C_{2-16}$alkenyl. In an embodiment, the tricyclic heterocyclyl ring system is selected from flourenyl, carbazolyl, dibenzofuranyl, phenoxazinyl, and xanthonyl which are optionally substituted with one or more substituents selected from OH, =O, halo, $C_{1-16}$alkyl, $C_{2-16}$alkenyl, $C_{2-16}$alkynyl, $OC_{1-16}$alkyl, $OC_{2-16}$alkenyl, $OC_{2-16}$alkynyl, $C_{1-16}$alkyleneOR$^8$, $C(O)C_{1-16}$alkyl, $C(O)C_{2-16}$alkenyl, $C(O)C_{2-16}$alkynyl, $C_{2-16}$alkenyleneOR$^8$, $C_{2-16}$alkynyleneOR$^8$, $C_{6-18}$ aryl, $C_{3-18}$ cycloalkyl, $C_{3-18}$heterocycloalkyl, and $C_{3-18}$heterocycloalkyl, the latter 4 groups being optionally substituted with one or more substituents selected from OH, halo, $C_{1-16}$alkyl, $OC_{1-16}$alkyl, and $C_{2-16}$alkenyl. In an embodiment, the tricyclic heterocyclyl ring system is a xanthonyl which is optionally substituted with one or more substituents selected from OH, $C_{1-16}$alkyl, $C_{2-16}$alkenyl, and $OC_{1-16}$alkyl. In an embodiment, the tricyclic heterocyclyl ring system is a xanthonyl which is optionally substituted with one or more OH. In an embodiment, the tricyclic heterocyclyl ring is

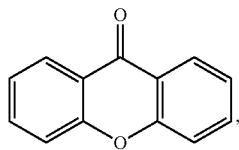 [SMILES: O=c1c2ccccc2oc2ccccc12]

which is optionally substituted with one or more substituents selected from OH, $C_{1-16}$alkyl, $C_{2-16}$alkenyl, and $OC_{1-16}$alkyl.

In an embodiment, the polycyclic heterocyclyl ring system is a tetracyclic heterocyclyl ring system which is optionally substituted with one or more substituents selected from OH, =O, halo, $C_{1-16}$alkyl, $C_{2-16}$alkenyl, $C_{2-16}$alkynyl, $OC_{1-16}$alkyl, $OC_{2-16}$alkenyl, $OC_{2-16}$alkynyl, $C_{1-16}$alkyleneOR$^8$, $C(O)C_{1-16}$alkyl, $C(O)C_{2-16}$alkenyl, $C(O)C_{2-16}$alkynyl, $C_{2-16}$alkenyleneOR$^8$, $C_{2-16}$alkynyleneOR$^8$, $C_{6-18}$ aryl, $C_{3-18}$ cycloalkyl, $C_{3-18}$heterocycloalkyl, and $C_{3-18}$heterocycloalkyl, the latter 4 groups being optionally substituted with one or more substituents selected from OH, halo, $C_{1-16}$alkyl, $OC_{1-16}$alkyl, and $C_{2-16}$alkenyl. In an embodiment, the tetracyclic heterocyclyl ring system is a benzofurochromenone which is optionally substituted with one or more substituents selected from OH, $C_{1-16}$alkyl, $C_{2-16}$alkenyl, and $OC_{1-16}$alkyl. In an embodiment, the tetracyclic heterocyclyl ring system is

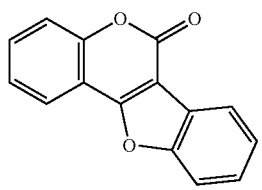 [SMILES: O=c1oc2ccccc2c2oc3ccccc3c12]

which is optionally substituted with one or more substituents selected from OH, $C_{1-16}$alkyl, $C_{2-16}$alkenyl, and $OC_{1-16}$alkyl.

In an embodiment, the polycyclic aryl ring system is selected from naphthalenyl, anthracenyl, phenanthrenyl, tetracenyl, chrysenyl, triphenylenyl, pyrenyl, pentacenyl, benzo[a]pyrenyl, corannulenyl, benzo[ghi]perylenyl, coronenyl, ovalenyl and benzo[c]fluorinyl which are optionally substituted with one or more substituents selected from OH, =O, halo, $C_{1-16}$alkyl, $C_{2-16}$alkenyl, $C_{2-16}$alkynyl, $OC_{1-16}$alkyl, $OC_{2-16}$alkenyl, $OC_{2-16}$alkynyl, $C_{1-16}$alkyleneOR$^8$, $C(O)$ $C_{1-16}$alkyl, $C(O)C_{2-16}$alkenyl, $C(O)C_{2-16}$alkynyl, $C_{2-16}$alkenyleneOR$^8$, $C_{2-16}$alkynyleneOR$^8$, $C_{6-18}$aryl, $C_{3-18}$ cycloalkyl, $C_{3-18}$heterocycloalkyl, and $C_{3-18}$heterocycloalkyl, the latter 4 groups being optionally substituted with one or more substituents selected from OH, halo, $C_{1-16}$alkyl, $OC_{1-16}$alkyl, and $C_{2-16}$alkenyl. In an embodiment, the polycyclic aryl ring system is naphthalenyl which is optionally substituted with one or more substituents selected from OH, =O, halo, $C_{1-16}$alkyl, $C_{2-16}$alkenyl, $C_{2-16}$alkynyl, $OC_{1-16}$alkyl, $OC_{2-16}$alkenyl, $OC_{2-16}$alkynyl, $C(O)C_{1-16}$alkyl, $C(O)C_{2-16}$alkenyl, $C(O)C_{2-16}$alkynyl, $C_{1-16}$alkyleneOR$^8$, $C_{2-16}$alkenyleneOR$^8$, $C_{2-16}$alkynyleneOR$^8$, $C_{6-18}$ aryl, $C_{3-18}$cycloalkyl, $C_{3-18}$heterocycloalkyl, and $C_{3-18}$heterocycloalkyl, the latter 4 groups being optionally substituted with one or more substituents selected from OH, halo, $C_{1-16}$alkyl, $OC_{1-16}$alkyl, and $C_{2-16}$alkenyl. In an embodiment, the polycyclic aryl ring system is naphthalenyl which is optionally substituted with one or more substituents selected from OH, $C_{1-16}$alkyl, $C_{2-16}$alkenyl, $C_{2-16}$alkynyl, $OC_{1-16}$alkyl, $OC_{2-16}$alkenyl, $OC_{2-16}$alkynyl, $C(O)O_{1-16}$alkyl, $C(O)C_{2-16}$alkenyl. In an embodiment, the polycyclic aryl ring system is naphthalenyl which is optionally substituted with one or more OH.

In an embodiment, when n is greater than 1, specifically when n is 2, two adjacent $R^1$ groups are linked together to form polycyclic ring system having 8 or more atoms together with the phenyl ring to which said groups are bonded, and in which one or more carbon atoms in said polycyclic ring system is optionally replaced with a heteromoiety selected from NR$^6$, O and S, wherein the polycyclic ring system is optionally substituted with one or more substituents selected from OH, =O, halo, $C_{1-16}$alkyl, $C_{2-16}$alkenyl, $C_{2-16}$alkynyl, $OC_{2-16}$alkenyl, $OC_{2-6}$alkynyl; $C_{1-16}$alkyleneOR$^8$, $C_{2-16}$alkenyleneOR$^8$, $C_{2-16}$alkynyleneOR$^8$, $C_{6-18}$aryl, $C_{3-18}$ cycloalkyl, $C_{3-18}$ heterocycloalkyl, and $C_{3-18}$heterocycloalkyl, the latter 4 groups being optionally substituted with one or more substituents selected from OH, halo, $C_{1-16}$alkyl, $OC_{1-16}$alkyl, and $C_{2-16}$alkenyl.

Therefore, when n is 2, in an embodiment, the compound of Formula (I) has the following structure

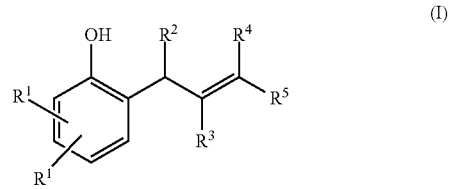

wherein:
the two $R^1$ groups are linked together to form a polycyclic ring system having 8 or more atoms together with the phenyl ring to which said groups are bonded, and in which one or more carbon atoms in said polycyclic ring system is optionally replaced with a heteromoiety selected from NR$^6$, O and S, wherein the polycyclic ring system is optionally substituted with one or more substituents selected from =O, OH, halo, $C_{1-16}$alkyl, $C_{2-16}$alkenyl, $C_{2-16}$alkynyl, $OC_{1-16}$alkyl, $OC_{2-16}$alkenyl, $OC_{2-16}$alkynyl; $C_{1-16}$alkyleneOR$^8$, $C_{2-16}$alkenyleneOR$^8$, $C_{2-16}$alkynyleneOR$^8$, $C_{6-18}$ aryl, $C_{3-18}$ cycloalkyl, $C_{3-18}$heterocycloalkyl, and $C_{5-18}$heteroaryl, the latter 4 groups being optionally substituted with one or more substituents selected from OH, halo, $C_{1-16}$alkyl, $OC_{1-16}$alkyl, and $C_{2-16}$alkenyl;

$R^2$ is H, $R^3$, $R^4$ and $R^5$ are as defined in Formula (I), and all alkyl, alkenyl, alkynyl, alkylene, alkenylene, alkynylene, cycloalkyl, and heterocycloalkyl groups are optionally fluoro-substituted.

In an embodiment, the two $R^1$ groups are linked together to form a polycyclic ring system having 10 or more atoms together with the carbon atoms to which said groups are bonded, and in which one or more carbon atoms in said polycyclic ring system is optionally replaced with a heteromoiety selected from $NR^6$, O and S, wherein the polycyclic ring system is optionally substituted with one or more substituents selected from =O, OH, halo, $C_{1-16}$alkyl, $C_{2-16}$alkenyl, $C_{2-16}$alkynyl, $OC_{1-16}$alkyl, $OC_{2-16}$alkenyl, $OC_{2-16}$alkynyl; $C_{1-16}$alkyleneOR$^8$, $C_{2-16}$alkenyleneOR$^8$, $C_{2-16}$alkynyleneOR$^8$, $C_{6-18}$ aryl, $C_{3-18}$ cycloalkyl, $C_{3-18}$heterocycloalkyl, and $C_{5-18}$heteroaryl, the latter 4 groups being optionally substituted with one or more substituents selected from OH, halo, $C_{1-16}$alkyl, $OC_{1-16}$alkyl, and $C_{2-16}$alkenyl as described above for the compounds of Formula (I) above.

In an embodiment, the polycyclic ring system is as described above.

In an embodiment, the compound of Formula (I) is a compound of Formula (I-A)

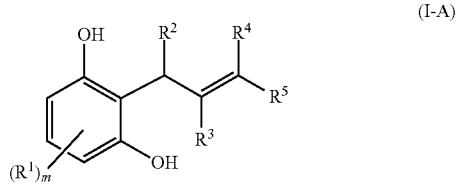

(I-A)

wherein:

each $R^1$ is independently selected from OH, halo, CN, $NO_2$, COOH, $C_{2-16}$alkenyl, $C_{2-16}$alkynyl, $C_{3-18}$cycloalkyl, $C_{1-16}$alkylene$C_{3-18}$ cycloalkyl, $C_{2-16}$alkenylene $C_{3-18}$ cycloalkyl, $C_{2-16}$alkynylene$C_{3-18}$ cycloalkyl, $C_{3-18}$heterocycloalkyl, $C_{1-16}$alkylene$C_{3-18}$heterocycloalkyl, $C_{1-10}$alkenylene$C_{3-18}$heterocycloalkyl, $C_{2-16}$alkynylene$C_{3-18}$heterocycloalkyl, $C_{6-18}$aryl, $C_{1-16}$alkylene$C_{6-18}$aryl, $C_{2-16}$alkenylene$C_{6-18}$aryl, $C_{2-16}$alkynylene$C_{6-18}$ aryl, $C_{5-18}$heteroaryl, $C_{2-16}$alkylene$C_{5-18}$heteroaryl, $C_{2-16}$alkenylene$C_{5-18}$heteroaryl, $C_{2-16}$alkynylene$C_{5-18}$heteroaryl, Z—$C_{1-16}$alkyl, Z—$C_{2-16}$alkenyl, Z—$C_{2-16}$alkynyl, Z—$C_{3-18}$ cycloalkyl, Z—$C_{1-16}$alkylene$C_{3-18}$cycloalkyl, Z—$C_{2-16}$alkenylene$C_{3-18}$ cycloalkyl, Z—$C_{2-16}$alkynylene$C_{3-18}$ cycloalkyl, Z—$C_{3-18}$heterocycloalkyl, Z—$C_{1-16}$alkylene$C_{3-18}$ heterocycloalkyl, Z—$C_{2-16}$alkenylene$C_{3-18}$heterocycloalkyl, Z—$C_{2-16}$alkynylene$C_{3-18}$ heterocycloalkyl, Z—$C_{6-18}$aryl, Z—$C_{1-16}$alkylene$C_{6-18}$aryl, Z—$C_{2-16}$alkenylene$C_{6-18}$aryl, Z—$C_{2-16}$ alkynylene$C_{6-18}$aryl, Z—$C_{5-18}$heteroaryl, Z—$C_{1-16}$alkylene$C_{5-18}$heteroaryl, Z—$C_{2-16}$alkenylene$C_{5-18}$ heteroaryl, and Z—$C_{2-16}$alkynylene$C_{5-18}$heteroaryl, wherein all alkyl, alkenyl, alkynyl, alkylene, alkenylene, alkynylene, cycloalkyl heterocycloalkyl, aryl, and heteroaryl groups are optionally substituted with one or more substituents selected from OH, halo, $C_{1-16}$alkyl, $C_{2-16}$alkenyl, $C_{2-16}$alkynyl, $OC_{1-16}$alkyl, $OC_{2-16}$alkenyl, and $OC_{2-16}$alkynyl; or when m is greater than 1, two $R^1$ groups are linked together to form a polycyclic ring system having 8 or more atoms together with the phenyl ring to which said groups are bonded, and in which one or more carbon atoms in said polycyclic ring system is optionally replaced with a heteromoiety selected from $NR^6$, O and S, wherein the polycyclic ring system is optionally substituted with one or more substituents selected from =O, OH, halo, $C_{1-16}$alkyl, $C_{2-16}$alkenyl, $C_{2-16}$alkynyl, $OC_{1-16}$alkyl, $OC_{2-16}$alkenyl, $OC_{2-16}$alkynyl; $C_{1-16}$alkyleneOR$^8$, $C_{2-16}$alkenyleneOR$^8$, $C_{2-16}$alkynyleneOR$^8$, $C_{6-18}$aryl, $C_{3-18}$cycloalkyl, $C_{3-18}$heterocycloalkyl, and $C_{5-18}$heteroaryl, the latter 4 groups being optionally substituted with one or more substituents selected from OH, halo, $C_{1-16}$alkyl, $OC_{1-16}$alkyl, and $C_{2-16}$alkenyl; and $R^2$, $R^3$, $R^4$ and $R^5$ are as defined in Formula (I), m is an integer selected from 0 to 3; and all alkyl, alkenyl, alkynyl, alkylene, alkenylene, alkynylene, cycloalkyl, and heterocycloalkyl groups are optionally fluoro-substituted.

In an embodiment, each $R^1$ in the compound of Formula (I-A) is independently selected from OH, $C_{1-12}$alkyl, $C_{2-16}$alkenyl, $C_{6-18}$aryl, $C_{1-12}$alkylene$C_{6-18}$aryl, $C_{2-16}$alkenylene$C_{6-18}$ aryl, $C_{5-18}$heteroaryl, Z—$C_{1-16}$alkylene $C_{6-18}$aryl, Z—$C_{6-18}$aryl, Z—$C_{2-16}$alkenylene$C_{6-18}$ aryl, Z—$C_{1-16}$alkylene$C_{3-18}$heterocycloalkyl, Z—$C_{5-18}$heteroaryl, Z—$C_{2-16}$alkenylene$C_{3-18}$heterocycloalkyl, Z—$C_{1-16}$alkylene$C_{5-18}$heteroaryl, and Z—$C_{2-16}$alkenylene$C_{6-18}$heteroaryl, wherein all alkyl, alkenyl, alkynyl, alkylene, alkenylene, aryl, heterocycloalkyl and heteroaryl groups are optionally substituted with one or more substituents selected from OH, halo, $C_{1-12}$alkyl, $C_{2-16}$alkenyl, $C_{2-6}$alkynyl, and $OC_{1-12}$alkyl.

In an embodiment, $R^1$ in the compound of Formula (I-A) is selected from $C_{1-12}$alkyl and $C_{2-16}$alkenyl. In an embodiment, m is 1 and $R^1$ in the compound of Formula (I-A) is $C_{1-6}$alkyl which is in a position meta to each of the hydroxy groups. In an embodiment, m is 1, and $R^1$ in the compound of Formula (I-A) is $C_{1-12}$alkyl. In an embodiment, m is 1 and $R^1$ in the compound of Formula (I-A) is $C_{1-12}$alkyl which is in a position meta to each of the hydroxy groups. In an embodiment, m is 1 and $R^1$ in the compound of Formula (I-A) is pentyl which is in a position meta to each of the hydroxy groups.

In an embodiment, each $R^1$ in the compound of Formula (I-A) is independently selected from OH, $C_{1-12}$alkyl, $C_{2-16}$alkenyl, $C_{1-12}$alkylene$C_{6-18}$ aryl, and $C_{2-16}$alkenylene$C_{6-18}$ aryl, wherein all alkyl, alkenyl, alkylene, alkenylene and aryl groups are optionally substituted with one to three substituents selected from OH, $C_{1-12}$alkyl, $C_{2-16}$alkenyl, and $OC_{1-12}$alkyl.

In an embodiment, one $R^1$ in the compound of Formula (I-A) is selected from $C_{1-6}$alkylene$C_{6-10}$aryl and $C_{2-6}$alkenylene$C_{6-10}$ aryl, wherein all alkylene, alkenylene and aryl groups are optionally substituted with one to three substituents selected from OH, $C_{1-12}$alkyl, $C_{2-16}$alkenyl, and $OC_{1-12}$alkyl.

In an embodiment, m is 1, and $R^1$ in the compound of Formula (I-A) is selected from $C_2$alkylenephenyl and $C_2$alkenylenephenyl, wherein the phenyl groups are optionally substituted with one to three substituents selected from OH and $C_{2-16}$alkenyl. In an embodiment, m is 1, and $R^1$ in the compound of Formula (I-A) is selected from $C_2$alkylenephenyl and $C_2$alkenylenephenyl, wherein the phenyl groups are optionally substituted with one to three substituents selected from OH and $C_{2-16}$alkenyl, and wherein $R^1$ is in a position meta to each of the hydroxy groups. Therefore, in an embodiment, the compound of Formula (I-A) is

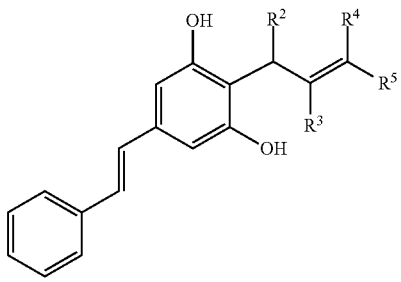

wherein the phenyl group is optionally substituted with one to three substituents selected from OH and $C_{2-16}$alkenyl.

In an embodiment, each $R^1$ in the compound of Formula (I-A) is independently selected from OH, $C_{2-16}$alkenyl, Z—$C_{1-16}$alkyl, Z—$C_{6-18}$ aryl, Z—$C_{1-16}$alkylene$C_{6-18}$aryl, Z—$C_{2-16}$alkenylene$C_{6-18}$ aryl, Z—$C_{1-16}$alkylene$C_{6-18}$heterocycloalkyl, Z—$C_{1-16}$alkenylene$C_{6-18}$heterocycloalkyl, Z—$C_{5-18}$ heteroaryl, Z—$C_{1-16}$alkylene$C_{5-18}$ heteroaryl, and Z—$C_{2-16}$alkenylene$C_{5-18}$ heteroaryl, wherein all alkyl, alkenyl, alkylene, alkenylene, aryl, heterocycloalkyl and heteroaryl groups are optionally substituted with one or more substituents selected from OH, halo, $C_{1-12}$alkyl, $C_{2-16}$alkenyl, $C_{2-6}$alkynyl, $OC_{1-12}$alkyl.

In an embodiment, Z is C(O) or O and one $R^1$ in the compound of Formula (I-A) is independently selected from C(O)$C_{1-16}$alkyl, C(O)$C_{6-18}$ aryl, C(O)$C_{1-16}$alkylene$C_{6-18}$aryl, C(O)$C_{2-16}$alkenylene$C_{6-18}$ aryl, C(O)$C_{1-16}$alkylene$C_{6-18}$heterocycloalkyl, C(O)$C_{1-16}$alkenylene$C_{6-18}$heterocycloalkyl, C(O)$C_{5-18}$ heteroaryl, C(O)$C_{1-16}$alkylene$C_{5-18}$heteroaryl, and C(O)$C_{2-16}$alkenylene$C_{5-18}$heteroaryl, wherein all alkyl, alkylene, alkenylene, aryl, heterocycloalkyl and heteroaryl groups are optionally substituted with one or more substituents selected from OH, halo, $C_{1-12}$alkyl, $C_{2-16}$alkenyl, $C_{2-6}$alkynyl, and $OC_{1-12}$alkyl.

In an embodiment, one $R^1$ in the compound of Formula (I-A) is C(O)$C_{1-16}$alkyl.

In an embodiment, one $R^1$ in the compound of Formula (I-A) is selected from C(O)$C_{1-6}$alkylene$C_{6-18}$ aryl, C(O)$C_{2-6}$alkenylene$C_{6-10}$ aryl, C(O)$C_{1-6}$alkylene$C_{3-10}$heterocycloalkyl, C(O)$C_{2-6}$alkenylene$C_{5-10}$heterocycloalkyl, C(O)$C_{1-6}$alkylene$C_{5-10}$heteroaryl, and C(O)$C_{2-16}$alkenylene$C_{5-10}$ heteroaryl, wherein all alkylene, alkenylene, aryl, heterocycloalkyl and heteroaryl groups are optionally substituted with one or more substituents selected from OH, $C_{1-12}$alkyl, $C_{2-16}$alkenyl, and $OC_{1-12}$alkyl.

In an embodiment, one $R^1$ in the compound of Formula (I-A) is selected from C(O)$C_{2-6}$alkenylene$C_{6-10}$aryl, and C(O)$C_{2-6}$alkenylene$C_{3-10}$heterocycloalkyl, wherein all, alkenylene, aryl, and heterocycloalkyl groups are optionally substituted with one or more substituents selected from OH, $C_{1-12}$alkyl, and $C_{2-16}$alkenyl.

In an embodiment, one $R^1$ in the compound of Formula (I-A) is selected from C(O)$C_2$alkenylenephenyl, and C(O)$C_2$alkenylene$C_{10}$heterocycloalkyl, wherein all alkenylene, phenyl, and heterocycloalkyl groups are optionally substituted with one or more substituents selected from OH, $C_{1-4}$alkyl, and $C_{2-6}$alkenyl.

In an embodiment, one $R^1$ in the compound of Formula (I-A) is $C_{5-10}$heteroaryl wherein the heteroaryl groups are optionally substituted with one or two OH. In an embodiment, the $C_{5-10}$heteroaryl in $R^1$ is benzofuran.

In an embodiment, when m greater than 1, two adjacent $R^1$ groups in the compound of Formula (I-A) are linked together to form a polycyclic ring system having 10 or more atoms together with the phenyl ring to which said groups are bonded, and in which one or more carbon atoms in said polycyclic ring system is optionally replaced with a heteromoiety selected from $NR^6$, O and S, wherein the polycyclic ring system is optionally substituted with one or more substituents selected from OH, =O, halo, $C_{1-16}$alkyl, $C_{2-16}$alkenyl, $C_{2-6}$alkynyl, $OC_{1-16}$alkyl, $OC_{2-16}$alkenyl, $OC_{2-6}$alkynyl; $C_{1-16}$alkylene$OR^8$, $C_{2-16}$alkenylene$OR^8$, $C_{2-16}$alkynylene$OR^8$, $C_{6-18}$aryl, $C_{3-18}$cycloalkyl, $C_{3-18}$heterocycloalkyl, and $C_{3-18}$heterocycloalkyl, the latter 4 groups being optionally substituted with one or more substituents selected from OH, halo, $C_{1-16}$alkyl, $OC_{1-16}$alkyl, and $C_{2-16}$alkenyl. In an embodiment, the polycyclic ring system is substituted with $C_{2-16}$alkenyl and further optionally substituted with one or more substituents selected from OH, =O, halo, $C_{1-16}$alkyl, $C_{2-16}$alkenyl, $C_{2-6}$alkynyl, $OC_{1-16}$alkyl, $OC_{2-16}$alkenyl, $OC_{2-6}$alkynyl; $C_{1-16}$alkylene$OR^8$, $C_{2-16}$alkenylene$OR^8$, $C_{2-16}$alkynylene$OR^8$, $C_{6-18}$ aryl, $C_{3-18}$cycloalkyl, $C_{3-18}$heterocycloalkyl, and $C_{3-18}$heterocycloalkyl, the latter 4 groups being optionally substituted with one or more substituents selected from OH, halo, $C_{1-16}$alkyl, $OC_{1-16}$alkyl, and $C_{2-16}$alkenyl.

In an embodiment, two adjacent $R^1$ groups in the compound of Formula (I-A) are linked together to form a bicyclic system having 10 atoms together with the phenyl ring to which said groups are bonded, and in which one or more carbon atoms in said bicyclic ring system is optionally replaced with a heteromoiety selected from O, wherein the polycyclic ring system is optionally substituted with one or more substituents selected from OH, =O, $C_{1-6}$alkyl, $OC_{1-6}$alkyl, $C_{6-18}$ aryl substituted with one or more substituents selected from OH, $C_{1-6}$alkyl, $OC_{1-6}$alkyl, and $C_{2-16}$alkenyl, and $C_{3-18}$heterocycloalkyl substituted with one or more substituents selected from OH, $C_{1-6}$alkyl, $OC_{1-6}$alkyl, and $C_{2-16}$alkenyl.

In an embodiment, the bicyclic system is substituted with $C_{2-16}$alkenyl and further is optionally substituted with one or more substituents selected from OH, =O, $C_{1-6}$alkyl, $OC_{1-6}$alkyl, $C_{6-18}$ aryl substituted with one or more substituents selected from OH, $C_{1-6}$alkyl, $OC_{1-6}$alkyl, and $C_{2-16}$alkenyl, and $C_{3-18}$heterocycloalkyl substituted with one or more substituents selected from OH, $C_{1-6}$alkyl, $OC_{1-6}$alkyl, and $C_{2-16}$alkenyl.

In an embodiment, two adjacent $R^1$ groups in the compound of Formula (I-A) are linked together to form, with the phenyl ring to which they are attached, a chromanone or a chromenone, which is optionally substituted with one or more substituents selected from OH, =O, $OC_{1-6}$alkyl, phenyl substituted with one or more substituents selected from OH, $C_{1-6}$alkyl, $OC_{1-6}$alkyl, and $C_{2-16}$alkenyl, and $C_{10}$heterocycloalkyl substituted with one or more substituents selected from OH and $C_{1-6}$alkyl]. In an embodiment, the chromanone or chromenone is substituted with $C_{2-16}$alkenyl and further optionally substituted with one or more substituents selected from OH, =O, $OC_{1-6}$alkyl, phenyl substituted with one or more substituents selected from OH, $C_{1-6}$alkyl, $OC_{1-6}$alkyl, and $C_{2-16}$alkenyl, and $C_{10}$heterocycloalkyl substituted with one or more substituents selected from OH and $C_{1-6}$alkyl. In an embodiment, two adjacent $R^1$ groups in the compound of Formula (I-A) are linked together to form, with the phenyl ring to which they are attached, a chroman-4-one (dihydrochromen-4-one) or a chromen-4-one, which is optionally substituted with one or more substituents selected from OH, =O, $OC_{1-6}$alkyl, and phenyl substituted with one or more substituents selected from OH, $C_{1-6}$alkyl, $OC_{1-6}$alkyl, and $C_{2-16}$alkenyl. In an embodiment, the chroman-4-one or a chromen-4-one is substituted with $C_{2-16}$alkenyl and further optionally substituted with one or more substituents selected from OH, =O, $OC_{1-6}$alkyl, and phenyl substituted with one or more substituents selected from OH, $C_{1-6}$alkyl, $OC_{1-6}$alkyl, and $C_{2-16}$alkenyl.

In an embodiment, two adjacent $R^1$ groups in the compound of Formula (I-A) are linked together to form, with the phenyl ring to which they are attached, a chroman-4-one or a chromen-4-one, which is optionally substituted with one or more substituents selected from OH, =O, $OC_{1-6}$alkyl, and phenyl substituted with one or more substituents selected from OH, $C_{1-6}$alkyl, $OC_{1-6}$alkyl, and $C_{2-16}$alkenyl.

Therefore, in an embodiment, two adjacent $R^1$ groups in the compound of Formula (I-A) are linked together to form, with the phenyl ring to which they are attached, a flavonol, isoflavonol, flavavonol or isoflavavonol which is optionally substituted with one or more substituents selected from OH, =O, $OC_{1-6}$alkyl, and phenyl substituted with one or more substituents selected from OH, $C_{1-6}$alkyl, $OC_{1-6}$alkyl, and $C_{2-16}$alkenyl.

In an embodiment, two adjacent $R^1$ groups in the compound of Formula (I-A) are linked together to form, with the phenyl ring to which they are attached, a polycyclic ring system having 14 or more atoms together with the two adjacent carbon atoms to which said groups are bonded, and in which one or more carbon atoms in said polycyclic ring system is optionally replaced with a heteromoiety that is O, wherein the polycyclic ring system is optionally substituted with one or more OH, =O, and $C_{2-16}$alkenyl. In an embodiment, polycyclic ring system having 14 or more atoms is substituted with $C_{2-16}$alkenyl and further optionally substituted with one or more substituents selected from OH, =O, and $C_{2-16}$alkenyl.

In an embodiment, two adjacent $R^1$ groups in the compound of Formula (I-A) are linked together to form, with the phenyl ring to which they are attached, a xanthone, wherein the xanthone is optionally substituted with one or more OH, =O and $C_{2-16}$alkenyl. In an embodiment, the xanthone is substituted with $C_{2-16}$alkenyl and further optionally substituted with one or more substituents selected from OH, =O, and $C_{2-16}$alkenyl.

In an embodiment, two adjacent $R^1$ groups in the compound of Formula (I-A) are linked together to form, with the phenyl ring to which they are attached, a xanthone, wherein the xanthone is optionally substituted with one or more OH.

In an embodiment, $R^3$ in the compounds of Formula (I), and (I-A) is selected from H, $CH_3$ and $CH_2CH_3$. In an embodiment, $R^3$ is selected from H and $CH_3$.

In an embodiment, $R^4$ in the compounds of Formula (I) and (I-A) is selected from H, $CH_3$, $CH_2CH_3$, $C_{6-10}$aryl, $C_{1-6}$alkylene$C_{6-18}$aryl, $C_{5-10}$ heteroaryl, and $C_{2-6}$alkylene $C_{5-10}$heteroaryl. In an embodiment, $R^4$ is selected from H, $CH_3$, $CH_2CH_3$, phenyl, and $C_{1-6}$alkylenephenyl. In an embodiment, $R^4$ is selected from H, $CH_3$, and phenyl.

In an embodiment, $R^5$ in the compounds of Formula (I) and (I-A) is selected from H, $C_{1-20}$alkyl, $C_{2-20}$alkenyl, $C_{2-20}$alkynyl, $C_{3-18}$ cycloalkyl, $C_{1-10}$alkylene$C_{3-18}$ cycloalkyl, $C_{2-10}$alkenylene$C_{3-18}$cycloalkyl, $C_{2-10}$alkynylene$C_{3-18}$ cycloalkyl, $C_{3-18}$heterocycloalkyl, $C_{1-10}$alkylene$C_{3-18}$heterocycloalkyl, $C_{1-10}$alkenylene$C_{3-18}$heterocycloalkyl, $C_{2-10}$alkynylene$C_{3-18}$heterocycloalkyl, $C_{6-10}$aryl, $C_{1-10}$alkylene$C_{6-10}$aryl; $C_{2-10}$alkenylene$C_{6-10}$aryl, $C_{2-10}$alkynylene$C_{6-10}$aryl, $C_{5-10}$heteroaryl, $C_{2-10}$alkylene$C_{5-10}$ heteroaryl, $C_{2-06}$alkenylene$C_{5-10}$heteroaryl, and $C_{2-10}$alkynylene $C_{5-18}$heteroaryl, wherein all cycloalkyl, heterocycloalkyl, aryl and heteroaryl are optionally substituted with one or more substituents selected from OH, $NO_2$, CN, halo, $C_{1-16}$alkyl, $C_{2-16}$alkenyl, $C_{2-6}$alkynyl, $OC_{1-16}$alkyl, $OC_{2-16}$alkenyl, $OC_{2-6}$alkynyl, $C_{1-16}$alkyleneOR$^9$ $C_{2-16}$alkenyleneOR$^9$, $C_{2-16}$alkynyleneOR$^9$, $SO_3C_{1-16}$alkyl, $SO_3C_{6-16}$aryl, and $SO_3C_{5-18}$heteroaryl substituted with $C_{1-16}$alkyl.

In an embodiment, $R^5$ in the compounds of Formula (I), and (I-A) is selected from H, $C_{1-10}$alkyl, $C_{2-20}$alkenyl, and $C_{6-10}$aryl, wherein aryl is optionally substituted with one or more substituents selected from OH, $NO_2$, CN, F, Cl, Br, $C_{1-6}$alkyl, $C_{2-16}$alkenyl, $C_{2-6}$alkynyl, $OC_{1-16}$alkyl and $SO_3C_{1-6}$alkyl.

In an embodiment, $R^5$ in the compounds of Formula (I), and (I-A) is selected from H, $C_{2-20}$alkenyl, and phenyl, wherein phenyl is optionally substituted with one or more substituents selected from OH, $NO_2$, CN, F, Cl, Br, $CH_3$, $CH_2CH_3$, $C_{2-16}$alkenyl, $OC_{1-6}$alkyl and $SO_3C_{1-6}$alkyl.

In an embodiment, $R^5$ in the compounds of Formula (I), and (I-A) is phenyl. In an embodiment, $R^5$ is phenyl which is substituted with one or more substituents selected from OH, $NO_2$, F, Cl, Br, $CH_3$, $OC_{1-6}$alkyl and $SO_3CH_3$.

In an embodiment, $R^4$ and $R^5$ in the compound of Formula (I), and (I-A) are both phenyl. In an embodiment, $R^4$ is H and $R^5$ is phenyl. In an embodiment, $R^4$ is H and $R^5$ is phenyl which is substituted with one or more substituents selected from OH, $NO_2$, F, Cl, Br, $CH_3$, $OC_{1-6}$alkyl and $SO_3CH_3$.

In an embodiment, $R^5$ in the compound of Formula (I), and (I-A) is H. In an embodiment, $R^5$ is $C_{1-10}$alkyl. In an embodiment, $R^5$ is selected from $CH_3$ and $CH_2CH_3$. In an embodiment, $R^5$ is $CH_3$.

In an embodiment, $R^5$ in the compound of Formula (I), and (I-A) is $C_{2-20}$alkenyl. In an embodiment, $R^5$ is selected from

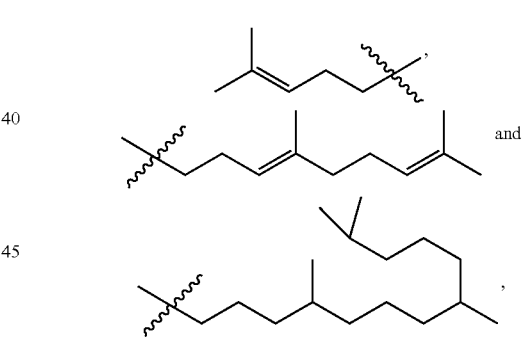

and wherein

represents a point of covalent attachment. In an embodiment, $R^5$ is

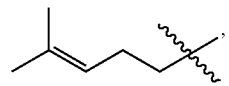, wherein

represents a point of covalent attachment. In an embodiment, $R^4$ and $R^5$ in the compound of Formula (I) and (I-A) are both $CH_3$. In an embodiment, $R^4$ is $CH_3$ and $R^5$ is

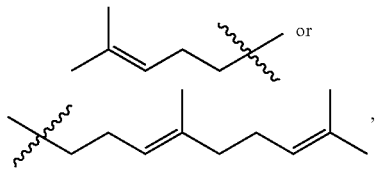

wherein

represents a point of covalent attachment.

Therefore, in an embodiment, the compound of Formula (I), and (I-A) comprises a prenyl functional group

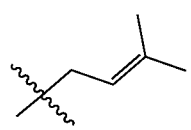 [SMILES: *CC=C(C)C]

or repeating prenyl functional groups such as prenyl, geranyl, phytyl, farnesyl, or neryl wherein

represents a point of covalent attachment. Therefore, in an embodiment, the compound of Formula (I), and (I-A) is an ortho-prenylated hydroxy aryl compound or ortho-polyprenylated hydroxy aryl compound also known as ortho-prenylated phenolics or ortho-polyprenylated phenolics.

In an embodiment, any two of $R^2$, $R^3$, $R^4$ and $R^5$ in the compound of Formula (I) or (I-A) are linked together to form an unsubstituted or substituted monocyclic or polycyclic ring system having 4 or more atoms together with the carbon atoms to which said any two of $R^2$, $R^3$, $R^4$ and $R^5$ are bonded, wherein the monocyclic or polycyclic ring system is optionally substituted with one or more substituents selected =O, OH, halo, $C_{1-16}$alkyl, $C_{2-16}$alkenyl, $C_{2-16}$alkynyl, $OC_{1-16}$alkyl, $OC_{2-16}$alkenyl, $OC_{2-16}$alkynyl; $C_{1-16}$alkyleneOR$^8$, $C_{2-16}$alkenyleneOR$^8$, $C_{2-16}$alkynyleneOR$^8$, $C_{6-18}$ aryl, $C_{3-18}$ cycloalkyl, $C_{3-18}$heterocycloalkyl, and $C_{5-18}$heteroaryl, the latter 4 groups being optionally substituted with one or more substituents selected from OH, halo, $C_{1-16}$alkyl, $OC_{1-16}$alkyl, and $C_{2-16}$alkenyl;

In an embodiment, $R^2$ and $R^5$ in the compound of Formula (I) or (I-A) are linked together to form an unsubstituted or substituted monocyclic ring system having 6 or more atoms together with the carbon atoms to which said $R^2$ and $R^5$ are bonded, wherein the monocyclic ring system is optionally substituted with one or more substituents selected OH, $C_{1-16}$alkyl, and $C_{2-16}$alkenyl.

In an embodiment, $R^2$ and $R^5$ in the compound of Formula (I-A) are linked together to form an unsubstituted or substituted monocyclic ring system having 6 or more atoms together with the carbon atoms to which said $R^2$ and $R^5$ are bonded, wherein the monocyclic ring system is optionally substituted with one or more substituents selected OH, $C_{1-16}$alkyl, and $C_{2-16}$alkenyl. In an embodiment, $R^2$ and $R^5$ in the compound of Formula (I-A) are linked together to form isopiperitenol. In an embodiment, $R^2$ and $R^5$ in the compound of Formula (I-A) are linked together to form

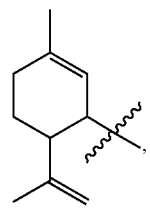

wherein

represents a point of covalent attachment.

In an embodiment, the compound of Formula (I) is selected from a cannabinoid. In an embodiment, the cannabinoid is selected from cannabidiol, cannabidivarin, cannabigerol, cannabigerorcin and cannabigerivarin. In an embodiment, the compound of Formula (I) is cannabidiol. In an embodiment, the compound of Formula (I) is selected from, cannabidivarin, cannabigerol, grifolin, cannabigerorcin, piperogalin and cannabigerivarin. In an embodiment, the compound of Formula (I) is selected from cannabigerol, piperogalin and grifolin.

In $R^2$ and $R^5$ in the compound of Formula (I-A) are linked together to form isopiperitenol and the compound of Formula (I-A) is cannabidiol.

In an embodiment, the compound of Formula (I), and (I-A) is a natural compound. In an embodiment, the compound of Formula (I), and (I-A) is a natural occurring phenolic compound. In an embodiment, the compound of Formula (I) and (I-A) is selected from a class of compound comprising cannabinoids, phenols, resorcinols, chalconoids, moracins, stilbenoidd, polycyclic aromatics, flavanonols, isoflavanonols, flavonols, isoflavonols, chromones, coumarins and xanthones.

In an embodiment, the compound of Formula (I), and (I-A) comprises a prenyl functional group

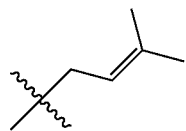 [SMILES: *CC=C(C)C]

or repeating prenyl functional groups, therefore the compound of Formula (I) and (I-A) is selected class of compound comprising prenylated or polyprenylated cannabinoids, phenols, resorcinols, chalconoids, moracins, stilbenoidd, polycyclic aromatics, flavanonols, isoflavanonols, flavonols, isoflavonols, chromones, coumarins and xanthones.

It would be appreciated by a person skilled in the art $R^1$ in a compound of Formula (II) and $R^2$, $R^3$, $R^4$ and $R^5$ for a compound of Formula (II) would correspond to $R^1$, $R^2$, $R^3$, $R^4$ and $R^5$ selected for the compound of Formula (I).

It would also be appreciated by a person skilled in the art that the compounds of Formula (I) can be further reacted to form further scaffolds of interest. For example, exemplary compounds of Formula (I), cannabidiol and cannabidivarin, can be further cyclized to form tetrahydrocannabinol and tetrahydrocannabivarin, respectively. Conditions for cyclization would be known a person skilled in the art.

In an embodiment, the compound of Formula (I) is selected from the compounds listed below:

| Compound I.D | Structure |
|---|---|
| I-1 | 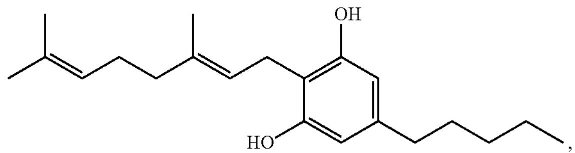 [SMILES: CCCCCc1cc(O)c(C/C=C(\C)CCC=C(C)C)c(O)c1] |
| I-2 | 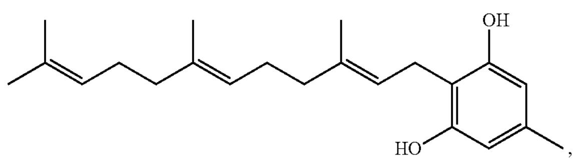 [SMILES: CC(C)=CCC/C(C)=C/CC/C(C)=C/Cc1c(O)cc(C)cc1O] |
| I-3 | 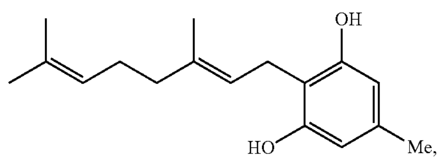 [SMILES: CC(C)=CCC/C(C)=C/Cc1c(O)cc(C)cc1O] |
| I-4 | 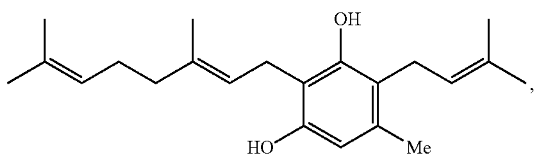 [SMILES: CC(C)=CCC/C(C)=C/Cc1c(O)cc(C)c(CC=C(C)C)c1O] |
| I-5 | 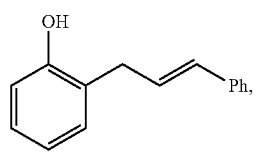 [SMILES: Oc1ccccc1C/C=C/c1ccccc1] |
| I-6 | 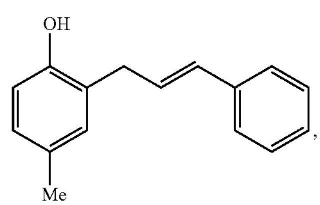 [SMILES: Cc1ccc(O)c(C/C=C/c2ccccc2)c1] |
| I-7 | 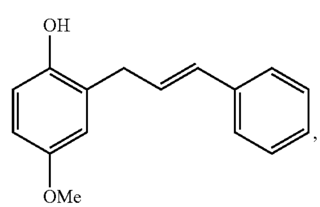 [SMILES: COc1ccc(O)c(C/C=C/c2ccccc2)c1] |

-continued

| Compound I.D | Structure |
|---|---|
| I-8 | 2-cinnamyl-4-chlorophenol |
| I-9 | 2-(3-(4-nitrophenyl)allyl)phenol |
| I-10 | 2-cinnamylnaphthalen-1-ol |
| I-11 | 1-cinnamylnaphthalen-2-ol |
| I-12 | 2-cinnamyl-3,5-dimethylphenol |
| I-13 | 2-cinnamyl-4,5-dimethylphenol |
| I-14 | 2-cinnamyl-4-methylphenol |
| I-15 | 2-cinnamylbenzene-1,3-diol |
| I-16 | 2-chloro-6-cinnamylphenol |

-continued
| Compound I.D | Structure |
|---|---|
| I-17 | 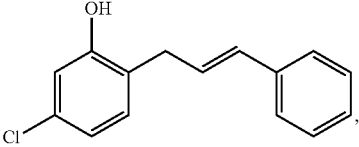 [SMILES: Oc1cc(Cl)ccc1C/C=C/c1ccccc1] |
| I-18 | 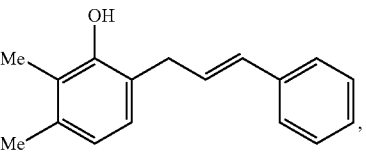 [SMILES: Cc1ccc(C/C=C/c2ccccc2)c(O)c1C] |
| I-19 | 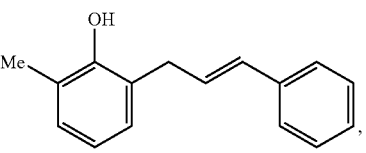 [SMILES: Cc1cccc(C/C=C/c2ccccc2)c1O] |
| I-20 | 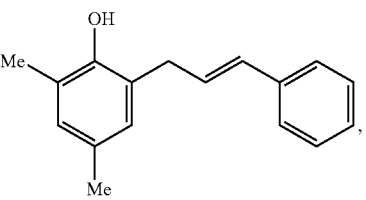 [SMILES: Cc1cc(C)c(O)c(C/C=C/c2ccccc2)c1] |
| I-21 | 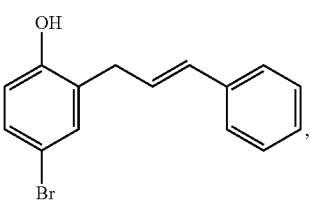 [SMILES: Oc1ccc(Br)cc1C/C=C/c1ccccc1] |
| I-22 | 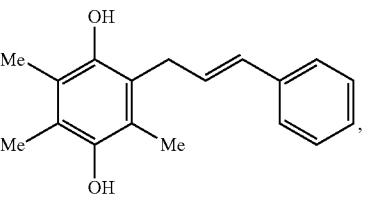 [SMILES: Cc1c(C)c(O)c(C/C=C/c2ccccc2)c(C)c1O] |
| I-23 | 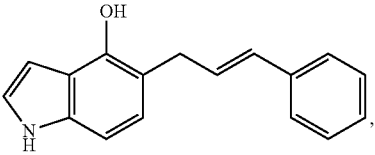 [SMILES: Oc1c(C/C=C/c2ccccc2)ccc2[nH]ccc12] |
| I-24 | 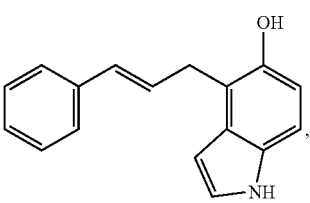 |

-continued
| Compound I.D | Structure |
|---|---|
| I-25 | 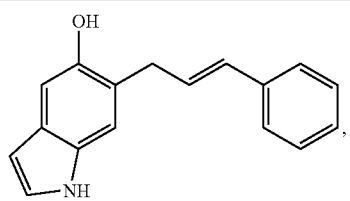 |
| I-26 | 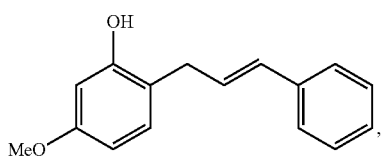 [SMILES: COc1ccc(C/C=C/c2ccccc2)c(O)c1] |
| I-27 | 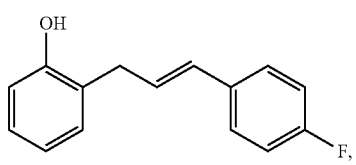 |
| I-28 | 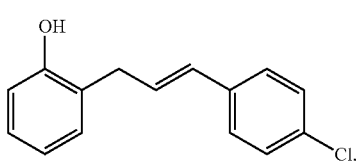 |
| I-29 | 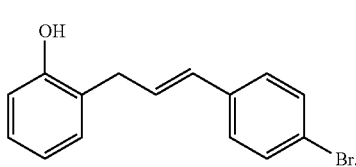 |
| I-30 | 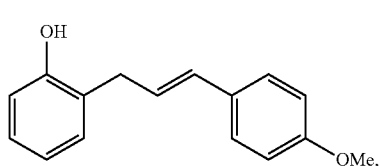 |
| I-31 | 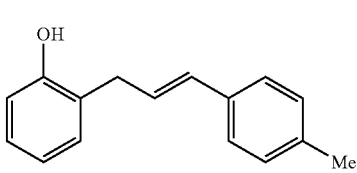 |
| I-32 | 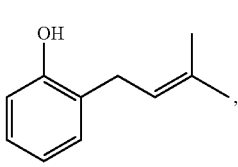 |
| I-33 | 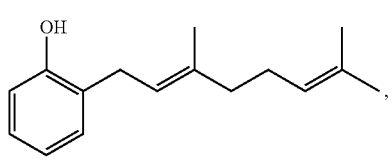 [SMILES: CC(C)=CCC/C(C)=C/Cc1ccccc1O] |

| Compound I.D | Structure |
|---|---|
| I-34 | 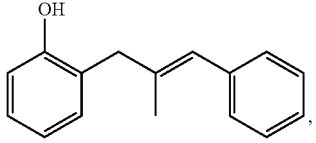 [SMILES: C/C(=C\c1ccccc1)Cc1ccccc1O] |
| I-35 | 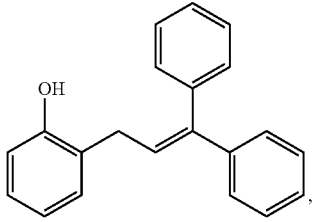 [SMILES: Oc1ccccc1CC=C(c1ccccc1)c1ccccc1] |
| I-36 | 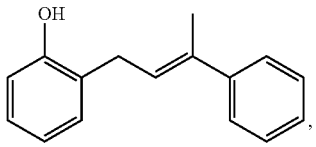 [SMILES: C/C(=C\Cc1ccccc1O)c1ccccc1] |
| I-37 | 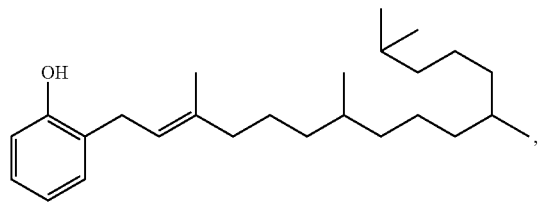 [SMILES: C/C(=C\Cc1ccccc1O)CCCC(C)CCCC(C)CCCC(C)C] |
| I-38 | 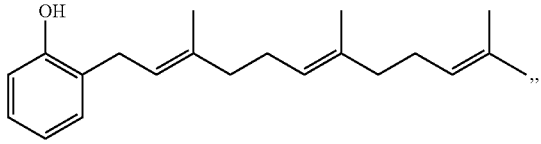 [SMILES: CC(C)=CCC/C(C)=C/CC/C(C)=C/Cc1ccccc1O] |
| I-39 | 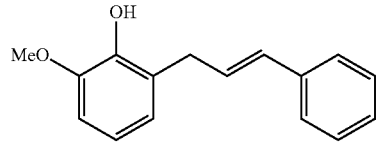 [SMILES: COc1cccc(C/C=C/c2ccccc2)c1O] |
| I-40 | 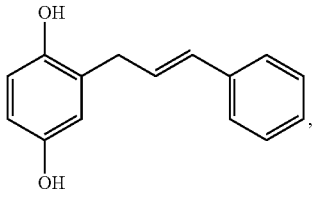 [SMILES: Oc1ccc(O)c(C/C=C/c2ccccc2)c1] |
| I-41 | 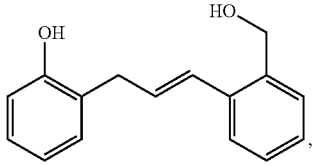 [SMILES: OCc1ccccc1/C=C/Cc1ccccc1O] |
| I-42 | 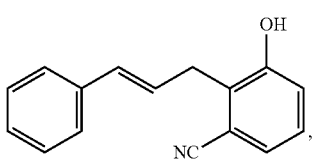 |

-continued
| Compound I.D | Structure |
|---|---|
| I-43 | 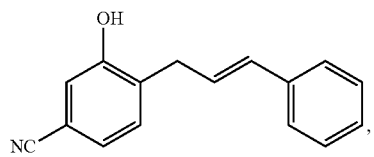 |
| I-44 | 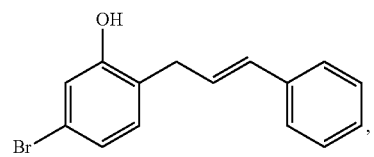 |
| I-45 | 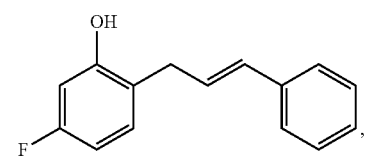 [SMILES: Oc1cc(F)ccc1C/C=C/c1ccccc1] |
| I-46 | 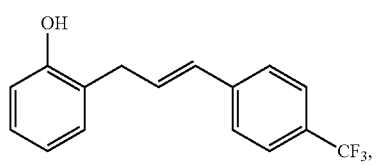 |
| I-47 | 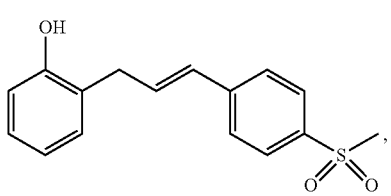 [SMILES: CS(=O)(=O)c1ccc(/C=C/Cc2ccccc2O)cc1] |
| I-48 | 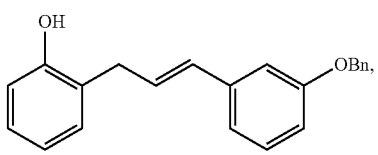 [SMILES: Oc1ccccc1C/C=C/c1cccc(OCc2ccccc2)c1] |
| I-49 | 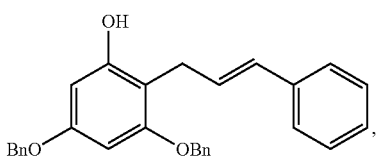 [SMILES: Oc1cc(OCc2ccccc2)cc(OCc2ccccc2)c1C/C=C/c1ccccc1] |
| I-51 | 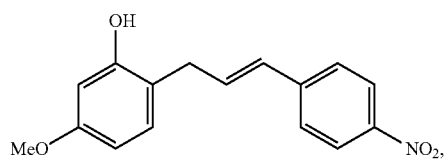 [SMILES: COc1ccc(C/C=C/c2ccc([N+](=O)[O-])cc2)c(O)c1] |
| I-52 | 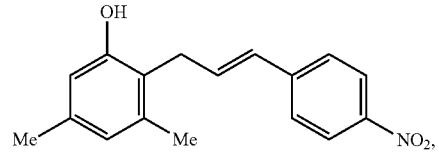 [SMILES: Cc1cc(C)c(C/C=C/c2ccc([N+](=O)[O-])cc2)c(O)c1] |

-continued

| Compound I.D | Structure |
|---|---|
| I-53 | [1-hydroxy-2-(3-(4-nitrophenyl)allyl)naphthalene] |
| I-54 | [2-hydroxy-1-(3-(4-nitrophenyl)allyl)naphthalene] |
| I-55 | [2-(cinnamyl)-3-nitrophenol] |
| I-56 | [2-cinnamyl-4-nitrophenol] |
| I-57 | [3,5-bis(benzyloxy)-2-(3-(3-(benzyloxy)phenyl)allyl)phenol] |
| I-58 | [2-cinnamyl-estradiol derivative] |
| I-59 | [2-cinnamyl-ethynyl-estradiol derivative] |
| I-60 | [2-cinnamyl-estrone derivative] |

| Compound I.D | Structure |
|---|---|
| I-61 | 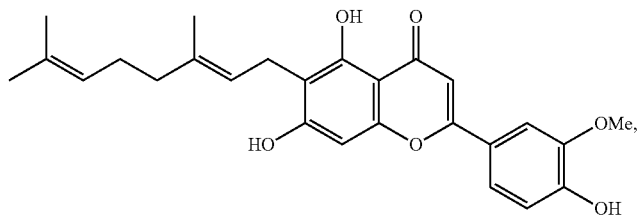 [SMILES: COc1cc(-c2cc(=O)c3c(O)c(C/C=C(\C)CCC=C(C)C)c(O)cc3o2)ccc1O] |
| I-62 | 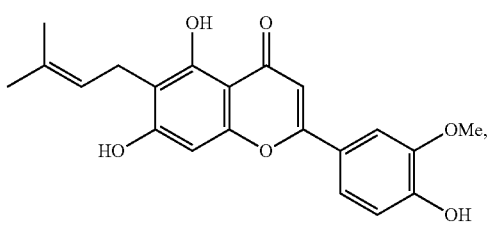 [SMILES: COc1cc(-c2cc(=O)c3c(O)c(CC=C(C)C)c(O)cc3o2)ccc1O] |
| I-63 | 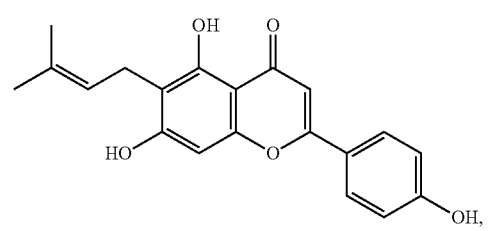 [SMILES: CC(C)=CCc1c(O)cc2oc(-c3ccc(O)cc3)cc(=O)c2c1O] |
| I-64 | 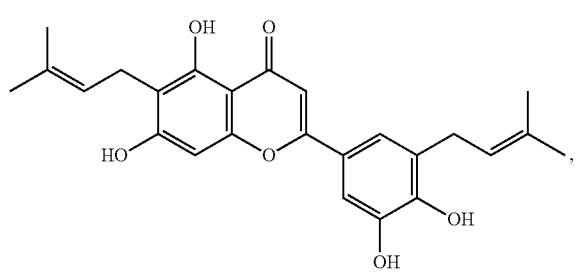 [SMILES: CC(C)=CCc1cc(-c2cc(=O)c3c(O)c(CC=C(C)C)c(O)cc3o2)cc(O)c1O] |
| I-65 | 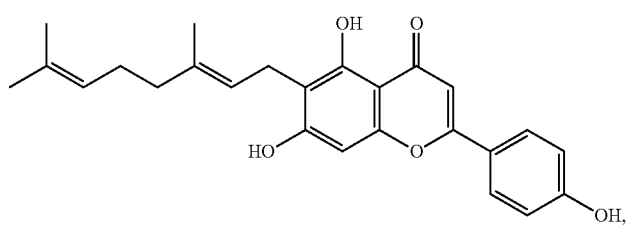 [SMILES: CC(C)=CCC/C(C)=C/Cc1c(O)cc2oc(-c3ccc(O)cc3)cc(=O)c2c1O] |
| I-66 | 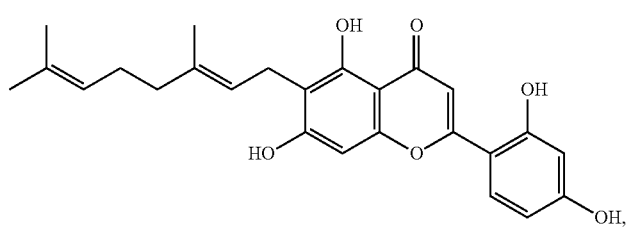 [SMILES: CC(C)=CCC/C(C)=C/Cc1c(O)cc2oc(-c3ccc(O)cc3O)cc(=O)c2c1O] |

-continued
| Compound I.D | Structure |
|---|---|
| I-67 | 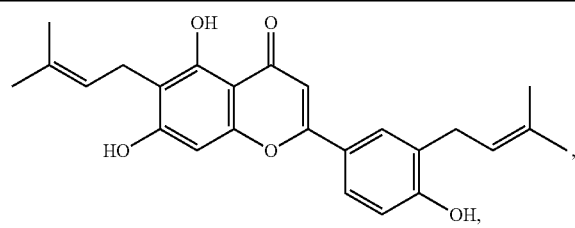 |
| I-68 | 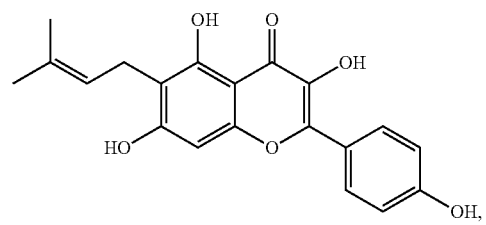 [SMILES: CC(C)=CCc1c(O)cc2oc(-c3ccc(O)cc3)c(O)c(=O)c2c1O] |
| I-69 | 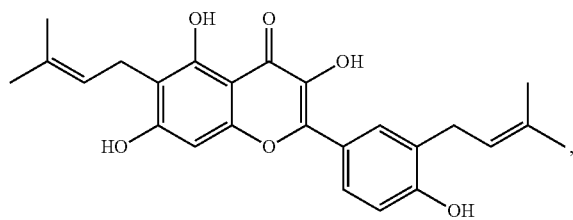 [SMILES: CC(C)=CCc1cc(-c2oc3cc(O)c(CC=C(C)C)c(O)c3c(=O)c2O)ccc1O] |
| I-70 | 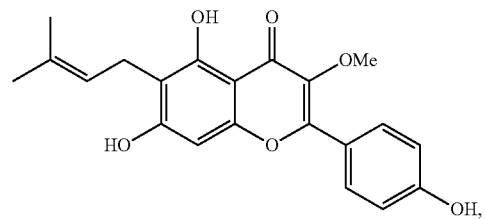 [SMILES: COc1c(-c2ccc(O)cc2)oc2cc(O)c(CC=C(C)C)c(O)c2c1=O] |
| I-71 | 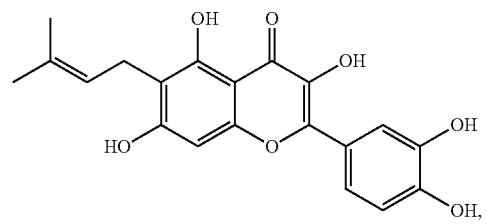 [SMILES: CC(C)=CCc1c(O)cc2oc(-c3ccc(O)c(O)c3)c(O)c(=O)c2c1O] |
| I-72 | 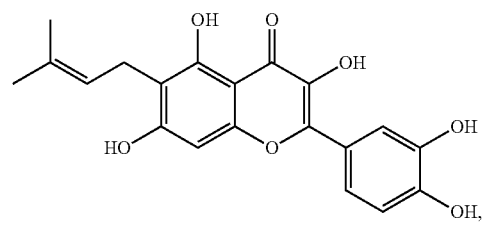 [SMILES: CC(C)=CCc1c(O)cc2oc(-c3ccc(O)c(O)c3)c(O)c(=O)c2c1O] |
| I-73 | 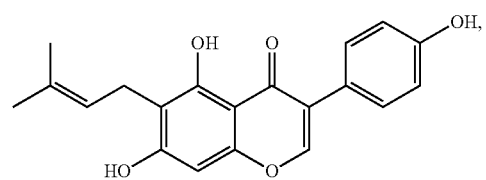 [SMILES: CC(C)=CCc1c(O)cc2occ(-c3ccc(O)cc3)c(=O)c2c1O] |

| Compound I.D | Structure |
|---|---|
| I-74 | 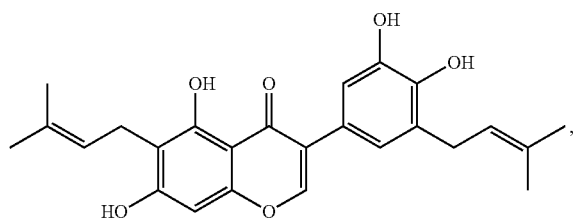 [SMILES: CC(C)=CCc1cc(-c2coc3cc(O)c(CC=C(C)C)c(O)c3c2=O)cc(O)c1O] |
| I-75 | 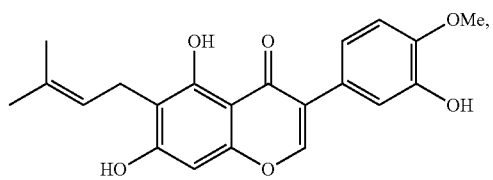 [SMILES: COc1ccc(-c2coc3cc(O)c(CC=C(C)C)c(O)c3c2=O)cc1O] |
| I-76 | 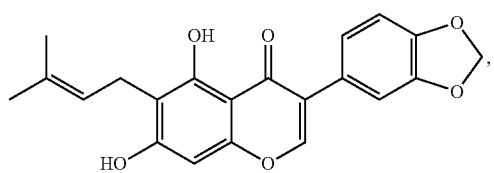 [SMILES: CC(C)=CCc1c(O)cc2occ(-c3ccc4c(c3)OCO4)c(=O)c2c1O] |
| I-77 | 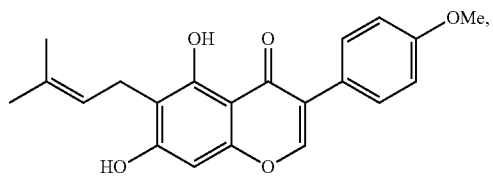 [SMILES: COc1ccc(-c2coc3cc(O)c(CC=C(C)C)c(O)c3c2=O)cc1] |
| I-78 | 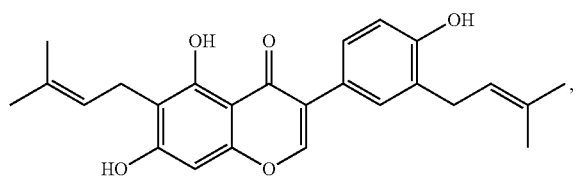 [SMILES: CC(C)=CCc1cc(-c2coc3cc(O)c(CC=C(C)C)c(O)c3c2=O)ccc1O] |
| I-79 | 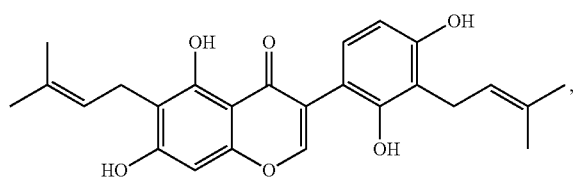 [SMILES: CC(C)=CCc1c(O)ccc(-c2coc3cc(O)c(CC=C(C)C)c(O)c3c2=O)c1O] |
| I-80 | 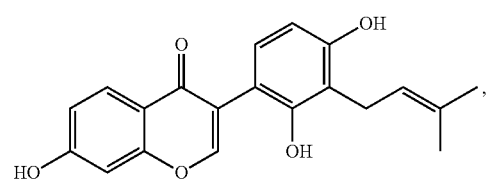 [SMILES: CC(C)=CCc1c(O)ccc(-c2coc3cc(O)ccc3c2=O)c1O] |
| I-81 | 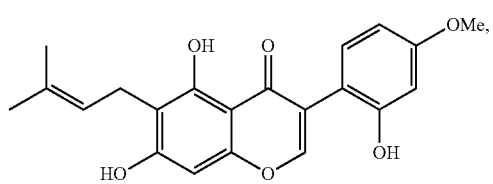 [SMILES: COc1ccc(-c2coc3cc(O)c(CC=C(C)C)c(O)c3c2=O)c(O)c1] |

| Compound I.D | Structure |
|---|---|
| I-82 | 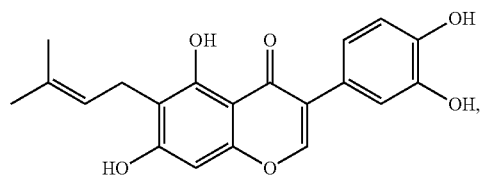 [SMILES: CC(C)=CCc1c(O)cc2occ(-c3ccc(O)c(O)c3)c(=O)c2c1O] |
| I-83 | 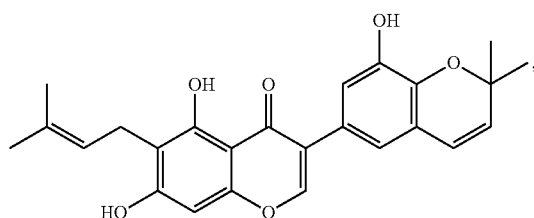 [SMILES: CC(C)=CCc1c(O)cc2occ(-c3cc(O)c4c(c3)C=CC(C)(C)O4)c(=O)c2c1O] |
| I-84 | 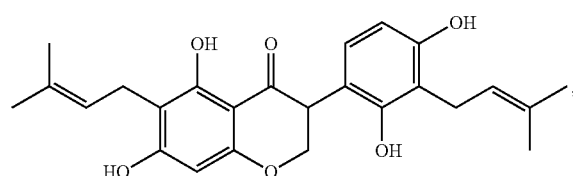 |
| I-85 | 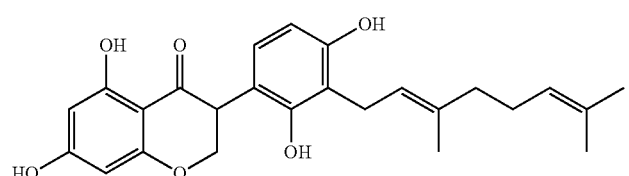 |
| I-86 | 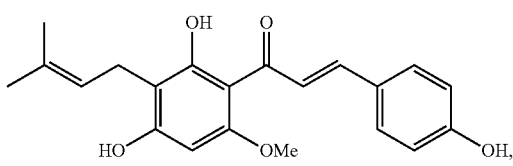 [SMILES: COc1cc(O)c(CC=C(C)C)c(O)c1C(=O)/C=C/c1ccc(O)cc1] |
| I-87 | 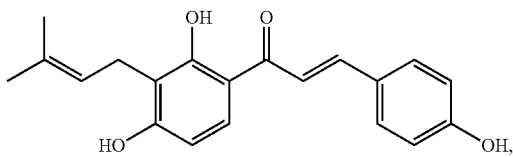 [SMILES: CC(C)=CCc1c(O)ccc(C(=O)/C=C/c2ccc(O)cc2)c1O] |
| I-88 | 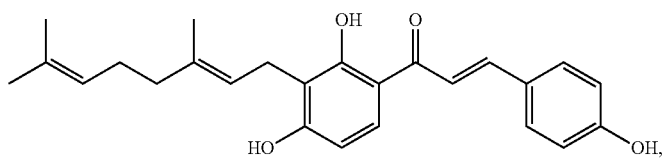 [SMILES: CC(C)=CCC/C(C)=C/Cc1c(O)ccc(C(=O)/C=C/c2ccc(O)cc2)c1O] |
| I-89 | 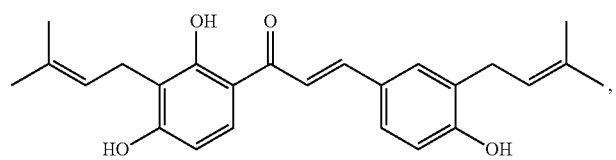 [SMILES: CC(C)=CCc1cc(/C=C/C(=O)c2ccc(O)c(CC=C(C)C)c2O)ccc1O] |
| I-90 | 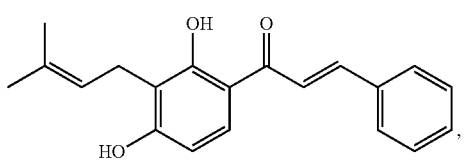 [SMILES: CC(C)=CCc1c(O)ccc(C(=O)/C=C/c2ccccc2)c1O] |

| Compound I.D | Structure |
|---|---|
| I-91 | 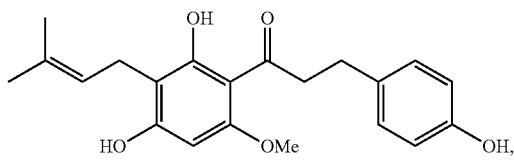 [SMILES: COc1cc(O)c(CC=C(C)C)c(O)c1C(=O)CCc1ccc(O)cc1] |
| I-92 | 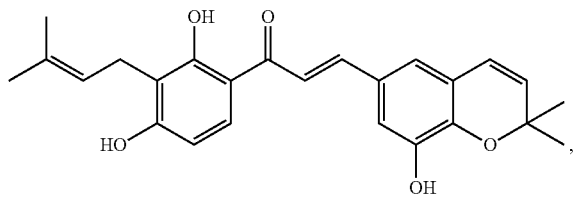 [SMILES: CC(C)=CCc1c(O)ccc(C(=O)/C=C/c2cc(O)c3c(c2)C=CC(C)(C)O3)c1O] |
| I-93 | 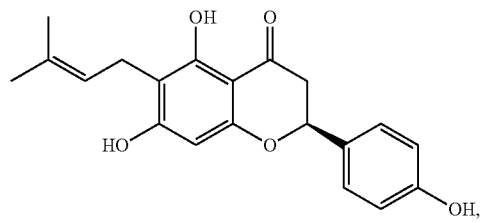 [SMILES: CC(C)=CCc1c(O)cc2c(c1O)C(=O)C[C@@H](c1ccc(O)cc1)O2] |
| I-94 | 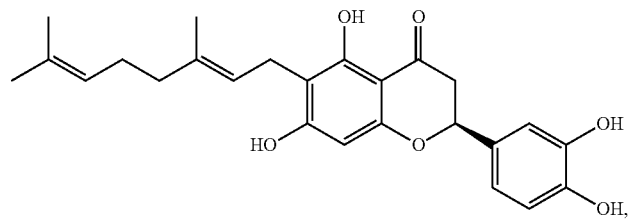 [SMILES: CC(C)=CCC/C(C)=C/Cc1c(O)cc2c(c1O)C(=O)C[C@@H](c1ccc(O)c(O)c1)O2] |
| I-95 | 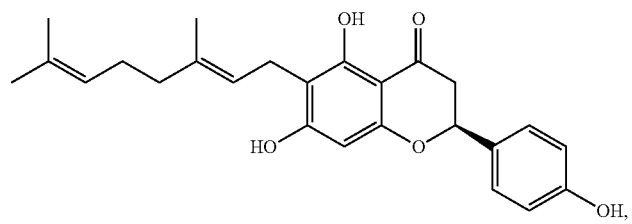 [SMILES: CC(C)=CCC/C(C)=C/Cc1c(O)cc2c(c1O)C(=O)C[C@@H](c1ccc(O)cc1)O2] |
| I-96 | 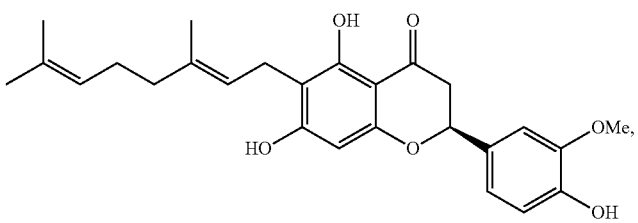 [SMILES: COc1cc([C@@H]2CC(=O)c3c(cc(O)c(C/C=C(\C)CCC=C(C)C)c3O)O2)ccc1O] |
| I-97 | 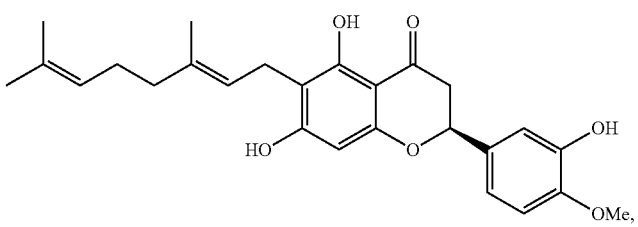 |

| Compound I.D | Structure |
|---|---|
| I-98 | 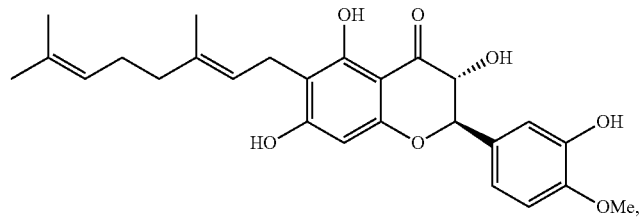 [SMILES: COc1ccc([C@H]2Oc3cc(O)c(C/C=C(\C)CCC=C(C)C)c(O)c3C(=O)[C@@H]2O)cc1O] |
| I-99 | 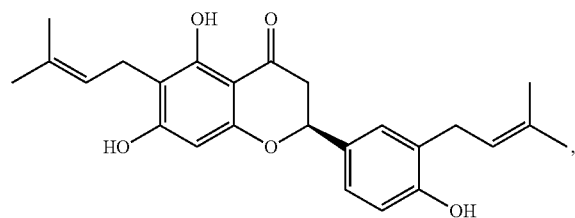 [SMILES: CC(C)=CCc1cc([C@@H]2CC(=O)c3c(cc(O)c(CC=C(C)C)c3O)O2)ccc1O] |
| I-100 | 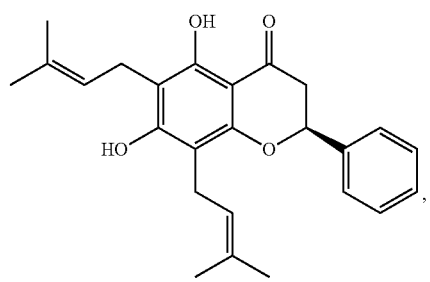 [SMILES: CC(C)=CCc1c(O)c(CC=C(C)C)c2c(c1O)C(=O)C[C@@H](c1ccccc1)O2] |
| I-101 | 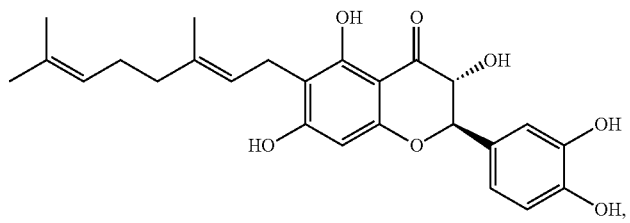 [SMILES: CC(C)=CCC/C(C)=C/Cc1c(O)cc2c(c1O)C(=O)[C@H](O)[C@@H](c1ccc(O)c(O)c1)O2] |
| I-102 | 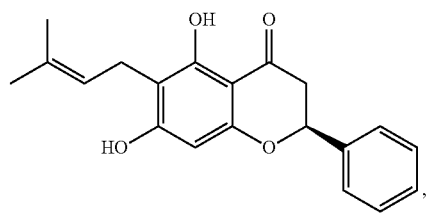 [SMILES: CC(C)=CCc1c(O)cc2c(c1O)C(=O)C[C@@H](c1ccccc1)O2] |
| I-103 | 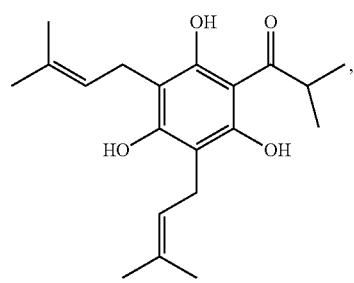 [SMILES: CC(C)=CCc1c(O)c(CC=C(C)C)c(O)c(C(=O)C(C)C)c1O] |

| Compound I.D | Structure |
|---|---|
| I-104 | 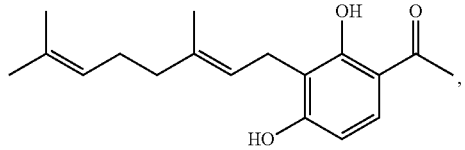 [SMILES: CC(=O)c1ccc(O)c(C/C=C(\C)CCC=C(C)C)c1O] |
| I-105 | 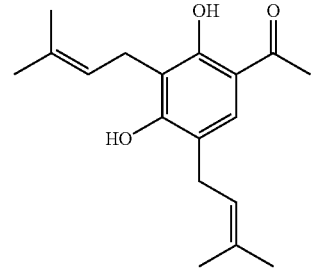 |
| I-106 | 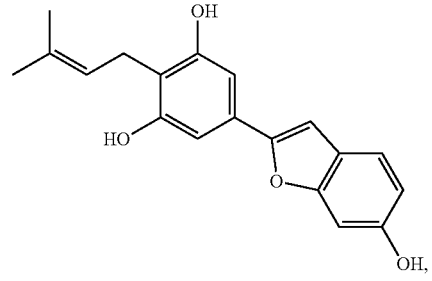 [SMILES: CC(C)=CCc1c(O)cc(-c2cc3ccc(O)cc3o2)cc1O] |
| I-107 | 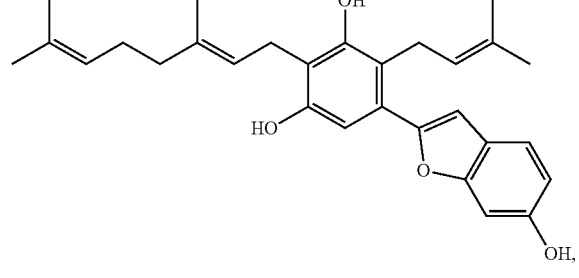 |
| I-108 | 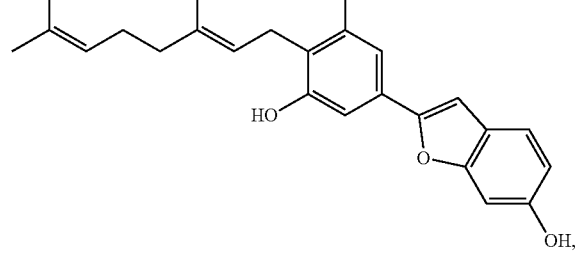 |
| I-109 | 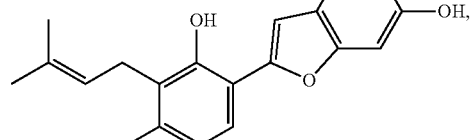 |

-continued

| Compound I.D | Structure |
|---|---|
| I-110 | (structure: 2-geranyl-resorcinol with 4-hydroxystyryl group) |
| I-111 | (structure: 2-geranyl-resorcinol with styryl group) |
| I-112 | (structure: 2-geranyl-resorcinol with 2,4-dihydroxystyryl group) |
| I-113 | (structure: 2-prenyl-resorcinol with 3,4-dihydroxystyryl group) |
| I-114 | (structure: 2-geranyl-resorcinol with phenethyl group) |
| I-115 | (structure: 2-prenyl-resorcinol with styryl group) |
| I-116 | (structure: 2-geranyl-resorcinol with stilbene bearing 3-geranyl-4,5-dihydroxyphenyl group) |

-continued
| Compound I.D | Structure |
|---|---|
| I-117 | 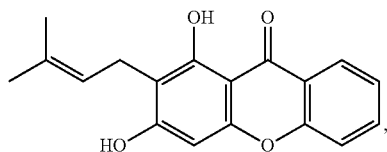 [SMILES: CC(C)=CCc1c(O)cc2oc3ccccc3c(=O)c2c1O] |
| I-118 | 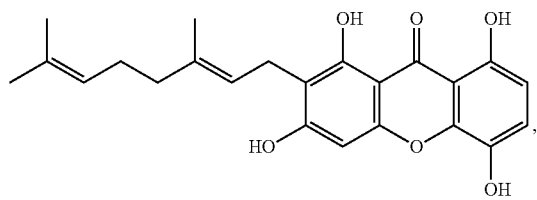 [SMILES: CC(C)=CCC/C(C)=C/Cc1c(O)cc2oc3c(O)ccc(O)c3c(=O)c2c1O] |
| I-119 | 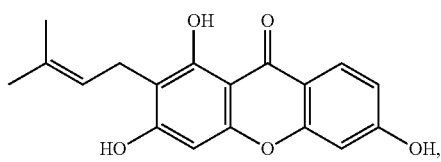 |
| I-120 | 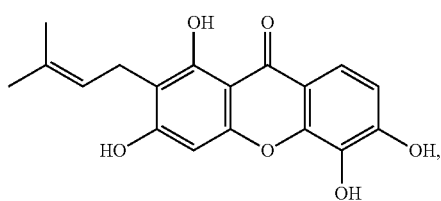 [SMILES: CC(C)=CCc1c(O)cc2oc3c(O)c(O)ccc3c(=O)c2c1O] |
| I-121 | 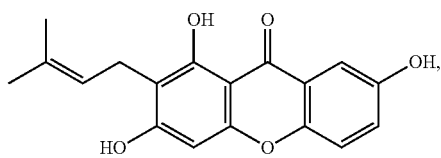 [SMILES: CC(C)=CCc1c(O)cc2oc3ccc(O)cc3c(=O)c2c1O] |
| I-122 | 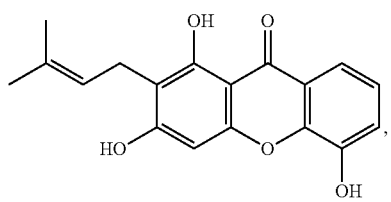 [SMILES: CC(C)=CCc1c(O)cc2oc3c(O)cccc3c(=O)c2c1O] |
| I-123 | 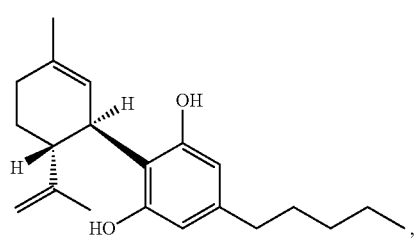 |
| I-124 | 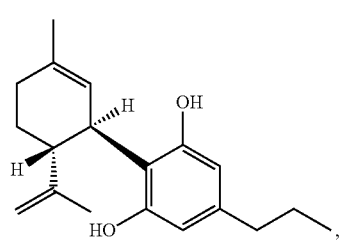 [SMILES: C=C(C)[C@@H]1CCC(C)=C[C@H]1c1c(O)cc(CCC)cc1O] |

| Compound I.D | Structure |
|---|---|
| I-125 | 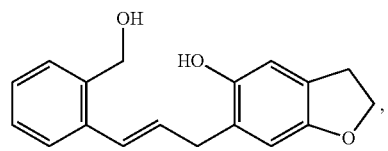 [SMILES: OCc1ccccc1/C=C/Cc1cc2c(cc1O)CCO2] |
| I-126 | 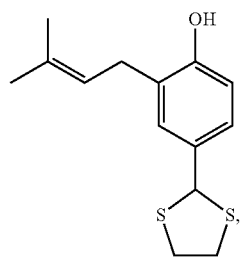 [SMILES: CC(C)=CCc1cc(C2SCCS2)ccc1O] |
| I-127 | 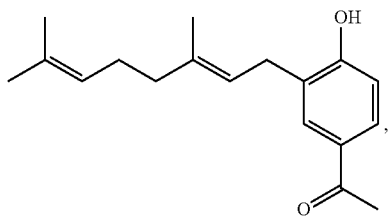 [SMILES: CC(=O)c1ccc(O)c(C/C=C(\C)CCC=C(C)C)c1] |
| I-128 | 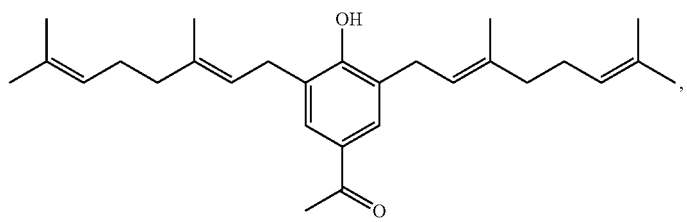 [SMILES: CC(=O)c1cc(C/C=C(\C)CCC=C(C)C)c(O)c(C/C=C(\C)CCC=C(C)C)c1] |
| I-129 | 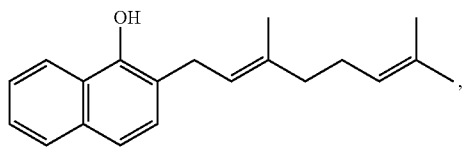 [SMILES: CC(C)=CCC/C(C)=C/Cc1ccc2ccccc2c1O] |
| I-130 | 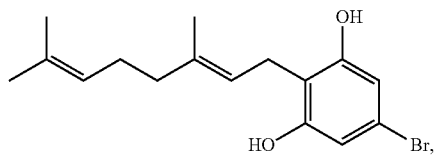 [SMILES: CC(C)=CCC/C(C)=C/Cc1c(O)cc(Br)cc1O] |
| I-131 | 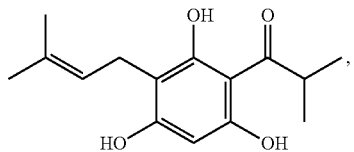 [SMILES: CC(C)=CCc1c(O)cc(O)c(C(=O)C(C)C)c1O] |
| I-132 | 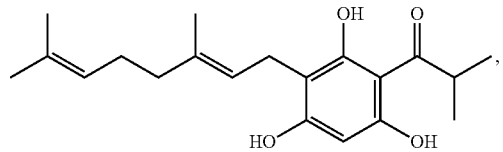 [SMILES: CC(C)=CCC/C(C)=C/Cc1c(O)cc(O)c(C(=O)C(C)C)c1O] |

| Compound I.D | Structure |
|---|---|
| I-133 | 1-(2,4,6-trihydroxy-3-(3-methylbut-2-en-1-yl)phenyl)-2-methylbutan-1-one |
| I-134 | 1-(2,4,6-trihydroxy-3-((2E)-3,7-dimethylocta-2,6-dien-1-yl)phenyl)-2-methylbutan-1-one |
| I-135 | (2,4,6-trihydroxy-3-(3-methylbut-2-en-1-yl)phenyl)(phenyl)methanone |
| I-136 | (2,4,6-trihydroxy-3-((2E)-3,7-dimethylocta-2,6-dien-1-yl)phenyl)(phenyl)methanone |
| I-137 | 1-(2,4,6-trihydroxy-3,5-bis(3-methylbut-2-en-1-yl)phenyl)-2-methylpropan-1-one |
| I-138 | 1-(2,4,6-trihydroxy-3,5-bis(3-methylbut-2-en-1-yl)phenyl)-2-methylbutan-1-one |
| I-139 | (2,4,6-trihydroxy-3,5-bis(3-methylbut-2-en-1-yl)phenyl)(phenyl)methanone |

-continued
| Compound I.D | Structure |
|---|---|
| I-140 | 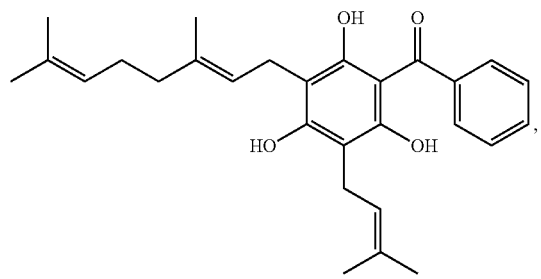 [SMILES: CC(C)=CCC/C(C)=C/Cc1c(O)c(CC=C(C)C)c(O)c(C(=O)c2ccccc2)c1O] |
| I-141 | 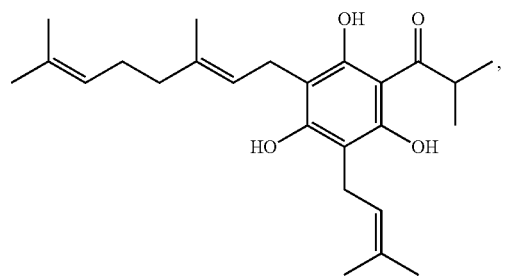 [SMILES: CC(C)=CCC/C(C)=C/Cc1c(O)c(CC=C(C)C)c(O)c(C(=O)C(C)C)c1O] |
| I-142 | 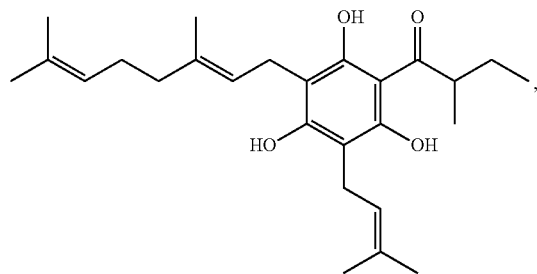 [SMILES: CCC(C)C(=O)c1c(O)c(CC=C(C)C)c(O)c(C/C=C(\C)CCC=C(C)C)c1O] |
| I-143 | 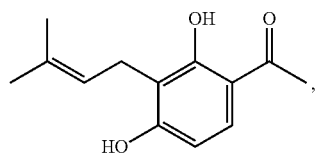 [SMILES: CC(=O)c1ccc(O)c(CC=C(C)C)c1O] |
| I-144 | 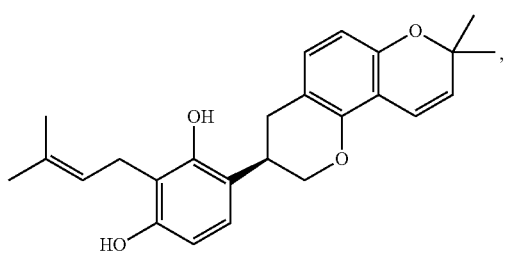 [SMILES: CC(C)=CCc1c(O)ccc([C@@H]2COc3c(ccc4c3C=CC(C)(C)O4)C2)c1O] |
| I-145 | 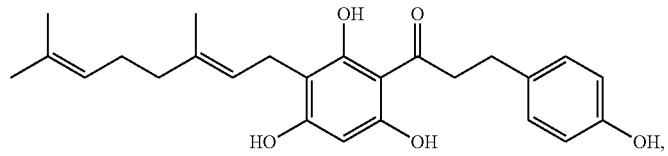 |

-continued
| Compound I.D | Structure |
|---|---|
| I-146 | 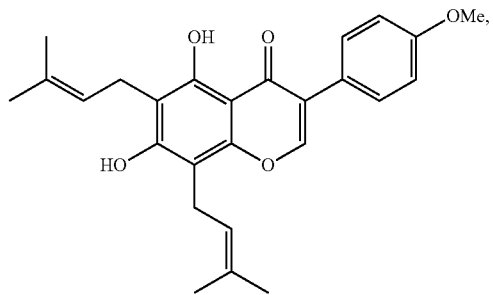 [SMILES: COc1ccc(-c2coc3c(CC=C(C)C)c(O)c(CC=C(C)C)c(O)c3c2=O)cc1] |
| I-147 | 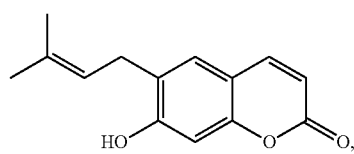 [SMILES: CC(C)=CCc1cc2ccc(=O)oc2cc1O] |
| I-148 | 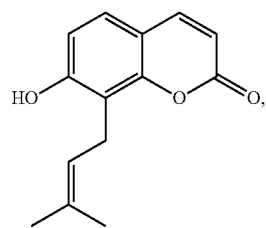 [SMILES: CC(C)=CCc1c(O)ccc2ccc(=O)oc12] |
| I-149 | 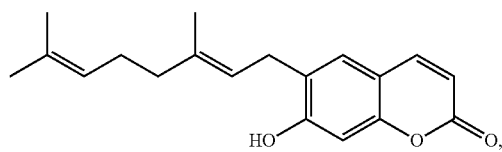 [SMILES: CC(C)=CCC/C(C)=C/Cc1cc2ccc(=O)oc2cc1O] |
| I-150 | 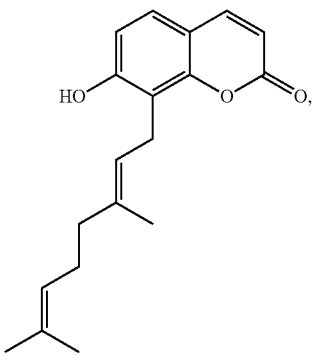 [SMILES: CC(C)=CCC/C(C)=C/Cc1c(O)ccc2ccc(=O)oc12] |
| I-151 | 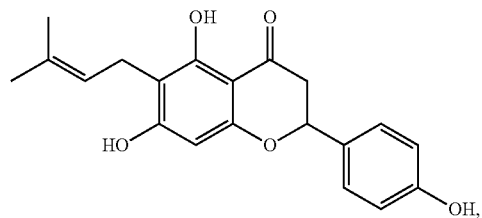 [SMILES: CC(C)=CCc1c(O)cc2c(c1O)C(=O)CC(c1ccc(O)cc1)O2] |

| Compound I.D | Structure |
|---|---|
| I-152 | 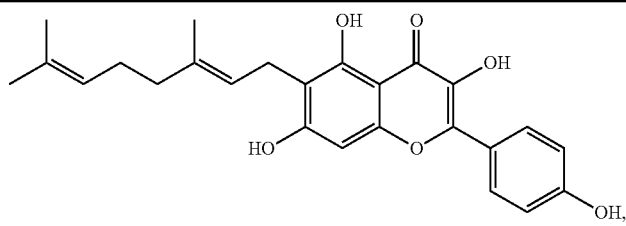 |
| I-153 | 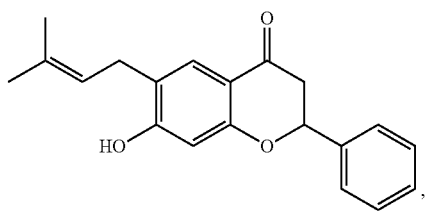 [SMILES: CC(C)=CCc1cc2c(cc1O)OC(c1ccccc1)CC2=O] |
| I-154 | 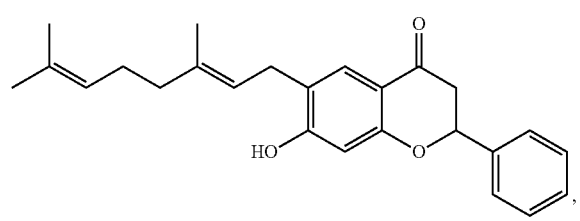 [SMILES: CC(C)=CCC/C(C)=C/Cc1cc2c(cc1O)OC(c1ccccc1)CC2=O] |
| I-155 | 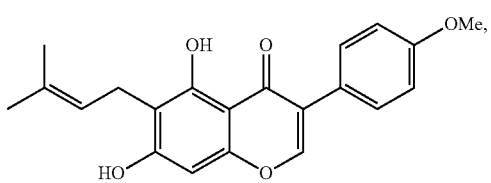 [SMILES: COc1ccc(-c2coc3cc(O)c(CC=C(C)C)c(O)c3c2=O)cc1] |
| I-156 | 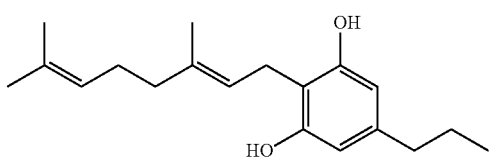 [SMILES: CCCc1cc(O)c(C/C=C(\C)CCC=C(C)C)c(O)c1] |
| I-157 | 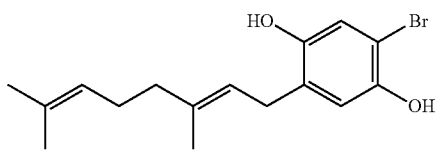 [SMILES: CC(C)=CCC/C(C)=C/Cc1cc(O)c(Br)cc1O] |
| I-158 | 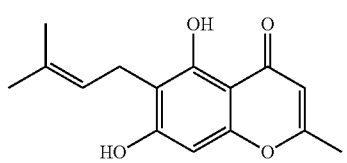 [SMILES: CC(C)=CCc1c(O)cc2oc(C)cc(=O)c2c1O] |
| I-159 | 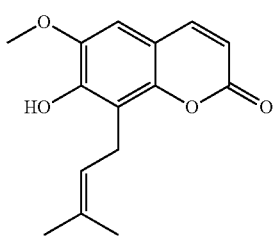 [SMILES: COc1cc2ccc(=O)oc2c(CC=C(C)C)c1O] |

| Compound I.D | Structure |
|---|---|
| I-160 | 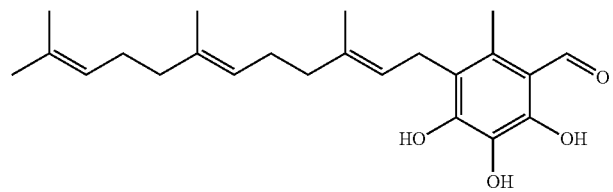 [SMILES: CC(C)=CCC/C(C)=C/CC/C(C)=C/Cc1c(C)c(C=O)c(O)c(O)c1O] |
| I-161 | 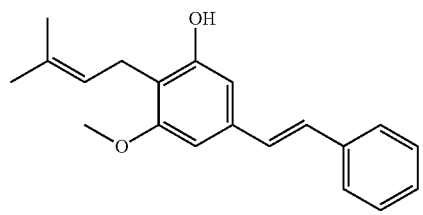 [SMILES: COc1cc(/C=C/c2ccccc2)cc(O)c1CC=C(C)C] |
| I-162 | 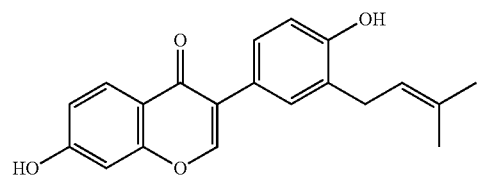 [SMILES: CC(C)=CCc1cc(-c2coc3cc(O)ccc3c2=O)ccc1O] |
| I-163 | 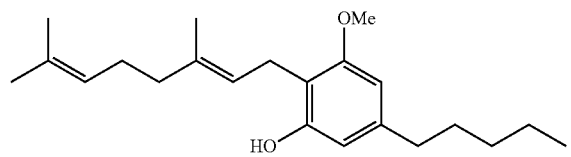 [SMILES: CCCCCc1cc(O)c(C/C=C(\C)CCC=C(C)C)c(OC)c1] |
| I-164 | 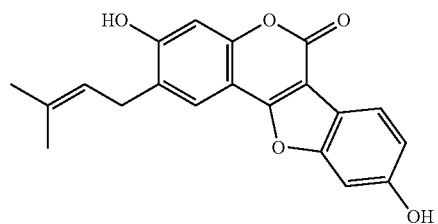 [SMILES: CC(C)=CCc1cc2c(cc1O)oc(=O)c1c3ccc(O)cc3oc21] |
| I-165 | 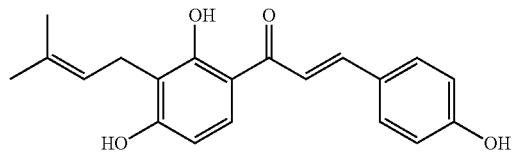 [SMILES: CC(C)=CCc1c(O)ccc(C(=O)/C=C/c2ccc(O)cc2)c1O] |
| I-166 | 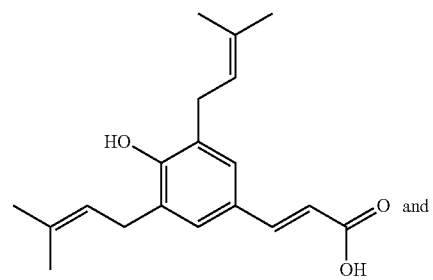 [SMILES: CC(C)=CCc1cc(/C=C/C(=O)O)cc(CC=C(C)C)c1O] and |

| Compound I.D | Structure |
|---|---|
| I-167 | 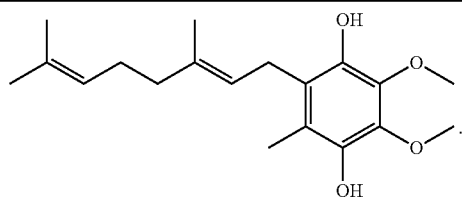 |
In an embodiment, the compound of Formula (I) is naturally occurring compound selected from the compounds I-1 to I-4, I-58 to I-124, I-31 to I-167.
In an embodiment, when n is greater than 1, the compound of Formula (I) is a compound selected from the compounds listed below:
| Compound I.D | Structure |
|---|---|
| I-10 | 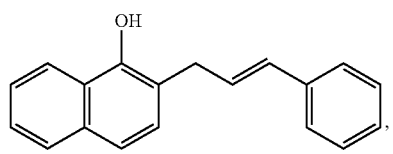 [SMILES: Oc1c(C/C=C/c2ccccc2)ccc2ccccc12] |
| I-11 | 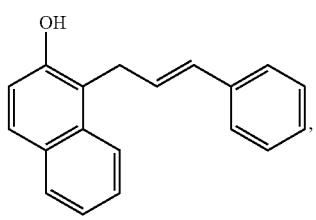 [SMILES: Oc1ccc2ccccc2c1C/C=C/c1ccccc1] |
| I-23 | 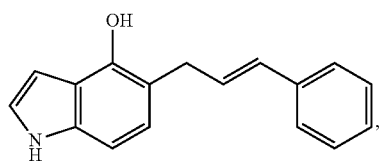 [SMILES: Oc1c(C/C=C/c2ccccc2)ccc2[nH]ccc12] |
| I-24 | 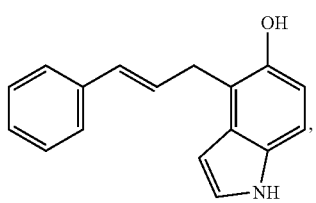 [SMILES: Oc1ccc2[nH]ccc2c1C/C=C/c1ccccc1] |
| I-25 | 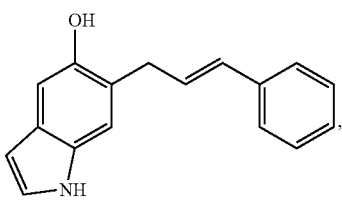 [SMILES: Oc1cc2cc[nH]c2cc1C/C=C/c1ccccc1] |
| I-53 | 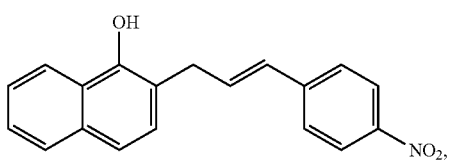 [SMILES: O=[N+]([O-])c1ccc(/C=C/Cc2ccc3ccccc3c2O)cc1] |

| Compound I.D | Structure |
|---|---|
| I-54 | (2-hydroxynaphthalen-1-yl)-CH2-CH=CH-(4-nitrophenyl) |
| I-58 | 2-cinnamyl-3-hydroxy-17β-hydroxy-estra-1,3,5(10)-triene |
| I-59 | 2-cinnamyl-3-hydroxy-17α-ethynyl-17β-hydroxy-estra-1,3,5(10)-triene |
| I-60 | 2-cinnamyl-3-hydroxy-estra-1,3,5(10)-trien-17-one |
| I-61 | 6-geranyl-5,7-dihydroxy-2-(4-hydroxy-3-methoxyphenyl)-4H-chromen-4-one |
| I-62 | 6-prenyl-5,7-dihydroxy-2-(4-hydroxy-3-methoxyphenyl)-4H-chromen-4-one |
| I-63 | 6-prenyl-5,7-dihydroxy-2-(4-hydroxyphenyl)-4H-chromen-4-one |

-continued
| Compound I.D | Structure |
|---|---|
| I-64 | 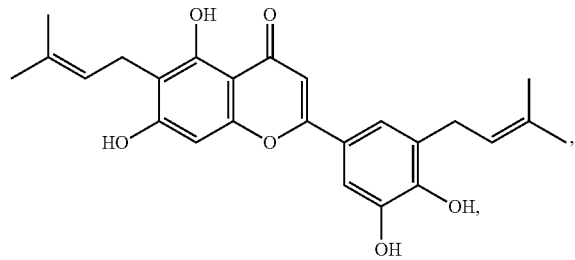 [SMILES: CC(C)=CCc1cc(-c2cc(=O)c3c(O)c(CC=C(C)C)c(O)cc3o2)cc(O)c1O] |
| I-65 | 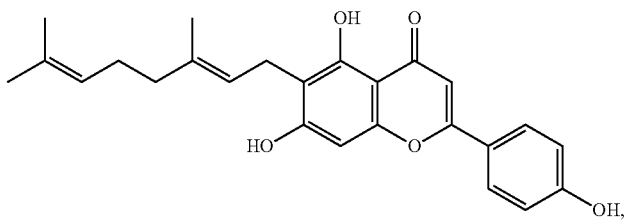 |
| I-66 | 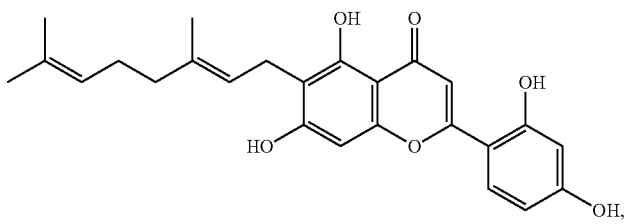 [SMILES: CC(C)=CCC/C(C)=C/Cc1c(O)cc2oc(-c3ccc(O)cc3O)cc(=O)c2c1O] |
| I-67 | 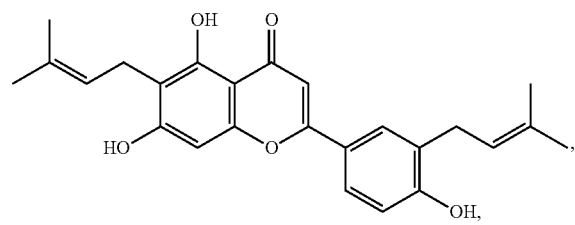 [SMILES: CC(C)=CCc1cc(-c2cc(=O)c3c(O)c(CC=C(C)C)c(O)cc3o2)ccc1O] |
| I-68 | 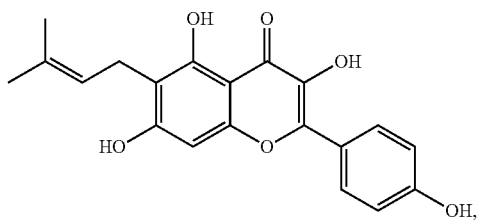 [SMILES: CC(C)=CCc1c(O)cc2oc(-c3ccc(O)cc3)c(O)c(=O)c2c1O] |
| I-69 | 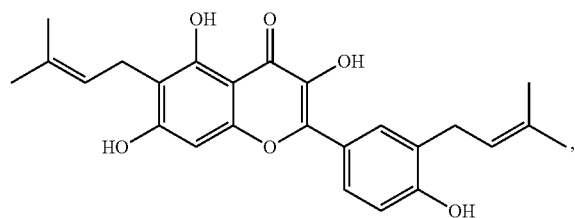 [SMILES: CC(C)=CCc1cc(-c2oc3cc(O)c(CC=C(C)C)c(O)c3c(=O)c2O)ccc1O] |

-continued

| Compound I.D | Structure |
| --- | --- |
| I-70 | 5,7-dihydroxy-3-methoxy-6-prenyl-2-(4-hydroxyphenyl)-4H-chromen-4-one |
| I-71 | 3,5,7-trihydroxy-6-prenyl-2-(3,4-dihydroxyphenyl)-4H-chromen-4-one |
| I-72 | 3,5,7-trihydroxy-6-prenyl-2-(3,4-dihydroxyphenyl)-4H-chromen-4-one |
| I-73 | 5,7-dihydroxy-6-prenyl-3-(4-hydroxyphenyl)-4H-chromen-4-one |
| I-74 | 5,7-dihydroxy-6-prenyl-3-(3,5-diprenyl-4,5-dihydroxyphenyl)-4H-chromen-4-one |
| I-75 | 5,7-dihydroxy-6-prenyl-3-(3-hydroxy-4-methoxyphenyl)-4H-chromen-4-one |
| I-76 | 5,7-dihydroxy-6-prenyl-3-(benzo[d][1,3]dioxol-5-yl)-4H-chromen-4-one |

-continued

| Compound I.D | Structure |
|---|---|
| I-77 | 5,7-dihydroxy-6-prenyl-3-(4-methoxyphenyl)-4H-chromen-4-one |
| I-78 | 5,7-dihydroxy-3-(4-hydroxy-3-prenylphenyl)-6-prenyl-4H-chromen-4-one |
| I-79 | 5,7-dihydroxy-3-(2,4-dihydroxy-3-prenylphenyl)-6-prenyl-4H-chromen-4-one |
| I-80 | 7-hydroxy-3-(2,4-dihydroxy-3-prenylphenyl)-4H-chromen-4-one |
| I-81 | 5,7-dihydroxy-3-(2-hydroxy-4-methoxyphenyl)-6-prenyl-4H-chromen-4-one |
| I-82 | 5,7-dihydroxy-3-(3,4-dihydroxyphenyl)-6-prenyl-4H-chromen-4-one |
| I-83 | 5,7-dihydroxy-3-(8-hydroxy-2,2-dimethyl-2H-chromen-6-yl)-6-prenyl-4H-chromen-4-one |
| I-84 | 5,7-dihydroxy-3-(2,4-dihydroxy-3-prenylphenyl)-6-prenyl-4H-chromen-4-one |

-continued

| Compound I.D | Structure |
|---|---|
| I-85 | 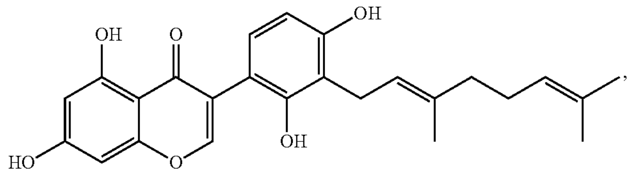 |
| I-93 | 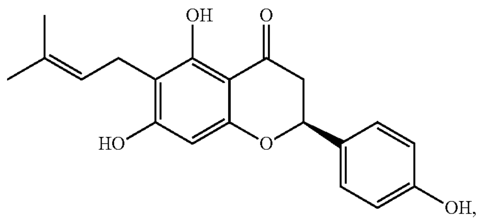 [SMILES: CC(C)=CCc1c(O)cc2c(c1O)C(=O)C[C@@H](c1ccc(O)cc1)O2] |
| I-94 | 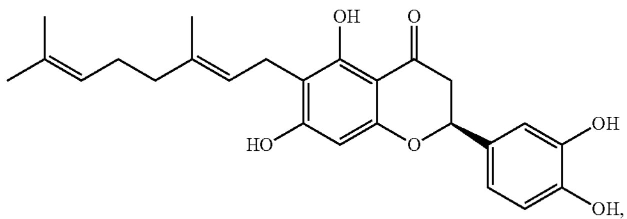 [SMILES: CC(C)=CCC/C(C)=C/Cc1c(O)cc2c(c1O)C(=O)C[C@@H](c1ccc(O)c(O)c1)O2] |
| I-95 | 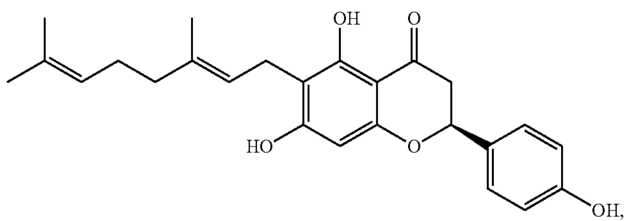 [SMILES: CC(C)=CCC/C(C)=C/Cc1c(O)cc2c(c1O)C(=O)C[C@@H](c1ccc(O)cc1)O2] |
| I-96 | 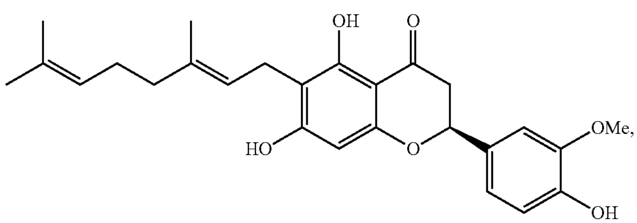 [SMILES: COc1cc([C@@H]2CC(=O)c3c(cc(O)c(C/C=C(\C)CCC=C(C)C)c3O)O2)ccc1O] |
| I-97 | 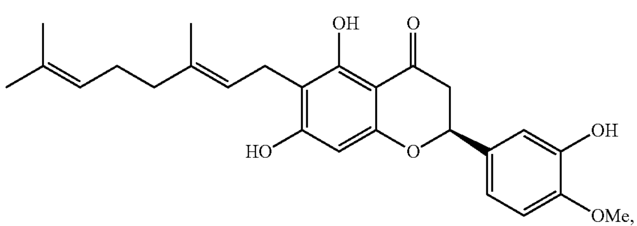 [SMILES: COc1ccc([C@@H]2CC(=O)c3c(cc(O)c(C/C=C(\C)CCC=C(C)C)c3O)O2)cc1O] |
| I-98 | 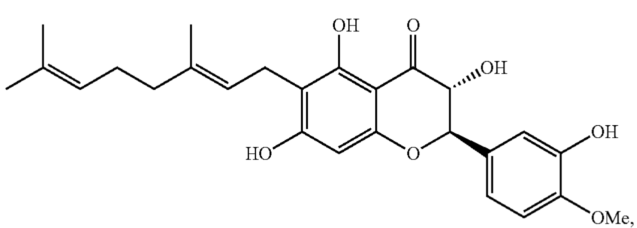 [SMILES: COc1ccc([C@H]2Oc3cc(O)c(C/C=C(\C)CCC=C(C)C)c(O)c3C(=O)[C@@H]2O)cc1O] |

-continued

| Compound I.D | Structure |
| --- | --- |
| I-99 | 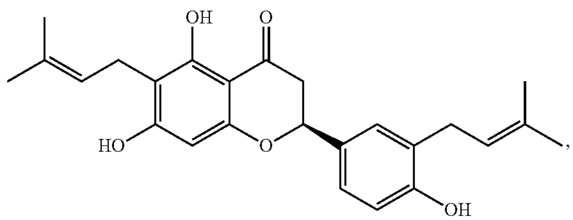 [SMILES: CC(C)=CCc1cc([C@@H]2CC(=O)c3c(cc(O)c(CC=C(C)C)c3O)O2)ccc1O] |
| I-100 | 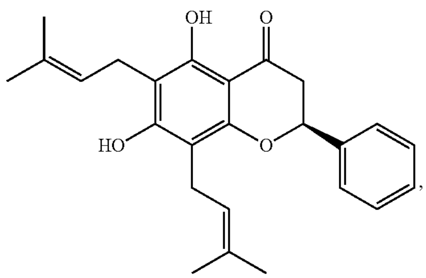 [SMILES: CC(C)=CCc1c(O)c(CC=C(C)C)c2c(c1O)C(=O)C[C@@H](c1ccccc1)O2] |
| I-101 | 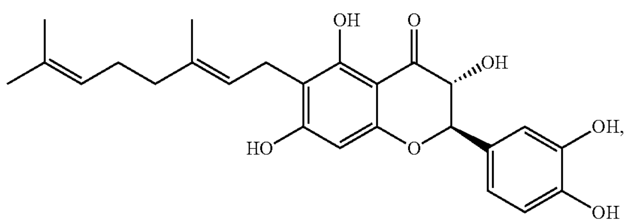 [SMILES: CC(C)=CCC/C(C)=C/Cc1c(O)cc2c(c1O)C(=O)[C@H](O)[C@@H](c1ccc(O)c(O)c1)O2] |
| I-102 | 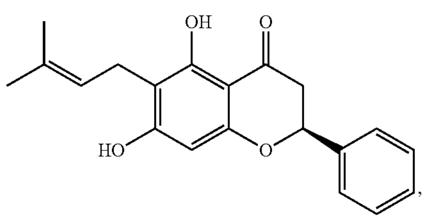 [SMILES: CC(C)=CCc1c(O)cc2c(c1O)C(=O)C[C@@H](c1ccccc1)O2] |
| I-117 | 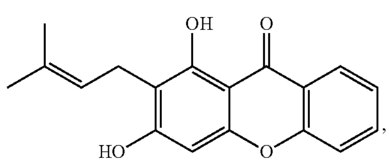 [SMILES: CC(C)=CCc1c(O)cc2oc3ccccc3c(=O)c2c1O] |
| I-118 | 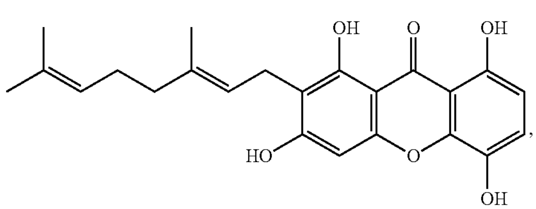 [SMILES: CC(C)=CCC/C(C)=C/Cc1c(O)cc2oc3c(O)ccc(O)c3c(=O)c2c1O] |
| I-119 | 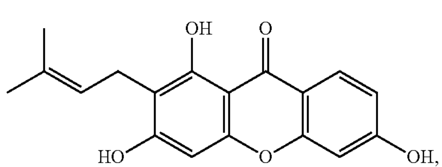 [SMILES: CC(C)=CCc1c(O)cc2oc3cc(O)ccc3c(=O)c2c1O] |

-continued

| Compound I.D | Structure |
|---|---|
| I-120 | a xanthone with 1-OH, 2-prenyl, 3-OH (HO), 5-OH, 6-OH, 8-OH substituents |
| I-121 | a xanthone with 1-OH, 2-prenyl, 3-OH, 7-OH substituents |
| I-122 | a xanthone with 1-OH, 2-prenyl, 3-OH, 8-OH substituents |
| I-129 | 2-geranyl-1-naphthol |
| I-146 | 5-OH, 6-prenyl, 7-OH, 8-prenyl chromone with 3-(4-methoxyphenyl) substituent |
| I-147 | 6-prenyl-7-hydroxycoumarin |
| I-148 | 7-hydroxy-8-prenylcoumarin |
| I-149 | 6-geranyl-7-hydroxycoumarin |

-continued
| Compound I.D | Structure |
|---|---|
| I-150 | 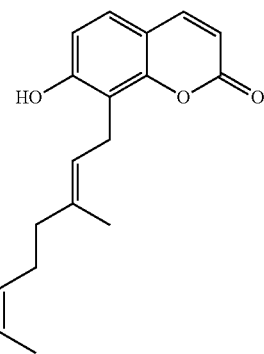 |
| I-151 | 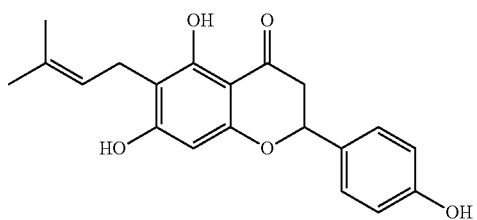 [SMILES: CC(C)=CCc1c(O)cc2c(c1O)C(=O)CC(c1ccc(O)cc1)O2] |
| I-152 | 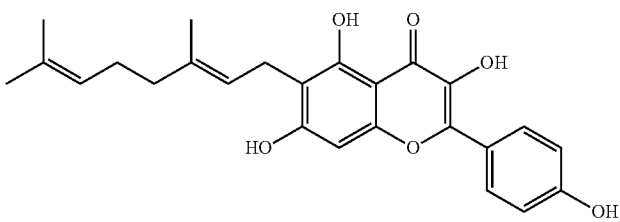 [SMILES: CC(C)=CCC/C(C)=C/Cc1c(O)cc2oc(-c3ccc(O)cc3)c(O)c(=O)c2c1O] |
| I-153 | 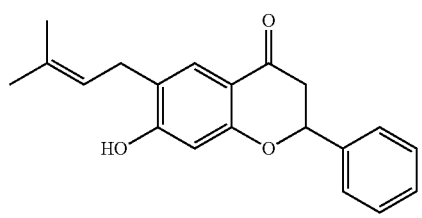 [SMILES: CC(C)=CCc1cc2c(cc1O)OC(c1ccccc1)CC2=O] |
| I-154 | 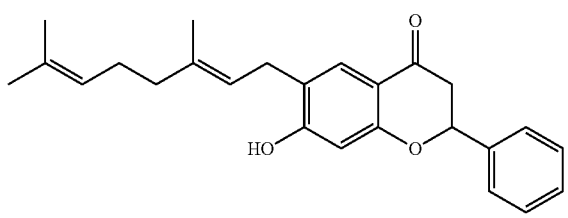 [SMILES: CC(C)=CCC/C(C)=C/Cc1cc2c(cc1O)OC(c1ccccc1)CC2=O] |
| I-155 | 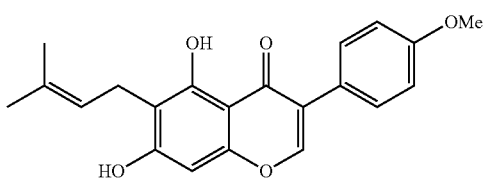 [SMILES: COc1ccc(-c2coc3cc(O)c(CC=C(C)C)c(O)c3c2=O)cc1] |

| Compound I.D | Structure |
|---|---|
| I-159 | 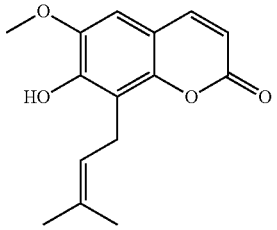 |
| I-162 | 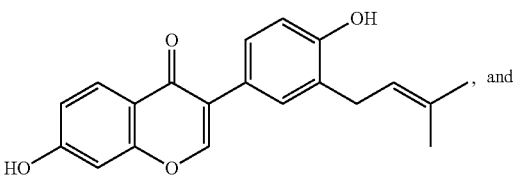 [SMILES: CC(C)=CCc1cc(-c2coc3cc(O)ccc3c2=O)ccc1O], and |
| I-164 | 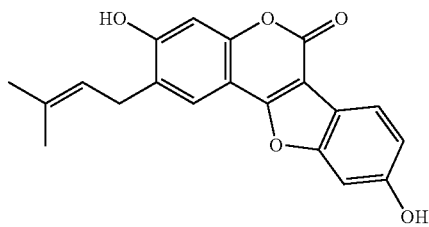 [SMILES: CC(C)=CCc1cc2c(cc1O)oc(=O)c1c3ccc(O)cc3oc21] |

In an embodiment, the forming of the compound of Formula (I) or (I-A) comprise mixing the compound of Formula (II), the compound of Formula (III) and the aluminum compound in the non-protic solvent under continuous flow reaction conditions using for example continuous processors. Continuous flow processors comprise a combination of mixing and conveying means that allow the reactants to flow into or through a mixing means, react to form products and allow the products to flow out of the mixing means for isolation and purification on a continuous basis. In the mixing and conveying means, the reaction conditions (such as temperature and pressure) can be controlled. Such continuous flow processors are well known in the art.

In an embodiment, the forming of the compound of Formula (I) or (I-A) comprise mixing the compound of Formula (II), the compound of Formula (III) and the aluminum compound in the non-protic solvent under batch reaction conditions.

In an embodiment, when forming a mono ortho-allylated compound of Formula I, the forming of the compound of Formula (I) or (I-A) further comprises mixing the compound of Formula (II), the compound of Formula (III) and the aluminum compound in the non-protic solvent with the addition of excess amounts of the compound of Formula (II). In an embodiment, the forming of the compound of Formula (I) or (I-A) comprises mixing the compound of Formula (II), the compound of Formula (III) and the aluminum compound in the non-protic solvent with the addition of, for example, about 1.1 to about 5, about 1.1 to about 4, about 1.1 to about 3, 1.5 to about 4, about 1.5 to about 5, about 2 to about 5, about 2 to about 4, about 3 to about 4, or about 1.5 to about 3 molar equivalents of the hydroxy aryl compound relative to the amount of the allylic alcohol. In an embodiment, the forming of the compound of Formula (I) or (I-A) comprises mixing the compound of Formula (II), the compound of Formula (III) and the aluminum compound in the non-protic solvent with the addition of, for example, about 1 to about 5, about 1 to about 4, about 1 to about 3, or about 1.5 to about 3 molar equivalents the compound of Formula (II) relative to the amount of the compound of Formula (III). In an embodiment, the forming of the compound of Formula (I) or (I-A) comprise mixing the compound of Formula (II), the compound of Formula (III) and the aluminum compound in the non-protic solvent with about 1.5 molar equivalents of the compound of Formula (II) relative to the amount of the compound of Formula (III).

The Applicants have shown that using greater than 1.5 molar equivalents of the compound of Formula (II) relative to the amount of the compound of Formula (III) provides improved yields of the compound of Formula (I) or (I-A). Therefore, in an embodiment, the forming of the compound of Formula (I) or (I-A) further comprise mixing the compound of Formula (II), the compound of Formula (III) and the aluminum compound in the non-protic solvent with 1.5 to about 4, about 1.5 to about 5, about 2 to about 5, about 2 to about 4, or about 3 to about 4 molar equivalents of the compound of Formula (II) relative to the amount of the compound of Formula (III). in an embodiment, the forming of the compound of Formula (I) or (I-A) further comprise mixing the compound of Formula (II), the compound of Formula (III) and the aluminum compound in the non-protic solvent with about 3 to about 4 molar equivalents of the compound of Formula (II) relative to the amount of the compound of Formula (III).

In an embodiment, when forming a mono ortho-allylated hydroxy aryl compound, the forming of the compound of Formula (I) or (I-A) further comprises mixing the compound of Formula (II), the compound of Formula (III) and the aluminum compound in the non-protic solvent with about 1.5 to about 4, about 1.5 to about 5, about 2 to about 5, about 2 to about 4, or about 3 to about 4 molar equivalents of compound of Formula (II) relative to the amount of the compound of Formula (III). In an embodiment, the forming of the compound of Formula (I) or (I-A) further comprises mixing the compound of Formula (II), the compound of Formula (III) and the aluminum compound in the non-protic solvent with about 3 to about 4 molar equivalents of the compound of Formula (II) relative to the amount of the compound of Formula (III).

In an embodiment, when it is desired to add additional allyl groups to the compound of Formula (I) or (I-A) (i.e. a polyallylated hydroxy aryl compound such as a di-, tri- and tetra-allylated hydroxy aryl compounds of Formula I or I-A) the forming of the compound of Formula (I) or (I-A) comprises mixing the compound of Formula (II), the compound of Formula (III) and the aluminum compound in the non-protic solvent with the addition of, for example, about 1.1 to about 5, about 1.1 to about 4, about 1.1 to about 3, 1.5 to about 4, about 1.5 to about 5, about 2 to about 5, about 2 to about 4, about 3 to about 4, or about 1.5 to about 3 molar equivalents the compound of Formula (III) relative to the amount of the compound of Formula (II). In an embodiment, the forming of the compound of Formula (I) or (I-A) comprises mixing the compound of Formula (II), the compound of Formula (III) and the aluminum compound in the non-protic solvent with the addition of, for example, about 3 to about 4, about 3 to about 5, or about 4 to about 5 molar equivalents the compound of Formula (III) relative to the amount of the compound of Formula (II).

In an embodiment, the forming of the compound of Formula (I) or (I-A) further comprise mixing the compound of Formula (II), the compound of Formula (III) and the aluminum compound in the non-protic solvent with the addition of alumina in the amount of about 1 g to about 3 g, about 1.5 g to about 3 g, or about 1.5 g to about 2 g per 1 mmol of the compound of Formula (III). In an embodiment, the forming of the compound of Formula (I) or (I-A) comprise mixing the compound of Formula (II), the compound of Formula (III) and the aluminum compound in the non-protic solvent with the addition of aluminum compound in the amount of about 2 g per 1 mmol of the compound of Formula II).

In an embodiment, the aluminum compound is alumina. In an embodiment, the alumina is acidic alumina. In an embodiment, the acidic alumina, has a pH of less than about 6.5, about 6, about 5.5, about 5.0, about 4.5 or about 4.0. In an embodiment, the alumina, has a pH of less than about 5.5, about 5.0, about 4.5 or about 4.0. In an embodiment, the alumina, has a pH of about 4.5.

In an embodiment, the alumina is basic alumina. In an embodiment, the basic alumina, has a pH of greater than about 7.5, about 8, about 8.5, about 9.0, about 9.5, about 10 or about 10.5. In an embodiment, the basic alumina has a pH of greater than about 9.0, about 9.5, about 10 or about 10.5. In an embodiment, the basic alumina has a pH of about 10.

In an embodiment, the alumina is neutral alumina. In an embodiment, the neutral alumina has a pH of about 7.

In an embodiment, the forming of the compound of Formula (I) or (I-A) further comprise mixing the compound of Formula (II), the compound of Formula (III) and the aluminum compound in the non-protic solvent to form a reaction mixture and heating the reaction mixture In an embodiment, the forming of the compound of Formula (I) or (I-A) comprise mixing the compound of Formula (II), the compound of Formula (III) and the aluminum compound in the non-protic solvent to form a reaction mixture and heating the reaction mixture to the boiling point (refluxing temperature) of the solvent. In an embodiment, the forming of the compound of Formula (I) or (I-A) comprise mixing the compound of Formula (II), the compound of Formula (III) and the aluminum compound in DCE to form a reaction mixture and heating the reaction mixture to about 40° C. to about 83° C., about 60° C. to about 83° C., about 70° C. to about 83° C., or about 83° C.

In an embodiment, the forming of the compound of Formula (I) or (I-A) further comprises mixing the compound of Formula (II), the compound of Formula (III) and the aluminum compound in the non-protic solvent to form a reaction mixture, and heating the reaction mixture for about 4 hours to about 24 hours, about 6 hours to about 24 hours, or about 12 hours to 24 hours.

In an embodiment, the forming of the compound of Formula (I) or (I-A) further comprises mixing the compound of Formula (II), the compound of Formula (III) and the aluminum compound in the non-protic solvent to form a reaction mixture, and heating the reaction mixture at the refluxing temperature of the solvent for about 24 hours.

In an embodiment, the forming of the compound of Formula (I) or (I-A) further comprises mixing the compound of Formula (II), the compound of Formula (III) and the aluminum compound in the non-protic solvent to form a reaction mixture and heating the reaction mixture under microwave synthesis conditions. Therefore, in an embodiment, the forming of the compound of Formula (I) or (I-A) further comprises mixing the compound of Formula (II), the compound of Formula (III) and the aluminum compound in the non-protic solvent to form a reaction mixture and heating the reaction mixture using microwave radiation. In an embodiment, the microwave synthesis conditions comprise heating the reaction mixture in a microwave reactor. In an embodiment, the microwave synthesis conditions comprise heating the reaction mixture in a microwave reactor to about 100° C. to about 175° C., about 125° C. to about 175° C., or about 150° C.

In an embodiment, after heating, the reaction mixture is cooled and filtered through a filter agent, such as Celite® or silica, and the filtrate is concentrated for example, by evapouration such as rotoevapouration, to provide a crude product that comprises the compound of Formula (I) or (I-A). In an embodiment, the crude product is then purified using chromatography such as column chromatography using a suitable solvent or mixture of solvents, or any other known purification method.

In an embodiment, the column chromatography is flash column chromatography. In an embodiment, the suitable mixture of solvents for column chromatography is ethyl acetate and hexane.

In an embodiment, the crude product is purified by crystallization. In an embodiment, the crude product is purified by crystallization without the use of chromatography. In an embodiment, the crude product is crystallized using hexane, hexanes, heptane, heptanes, cyclohexane, toluene, xylene and the like. In an embodiment, the crude product is a crude ortho-allylated cannabinoid and the crude product is crystallized using hexane, hexanes, heptane, heptanes, or cyclohexane. In an embodiment, the crude product is a crude ortho-allylated cannabinoid and the crude product is crystallized with heptane.

In an embodiment, the crude product is purified by distillation. In an embodiment, the crude product is purified by distillation without the use of chromatography. In an embodiment, the crude product is a crude ortho-allylated cannabinoid and the crude product is purified by distillation.

In an embodiment, the process of the application can be performed consecutively such that the compound of Formula (I) or (I-A) formed from a first process of the application is used as the compound of Formula (II) in a subsequent process of the application. Accordingly, in the embodiment, the compound of Formula (II) compound is the compound of Formula (I) formed by a process of the application described above.

In an embodiment, the process provides the compound of Formula (I) or (I-A) as the as the major product of the process. In an embodiment, the process provides the compound of Formula (I) or (I-A) in a yield of greater than about 15%, about 20%, about 25%, about 30%, about 35%, about 40%, about 45%, about 50%, about 55%, about 60%, about 65%, about 70%, about 75%, about 80%, about 85%, about 90% or about 95%. In an embodiment, the process provides the compound of Formula (I) or (I-A) in a yield of greater an about 55%, about 60%, about 65%, about 70%, about 75%, about 80%, about 85%, about 90% or about 95%. In an embodiment, the process provides the compound o Formula (I) or (I-A), in a yield of greater an about 70%, about 75%, about 80%, about 85%, about 90% or about 95%.

The Applicants have shown that the compound of Formula (I) can be formed by reacting the compound of Formula (II) with a compound of Formula (III) in the presence of alumina and further additives including dehydrating reagents such as and magnesium sulfate and/or various acids. Therefore, in an embodiment, the process of the application comprises reacting the compound of Formula (II) with a compound of Formula (III) in the presence of alumina and a dehydrating agent and in a non-protic solvent to form the compound of Formula (I).

Accordingly, the application further includes a process for preparing a compound of Formula (I) comprising:

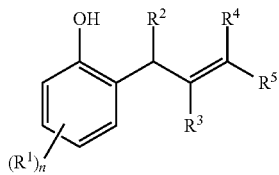
(I)

reacting a compound of Formula (II)

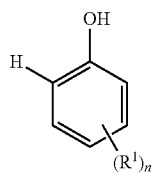
(II)

with a compound of Formula (III)

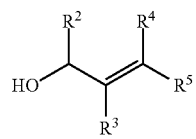
(III)

in the presence of alumina and a dehydrating agent and in a non-protic solvent to form the compound of Formula (I), wherein:
each $R^1$ is independently selected from OH, halo, CN, $NO_2$, COOH, $C_{2-16}$alkenyl, $C_{2-16}$alkynyl, $C_{3-18}$ cycloalkyl, $C_{1-16}$alkylene$C_{3-18}$ cycloalkyl, $C_{2-16}$alkenylene$C_{3-18}$cycloalkyl, $C_{2-16}$alkynylene$C_{3-18}$ cycloalkyl, $C_{3-18}$heterocycloalkyl, $C_{1-16}$alkylene$C_{3-18}$heterocycloalkyl, $C_{1-10}$alkenylene$C_{3-18}$heterocycloalkyl, $C_{2-16}$alkynylene$C_{3-18}$heterocycloalkyl, $C_{6-18}$aryl, $C_{1-16}$alkylene$C_{6-18}$aryl, $C_{2-16}$alkenylene$C_{6-18}$aryl, $C_{2-16}$alkynylene$C_{6-18}$ aryl, $C_{5-18}$heteroaryl, $C_{2-16}$alkylene$C_{5-18}$heteroaryl, $C_{2-16}$alkenylene$C_{5-18}$heteroaryl, $C_{2-16}$alkynylene$C_{5-18}$heteroaryl, Z—$C_{1-16}$alkyl, Z—$C_{2-16}$alkenyl, Z—$C_{2-16}$alkynyl, Z—$C_{5-18}$ cycloalkyl, Z—$C_{1-16}$alkylene$C_{3-18}$cycloalkyl, Z—$C_{2-16}$alkenylene$C_{3-18}$ cycloalkyl, Z—$C_{2-16}$alkynylene$C_{3-18}$ cycloalkyl, Z—$C_{3-18}$heterocycloalkyl, Z—$C_{1-16}$alkylene$C_{3-18}$ heterocycloalkyl, Z—$C_{2-16}$alkenylene$C_{3-18}$heterocycloalkyl, Z—$C_{2-16}$alkynylene $C_{3-18}$ heterocycloalkyl, Z—$C_{6-18}$aryl, Z—$C_{1-16}$alkylene$C_{6-18}$aryl, Z—$C_{2-16}$alkenylene$C_{6-18}$aryl, Z—$C_{2-16}$ alkynylene$C_{6-18}$aryl, Z—$C_{5-18}$heteroaryl, Z—$C_{1-16}$alkylene$C_{5-18}$heteroaryl, Z—$C_{2-16}$alkenylene$C_{5-18}$ heteroaryl, and Z—$C_{2-16}$alkynylene$C_{5-18}$heteroaryl, wherein all alkyl, alkenyl, alkynyl, alkylene, alkenylene, alkynylene, cycloalkyl heterocycloalkyl, aryl, and heteroaryl groups are optionally substituted with one or more substituents selected from OH, halo, $C_{1-16}$alkyl, $C_{2-16}$alkenyl, $C_{2-6}$alkynyl, $OC_{1-16}$alkyl, $OC_{2-16}$alkenyl, and $OC_{2-16}$alkynyl; or when n is greater than 1, two $R^1$ groups are linked together to form a polycyclic ring system having 8 or more atoms together with the phenyl ring to which said groups are bonded, and in which one or more carbon atoms in said polycyclic ring system is optionally replaced with a heteromoiety selected from $NR^6$, O and S, wherein the polycyclic ring system is optionally substituted with one or more substituents selected from =O, OH, halo, $C_{1-16}$alkyl, $C_{2-16}$alkenyl, $C_{2-16}$alkynyl, $OC_{2-16}$alkenyl, $OC_{2-16}$alkynyl, $C(O)C_{1-16}$alkyl, $C(O)$ $C_{2-16}$alkenyl, $C(O)C_{2-16}$alkynyl, $C_{1-16}$alkyleneOR$^8$, $C_{2-16}$alkenyleneOR$^8$, $C_{2-16}$alkynyleneOR$^8$, $C_{6-18}$aryl, $C_{3-18}$ cycloalkyl, $C_{3-18}$heterocycloalkyl, and $C_{3-18}$heteroaryl, the latter 4 groups being optionally substituted with one or more substituents selected from OH, halo, $C_{1-16}$alkyl, $OC_{1-16}$alkyl, and $C_{2-16}$alkenyl;

Z is selected from O, C(O), $CO_2$, S, $SO_2$, SO, and $NR^7$;
$R^2$ is H,
$R^3$ is selected from H and $C_{1-6}$alkyl,
$R^4$ is selected from H, $C_{1-6}$alkyl, $C_{6-18}$aryl, $C_{1-16}$alkylene$C_{6-18}$aryl, $C_{5-18}$ heteroaryl, and $C_{2-16}$alkylene $C_{5-18}$heteroaryl;
$R^5$ is selected from H, $C_{1-26}$alkyl, $C_{2-26}$alkenyl, $C_{2-26}$alkynyl, $C_{3-18}$ cycloalkyl, $C_{1-16}$alkylene$C_{3-18}$ cycloalkyl, $C_{2-16}$alkenylene$C_{3-18}$ cycloalkyl, $C_{2-16}$alkynylene $C_{3-18}$cycloalkyl, $C_{3-18}$ heterocycloalkyl, $C_{1-16}$alkylene$C_{3-18}$ heterocycloalkyl, 16alkenylene$C_{3-18}$ heterocycloalkyl, $C_{2-16}$alkynylene$C_{3-18}$ heterocycloalkyl, $C_{6-18}$aryl, $C_{1-16}$alkylene$C_{6-18}$ aryl, $C_{2-16}$alkenylene $C_{6-18}$aryl, $C_{2-16}$alkynylene$C_{6-18}$aryl, $C_{5-18}$heteroaryl, $C_{2-16}$alkylene$C_{5-18}$heteroaryl, $C_{2-16}$alkenylene$C_{5-18}$ heteroaryl, $C_{2-16}$alkynylene$C_{5-18}$heteroaryl, wherein all cycloalkyl, heterocycloalkyl, aryl and heteroaryl are optionally substituted with one or more substituents selected from OH, $NO_2$, CN, halo, $C_{1-16}$alkyl, $C_{2-16}$alkenyl, $C_{2-16}$alkynyl, $OC_{2-16}$alkenyl, $OC_{2-16}$alkynyl, $C_{1-16}$alkyleneOR$^9$ $C_{2-16}$alkenyleneOR$^9$, $C_{2-16}$alkynyleneOR$^9$, SO$_3$C$_{1-16}$alkyl, SO$_3$C$_{6-16}$aryl, and SO$_3$C$_{5-18}$ heteroaryl substituted with C$_{1-16}$alkyl; or any two of R$^2$, R$^3$, R$^4$ and R$^5$ are linked together to form an unsubstituted or substituted monocyclic or polycyclic ring system having 4 or more atoms together with the carbon atoms to which said any two of R$^2$, R$^3$, R$^4$ and R$^5$ are bonded, wherein the monocyclic or polycyclic ring system is optionally substituted with one or more substituents selected =O, OH, halo, C$_{1-16}$alkyl, C$_{2-16}$alkenyl, C$_{2-16}$alkynyl, OC$_{1-16}$alkyl, OC$_{2-16}$alkenyl, OC$_{2-16}$alkynyl; C$_{1-16}$alkyleneOR$^8$, C$_{2-16}$alkenyleneOR$^8$, C$_{2-16}$alkynyleneOR$^8$, C$_{6-18}$ aryl, C$_{3-18}$ cycloalkyl, C$_{3-18}$ heterocycloalkyl, and C$_{5-18}$heteroaryl, the latter 4 groups being optionally substituted with one or more substituents selected from OH, halo, C$_{1-16}$alkyl, OC$_{1-16}$alkyl, and C$_{2-16}$alkenyl;

R$^6$, R$^7$, R$^8$ and R$^9$ are independently selected from H and C$_{1-6}$alkyl;

n is an integer selected from 0 to 4, and all alkyl, alkenyl, alkynyl, alkylene, alkenylene, alkynylene, cycloalkyl, and heterocycloalkyl groups are optionally fluoro-substituted.

In an embodiment, the compound of Formula (I), compound of Formula (II) and compound of Formula (III) are as defined above.

In an embodiment, the dehydrating agent is selected from magnesium sulfate, sodium sulfate, aluminium phosphate, calcium oxide, cyanuric chloride, orthoformic acid, phosphorus pentoxide, sulfuric acid and molecular sieves, and combinations thereof. In an embodiment, the dehydrating agent is selected from magnesium sulfate, sodium sulfate, aluminium phosphate, calcium oxide, cyanuric chloride, orthoformic acid, phosphorus pentoxide, and molecular sieves, and combinations thereof. In an embodiment, the dehydrating agent is magnesium sulfate.

The Applicants have found that the alumina can be acidic alumina. Therefore, it would be appreciated by a person skilled in the art that acid can be added to the alumina in process of the application. Therefore, in an embodiment, the application also includes a process for preparing the compound of Formula (I) comprising reacting a compound of Formula (II) with a compound of Formula (III) in the presence of alumina and an acid and in a non-protic solvent to form the compound of Formula (I), wherein the compounds of Formula (I), (II) and (III) are as defined above.

In an embodiment the acid is selected from a Lewis acid and a Bronsted acid, and a combination thereof. In an embodiment, the Lewis Acids is selected from boron trichloride, boron trifluoride, boron trifluoride diethyl etherate, iron (III) bromide, iron (III) chloride, aluminum chloride, aluminum bromide, tin (IV) chloride, titanium (IV) chloride, and titanium (IV) isopropoxide and a combination thereof. In an embodiment, the Bronsted acids is selected from hydrochloric acid, sulfuric acid, nitric acid, phosphoric acid, acetic acid, trifluoroacetic acid, toluene sulfonic acid, trichloroacetic acid, boric acid, oleic acid, palmitic acid, and camphor sulfonic acid and a combination thereof.

In an embodiment, the forming of the compound of Formula (I) in the presence of alumina and a further additive such as a dehydrating agent and/or an acid in a non-protic solvent are under conditions as described above for the forming of the compound of Formula (I) in the presence of alumina in a non-protic solvent.

In an embodiment, the compound of Formula (I) is a compound of Formula (I-A) as defined above.

The Applicants have also shown that compound of Formula (I) can be formed by reacting the compound of Formula (II) with a compound of Formula (III) in the presence of an aluminum alkoxide such as aluminum isopropoxide to provide a compound of Formula (I). Therefore, in an embodiment, the aluminum compound is aluminum alkoxide.

Accordingly, the application also includes a process for preparing a compound of Formula (I) comprising:

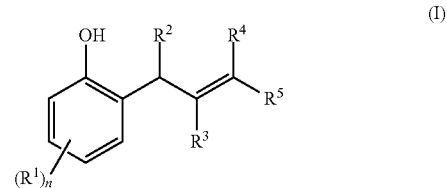

reacting a compound of Formula (II)

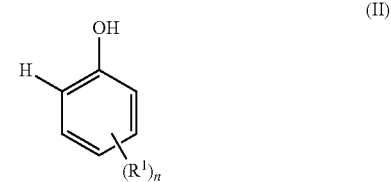

with a compound of Formula (III)

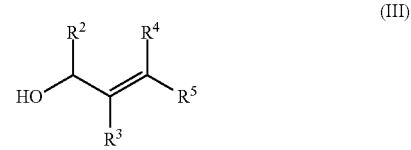

in the presence of an aluminum alkoxide and in a non-protic solvent to form the compound of Formula (I), wherein:

each R$^1$ is independently selected from OH, halo, CN, NO$_2$, COOH, C$_{2-16}$alkenyl, C$_{2-16}$alkynyl, C$_{3-18}$cycloalkyl, C$_{1-16}$alkyleneC$_{3-18}$cycloalkyl, C$_{2-16}$alkenylene C$_{3-18}$cycloalkyl, C$_{2-16}$alkynyleneC$_{3-18}$ cycloalkyl, O$_{3-18}$heterocycloalkyl, C$_{1-16}$alkyleneC$_{3-18}$heterocycloalkyl, C$_{1-10}$alkenyleneC$_{3-18}$heterocycloalkyl, C$_{2-16}$alkynyleneC$_{3-18}$heterocycloalkyl, C$_{6-18}$aryl, C$_{1-16}$alkyleneC$_{6-18}$aryl, C$_{2-16}$alkenyleneC$_{6-18}$ aryl, C$_{2-16}$alkynyleneC$_{6-18}$ aryl, C$_{5-18}$heteroaryl, C$_{2-16}$alkyleneC$_{5-18}$heteroaryl, C$_{2-16}$alkenyleneC$_{5-18}$heteroaryl, C$_{2-16}$alkynyleneC$_{5-18}$heteroaryl, Z—C$_{1-16}$alkyl, Z—C$_{2-16}$alkenyl, Z—C$_{2-16}$alkynyl, Z—C$_{3-18}$cycloalkyl, Z—C$_{1-16}$alkyleneC$_{3-18}$cycloalkyl, Z—C$_{2-16}$alkenyleneC$_{3-18}$ cycloalkyl, Z—C$_{2-16}$alkynyleneC$_{3-18}$ cycloalkyl, Z—C$_{3-18}$ heterocycloalkyl, Z—C$_{1-16}$alkyleneC$_{3-18}$ heterocycloalkyl, Z—C$_{2-16}$alkenyleneC$_{3-18}$heterocycloalkyl, Z—C$_{2-16}$alkynyleneC$_{3-18}$ heterocycloalkyl, Z—C$_{6-18}$ aryl, Z—C$_{1-16}$alkyleneC$_{6-18}$aryl, Z—C$_{2-16}$alkenyleneC$_{6-18}$aryl, Z—C$_{2-16}$alkynyleneC$_{6-18}$aryl, Z—C$_{5-18}$heteroaryl, Z—C$_{1-16}$alkyleneC$_{5-18}$heteroaryl, Z—C$_{2-16}$alkenyleneC$_{5-18}$heteroaryl, and Z—C$_{2-16}$alkynyleneC$_{5-18}$heteroaryl, wherein all alkyl, alkenyl, alkynyl, alkylene, alkenylene, alkynylene, cycloalkyl heterocycloalkyl, aryl, and heteroaryl groups are optionally substituted with one or more substituents selected from OH, halo, $C_{1-16}$alkyl, $C_{2-16}$alkenyl, $C_{2-6}$alkynyl, $OC_{1-16}$alkyl, $OC_{2-16}$alkenyl, and $OC_{2-16}$alkynyl; or when n is greater than 1, two $R^1$ groups are linked together to form a polycyclic ring system having 8 or more atoms together with the phenyl ring to which said groups are bonded, and in which one or more carbon atoms in said polycyclic ring system is optionally replaced with a heteromoiety selected from $NR^6$, O and S, wherein the polycyclic ring system is optionally substituted with one or more substituents selected from =O, OH, halo, $C_{1-16}$alkyl, $C_{2-16}$alkenyl, $C_{2-16}$alkynyl, $OC_{2-16}$alkenyl, $OC_{2-16}$alkynyl, $C(O)C_{1-16}$alkyl, $C(O)C_{2-16}$alkenyl, $C(O)C_{2-16}$alkynyl, $C_{1-16}$alkyleneOR$^8$, $C_{2-16}$alkenyleneOR$^8$, $C_{2-16}$alkynyleneOR$^8$, $O_{6-18}$aryl, $C_{3-18}$cycloalkyl, $C_{3-18}$heterocycloalkyl, and $C_{3-18}$heteroaryl, the latter 4 groups being optionally substituted with one or more substituents selected from OH, halo, $C_{1-16}$alkyl, $OC_{1-16}$alkyl, and $C_{2-16}$alkenyl;

Z is selected from O, C(O), $CO_2$, S, $SO_2$, SO, and $NR^7$;
$R^2$ is H,
$R^3$ is selected from H and $C_{1-6}$alkyl,
$R^4$ is selected from H, $C_{1-6}$alkyl, $C_{6-18}$aryl, $C_{1-16}$alkylene$C_{6-18}$aryl, $C_{5-18}$heteroaryl, and $C_{2-16}$alkylene$C_{5-18}$heteroaryl;
$R^5$ is selected from H, $C_{1-26}$alkyl, $C_{2-26}$alkenyl, $C_{2-26}$alkynyl, $C_{3-18}$ cycloalkyl, $C_{1-16}$alkylene$C_{3-18}$ cycloalkyl, $C_{2-16}$alkenylene$C_{3-18}$ cycloalkyl, $C_{2-16}$alkynylene$C_{3-18}$cycloalkyl, $C_{3-18}$ heterocycloalkyl, $C_{1-16}$alkylene$C_{3-18}$ heterocycloalkyl, $C_{1-16}$alkenylene$C_{3-18}$ heterocycloalkyl, $C_{2-16}$alkynylene$C_{3-18}$ heterocycloalkyl, $C_{6-18}$aryl, $C_{1-16}$alkylene$C_{6-18}$ aryl, $C_{2-16}$alkenylene$C_{6-18}$aryl, $C_{2-16}$alkynylene$C_{6-18}$aryl, $C_{5-18}$heteroaryl, $C_{2-16}$alkylene$C_{5-18}$heteroaryl, $C_{2-16}$alkenylene$C_{5-18}$heteroaryl, $C_{2-16}$alkynylene$C_{5-18}$heteroaryl, wherein all cycloalkyl, heterocycloalkyl, aryl and heteroaryl are optionally substituted with one or more substituents selected from OH, $NO_2$, CN, halo, $C_{1-16}$alkyl, $C_{2-16}$alkenyl, $C_{2-16}$alkynyl, $OC_{1-16}$alkyl, $OC_{2-16}$alkenyl, $OC_{2-16}$alkynyl, $C_{1-16}$alkyleneOR$^9$ $C_{2-16}$alkenyleneOR$^9$, $C_{2-16}$alkynyleneOR$^9$, $SO_3C_{1-16}$alkyl, $SO_3C_{6-16}$aryl, and $SO_3C_{5-18}$ heteroaryl substituted with $C_{1-16}$alkyl; or any two of $R^2$, $R^3$, $R^4$ and $R^5$ are linked together to form an unsubstituted or substituted monocyclic or polycyclic ring system having 4 or more atoms together with the carbon atoms to which said any two of $R^2$, $R^3$, $R^4$ and $R^5$ are bonded, wherein the monocyclic or polycyclic ring system is optionally substituted with one or more substituents selected =O, OH, halo, $C_{1-16}$alkyl, $C_{2-16}$alkenyl, $C_{2-16}$alkynyl, $OC_{1-16}$alkyl, $OC_{2-16}$alkenyl, $OC_{2-16}$alkynyl; $C_{1-16}$alkyleneOR$^8$, $C_{2-16}$alkenyleneOR$^8$, $C_{2-16}$alkynyleneOR$^8$, $C_{6-18}$ aryl, $C_{3-18}$cycloalkyl, $C_{3-18}$heterocycloalkyl, and $C_{5-18}$heteroaryl, the latter 4 groups being optionally substituted with one or more substituents selected from OH, halo, $C_{1-16}$alkyl, $OC_{1-16}$alkyl, and $C_{2-16}$alkenyl;

$R^6$, $R^7$, $R^8$ and $R^9$ are independently selected from H and $C_{1-6}$alkyl;

n is an integer selected from 0 to 4, and all alkyl, alkenyl, alkynyl, alkylene, alkenylene, alkynylene, cycloalkyl, and heterocycloalkyl groups are optionally fluoro-substituted.

In an embodiment, the compound of Formula (I), compound of Formula (II) and compound of Formula (III) are as defined above.

In an embodiment, the forming of the compound of Formula (I) in the presence of aluminum alkoxide in a non-protic solvent are under conditions as described above for the forming of the compound of Formula (I) in the presence of alumina in a non-protic solvent.

In an embodiment, the aluminum alkoxide is an aluminum $C_{1-10}$alkoxide. In an embodiment, the aluminum alkoxide is an aluminum $C_{1-6}$alkoxide. In an embodiment, the aluminum alkoxide is selected from aluminum methoxide, aluminum ethoxide, aluminum-n-propoxide, aluminum iso-propoxide, aluminum-n-butoxide, aluminum-sec-butoxide, aluminum-iso-propoxide and aluminum tert-butoxide. In an embodiment, the aluminum alkoxide is aluminum isopropoxide.

In an embodiment, it would be appreciated by a person skilled in the art that that the aluminum alkoxide can be conjugated to any solid support known in the art.

In an embodiment, compound of Formula (II) and the compound of Formula (III) are both available from commercial sources or can be prepared using methods known in the art.

In an embodiment, it would also be appreciated that the compound of Formula (I) can be formed by reacting the compound of Formula (II) with a compound of Formula (III) in the presence of aluminum alkoxide in combination with further additives including dehydrating reagents such as and magnesium sulfate and/or various acids as described above.

In an embodiment, it would also be appreciated that the compound of Formula (I) can be formed by reacting the compound of Formula (II) with a compound of Formula (III) in the presence of aluminum alkoxide in combination with further additives including dehydrating reagents such as magnesium sulfate and/or various acids as described above.

In an embodiment, the alumina (e.g., neutral, basic and acidic alumina) is available from commercial sources.

In an embodiment, the aluminum alkoxide (e.g. aluminum isopropoxide) is available from commercial sources.

III. Compounds of the Application

The present application also includes novel compounds of Formula (I).

Accordingly, the present application includes compounds of Formula (I) selected from the compounds listed below or a salt, solvate and/or prodrug thereof:

| Compound I.D | Structure |
|---|---|
| I-18 | 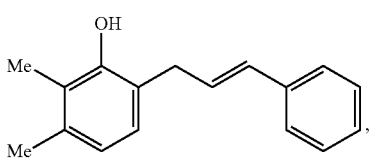 |

-continued
| Compound I.D | Structure |
|---|---|
| I-23 | 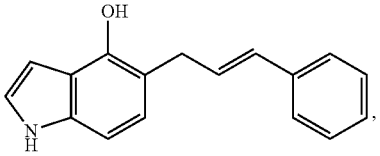 [SMILES: Oc1c(C/C=C/c2ccccc2)ccc2[nH]ccc12] |
| I-24 | 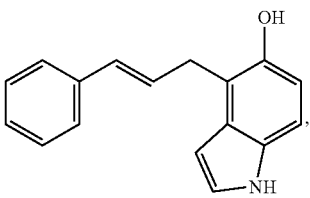 [SMILES: Oc1ccc2[nH]ccc2c1C/C=C/c1ccccc1] |
| I-27 | 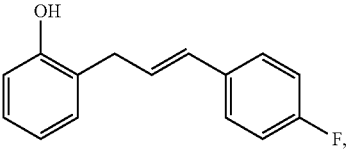 [SMILES: Oc1ccccc1C/C=C/c1ccc(F)cc1] |
| I-34 | 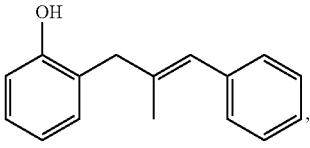 [SMILES: C/C(=C\c1ccccc1)Cc1ccccc1O] |
| I-42 | 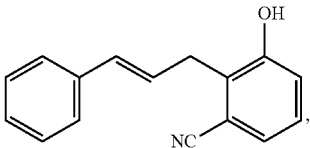 [SMILES: N#Cc1cccc(O)c1C/C=C/c1ccccc1] |
| I-43 | 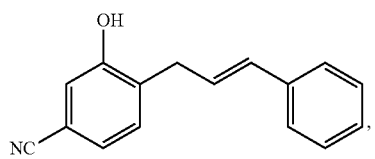 |
| I-45 | 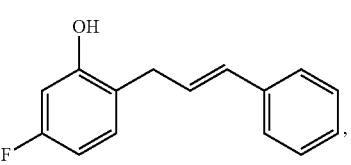 [SMILES: Oc1cc(F)ccc1C/C=C/c1ccccc1] |
| I-47 | 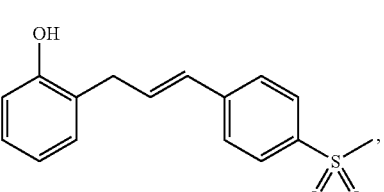 |
| I-48 | 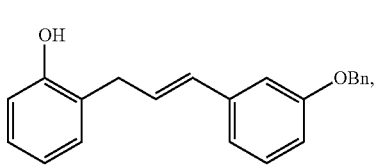 |

| Compound I.D | Structure |
|---|---|
| I-51 | 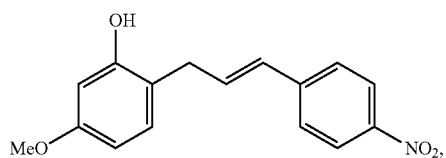 [SMILES: COc1ccc(C/C=C/c2ccc([N+](=O)[O-])cc2)c(O)c1] |
| I-52 | 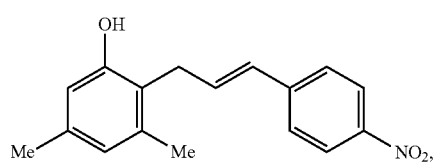 [SMILES: Cc1cc(C)c(C/C=C/c2ccc([N+](=O)[O-])cc2)c(O)c1] |
| I-53 | 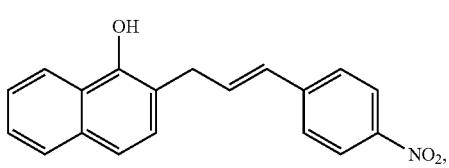 [SMILES: O=[N+]([O-])c1ccc(/C=C/Cc2ccc3ccccc3c2O)cc1] |
| I-55 | 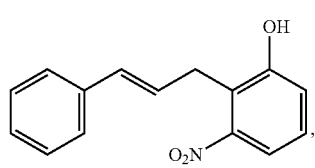 [SMILES: O=[N+]([O-])c1cccc(O)c1C/C=C/c1ccccc1] |
| I-56 | 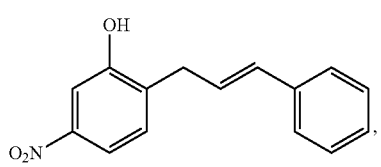 [SMILES: O=[N+]([O-])c1ccc(C/C=C/c2ccccc2)c(O)c1] |
| I-58 | 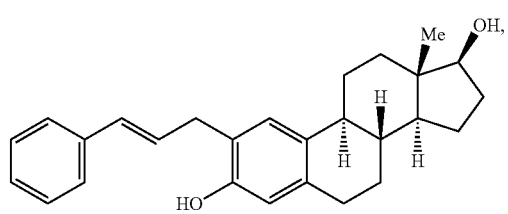 |
| I-59 | 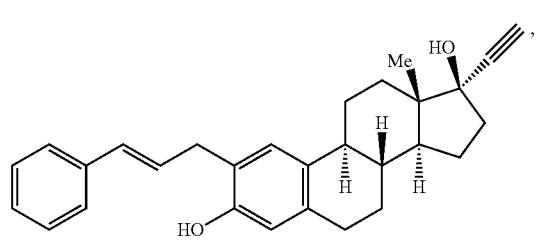 |
| I-60 | 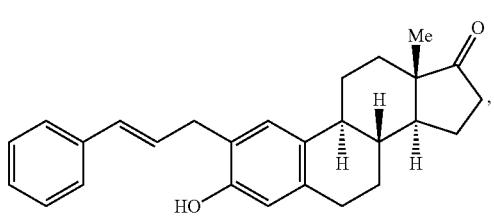 |

| Compound I.D | Structure |
|---|---|
| I-126 | 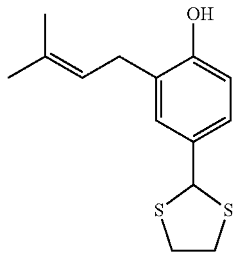 [SMILES: CC(C)=CCc1cc(C2SCCS2)ccc1O] |
| I-127 | 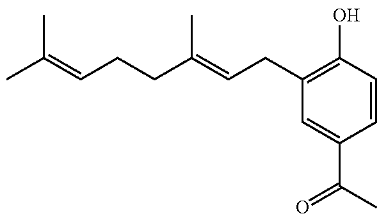 [SMILES: CC(=O)c1ccc(O)c(C/C=C(\C)CCC=C(C)C)c1] |
| I-128 | 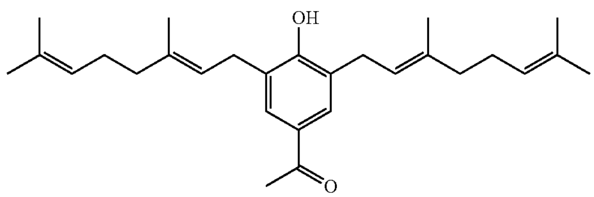 [SMILES: CC(=O)c1cc(C/C=C(\C)CCC=C(C)C)c(O)c(C/C=C(\C)CCC=C(C)C)c1] |
| I-141 | and |
| I-142 | 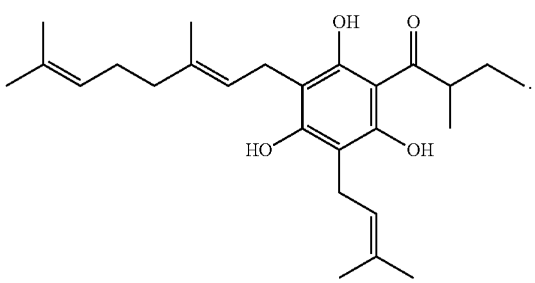 [SMILES: CCC(C)C(=O)c1c(O)c(CC=C(C)C)c(O)c(C/C=C(\C)CCC=C(C)C)c1O] |

In some embodiments, the salt, solvate and/or prodrug of the compound of Formula I is a pharmaceutically acceptable salt, solvate and/or prodrug.

In some embodiments, the pharmaceutically acceptable salt is an acid addition salt or a base addition salt. The selection of a suitable salt may be made by a person skilled in the art. Suitable salts include acid addition salts that may, for example, be formed by mixing a solution of a compound with a solution of a pharmaceutically acceptable acid such as hydrochloric acid, sulfuric acid, acetic acid, trifluoroacetic acid, or benzoic acid. Additionally, acids that are generally considered suitable for the formation of pharmaceutically useful salts from basic pharmaceutical compounds are discussed, for example, by P. Stahl et al, Camille G. (eds.) and Handbook of Pharmaceutical Salts. Properties, Selection and Use. (2002) Zurich: Wiley VCH; S. Berge et al, Journal of Pharmaceutical Sciences 1977 66(1) 1-19; P. Gould, International J. of Pharmaceutics (1986) 33 201-217; Anderson et al, The Practice of Medicinal Chemistry (1996), Academic Press, New York; and in The Orange Book (Food & Drug Administration, Washington, D.C. on their website).

An acid addition salt suitable for, or compatible with, the treatment of subjects is any non-toxic organic or inorganic acid addition salt of any basic compound. Basic compounds that form an acid addition salt include, for example, compounds comprising an amine group. Illustrative inorganic acids which form suitable salts include hydrochloric, hydrobromic, sulfuric, nitric and phosphoric acids, as well as acidic metal salts such as sodium monohydrogen orthophosphate and potassium hydrogen sulfate. Illustrative organic acids which form suitable salts include mono-, di- and tricarboxylic acids. Illustrative of such organic acids are, for example, acetic, trifluoroacetic, propionic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, mandelic, salicylic, 2-phenoxybenzoic, p-toluenesulfonic acid and other sulfonic acids such as methanesulfonic acid, ethanesulfonic acid and 2-hydroxyethanesulfonic acid. In some embodiments, exemplary acid addition salts also include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates ("mesylates"), naphthalenesulfonates, nitrates, oxalates, phosphates, propionates, salicylates, succinates, sulfates, tartarates, thiocyanates, toluenesulfonates (also known as tosylates) and the like. In some embodiments, the mono- or di-acid salts are formed and such salts exist in either a hydrated, solvated or substantially anhydrous form. In general, acid addition salts are more soluble in water and various protic organic solvents and generally demonstrate higher melting points in comparison to their free base forms. The selection criteria for the appropriate salt will be known to one skilled in the art. Other non-pharmaceutically acceptable salts such as but not limited to oxalates may be used, for example in the isolation of compounds of the application for laboratory use, or for subsequent conversion to a pharmaceutically acceptable acid addition salt.

A base addition salt suitable for, or compatible with, the treatment of subjects is any non-toxic organic or inorganic base addition salt of any acidic compound. Acidic compounds that form a basic addition salt include, for example, compounds comprising a carboxylic acid group. Illustrative inorganic bases which form suitable salts include lithium, sodium, potassium, calcium, magnesium or barium hydroxide as well as ammonia. Illustrative organic bases which form suitable salts include aliphatic, alicyclic or aromatic organic amines such as isopropylamine, methylamine, trimethylamine, picoline, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Exemplary organic bases are isopropylamine, diethylamine, ethanolamine, trimethylamine, dicyclohexylamine, choline and caffeine. The selection of the appropriate salt may be useful, for example, so that an ester functionality, if any, elsewhere in a compound is not hydrolyzed. The selection criteria for the appropriate salt will be known to one skilled in the art. In some embodiments, exemplary basic salts also include ammonium salts, alkali metal salts such as sodium, lithium and potassium salts, alkaline earth metal salts such as calcium and magnesium salts, salts with organic bases (for example, organic amines) such as dicyclohexylamine, Abutyl amine, choline and salts with amino acids such as arginine, lysine and the like. Basic nitrogen containing groups may be quaternized with agents such as lower alkyl halides (e.g., methyl, ethyl and butyl chlorides, bromides and iodides), dialkyl sulfates (e.g., dimethyl, diethyl and dibutyl sulfates), long chain halides (e.g., decyl, lauryl and stearyl chlorides, bromides and iodides), aralkyl halides (e.g., benzyl and phenethyl bromides) and others. Compounds carrying an acidic moiety can be mixed with suitable pharmaceutically acceptable salts to provide, for example, alkali metal salts (e.g., sodium or potassium salts), alkaline earth metal salts (e.g., calcium or magnesium salts) and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

All such acid salts and base salts are intended to be pharmaceutically acceptable salts within the scope of the application and all acid and base salts are considered equivalent to the free forms of the corresponding compounds for purposes of the application. In addition, when a compound of the application contains both a basic moiety, such as, but not limited to an aliphatic primary, secondary, tertiary or cyclic amine, an aromatic or heteroaryl amine, pyridine or imidazole and an acidic moiety, such as, but not limited to tetrazole or carboxylic acid, zwitterions ("inner salts") may be formed and are included within the terms "salt(s)" as used herein. It is understood that certain compounds of the application may exist in zwitterionic form, having both anionic and cationic centers within the same compound and a net neutral charge. Such zwitterions are included within the application.

Solvates of compounds of the application include, for example, those made with solvents that are pharmaceutically acceptable. Examples of such solvents include water (resulting solvate is called a hydrate) and ethanol and the like. Suitable solvents are physiologically tolerable at the dosage administered.

EXAMPLES

The following non-limiting examples are illustrative of the present application.

Example 1

General Experimental Procedures

Alumina was purchased from Millipore Sigma (activated, acidic, Brockmann I, catalogue #199966; activated neutral, Brockmann I, catalogue #199974; activated, basic, Brockmann I, catalogue #199443). Substrates were purchased from AKScientific and used as obtained. Solvents were purchased from Fisher Scientific, reagent grade, and used without further purification.

$^1$H NMR spectra were acquired at 700 MHz with a default digital resolution (Bruker parameter: FIDRES) of 0.15 Hz/point. Coupling constants reported herein therefore have uncertainties of ±0.30 Hz. Chemical shifts in $^1$H NMR and $^{13}$C NMR spectra are reported in parts per million (ppm) with reference to residual chloroform ($\delta_H$ 7.26) and deuterated chloroform ($\delta_C$ 77.16). Peak multiplicities are reported using the following abbreviations: s, singlet; d, doublet; t, triplet; q, quartet; dd, doublet of doublets; m, multiplet. Reaction progress was monitored by thin layer chromatography (TLC, EMD Chemicals, Inc., silica gel 60 F254). TLC plates were developed via capillary action in hexane-ethyl acetate solvent mixtures then visualized under UV light followed by p-anisaldehyde stain. An automated flash chromatography system (Teledyne CombiFlash $R_f$ 200) was used for the purification of compounds on silica gel (either 40-60 μM particle size).

Cannabigerol (CBG, I-1)

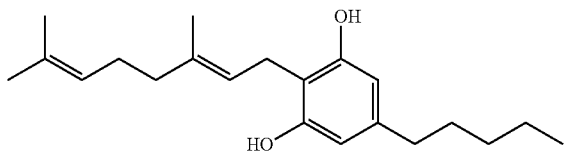 [SMILES: CCCCCc1cc(O)c(C/C=C(\C)CCC=C(C)C)c(O)c1]

To a solution of geraniol (173.5 µL, 1.0 mmol) and olivetol (270.4 mg, 1.5 mmol) in DCE (5 mL) was added alumina (2.0 g). The heterogenous mixture was stirred at reflux temperature for 6 hours then cooled to ambient temperature and filtered through a Celite® plug. The filter cake was rinsed with ethyl acetate (3×10 mL portions) and the filtrate was concentrated in vacuo to afford a yellow oil. This residue was purified via chromatography using a silica gel eluted with hexane and ethyl acetate. Product rich fractions were pooled and evaporated to afford I-1 (162 mg, 62%) as a yellow oil. $R_f$=0.49 (ethyl acetate/hexane 30:70). $^1$H NMR (700 MHz, CDCl$_3$): δ 6.25 (2H, s), 5.27 (1H, td, J=7.1, 1.0 Hz,), 5.05 (3H, m), 3.39 (2H, d, J=7.1 Hz,), 2.46 (2H, t, J=7.8 Hz,), 2.11 (2H, q, J=7.4 Hz), 2.06 (2H, d, J=7.4 Hz), 1.81 (3H, s), 1.68 (3H, s), 1.60 (3H, s), 1.56 (2H, q, J=7.2 Hz), 1.36-1.28 (4H, m), 0.89 (3H, t, J=6.9 Hz). DEPTQ $^{13}$C NMR (176 MHz, CDCl$_3$): δ 154.9 (C), 142.9 (C), 139.1 (C), 132.2 (C), 123.9 (CH), 121.8 (CH), 110.7 (C), 108.5 (CH), 39.8 (CH$_2$), 35.7 (CH$_2$), 31.6 (CH$_2$), 30.9 (CH$_2$), 26.5 (CH$_2$), 25.8 (CH$_3$), 22.7 (CH$_2$), 22.4 (CH$_2$), 17.8 (CH$_3$), 16.3 (CH$_3$), 14.2 (CH$_3$).

Grifolin, (E)-2-(3,7-dimethylocta-2,6-dien-1-yl)-5-methylbenzene-1,3-diol (I-2)

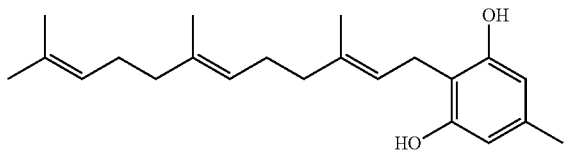 [SMILES: CC(C)=CCC/C(C)=C/CC/C(C)=C/Cc1c(O)cc(C)cc1O]

To a solution of farnesol (251 µL, 1.0 mmol) and orcinol (372 mg, 3.0 mmol) in DCE (5 mL) was added acidic alumina (2.0 g). The heterogeneous mixture was stirred at reflux temperature for 7 hours then cooled to ambient temperature and filtered through a Celite® plug. The filter cake was rinsed with ethyl acetate (3×10 mL portions) and the filtrate was concentrated in vacuo to afford a yellow oil. This residue was purified via chromatography using a silica gel eluted with hexane and ethyl acetate. Product rich fractions were pooled and evaporated to afford I-2 (121 mg, 37%) as a yellow oil. $R_f$=0.57 (EtOAc/Hex 25:75). $^1$H NMR (700 MHz, CDCl$_3$): δ 6.25 (2H, s), 5.48 (2H, s), 5.29 (1H, t, J=7.0 Hz), 5.12 (2H, q, J=7.1 Hz), 3.42 (2H, d, J=7.1 Hz), 2.21 (3H, s), 2.10 (2H, q, J=6.9 Hz), 2.09-2.07 (4H, m), 2.01-1.99 (2H, m), 1.83 (3H, s), 1.70 (3H, s), 1.63 (3H, s), 1.61 (3H, s). DEPTQ $^{13}$C NMR (176 MHz, CDCl$_3$) δ 154.9 (C), 138.9 (C), 137.5 (C), 135.7 (C), 131.4 (C), 124.5 (CH), 123.7 (CH), 121.9 (CH), 110.7 (C), 109.2 (CH), 39.8 (CH$_2$), 39.8 (CH$_2$), 26.8 (CH$_2$), 26.5 (CH$_2$), 25.8 (CH$_3$), 22.3 (CH$_2$), 21.1 (CH$_3$), 17.8 (CH$_3$), 16.3 (CH$_3$), 16.1 (CH$_3$).

Cannabigerorcin, E)-2-(3,7-dimethylocta-2,6-dien-1-yl)-5-methylbenzene-1,3-diol (I-3)

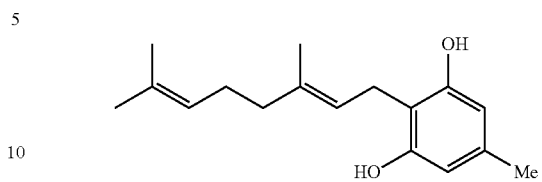

To a solution of geraniol (838 µL, 4.0 mmol) and orcinol (617 mg, 6.0 mmol) in DCE was added acidic alumina (2.0 g). The heterogenous mixture was stirred at reflux temperature for 24 hours then cooled to ambient temperature and filtered through a Celite® plug. The filter cake was rinsed with ethyl acetate (3×15 mL portions) and the filtrate was concentrated in vacuo to afford a yellow oil. This residue was purified via chromatography using a silica gel eluted with hexane and ethyl acetate. Product rich fractions were pooled and evaporated to afford I-3 (492 mg, 47%) as a yellow oil. $R_f$=0.41 (ethyl acetate/hexane 25:75). δ $^1$H NMR (700 MHz, CDCl$_3$) δ 6.24 (2H, s), 5.28-5.26 (1H, m), 5.07 (2H, s), 5.05 (1H, d, J=6.9 Hz), 3.39 (2H, d, J=7.1 Hz), 2.21 (3H, s), 2.10 (2H, dd, J=7.3, 6.9 Hz), 2.06 (2H, dd, J=8.7, 6.3 Hz), 1.81 (3H, s), 1.68 (4H, s), 1.59 (3H, s). DEPTQ $^{13}$C NMR (175 MHz, CDCl$_3$): δ 154.8 (C), 139.0 (C), 137.6 (C), 132.1 (C), 123.8 (CH), 121.7 (CH), 110.5 (C), 109.1 (CH), 39.7 (CH$_2$), 26.4 (CH$_2$), 25.7 (CH$_3$), 22.2 (CH$_2$), 21.1 (CH$_3$), 17.7 (CH$_3$), 16.2 (CH$_3$).

Piperogalin, (E)-2-(3,7-dimethylocta-2,6-dien-1-yl)-5-methyl-4-(3-methylbut-2-en-1-yl)benzene-1,3-diol (I-4)

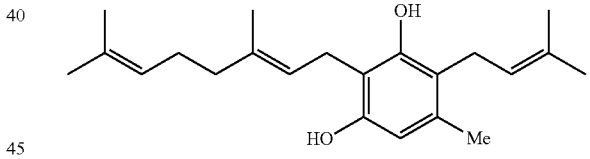

To a solution of cannabigerorcin (78 mg, 0.3 mmol) and 3-methylbut-2-en-1-ol (20.3 µL, 0.2 mmol) in heptanes (3.0 mL) was added acidic alumina (300 mg). The reaction was heated to 80° C. for 14 hours then cooled to ambient temperature and filtered through a Celite® pad. The filter cake was rinsed with ethyl acetate (3×10 mL) and the filtrate was concentrated in vacuo to afford a yellow oil. This residue was purified via chromatography using a silica gel eluted with hexane and ethyl acetate. Product rich fractions were pooled and evaporated to afford I-4 (37.5 mg, 57%) as a yellow oil. $R_f$=0.46 (EtOAc/Hex 1:6). $^1$H NMR (700 MHz, CDCl$_3$): δ 6.27 (1H, s), 5.38 (1H, s), 5.25 (1H, t, J=7.0 Hz), 5.14 (1H, t, J=6.4 Hz), 5.06 (1H, t, J=6.4 Hz), 4.90 (1H, s), 3.40 (2H, d, J=7.0 Hz), 3.29 (2H, d, J=7.0 Hz), 2.21 (3H, s,), 2.11 (2H, q, J=7.5 Hz), 2.07-2.04 (2H, m), 1.81 (3H, s), 1.80 (3H, s), 1.73 (3H, s), 1.68 (3H, s), 1.59 (3H, s). DEPTQ $^{13}$C NMR (176 MHz, CDCl$_3$): δ 153.6 (C), 152.8 (C), 138.8 (C), 135.4 (C), 133.7 (C), 132.1 (C), 124.0 (CH), 122.6 (CH), 122.1 (CH), 118.2 (C), 111.5 (C), 109.9 (CH), 39.8 (CH$_2$), 26.5 (CH$_2$), 25.9 (CH$_3$), 25.8 (CH$_3$), 25.7 (CH$_3$), 22.7 (CH$_2$), 20.0 (CH$_3$), 18.0 (CH$_3$), 17.8 (CH$_3$), 16.3 (CH$_3$).

Results and Discussion

Two syntheses of an exemplary compound of Formula (I), cannabigerol (CBG) (I-1), are reported in the literature, both proceeding via C-alkylation of an exemplary compound of Formula (II), olivetol (II-1) with an exemplary compound of Formula (III), geraniol (III-1) (Scheme 1). In 1995, Baek and co-workers treated these two substrates with boron trifluoride etherate on silica in dichloromethane to afford cannabigerol in 29% yield (Scheme 1).[18] One year later, Morimoto and co-workers reported the use of p-toluene-sulfonic acid in chloroform to obtain cannabigerol from the same two substrates in 40% yield,[19] following a similar procedure to that described in 1969 by Mechoulam and Yagen.[29] (Table 1).

Scheme 1. General synthetic scheme for the Syntheses of exemplary compound of Formula (I), CBG (I-1).

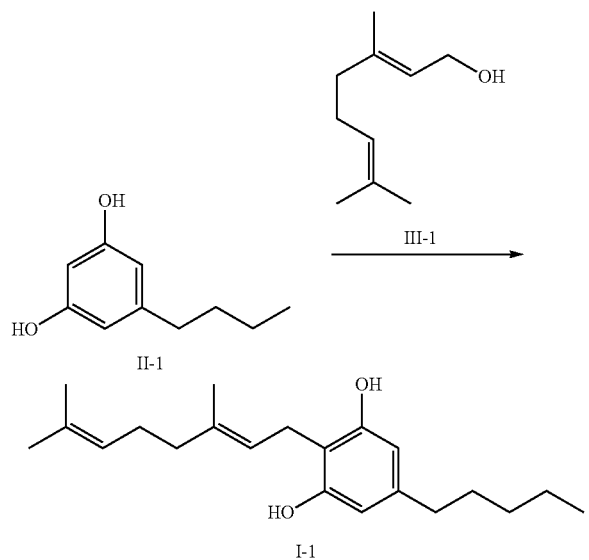

TABLE 1

| | Conditions | Reported Yield |
| --- | --- | --- |
| Baek, 1995[18] | BF$_3$•EtO$_2$, SiO$_2$, CH$_2$Cl$_2$, r.t., | 29% |
| Morimoto, 1996 [19] | TSOH, CH$_3$Cl, r.t., | 40% |

The pairing of acidic alumina with non-protic solvents like hexane or 1,2-dichloroethane (DCE) as useful conditions for promoting an indole alkylation reaction was recently identified.[21] When analogous conditions were applied to the reaction of exemplary compound of Formula (II), olivetol (II-1), with III-1 a relatively selective and clean formation of I-1 in 34% yield (Table 2, entry 1) was surprisingly observed. The only other observable product was di-geranylated compound A, in 11% yield. A preliminary optimization study of this process (scheme 2) is summarized in Table 2. It was found that acidic alumina was better to basic and neutral aluminas (entries I-3) and that (1,2-dichloroethane) DCE was a suitable solvent (entries 6-10). Under these conditions (e.g., acidic alumina and DCE solvent) byproduct A was formed in 10% NMR yield and easily removed using silica chromatography. Ultimately, CBG (I-1) was obtained 62% isolated yield under the following conditions (entry 8): excess I-1 (1.5 equiv.) in DCE at reflux temperature (83° C.) for 6 hours in the presence of acidic alumina (2 g/mmol with respect to III-1).

To the best of the Applicant's knowledge, this constitutes the most efficient synthesis of this natural product reported to date. Notably, cannabigerol (CBG, I-1) is of industrial significance as a substrate for a bioenzymatic synthesis of tetrahydrocannabinol (THC).[22]

Scheme 2

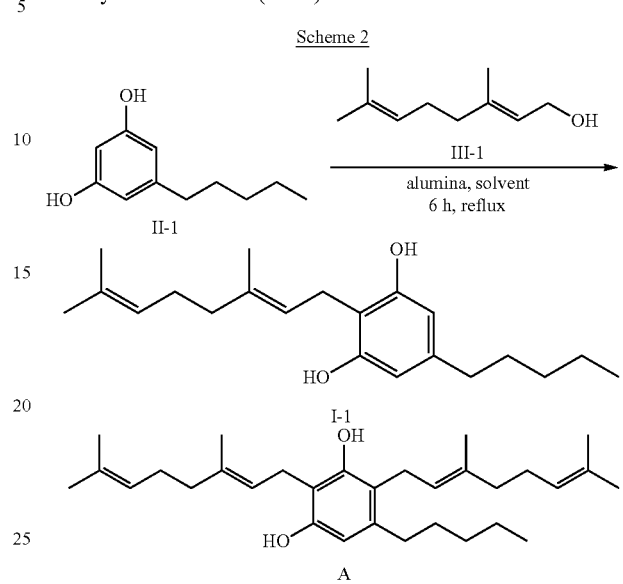

TABLE 2

Optimization study of alumina-promoted CBG synthesis

| | Alumina | | | II-1 | III-1 | I-1 | A |
| --- | --- | --- | --- | --- | --- | --- | --- |
| Entry | Type | Amt (g) | Solvent | (mmol) | (mmol) | (%)$^a$ | (%)$^a$ |
| 1 | Acidic | 2 | Hexane | 1 | 1 | 34 | 11 |
| 2 | Neutral | 2 | Hexane | 1 | 1 | 12 | 2 |
| 3 | Basic | 2 | Hexane | 1 | 1 | 4 | 1 |
| 4 | Acidic | 2 | Hexane | 1 | 1.5 | 39 | 13 |
| 5 | Acidic | 2 | Hexane | 1.5 | 1 | 53 | 12 |
| 6 | Acidic | 1 | Hexane | 1.5 | 1 | 22 | 13 |
| 7 | Acidic | 2 | Heptanes | 1.5 | 1 | 15 | 13 |
| 8 | Acidic | 2 | DCE | 1.5 | 1 | 67 (62$^b$) | 10 |
| 9 | Acidic | 2 | CH$_3$CN | 1.5 | 1 | 9 | 3 |
| 10 | Acidic | 2 | MeOH | 1.5 | 1 | 0 | 0 |
| 11 | none | 0 | DCE | 1.5 | 1 | 0 | 0 |

$^a$Yield determined by $^1$H NMR with dibromomethane as the internal standard.
$^b$Isolated yield after chromatography.

Cannabigerol is structurally analogous to exemplary compound, grifolin (II-2), a natural product isolated in 1950 by Hirata from the mushroom Grifola confluens (Scheme 3).[23] Extensive bioactivity investigations of II-2 have shown it to be a tyrosinase inhibitor,[24] an antioxidant,[25] an antihistamine agent,[26] an antitumor agent,[27-36] an antimicrobial,[21] hypocholesterolemic,[31] a carbonic anhydrase inhibitor,[32] and an inhibitor of nitric oxide production.[33] Whether a simple one step synthesis of II-2 was possible using a process analogous to the cannabigerol synthesis described was investigated. Indeed, after a cursory optimization of substrate ratios it was found that a refluxing mixture of exemplary compound of Formula (III), farnesol (III-2, 1.0 mmol) and exemplary compound of Formula (II), orcinol (II-2, 3.0 mmol) and acidic alumina (2.0 g) in DCE offered II-2 in 37% isolated yield after a 7 hour reaction time (Scheme 3). This simple one step process compares favorably with four previous synthetic preparations of this compound which utilized reaction sequences ranging from four to seven steps in length (Scheme 2).[34-37]

Scheme 3. Exemplary synthesis and four comparative syntheses of grifolin (II-2).

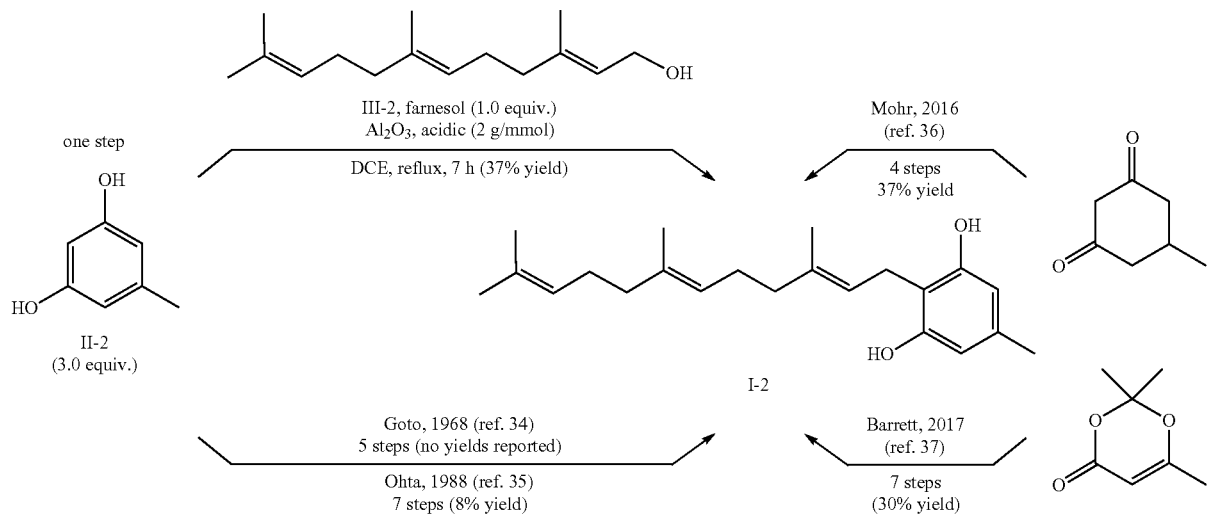

Seeking to further demonstrate the utility of this alumina-promoted allylation reaction, a third natural product called piperogalin (I-4) which was isolated in 1995 from *Peperomia galioides*,[38] and later from *Peperomia obtusifolia* but had yet to be accessed via chemical synthesis (Scheme 3),[39] was investigated. I-4 has demonstrated antiparasitic activity against *Leishmania* and *Trypanosoma cruzi*.[40]% s illustrated in Scheme 4, the two step sequence began with a geranylation of II-2. In this case, the reaction was run on a 4 mmol scale and it was opted to reduce the alumina loading to 2 g/mmol to facilitate magnetic stirring of the heterogenous reaction mixture. The reaction required 24 hours in refluxing DCE and offered cannabigerocin (I-3) in 47% isolated yield. Next, prenylation of I-3 was initially low yielding in DCE and required some effort to optimize solvent, reaction temperature, and substrate ratios. Ultimately, I-4 was obtained in 57% yield when the reaction was run in heptanes, with 1.5 equiv. of prenol and 1.5 g/mmol of alumina relative to I-3, and the temperature maintained at 80° C. for 14 hours. Considerably reduced yields were observed when the reaction was performed at 98° C., the reflux temperature of heptanes, as I-4 appeared to be prone to further reactions resulting in a complex mixture of unidentified byproducts evident in the crude $^1$H NMR spectrum. Overall, this regioselective geranylation and prenylation sequence offered the first total synthesis of I-4 in 27% overall yield in two steps from II-2.

Scheme 4. Synthesis of exemplary compounds of Formula (I), cannabigerorcin (I-3) and piperogalin (I-4).

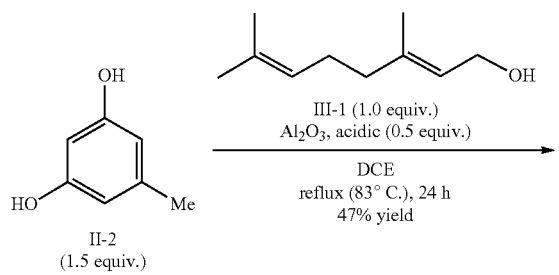

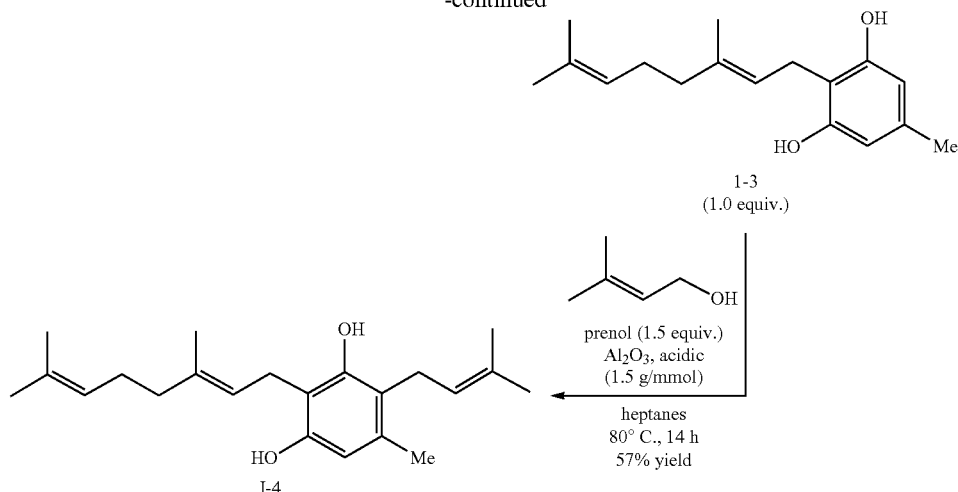

Accordingly, the utility of an exemplary regioselective alumina-promoted allylation reaction of resorcinols was investigated which has enabled efficient syntheses of the natural products cannabigerol (CBG, I-1), grifolin (I-2), cannabigerorcin (I-3) and piperogalin (I-4).

Example 2

The allylation of model compound of Formula (II) (phenol II-3, wherein n is 1 and $R^1$ is H) with a compound of Formula (III) ((E)-3-phenylprop-2-en-1-ol wherein $R^2$ to $R^4$ are H and $R^5$ is phenyl (III-3, cinnamyl alcohol)) using the alumina (acidic) in DCE according to the process described herein in comparison with other reaction conditions known in the art was investigated (Scheme 5). A summary of the results of the investigation is provided in Table 3.

Conditions: II-3 (0.75 mmol), III-3 (0.5 mmol), acidic alumina (1 g) and solvent (5 mL) in a 40 mL reaction vial, charged with a stir bar, the mixture was heated at refluxing temperature for 24 h. Then was filtered through a pad of Cellite®. The residue was washed by EtOAc 3 times, solvent was removed in vacuo.

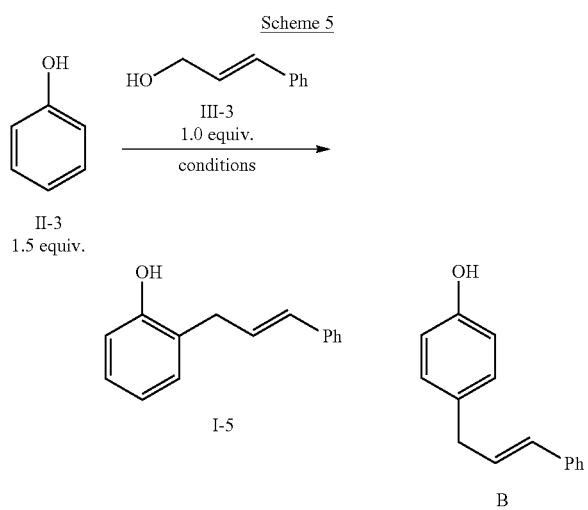

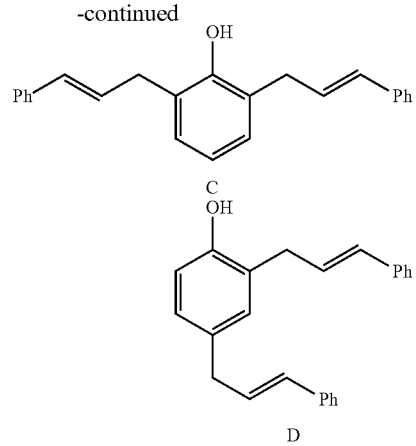

TABLE 3

| Reaction Conditions | I-5 | B | C | D |
|---|---|---|---|---|
| Alumina (acidic) DCE, reflux, 24 hr | 79% | 0% | 10% | 0% |
| BF$_3$•OEt$_2$ (1.0 equiv), DCE, r.t., 15 min | 10% | 42% | 0% | 9% |
| ZnBr$_2$ (1.0 equiv) DCE, r.t., 2 hr | 7% | 34% | 0% | 6% |
| TsOH (1.0 equiv) DCE, r.t., 24 hr | 21% | 30% | 0% | 8% |
| FeCl$_3$ (1.0 equiv) DCE, r.t., 30 min | 4% | 35% | 0% | Trace |
| Sc(OTf)$_3$ (1.0 equiv) DCE, r.t., 30 min | Trace | 22% | 0% | Trace |
| AgOTf (1.0 equiv) DCE, r.t., 1 hr | 21% | 36% | 0% | 9% |
| ZrCl$_4$ (1.0 equiv) DCE, r.t., 30 min | 0% | 10% | 0% | 0% |
| TFA (1.0 equiv) DCE, r.t., 3 days | 9% | 35% | 0% | 5% |

Discussion

The alumina-mediated allylation yielded primarily I-5 and the o,o-disubstituted phenol compound C (Scheme 5). In contrast, the 8 other Lewis or Bronsted acids evaluated all resulted in the para-allylation product compound B as the major product of the reaction. In contrast to the other acids, formation of para-substitution products, compounds B and D, was not observed with alumina. Instead, the only products observed via ¹H NMR spectrum of the crude reaction mixtures were ortho-substituted I-5, in 79% yield, and ortho-disubstituted compound C, in 10% yield. This reaction was not inhibited by the radical scavenger BHT, ruling out a potential radical process.

Example 3

An study of an exemplary process of the application with model compound of Formula (II) wherein n is 1 and R¹ is H

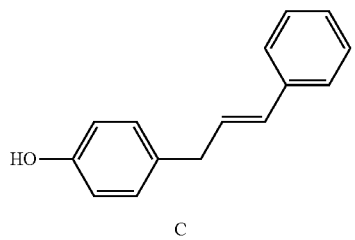

C

TABLE 4

| Entry | Deviation from acid alumina and DCE | (%) Yield I-5[a] | (%) Yield B[a] | (%) Yield C[a] |
|---|---|---|---|---|
| 1 | None | 79 (73[b]) | 10 (9[b]) | 0 |
| 2 | Neutral alumina instead of Acidic alumina | 20 | 1 | 0 |
| 3 | Basic alumina instead of Acidic alumina | 48 | 10 | 0 |
| 4 | Hexane instead of DCE | 55 | 8 | 0 |
| 5 | Toluene instead of DCE | 48 | 10 | 0 |
| 6 | DCM instead of DCE | 0 | 0 | 0 |
| 7 | DCM at 84° C. instead of DCE[c] | 68 | 8 | 0 |
| 8 | Et₂O instead of DCE | 0 | 0 | 0 |
| 9 | EtOAc instead of DCE | 0 | 0 | 0 |
| 10 | CH₃CN instead of DCE | 0 | 0 | 0 |
| 11 | EtOH instead of DCE | 0 | 0 | 0 |
| 12 | II-3:III-3 (2.0:1.0) | 68 | 8 | 0 |
| 13 | II-3:III-3 (1.0:1.0) | 43 | 13 | 0 |
| 14 | II-3:III-3 (1.0:1.5) | 43 | 21 | 0 |
| 15 | II-3:III-3 (1.0:2.0) | 42 | 20 | 0 |
| 16 | Acidic alumina (0.5 g) | 55 | 3 | 0 |
| 17 | Acidic alumina (0 g) | 0 | 0 | 0 |

[a]Yields were determined by ¹H NMR analysis of the crude reaction mixture with an internal standard CH₂Br₂;
[b]Isolated yield;
[c]Reaction in pressure tube.

(phenol (II-3), with a compound of Formula (III) wherein R² to R⁴ are H and R⁵ is phenyl ((E)-3-phenylprop-2-en-1-ol, III-3, cinnamyl alcohol) was conducted (Scheme 6). A summary of the results of the study is provided in Table 4.

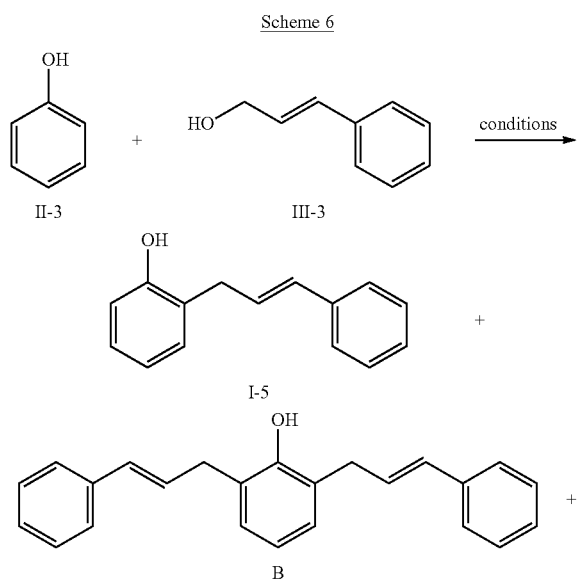

Conditions for reaction: II-2 (0.75 mmol), III-3 (0.5 mmol), acidic alumina (1 g), dichloroethane (5 mL), reflux, 24 h; then filtration through pad of Celite®, rinsed with EtOAc (×3); solvent removed in vacuo. [a]Yields were determined by ¹H NMR analysis of the crude reaction mixture using CH₂Br₂ as an internal standard;[b]Isolated yield;[c]Reaction was performed in a pressure tube.

Consistent yields of I-5 were obtained with six acidic aluminas purchased from different vendors (see Example 4). Spent alumina is easily recovered from this reaction by filtration. When the spent alumina was dried by heating at 90° C. under a strong vacuum for five hours, it was found that it could be reused in repeated reactions with a consistently high yield of I-5 obtained over, for example, five cycles.

Example 4

The effect of various commercially available acidic alumina on an exemplary process of the application (Scheme 7) was investigated. The results are summarized in Table 5.

Conditions: II-3 (1.5 mmol), III-3 (1.0 mmol), acidic alumina (2 g) and DCE (10 mL) in a 40 mL reaction vial, charged with a stir bar, the mixture was heated at refluxing temperature for 24 h. Then was filtered through a pad of Cellite. The residue was washed by EtOAc 3 times, solvent was removed in vacuo.

Scheme 7

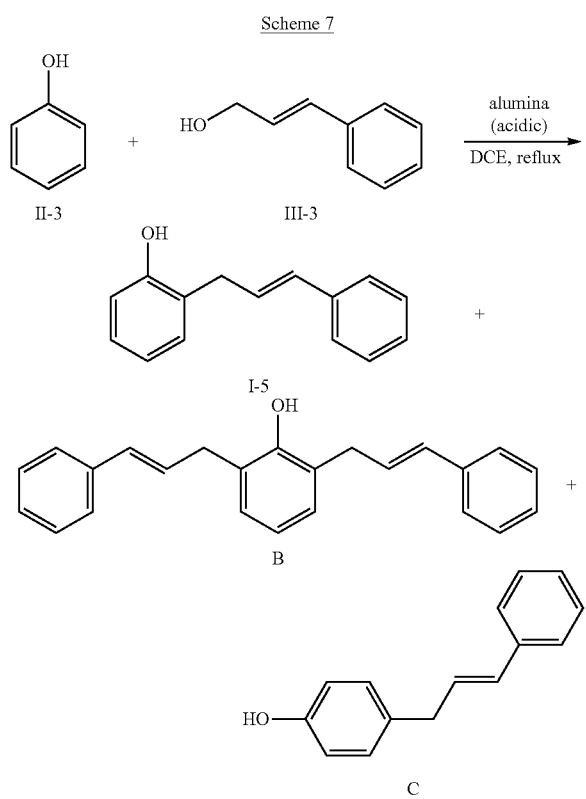

TABLE 5

| Entry | Alumina (acidic) | (%) Yield I-5 | (%) Yield B[a] | (%) Yield C[a] |
|---|---|---|---|---|
| 1 | Millipore | 73 | 13 | 0 |
| 2 | Acros | 74 | 11 | 0 |
| 3 | MP | 75 | 13 | 0 |
| 4 | Honeywell | 72 | 11 | 0 |
| 5 | Alfa Aesar | 76 | 12 | 0 |
| 6 | Fisher | 72 | 11 | 0 |

[a]Yields were determined by $^1$H NMR analysis of the crude reaction mixture with an internal standard $CH_2Br_2$ Discussion:

The 6 aluminas obtained from different manufacturers all resulted in comparable yields of I-5 and compound B with no observable para-substitution product (compound C) in any of the reactions.

Example 5: Preparation of Exemplary Compounds of Formula (I) Using the Process of the Application To probe the synthetic utility of this reaction, a range of sterically and electronically diverse phenols and allylic alcohols were subjected to the conditions as described in Example 4. A steric hindrance effect was observed for ortho substituted phenols (I-19, I-39 and I-16). As steric bulk increased, reaction yields lowered and reaction rates were slower. Substrates I-19 and I-39 showed incomplete consumption of cinnamyl alcohol after two days. Additionally, meta substituted phenols (I-14 to I-17, I-44, I-26, I-51 and I-13) were preferentially allylated at the less hindered position. Exceptions to this included resorcinol (I-15) and 2-naphthol (I-11 and I-53). Electron-poor phenols had reduced selectivity and lower yields (I-55, I-56, I-42, I-43). Additionally, indoles I-24 and I-24 demonstrated poor regioselectivity. Notably, the 1,4-quinone corresponding to the 1,4-dihydroxyl benzene (I-13) which presumably resulted from air-oxidation was isolated. Evaluation of allylic alcohols demonstrated that this reaction is effective for electron-rich, electron-poor, and aliphatic alcohols (I-27, I-28, I-29, I-9, I-47, I-46, I-30, I-31, I-41, I-48, I-32, I-33, I-38, I-37). The natural hormones estrone, estradiol and the birth control drug ethinylestradiol underwent cinnamylation at less hindered ortho-positions relative to phenolic hydroxyl group (I-58 to I-60). These substrates highlight the potential applicability of this allylation reaction to late-stage functionalization of phenolic natural products and pharmaceuticals.

Table 6 is a summary of exemplary compound of Formula (I) prepared using the process of the application and the corresponding yields of the reaction.

TABLE 6

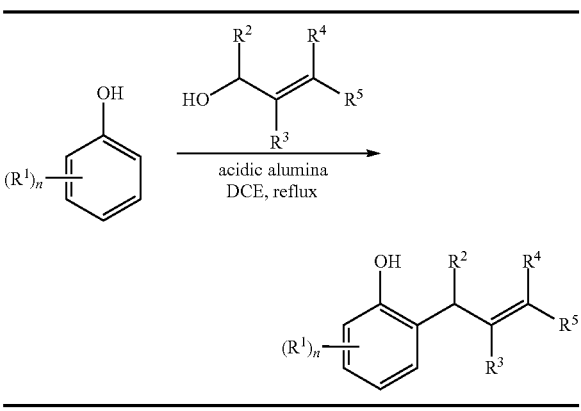

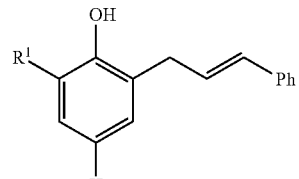

I-5  R$^1$ = H     73%
I-19 R$^1$ = Me    23%
I-39 R$^1$ = OMe   15%
I-16 R$^1$ = Cl    73%

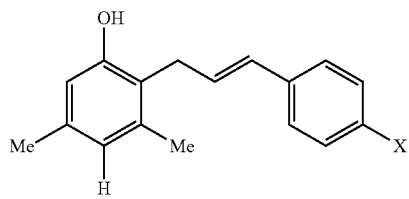

I-12 X = H     81%
I-52 X = NO$_2$ 62%

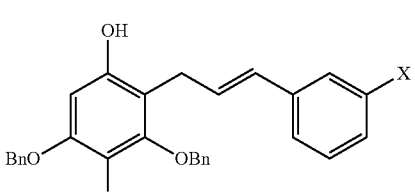

I-49 X = H     68%
I-57 X = OBn   71%

TABLE 6-continued
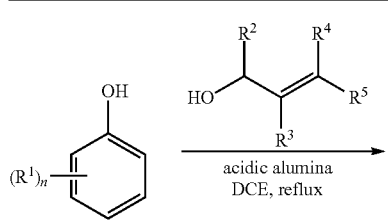
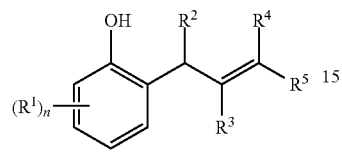
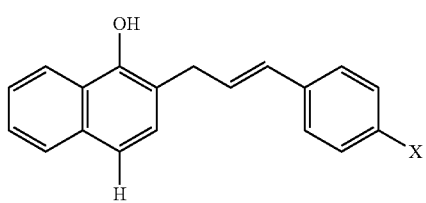
I-10 X = H 82%
I-53 X = NO₂ 79%
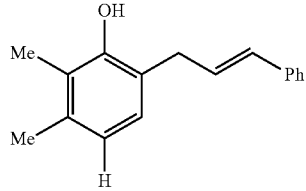
I-18 82%
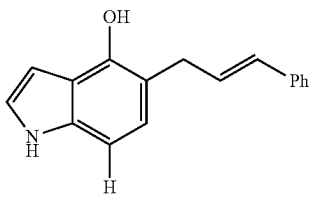
I-23 87%
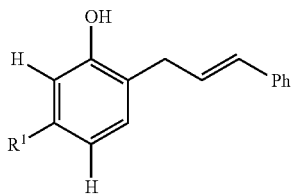
I-14 R¹ = Me 86%
I-45 R¹ = F 79%
I-17 R¹ = Cl 64%
I-44 R¹ = Br 75%
TABLE 6-continued
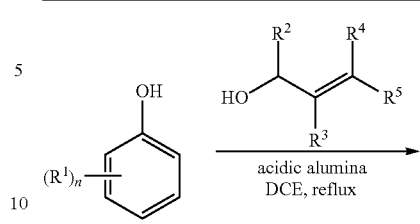
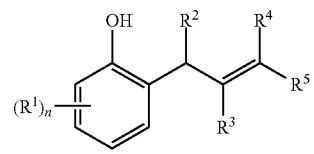
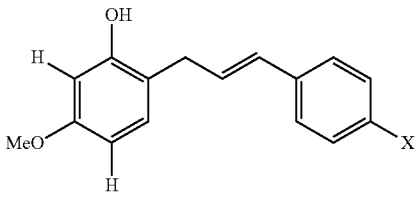
I-26 X = H 91%
I-51 X = NO₂ 77%
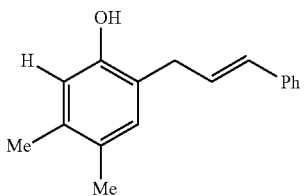
I-13 85%
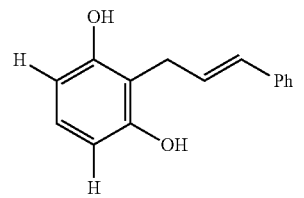
I-15 53%
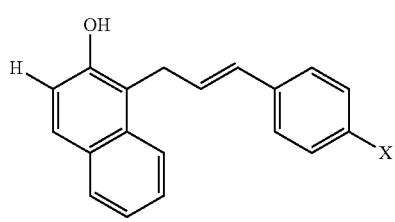
I-11 X = H 93%
I-54 X = NO₂ 88%

TABLE 6-continued
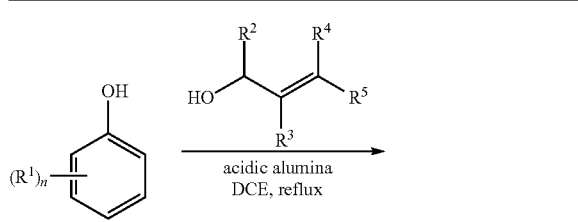
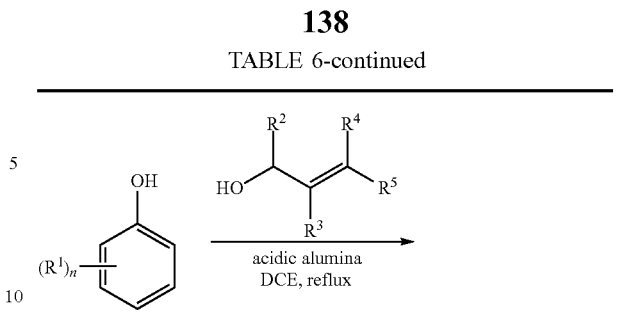
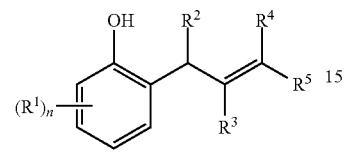
I-6  R¹ = Me  78%
I-7  R¹ = OMe  71%
I-8  R¹ = Cl  91%
I-21  R¹ = Br  84%
I-40  R¹ = OH  52%
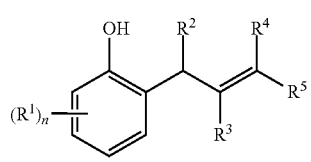
I-55 9%   I-56 14%
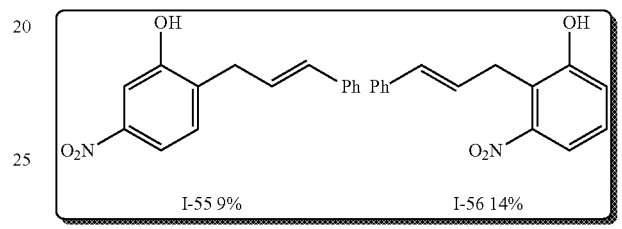
I-42   I-43 10%
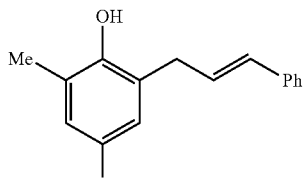
I-20 84%
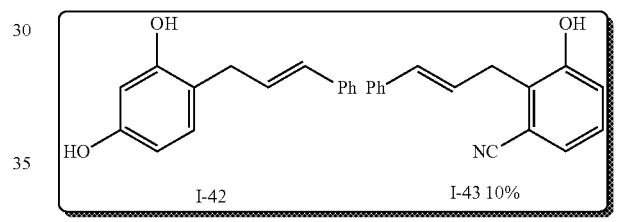
I-27  X = F  77%
I-28  X = Cl  80%
I-39  X = Br  77%
I-9   X = NO₂  84%
I-47  X = Ms  52%
I-46  X = CF₃  75%
I-30  X = OMe  34%
I-31  X = Me  83%
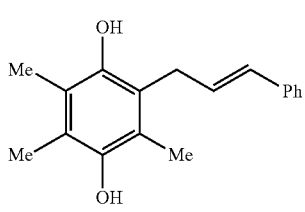
I-22 55%
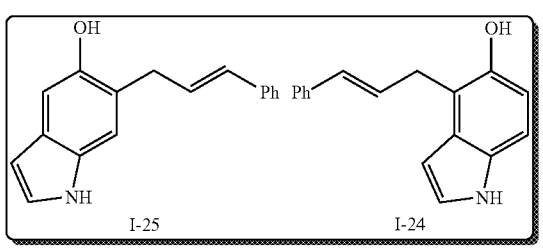
I-25   I-24
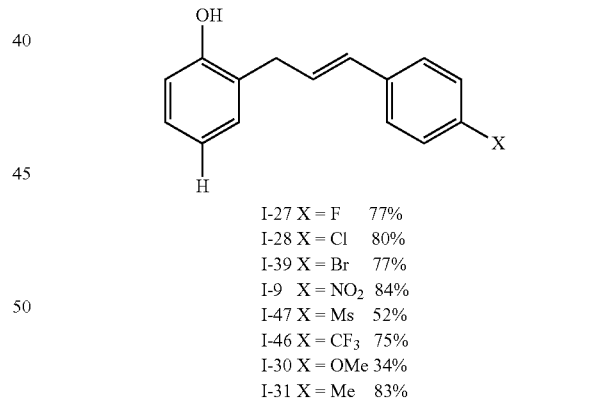
I-41 47%

TABLE 6-continued
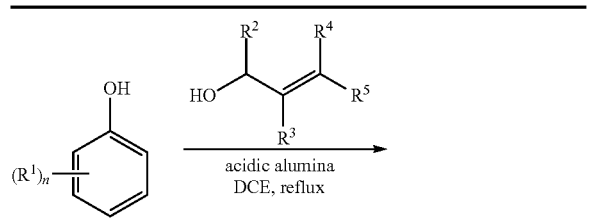
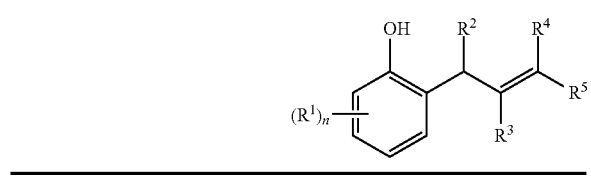
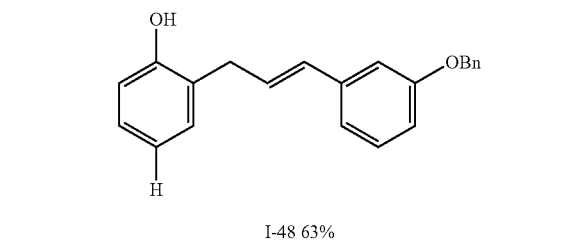 [SMILES: Oc1ccccc1C/C=C/c1cccc(OCc2ccccc2)c1]
I-48 63%
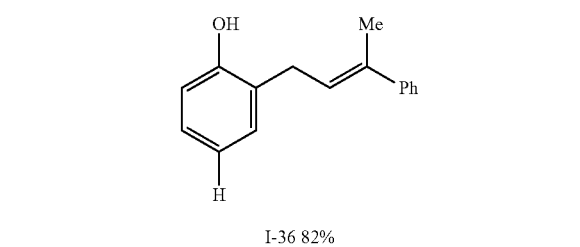 [SMILES: C/C(=C\Cc1ccccc1O)c1ccccc1]
I-36 82%
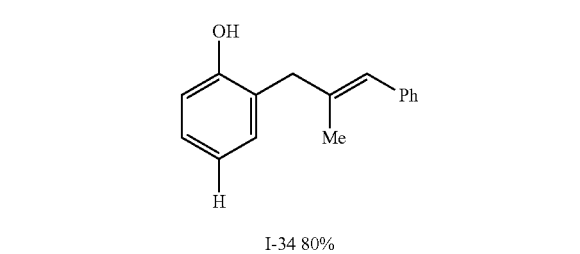 [SMILES: C/C(=C\c1ccccc1)Cc1ccccc1O]
I-34 80%
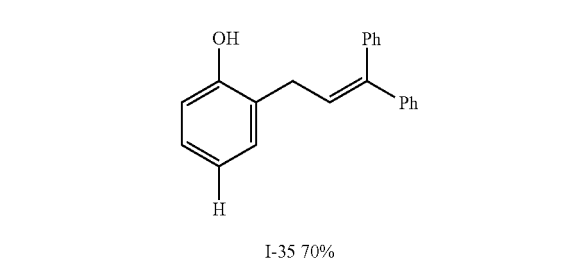 [SMILES: Oc1ccccc1CC=C(c1ccccc1)c1ccccc1]
I-35 70%
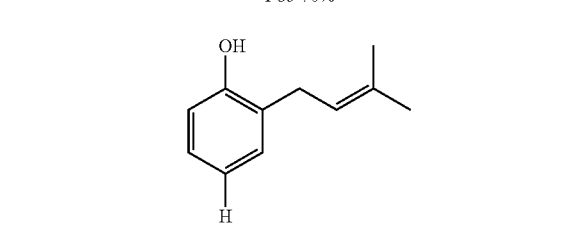
I-32 55%
TABLE 6-continued
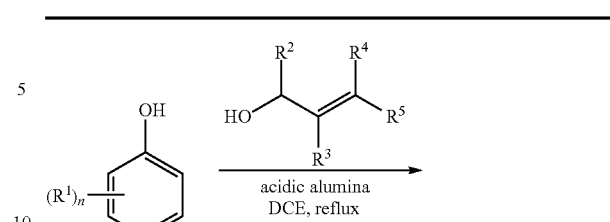
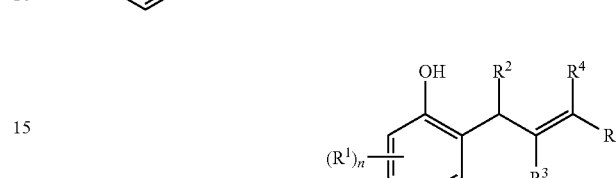
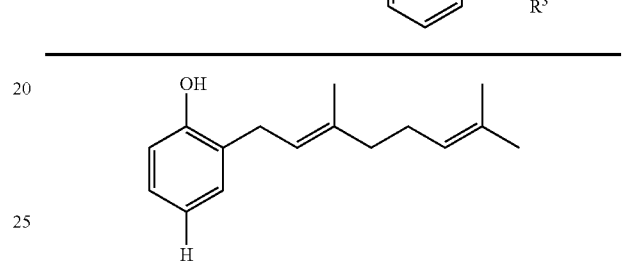
I-33 72%
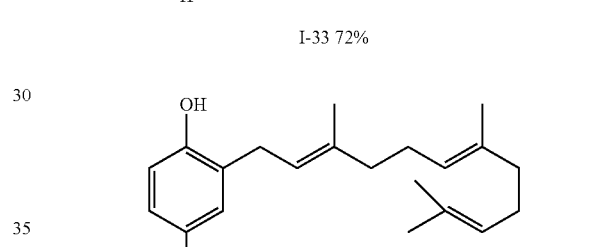
I-38 80%
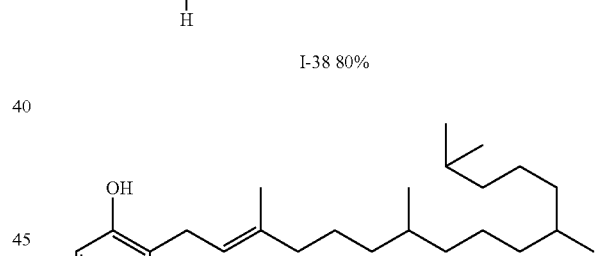
I-37 65%
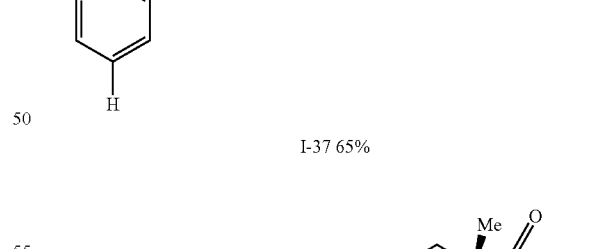
I-60 (estrone) 62%

TABLE 6-continued

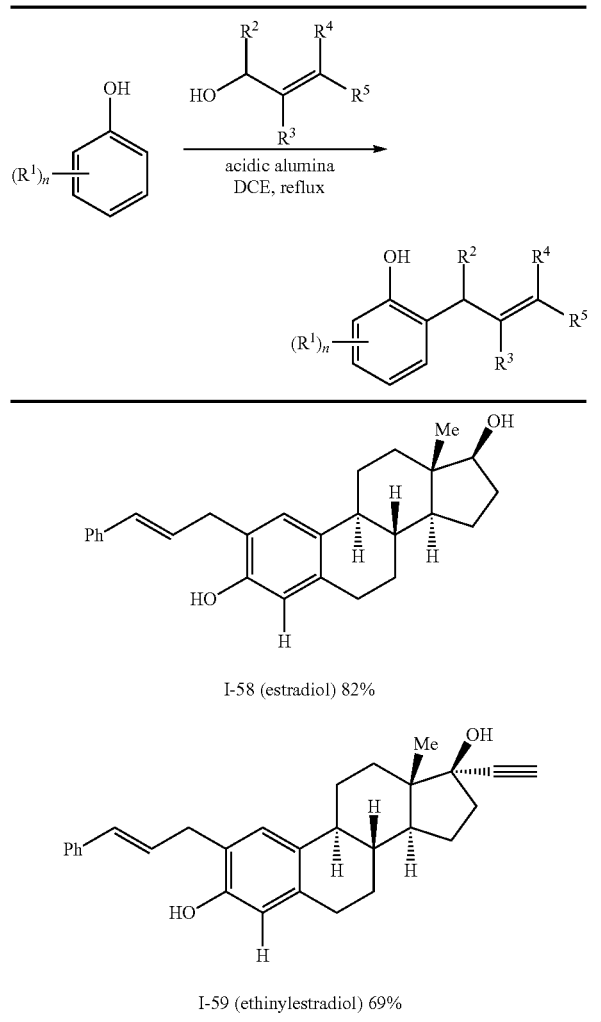

I-58 (estradiol) 82%

I-59 (ethinylestradiol) 69%

Synthesis of Exemplary Compounds of Formula (I) from Table 6

Synthesis of I-5

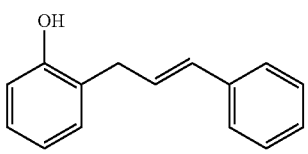 [SMILES: Oc1ccccc1C/C=C/c1ccccc1]

General Procedure: To a 40 mL reaction vial containing a magnetic stir were added cinnamyl alcohol (134.2 mg, 1.0 mmol), 1,2-dichloroethane (10 mL), acidic aluminum oxide (2.0 g), and phenol (141.2 mg, 1.5 mmol). The suspension was stirred and heated at reflux temperature for 24 hours at which point TLC analysis indicated complete consumption of the cinnamyl alcohol substrate. The reaction mixture was cooled and filtered through a pad of Celite®. The solids were washed with EtOAc (3×30 mL) and the filtrates combined and concentrated in vacuo. Unless otherwise specified, the crude residue was purified via flash column chromatography on silica gel using gradient elution with hexane and ethyl acetate. Compound I-5 was isolated as a white solid in 9% yield (29.3 mg, 0.09 mmol) and Compound MLAP-1909 was isolated as a colorless oil in 73% yield (153.8 mg, 0.73 mmol). $R_f$=0.63 (Hexane:EtOAc=7:3); $^1$H NMR (700 MHz, Chloroform-d) δ 7.36 (d, J=7.6 Hz, 2H), 7.30 (t, J=7.6 Hz, 2H), 7.22 (t, J=7.3 Hz, 1H), 7.18 (d, J=7.5 Hz, 1H), 7.16 (t, J=7.7 Hz, 1H), 6.92 (t, J=7.4 Hz, 1H), 6.82 (d, J=7.9 Hz, 1H), 6.52 (d, J=15.9 Hz, 1H), 6.40 (dt, J=15.9, 6.6 Hz, 1H), 4.90 (s, 1H), 3.58 (d, J=6.4 Hz, 2H); $^{13}$C NMR (176 MHz, Chloroform-d) δ 154.15, 137.22, 131.67, 130.62, 128.67, 128.07, 128.04, 127.47, 126.34, 125.79, 121.17, 115.91, 34.25; HRMS: calculated for C15H13O (M-H)$^-$ 209.0966; found 209.0964.

Synthesis of I-6

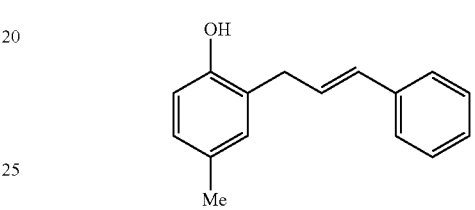

The general procedure was used with cinnamyl alcohol (67.1 mg, 0.5 mmol), p-cresol (81.1 mg, 0.75 mmol), acidic alumina (1 g), and 1,2-dichloroethane (5 mL). TLC analysis at 11 hours indicated complete consumption of cinnamyl alcohol. Compound I-6 was isolated as a colorless oil (87.2 mg, 0.39 mmol, 78% yield); $R_f$=0.68 (Hexane:EtOAc=7:3); $^1$H NMR (700 MHz, Chloroform-d) δ 7.37 (d, J=7.3 Hz, 2H), 7.31 (t, J=7.7 Hz, 2H), 7.22 (t, J=7.3 Hz, 1H), 6.99 (s, 1H), 6.95 (d, J=7.9 Hz, 1H), 6.73 (d, J=8.1 Hz, 1H), 6.52 (d, J=15.9 Hz, 1H), 6.40 (dt, J=15.7, 6.6 Hz, 1H), 4.80 (s, 1H), 3.55 (d, J=6.6 Hz, 2H), 2.29 (s, 3H); $^{13}$C NMR (176 MHz, Chloroform-d) δ 151.84, 137.28, 131.50, 131.12, 130.34, 128.65, 128.39, 128.21, 127.42, 126.33, 125.53, 115.74, 34.24, 20.63; HRMS: calculated for C16H15O (M-H)$^-$ 223.1123; found 223.1124.

Synthesis of I-7

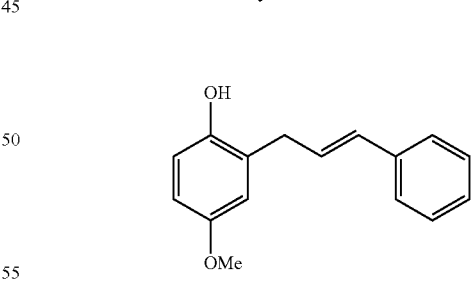

The general procedure was used with cinnamyl alcohol (67.1 mg, 0.5 mmol), p-methoxylphenol (93.1 mg, 0.75 mmol), acidic alumina (1 g), and 1,2-dichloroethane (5 mL). TLC analysis at 23 hours indicated complete consumption of cinnamyl alcohol. Compound I-7 was isolated as a colorless oil (85.1 mg, 0.354 mmol, 71% yield); $R_f$=0.55 (Hexane: EtOAc=7:3); $^1$H NMR (700 MHz, Chloroform-d) δ 7.37-7.34 (m, 2H), 7.29 (t, J=7.6 Hz, 2H), 7.23-7.20 (m, 1H), 6.78-6.73 (m, 2H), 6.69 (dd, J=8.7, 3.1 Hz, 1H), 6.50 (dt, J=16.0, 1.6 Hz, 1H), 6.37 (dt, J=15.9, 6.6 Hz, 1H), 4.57 (s, 1H), 3.76 (s, 3H), 3.54 (dd, J=6.6, 1.7 Hz, 2H); $^{13}$C NMR (176 MHz, Chloroform-d) δ 153.99, 148.06, 137.21, 131.72, 128.65, 127.84, 127.43, 126.99, 126.34, 116.61, 116.13, 112.74, 55.88, 34.48; HRMS: calculated for C16H15O2 (M-H)⁻ 239.1072; found 239.1084.

Synthesis of I-8

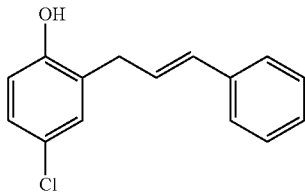 [SMILES: Oc1ccc(Cl)cc1C/C=C/c1ccccc1]

The general procedure was used with cinnamyl alcohol (67.1 mg, 0.5 mmol), 4-chlorophenol (96.4 mg, 0.75 mmol), acidic alumina (1 g), and 1,2-dichloroethane (5 mL). TLC analysis at 24 hours indicated complete consumption of cinnamyl alcohol. Compound I-8 was isolated as a colorless oil (85.1 mg, 0.354 mmol, 71% yield); $R_f$=0.57 (Hexane: EtOAc=7:3); ¹H NMR (700 MHz, Chloroform-d) δ 7.39-7.34 (m, 2H), 7.31 (t, J=7.7 Hz, 2H), 7.23 (td, J=7.1, 1.3 Hz, 1H), 7.15 (d, J=2.5 Hz, 1H), 7.10 (dd, J=8.5, 2.6 Hz, 1H), 6.75 (dd, J=10.5, 8.7 Hz, 1H), 6.51 (dt, J=15.9, 1.7 Hz, 1H), 6.34 (dt, J=15.8, 6.7 Hz, 1H), 5.11 (s, 1H), 3.53 (dd, J=6.7, 1.6 Hz, 2H); ¹³C NMR (176 MHz, Chloroform-d) δ 152.71, 137.01, 132.21, 130.22, 129.64, 128.71, 127.76, 127.70, 127.63, 127.05, 126.37, 125.73, 117.06, 116.79, 33.95; HRMS: calculated for 015H12010 (M-H)⁻ 243.0577; found 243.0564.

Synthesis of I-9

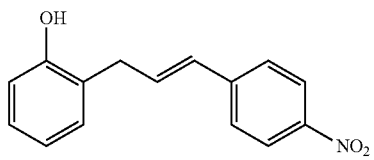 [SMILES: O=[N+]([O-])c1ccc(/C=C/Cc2ccccc2O)cc1]

The general procedure was used with 4-nitrocinnamyl alcohol (89.6 mg, 0.5 mmol), phenol (70.6 mg, 0.75 mmol), acidic alumina (1 g), and 1,2-dichloroethane (5 mL). TLC analysis at 24 hours indicated complete consumption of 4-nitrocinnamyl. Com I-9 was isolated as a yellow crystal solid (71.3 mg, 0.279 mmol, 56% yield); $R_f$=0.45 (Hexane: EtOAc=7:3); ¹H NMR (700 MHz, Chloroform-d)) δ 8.14 (d, J=8.8 Hz, 2H), 7.46 (d, J=8.8 Hz, 2H), 7.16 (ddd, J=9.3, 7.4, 1.6 Hz, 2H), 6.94-6.91 (m, 1H), 6.81 (d, J=7.9 Hz, 1H), 6.61 (dt, J=15.9, 6.6 Hz, 1H), 6.50 (dd, J=15.9, 1.7 Hz, 1H), 4.80 (s, 1H), 3.61 (dd, J=6.6, 1.6 Hz, 2H); ¹³C NMR (176 MHz, Chloroform-d) δ 153.73, 146.77, 144.05, 133.80, 130.74, 129.28, 128.24, 126.75, 125.25, 124.11, 121.34, 115.73, 34.04; HRMS: calculated for C15H12NO3 (M-H)⁻ 254.0817; found 254.0808.

Synthesis of I-10

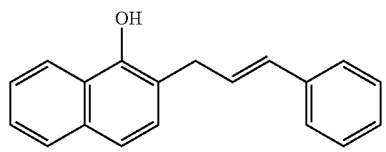 [SMILES: Oc1c(C/C=C/c2ccccc2)ccc2ccccc12]

The general procedure was used with cinnamyl alcohol (67.1 mg, 0.5 mmol), 1-naphthol (108.1 mg, 0.75 mmol), acidic alumina (1 g), and 1,2-dichloroethane (5 mL). TLC analysis at 24 hours indicated complete consumption of cinnamyl alcohol. Compound I-10 was isolated as a white solid (107.0 mg, 0.411 mmol, 82% yield); $R_f$=0.63 (Hexane: EtOAc=7:3); ¹H NMR (700 MHz, Chloroform-d) δ 8.16 (d, J=7.8 Hz, 1H), 7.80 (d, J=7.3 Hz, 1H), 7.50-7.43 (m, 3H), 7.36 (d, J=7.5 Hz, 2H), 7.32-7.27 (m, 3H), 7.23 (t, J=7.3 Hz, 1H), 6.60 (d, J=15.9 Hz, 1H), 6.45 (dt, J=15.9, 6.4 Hz, 1H), 5.52 (s, 1H), 3.74 (d, J=5.4 Hz, 2H); ¹³C NMR (176 MHz, Chloroform-d) δ 149.56, 136.69, 133.80, 131.99, 128.61, 128.44, 127.61, 127.46, 126.29, 125.84, 125.38, 124.81, 121.27, 120.48, 118.18, 34.78; HRMS: calculated for C19H15O (M-H)⁻ 259.1123; found 259.1112.

Synthesis of I-11

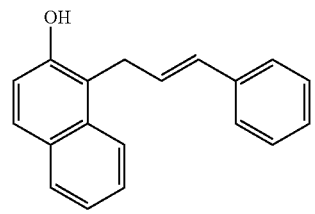 [SMILES: Oc1ccc2ccccc2c1C/C=C/c1ccccc1]

The general procedure was used with cinnamyl alcohol (67.1 mg, 0.5 mmol), 2-naphthol (108.1 mg, 0.75 mmol), acidic alumina (1 g), and 1,2-dichloroethane (5 mL). TLC analysis at 24 hours indicated complete consumption of cinnamyl alcohol. Compound I-11 was isolated as a white solid (120.5 mg, 0.463 mmol, 93% yield); $R_f$=0.49 (Hexane: EtOAc=7:3); ¹H NMR (700 MHz, Chloroform-d)) δ 7.97 (d, J=8.5 Hz, 1H), 7.80 (d, J=8.1 Hz, 1H), 7.70 (d, J=8.7 Hz, 1H), 7.51-7.48 (m, 1H), 7.36 (t, J=7.5 Hz, 1H), 7.30 (d, J=7.3 Hz, 2H), 7.27-7.23 (m, 2H), 7.17 (t, J=7.3 Hz, 1H), 7.12 (d, J=8.8 Hz, 1H), 6.44 (d, J=3.4 Hz, 2H), 5.02 (s, 1H), 3.99 (d, J=3.3 Hz, 2H); ¹³C NMR (176 MHz, Chloroform-d) δ 151.31, 137.31, 133.42, 131.10, 129.64, 128.76, 128.59, 128.57, 127.70, 127.32, 126.78, 126.28, 123.40, 123.22, 118.09, 117.22, 28.62; HRMS: calculated for C19H15O (M-H)⁻ 259.1123; found 259.1113.

Synthesis of I-12

The general procedure was used with cinnamyl alcohol (67.1 mg, 0.5 mmol), 3,5-dimethylphenol (91.6 mg, 0.75 mmol), acidic alumina (1 g), and 1,2-dichloroethane (5 mL). TLC analysis at 24 hours indicated complete consumption of cinnamyl alcohol. Compound I-12 was isolated as a white solid (96.1 mg, 0.403 mmol, 81% yield); $R_f$=0.60 (Hexane:EtOAc=7:3); $^1$H NMR (700 MHz, Chloroform-d)) δ 7.32 (d, J=7.1 Hz, 2H), 7.28-7.25 (m, 2H), 7.20-7.16 (m, 1H), 6.63 (s, 1H), 6.52 (s, 1H), 6.40-6.36 (m, 1H), 6.32 (dt, J=15.8, 5.9 Hz, 1H), 4.70 (s, 1H), 3.55 (dd, J=5.9, 1.5 Hz, 2H), 2.30 (s, 3H), 2.26 (s, 3H); $^{13}$C NMR (176 MHz, Chloroform-d) δ 153.87, 137.98, 137.35, 137.02, 130.34, 128.45, 127.65, 127.08, 126.12, 123.79, 120.94, 114.09, 29.53, 20.97, 19.63; HRMS: calculated for C17H17O (M-H)$^-$ 237.1279; found 237.1289.

Synthesis of I-13

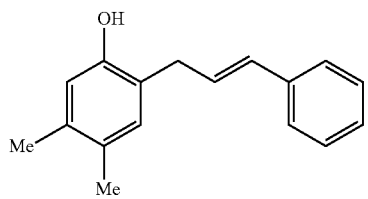 [SMILES: Cc1cc(O)c(C/C=C/c2ccccc2)cc1C]

The general procedure was used with cinnamyl alcohol (67.1 mg, 0.5 mmol), 3,4-dimethylphenol (91.6 mg, 0.75 mmol), acidic alumina (1 g), and 1,2-dichloroethane (5 mL). TLC analysis at 24 hours indicated complete consumption of cinnamyl alcohol. Compound I-13 was isolated as a white crystal solid (121.0 mg, 0.427 mmol, 85% yield); $R_f$=0.61 (Hexane:EtOAc=7:3); $^1$H NMR (700 MHz, Chloroform-d) δ 7.38 (d, J=7.6 Hz, 2H), 7.31 (t, J=7.7 Hz, 2H), 7.23 (t, J=7.3 Hz, 1H), 6.94 (s, 1H), 6.66 (s, 1H), 6.53 (d, J=15.9 Hz, 1H), 6.40 (dt, J=15.9, 6.6 Hz, 1H), 4.70 (s, 1H), 3.53 (d, J=6.4 Hz, 2H), 2.23 (s, 3H), 2.21 (s, 3H); $^{13}$C NMR (176 MHz, Chloroform-d) δ 151.97, 137.31, 136.27, 131.63, 131.33, 128.92, 128.65, 128.49, 127.39, 126.34, 122.66, 117.28, 33.91, 19.58, 18.86; HRMS: calculated for C17H17O (M-H)$^-$ 237.1279; found 237.1280.

Synthesis of I-14

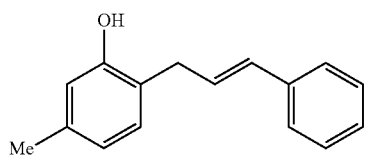 [SMILES: Cc1ccc(C/C=C/c2ccccc2)c(O)c1]

The general procedure was used with cinnamyl alcohol (67.1 mg, 0.5 mmol), 3-methylphenol (81.1 mg, 0.75 mmol), acidic alumina (1 g), and 1,2-dichloroethane (5 mL). TLC analysis at 24 hours indicated complete consumption of cinnamyl alcohol. Compound I-14 was isolated as a white solid (96.1 mg, 0.403 mmol, 86% Yield); $R_f$=0.55 (Hexane/EtOAc=7:3); $^1$H NMR (700 MHz, Chloroform-d) δ 7.35 (d, J=7.5 Hz, 2H), 7.29 (t, J=7.6 Hz, 2H), 7.21 (t, J=7.3 Hz, 1H), 7.05 (d, J=7.6 Hz, 1H), 6.73 (d, J=7.6 Hz, 1H), 6.65 (s, 1H), 6.50 (d, J=15.9 Hz, 1H), 6.38 (dt, J=15.7, 6.6 Hz, 1H), 4.82 (s, 1H), 3.53 (d, J=6.4 Hz, 2H), 2.30 (s, 3H); $^{13}$C NMR (176 MHz, Chloroform-d) 153.87, 138.01, 137.14, 131.35, 130.28, 128.53, 128.20, 127.29, 126.20, 126.12, 122.46, 121.74, 116.51, 33.81, 21.03; HRMS: calculated for C16H15O (M-H)$^-$ 223.1123; found 223.1115.

Synthesis of I-15

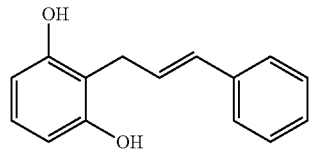 [SMILES: Oc1cccc(O)c1C/C=C/c1ccccc1]

The general procedure was used with cinnamyl alcohol (268.4 mg, 2.0 mmol), 3-hydroxyphenol (330.3 mg 3.0 mmol), acidic alumina (4 g), and 1,2-dichloroethane (520 mL). TLC analysis at 24 hours indicated complete consumption of cinnamyl alcohol. Compound I-15 was isolated as a white solid (238.4 mg, 1.054 mmol, 53% Yield); $R_f$=0.58 (Hexane/EtOAc=6:4); $^1$H NMR (700 MHz, Chloroform-d) δ 7.34 (dd, J=8.1, 1.4 Hz, 2H), 7.28 (t, J=7.7 Hz, 2H), 7.21-7.18 (m, 1H), 6.99 (t, J=8.1 Hz, 1H), 6.52 (dt, J=15.8, 1.8 Hz, 1H), 6.44 (d, J=8.1 Hz, 2H), 6.37 (dt, J=15.9, 6.4 Hz, 1H), 4.90 (d, J=1.2 Hz, 2H), 3.63 (dd, J=6.3, 1.7 Hz, 2H); $^{13}$C NMR (176 MHz, Chloroform-d) δ 155.29, 137.26, 131.02, 128.59, 127.75, 127.70, 127.34, 126.32, 112.54, 108.33, 31.08, 26.80; HRMS: calculated for C15H13O2 (M-H)$^-$ 225.0916; found 225.0923.

Synthesis of I-16

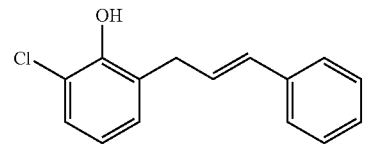 [SMILES: Oc1c(Cl)cccc1C/C=C/c1ccccc1]

The general procedure was used with cinnamyl alcohol (67.1 mg, 0.5 mmol), 2-chlorophenol (96.4 mg, 0.75 mmol), acidic alumina (1 g), and 1,2-dichloroethane (5 mL). TLC analysis at 24 hours indicated complete consumption of cinnamyl alcohol. Compound I-16 was isolated as a yellow oil (113.6 mg, 0.464 mmol, 86% yield); $R_f$=0.62 (Hexane/EtOAc=7:3); $^1$H NMR (700 MHz, Chloroform-d) δ 7.36 (d, J=7.6 Hz, 2H), 7.33-7.28 (m, 3H), 7.24 (dd, J=8.2, 2.5 Hz, 2H), 6.70 (d, J=8.5 Hz, 1H), 6.51 (d, J=15.8 Hz, 1H), 6.34 (dt, J=15.9, 6.7 Hz, 1H), 4.99 (s, 1H), 3.53 (d, J=6.7 Hz, 2H); $^{13}$C NMR (176 MHz, Chloroform-d) δ 153.24, 136.97, 133.11, 132.27, 130.71, 128.72, 128.23, 127.66, 126.98, 126.38, 117.60, 113.09, 33.96; HRMS: calculated for 015H12010 (M-H)$^-$ 243.0577; found 243.0565.

Synthesis of I-17

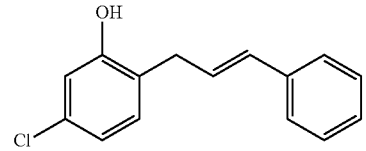 [SMILES: Oc1cc(Cl)ccc1C/C=C/c1ccccc1]

The general procedure was used with cinnamyl alcohol (67.1 mg, 0.5 mmol), 3-chlorophenol (96.4 mg, 0.75 mmol), acidic alumina (1 g), and 1,2-dichloroethane (5 mL). TLC analysis at 24 hours indicated complete consumption of cinnamyl alcohol. Compound I-17 was isolated as a white solid (78.4 mg, 0.32 mmol, 64% yield); $R_f$=0.74 (Hexane/EtOAc=7:3); $^1$H NMR (700 MHz, Chloroform-d) δ 7.37 (d, J=7.6 Hz, 2H), 7.30 (t, J=7.6 Hz, 2H), 7.24-7.19 (m, 2H), 7.11 (d, J=7.5 Hz, 1H), 6.83 (t, J=7.8 Hz, 1H), 6.48 (d, J=15.9 Hz, 1H), 6.39 (dt, J=15.7, 6.8 Hz, 1H), 5.67 (s, 1H), 3.60 (d, J=6.7 Hz, 2H); $^{13}$C NMR (176 MHz, Chloroform-d) δ 149.41, 137.54, 131.48, 129.06, 128.63, 128.12, 127.84, 127.28, 127.07, 126.27, 121.03, 120.06, 33.88; HRMS: calculated for C15H12ClO (M-H)$^-$ 243.0577; found 243.0571.

Synthesis of I-18

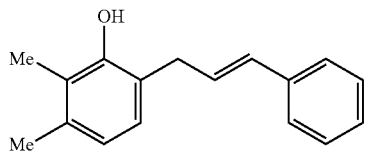 [SMILES: Cc1ccc(C/C=C/c2ccccc2)c(O)c1C]

The general procedure was used with cinnamyl alcohol (67.1 mg, 0.5 mmol), 2,3-dimethylphenol (91.6 mg, 0.75 mmol), acidic alumina (1 g), and 1,2-dichloroethane (5 mL). TLC analysis at 24 hours indicated complete consumption of cinnamyl alcohol. Compound I-18 was isolated as a colorless oil (97.9 mg, 0.41 mmol, 82% yield); $R_f$=0.69 (Hexane/EtOAc=7:3); $^1$H NMR (700 MHz, Chloroform-d) δ 7.37 (d, J=7.5 Hz, 2H), 7.31 (t, J=7.6 Hz, 2H), 7.25-7.21 (m, 1H), 6.93 (d, J=7.6 Hz, 1H), 6.76 (d, J=7.6 Hz, 1H), 6.56 (d, J=16.0 Hz, 1H), 6.39 (dt, J=16.0, 6.6 Hz, 1H), 5.00 (d, J=1.1 Hz, 1H), 3.56 (dd, J=6.7, 1.6 Hz, 2H), 2.29 (s, 3H), 2.19 (s, 3H); $^{13}$C NMR (176 MHz, Chloroform-d) δ 152.39, 136.97, 136.60, 131.63, 128.57, 128.18, 127.43, 127.04, 126.27, 122.95, 122.34, 122.06, 34.83, 20.10, 11.68; HRMS: calculated for C17H17O (M-H)$^-$ 237.1279; found 237.1231.

Synthesis of I-19

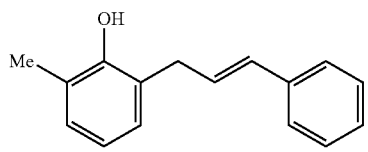 [SMILES: Cc1cccc(C/C=C/c2ccccc2)c1O]

The general procedure was used with cinnamyl alcohol (67.1 mg, 0.5 mmol), 2-methylphenol (81.1 mg, 0.75 mmol), acidic alumina (1 g), and 1,2-dichloroethane (5 mL). TLC analysis at 48 hours indicated cinnamyl alcohol was still existed. Compound I-19 was isolated as a colorless oil (25.8 mg, 0115 mmol, 23% yield); $R_f$=0.74 (Hexane/EtOAc=7:3); $^1$H NMR (700 MHz, Chloroform-d) δ 7.36 (d, J=7.6 Hz, 2H), 7.30 (t, J=7.6 Hz, 2H), 7.22 (t, J=7.3 Hz, 1H), 7.04 (dd, J=12.6, 7.5 Hz, 2H), 6.83 (t, J=7.5 Hz, 1H), 6.54 (d, J=15.9 Hz, 1H), 6.40 (dt, J=15.9, 6.7 Hz, 1H), 4.95 (s, 1H), 3.58 (d, J=6.4 Hz, 2H), 2.26 (s, 3H); $^{13}$C NMR (176 MHz, Chloroform-d) δ 152.67, 137.13, 131.76, 129.53, 128.68, 128.24, 128.16, 127.52, 126.36, 125.08, 124.20, 120.61, 34.72, 16.01; HRMS: calculated for C16H15O (M-H)$^-$ 223.1123; found 223.1132.

Synthesis of I-20

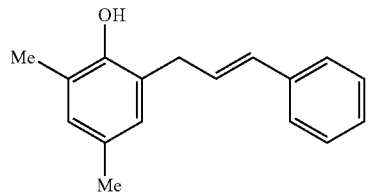 [SMILES: Cc1cc(C)c(O)c(C/C=C/c2ccccc2)c1]

The general procedure was used with cinnamyl alcohol (67.1 mg, 0.5 mmol), 2,4-dimethylphenol (91.6 mg, 0.75 mmol), acidic alumina (1 g), and 1,2-dichloroethane (5 mL). TLC analysis at 24 hours indicated complete consumption of cinnamyl alcohol. Compound I-20 was isolated as a colorless oil (100.2 mg, 0.42 mmol, 84% yield); $R_f$=0.73 (Hexane/EtOAc=7:3); $^1$H NMR (700 MHz, Chloroform-d) δ 7.37 (d, J=7.3 Hz, 2H), 7.31 (t, J=7.7 Hz, 2H), 7.22 (t, J=7.3 Hz, 1H), 6.87 (s, 1H), 6.84 (s, 1H), 6.54 (d, J=15.9 Hz, 1H), 6.39 (dt, J=15.9, 6.7 Hz, 1H), 4.77 (s, 1H), 3.54 (d, J=5.8 Hz, 2H), 2.26 (s, 3H), 2.23 (s, 3H); $^{13}$C NMR (176 MHz, Chloroform-d) δ 150.34, 137.18, 131.60, 130.08, 129.74, 128.67, 128.66, 128.31, 127.48, 126.36, 124.91, 124.00, 34.71, 20.60, 15.97; HRMS: calculated for C17H17O (M-H)$^-$ 237.1279; found 237.1286.

Synthesis of I-21

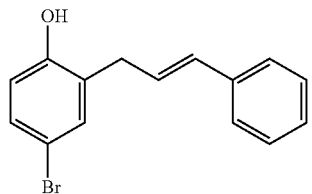 [SMILES: Oc1ccc(Br)cc1C/C=C/c1ccccc1]

The general procedure was used with cinnamyl alcohol (67.1 mg, 0.5 mmol), 4-bromophenol (129.8 mg, 0.75 mmol), acidic alumina (1 g), and 1,2-dichloroethane (5 mL). TLC analysis at 12 hours indicated complete consumption of cinnamyl alcohol. Compound I-21 was isolated as a yellow oil (121.2 mg, 0.42 mmol, 84% yield); $R_f$=0.56 (Hexane/EtOAc=7:3); $^1$H NMR (700 MHz, Chloroform-d) δ 7.36 (d, J=7.6 Hz, 2H), 7.33-7.28 (m, 3H), 7.24 (dd, J=8.2, 2.5 Hz, 2H), 6.70 (d, J=8.5 Hz, 1H), 6.51 (d, J=15.8 Hz, 1H), 6.34 (dt, J=15.9, 6.7 Hz, 1H), 4.99 (s, 1H), 3.53 (d, J=6.7 Hz, 2H); $^{13}$C NMR (176 MHz, Chloroform-d) δ 153.24, 136.97, 133.11, 132.27, 130.71, 128.72, 128.23, 127.66, 126.98, 126.38, 117.60, 113.09, 33.96; HRMS: calculated for C15H12BrO (M-H)$^-$ 287.0072; found 287.0078.

Synthesis of I-22

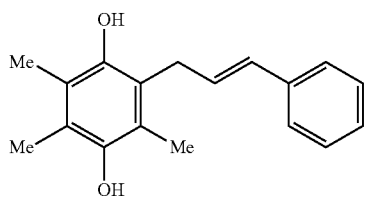 [SMILES: Cc1c(C)c(O)c(C/C=C/c2ccccc2)c(C)c1O]

The general procedure was used with cinnamyl alcohol (67.1 mg, 0.5 mmol), trimethylhydroquinone (114.1 mg, 0.75 mmol), acidic alumina (1 g), and 1,2-dichloroethane (5 mL). TLC analysis at 24 hours indicated complete consumption of cinnamyl alcohol. Compound I-22 was isolated as a yellow oil (74.4 mg, 0.277 mmol, 55% yield); $R_f$=0.76 (Hexane/EtOAc=7:3); $^1$H NMR (700 MHz, Chloroform-d) δ 7.32-7.30 (m, 2H), 7.29-7.26 (m, 3H), 7.21-7.17 (m, 1H), 6.42 (dd, J=15.8, 1.7 Hz, 1H), 6.13 (dt, J=15.8, 6.8 Hz, 1H), 3.41 (dd, J=6.8, 1.5 Hz, 2H), 2.09 (s, 3H), 2.03 (d, J=2.1 Hz, 6H); $^{13}$C NMR (176 MHz, Chloroform-d) δ 187.87, 186.93, 141.56, 141.25, 140.76, 140.59, 137.25, 131.85, 128.64, 127.46, 126.24, 125.40, 30.00, 12.56, 12.54, 12.37;

Synthesis of I-23

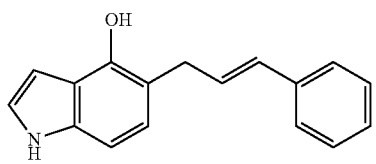 [SMILES: Oc1c(C/C=C/c2ccccc2)ccc2[nH]ccc12]

The general procedure was used with cinnamyl alcohol (67.1 mg, 0.5 mmol), 4-hydroxyindole (99.9 mg, 0.75 mmol), acidic alumina (1 g), and 1,2-dichloroethane (5 mL). TLC analysis at 5 hours indicated complete consumption of cinnamyl alcohol. Compound I-23 was isolated as a white crystal solid (108.1 mg, 0.277 mmol, 55% yield); $R_f$=0.73 (Hexane/EtOAc=7:3); $^1$H NMR (700 MHz, Chloroform-d) δ 8.10 (s, 1H), 7.35 (d, J=7.8 Hz, 2H), 7.29 (t, J=7.6 Hz, 2H), 7.20 (t, J=7.3 Hz, 1H), 7.13 (d, J=2.4 Hz, 1H), 7.01 (d, J=8.2 Hz, 1H), 6.98 (d, J=8.2 Hz, 1H), 6.58 (s, 1H), 6.54 (d, J=16.0 Hz, 1H), 6.45 (dt, J=15.9, 6.5 Hz, 1H), 5.20 (s, 1H), 3.68 (d, J=6.3 Hz, 2H); $^{13}$C NMR (176 MHz, Chloroform-d) δ 147.04, 137.38, 136.87, 130.94, 129.34, 128.63, 127.31, 126.33, 125.11, 123.43, 118.31, 114.04, 104.11, 98.76, 34.01; HRMS: calculated for C15H12BrO (M-H)$^-$ 248.1075; found 248.1081.

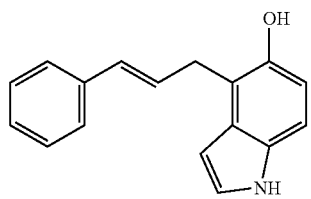 [SMILES: Oc1ccc2[nH]ccc2c1C/C=C/c1ccccc1]

Synthesis of I-24

The general procedure was used with cinnamyl alcohol (67.1 mg, 0.5 mmol), 5-hydrooxyindole (99.9 mg, 0.75 mmol), acidic aluminum oxide (1 g), and dichloroethane (5 mL). TLC analysis at 24 hours indicated complete consumption of cinnamyl alcohol. Compound I-24 was isolated as a colorless oil (42.5 mg, 0.170 mmol, 34% yield); $R_f$=0.65 (DCM/MeOH=98:2); $^1$H NMR (700 MHz, Chloroform-d) δ 8.07 (s, 1H), 7.33 (d, J=7.6 Hz, 2H), 7.28-7.24 (m, 2H), 7.18 (dt, J=12.0, 3.2 Hz, 3H), 6.80 (d, J=8.6 Hz, 1H), 6.57-6.52 (m, 2H), 6.45 (dt, J=15.9, 6.3 Hz, 1H), 4.69 (s, 1H), 3.84 (dd, J=6.3, 1.2 Hz, 2H); $^{13}$C NMR (176 MHz, Chloroform-d) δ 147.52, 137.40, 131.24, 130.94, 128.75, 128.58, 128.19, 127.27, 126.32, 124.98, 115.28, 112.82, 110.01, 100.99, 31.01;

Synthesis of I-25

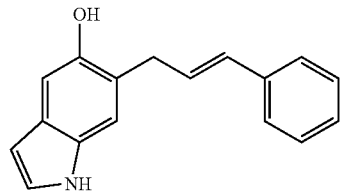 [SMILES: Oc1cc2cc[nH]c2cc1C/C=C/c1ccccc1]

The general procedure was used with cinnamyl alcohol (67.1 mg, 0.5 mmol), 5-hydroxyindole (99.9 mg, 0.75 mmol), acidic alumina (1 g), and 1,2-dichloroethane (5 mL). TLC analysis at 24 hours indicated complete consumption of cinnamyl alcohol. Compound I-25 was isolated as a white solid (40.4 mg, 0.162 mmol, 32% yield); $R_f$=0.75 (Hexane/EtOAc=7:3); $^1$H NMR (700 MHz, Chloroform-d) δ 7.96 (s, 1H), 7.36 (d, J=7.3 Hz, 2H), 7.30 (t, J=7.7 Hz, 2H), 7.21 (t, J=7.3 Hz, 1H), 7.19 (s, 1H), 7.14 (t, J=2.8 Hz, 1H), 7.07 (s, 1H), 6.54-6.42 (m, 3H), 4.66 (d, J=3.0 Hz, 1H), 3.67 (d, J=6.0 Hz, 2H); $^{13}$C NMR (176 MHz, Chloroform-d) δ 148.42, 137.43, 131.54, 131.29, 128.91, 128.65, 127.34, 127.31, 126.31, 124.76, 122.50, 112.03, 105.80, 101.98, 34.77; HRMS: calculated for C15H12BrO (M-H)$^-$ 248.1075; found 248.1069.

Synthesis of I-26

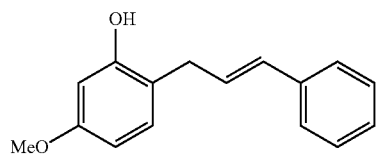 [SMILES: COc1ccc(C/C=C/c2ccccc2)c(O)c1]

The general procedure was used with cinnamyl alcohol (67.1 mg, 0.5 mmol), 3-methoxyphenol (93.1 mg, 0.75 mmol), acidic alumina (1 g), and 1,2-dichloroethane (5 mL). TLC analysis at 11 hours indicated complete consumption of cinnamyl alcohol. Compound I-26 was isolated as a colorless oil (108.9 mg, 0.454 mmol, 91% yield); $R_f$=0.52 (Hexane/EtOAc=7:3); $^1$H NMR (700 MHz, Chloroform-d) δ 7.36 (d, J=7.5 Hz, 2H), 7.30 (t, J=7.6 Hz, 2H), 7.22 (t, J=7.3 Hz, 1H), 7.06 (d, J=8.2 Hz, 1H), 6.52-6.43 (m, 3H), 6.38 (dt, J=15.9, 6.5 Hz, 1H), 5.23 (s, 1H), 3.78 (s, 3H), 3.51 (d, J=6.4

Hz, 2H); $^{13}$C NMR (176 MHz, Chloroform-d) δ 159.74, 155.13, 137.23, 131.37, 131.01, 128.65, 128.50, 127.42, 126.32, 117.90, 106.40, 102.19, 55.48, 33.63; HRMS: calculated for O16H15O2 (M-H)$^-$ 239.1072; found 239.1067.

Synthesis of I-27

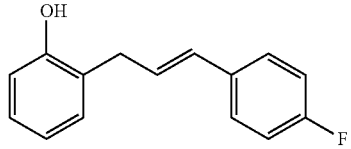 [SMILES: Oc1ccccc1C/C=C/c1ccc(F)cc1]

The general procedure was used with (E)-3-(4-fluorophenyl)prop-2-en-1-ol (76.1 mg, 0.5 mmol), phenol (70.6 mg, 0.75 mmol), acidic alumina (1 g), and 1,2-dichloroethane (5 mL). TLC analysis at 72 hours indicated complete consumption of (E)-3-(4-fluorophenyl)prop-2-en-1-ol. Compound I-27 was isolated as a colorless oil (87.7 mg, 38.4 mmol, 77% yield); R$_f$=0.52 (Hexane/EtOAc=7:3); $^1$H NMR (700 MHz, Chloroform-d) δ 7.34-7.30 (m, 2H), 7.20-7.14 (m, 2H), 6.99 (t, J=8.7 Hz, 2H), 6.92 (t, J=7.5 Hz, 1H), 6.82 (d, J=7.9 Hz, 1H), 6.46 (d, J=15.9 Hz, 1H), 6.31 (dt, J=15.7, 6.6 Hz, 1H), 5.00-4.92 (m, 2H), 3.57 (d, J=6.4 Hz, 2H); $^{13}$C NMR (176 MHz, Chloroform-d) δ 162.96, 161.56, 154.02, 133.45, 130.61, 130.33, 128.06, 127.87, 127.79, 127.75, 125.80, 121.19, 115.85, 115.57, 115.45, 34.06; HRMS: calculated for C15H12FO (M-H)$^-$ 227.0872; found 227.0883.

Synthesis of I-28

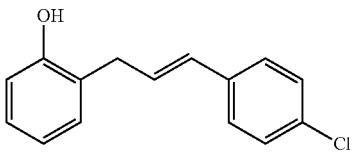 [SMILES: Oc1ccccc1C/C=C/c1ccc(Cl)cc1]

The general procedure was used with (E)-3-(4-chlorophenyl)prop-2-en-1-ol (84.3 mg, 0.5 mmol), phenol (70.6 mg, 0.75 mmol), acidic alumina (1 g), and 1,2-dichloroethane (5 mL). TLC analysis at 24 hours indicated complete consumption of (E)-3-(4-chlorophenyl)prop-2-en-1-ol. Compound I-28 was isolated as a white crystal solid (98.1 mg, 0.40 mmol, 80% yield); R$_f$=0.46 (Hexane/EtOAc=8:2); $^1$H NMR (700 MHz, Chloroform-d) δ 7.14-7.10 (m, 4H), 7.04-6.99 (m, 2H), 6.79-6.76 (m, 1H), 6.67 (d, J=7.9 Hz, 1H), 6.29 (d, J=15.9 Hz, 1H), 6.23 (dt, J=15.9, 6.4 Hz, 1H), 4.82 (s, 1H), 3.42 (d, J=6.3 Hz, 2H); $^{13}$C NMR (176 MHz, Chloroform-d) δ 153.95, 135.82, 132.93, 130.63, 130.22, 128.92, 128.77, 128.08, 127.50, 125.70, 121.20, 115.81, 34.02; HRMS: calculated for C15H12ClO (M-H)– 243.0577; found 243.0578.

Synthesis of I-29

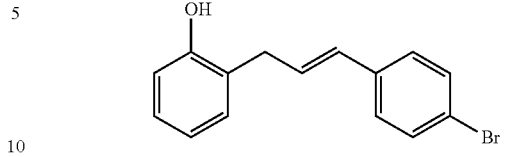

The general procedure was used with (E)-3-(4-bromophenyl)prop-2-en-1-ol (106.6 mg, 0.5 mmol), phenol (70.6 mg, 0.75 mmol), acidic alumina (1 g), and 1,2-dichloroethane (5 mL). TLC analysis at 72 hours indicated complete consumption of (E) (4-bromophenyl)prop-2-en-1-ol. Compound I-29 was isolated as a white solid (111.4 mg, 0.385 mmol, 77% yield); R$_f$=0.44 (Hexane/EtOAc=8:2); $^1$H NMR (700 MHz, Chloroform-d) 7.42-7.39 (m, 2H), 7.23-7.19 (m, 2H), 7.17-7.13 (m, 2H), 6.91 (td, J=7.5, 1.2 Hz, 1H), 6.81 (dd, J=7.9, 1.3 Hz, 1H), 6.45-6.34 (m, 2H), 4.90 (s, 1H), 3.55 (d, J=5.3 Hz, 2H); $^{13}$C NMR (176 MHz, Chloroform-d) δ 153.84, 136.15, 131.60, 130.51, 130.15, 128.95, 127.97, 127.72, 125.52, 121.08, 120.95, 115.69, 33.93; HRMS: calculated for C15H12BrO (M-H)$^-$ 287.0072; found 287.0085.

Synthesis of I-30

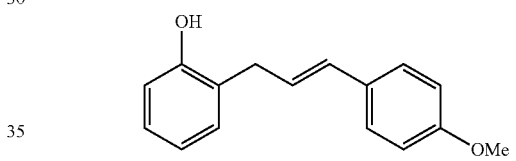

The general procedure was used with (E)-3-(4-methoxyphenyl)prop-2-en-1-ol (82.1 mg, 0.5 mmol), phenol (70.6 mg, 0.75 mmol), acidic alumina (1 g), and 1,2-dichloroethane (5 mL). TLC analysis at 5 hours indicated complete consumption of (E)-3-(4-methoxyphenyl)prop-2-en-1-ol. Compound I-30 was isolated as a white solid (40.6 mg, 0.169 mmol, 34% yield); R$_f$=0.62 (Hexane/EtOAc=7:3); $^1$H NMR (700 MHz, Chloroform-d) δ 7.30 (d, J=8.7 Hz, 2H), 7.18 (d, J=7.5 Hz, 1H), 7.15 (td, J=7.8, 1.5 Hz, 1H), 6.91 (td, J=7.5, 1.0 Hz, 1H), 6.86-6.82 (m, 4H), 6.47 (d, J=15.9 Hz, 1H), 6.25 (dt, J=15.9, 6.7 Hz, 1H), 5.05 (s, 1H), 3.81 (s, 3H), 3.56 (d, J=6.7 Hz, 2H); $^{13}$C NMR (176 MHz, Chloroform-d) δ 159.15, 154.26, 131.13, 130.57, 130.02, 128.02, 127.48, 125.97, 125.76, 121.08, 115.92, 114.09, 55.43, 34.31; HRMS: calculated for C16H15O2 (M-H)$^-$ 239.1072; found 239.1079.

Synthesis of I-31

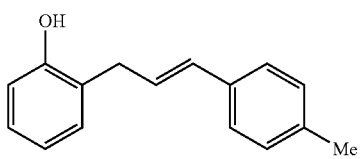 [SMILES: Cc1ccc(/C=C/Cc2ccccc2O)cc1]

The general procedure was used with (E)-3-(4-methylphenyl)prop-2-en-1-ol (74.1 mg, 0.5 mmol), phenol (70.6 mg, 0.75 mmol), acidic alumina (1 g), and 1,2-dichloroethane (5 mL). TLC analysis at 48 hours indicated complete consumption of (E)-3-(4-methylphenyl)prop-2-en-1-ol. Compound I-31 was isolated as a colorless oil (93.5 mg, 0.417 mmol, 83% yield); $R_f$=0.48 (Hexane/EtOAc=8:2); $^1$H NMR (700 MHz, Chloroform-d) δ 7.28-7.24 (m, 2H), 7.19-7.13 (m, 2H), 7.13-7.09 (m, 2H), 6.91 (tt, J=7.5, 1.5 Hz, 1H), 6.83 (d, J=8.0 Hz, 1H), 6.49 (dd, J=15.9, 1.8 Hz, 1H), 6.34 (dtd, J=15.5, 6.7, 1.7 Hz, 1H), 5.02-4.88 (m, 1H), 3.57 (d, J=6.6 Hz, 2H), 2.33 (s, 3H); $^{13}$C NMR (176 MHz, Chloroform-d) δ 154.23, 137.28, 134.39, 131.61, 130.59, 129.37, 128.04, 126.91, 126.25, 125.87, 121.12, 115.94, 34.31, 21.30; HRMS: calculated for C16H15O (M-H)$^-$ 223.1123; found 223.1120.

Synthesis of I-32

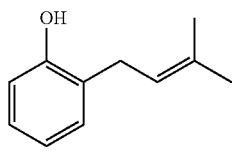

The general procedure was used with prenol (43.1 mg, 0.5 mmol, 50.8 uL), phenol (70.6 mg, 0.75 mmol), acidic alumina (1 g), and 1,2-dichloroethane (5 mL). TLC analysis at 22 hours indicated complete consumption of prenol. Compound I-32 was isolated as a colorless oil (40.8 mg, 0.251 mmol, 50% yield); $R_f$=0.73 (Hexane/EtOAc=7:3); $^1$H NMR (700 MHz, Chloroform-d) δ 7.11 (t, J=7.8 Hz, 2H), 6.87 (t, J=7.4 Hz, 1H), 6.80 (d, J=7.8 Hz, 1H), 5.33 (t, J=6.9 Hz, 1H), 5.07 (s, 1H), 3.36 (d, J=7.2 Hz, 2H), 1.79 (s, 3H), 1.78 (s, 3H); $^{13}$C NMR (176 MHz, Chloroform-d) δ 154.44, 134.94, 130.11, 127.68, 126.93, 121.92, 120.90, 115.85, 29.96, 25.93, 18.01;

Synthesis of I-33

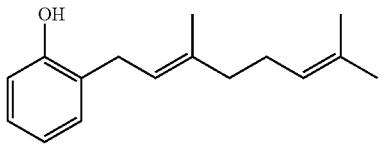 [SMILES: CC(C)=CCC/C(C)=C/Cc1ccccc1O]

The general procedure was used with geraniol (77.1 mg, 0.5 mmol, 86.8 uL), phenol (70.6 mg, 0.75 mmol), acidic alumina (1 g), and 1,2-dichloroethane (5 mL). TLC analysis at 29 hours indicated complete consumption of geraniol. Compound I-33 was isolated as a colorless oil (83.3 mg, 0.362 mmol, 72% yield); $R_f$=0.73 (Hexane/EtOAc=7:3); $^1$H NMR (700 MHz, Chloroform-d) δ 7.11 (d, J=7.6 Hz, 2H), 6.87 (t, J=7.4 Hz, 1H), 6.81 (d, J=7.8 Hz, 1H), 5.33 (t, J=7.1 Hz, 1H), 5.09-5.07 (m, 2H), 3.37 (d, J=7.2 Hz, 2H), 2.15-2.11 (m, 2H), 2.11-2.07 (m, 2H), 1.78 (s, 3H), 1.69 (s, 3H), 1.60 (s, 3H); $^{13}$C NMR (176 MHz, Chloroform-d) δ 154.59, 138.72, 132.13, 131.83, 130.08, 127.68, 126.94, 123.99, 121.78, 120.87, 115.96, 39.84, 29.94, 26.56, 25.84, 17.85, 16.32; HRMS: calculated for C16H21O (M-H)$^-$ 229.1592; found 229.1583.

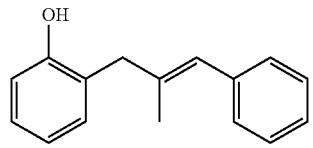 [SMILES: C/C(=C\c1ccccc1)Cc1ccccc1O]

Synthesis of I-34

The general procedure was used with (E)-2-methyl-3-phenylprop-2-en-1-ol (74.1 mg, 0.5 mmol, 71.9 uL), phenol (70.6 mg, 0.75 mmol), acidic alumina (1 g), and 1,2-dichloroethane (5 mL). TLC analysis at 48 hours indicated complete consumption of geraniol. Compound I-34 was isolated as a colorless oil (89.2 mg, 0.398 mmol, 80% yield); $R_f$=0.73 (Hexane/EtOAc=7:3); $^1$H NMR (700 MHz, Chloroform-d) δ 7.33 (t, J=7.6 Hz, 2H), 7.28-7.24 (m, 3H), 7.22 (t, J=7.3 Hz, 1H), 7.17 (d, J=7.3 Hz, 2H), 6.91 (t, J=7.4 Hz, 1H), 6.85 (d, J=8.2 Hz, 1H), 6.48 (s, 1H), 5.19 (s, 1H), 3.55 (s, 2H), 1.87 (s, 3H); $^{13}$C NMR (176 MHz, Chloroform-d) δ 154.93, 137.83, 137.69, 131.17, 128.98, 128.25, 128.16, 127.03, 126.50, 125.02, 120.88, 116.07, 42.11, 17.87; HRMS: calculated for C16H15O (M-H)$^-$ 223.1123; found 223.1113.

Synthesis of I-35

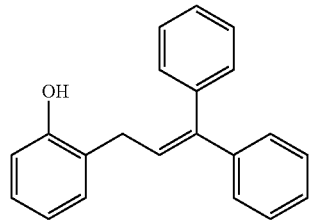 [SMILES: Oc1ccccc1CC=C(c1ccccc1)c1ccccc1]

The general procedure was used with 3,3-diphenylprop-2-en-1-ol (105.1 mg, 0.5 mmol), phenol (70.6 mg, 0.75 mmol), acidic alumina (1 g), and 1,2-dichloroethane (5 mL). TLC analysis at 48 hours indicated complete consumption of 3,3-diphenylprop-2-en-1-ol. Compound I-35 was isolated as a colorless oil (100.2 mg, 0.350 mmol, 70% yield); $R_f$=0.64 (100% DCM); $^1$H NMR (700 MHz, Chloroform-d) δ 7.43 (q, J=6.4, 5.3 Hz, 2H), 7.37 (t, J=7.4 Hz, 1H), 7.27 (qd, J=10.7, 9.8, 6.5 Hz, 7H), 7.19-7.10 (m, 2H), 6.90 (q, J=6.6, 5.8 Hz, 1H), 6.79 (dd, J=8.2, 3.0 Hz, 1H), 6.28 (t, J=7.5 Hz, 1H), 4.78-4.69 (m, 1H), 3.48 (dt, J=898.6, 6.5 Hz, 2H); $^{13}$C NMR (176 MHz, Chloroform-d) δ 153.97, 143.31, 142.27, 139.57, 130.10, 130.03, 128.64, 128.29, 127.82, 127.59, 127.51, 127.37, 126.69, 126.52, 121.05, 115.64, 30.96; HRMS: calculated for C21H17O (M-H)$^-$ 285.1279; found 285.1274.

Synthesis of I-36

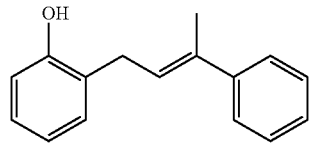 [SMILES: C/C(=C\Cc1ccccc1O)c1ccccc1]

The general procedure was used with (E)-3-phenylbut-2-en-1-ol (74.1 mg, 0.5 mmol), phenol (70.6 mg, 0.75 mmol), acidic aluminum oxide (1 g) and dichloroethane (5 mL). TLC analysis at 24 hours indicated complete consumption of (E)-3-phenylbut-2-en-1-ol. Compound I-36 was isolated as a yellow oil (92.3 mg, 0.411 mmol, 82% yield); $R_f$=0.63 (Hexane/EtOAc=7:3); $^1$H NMR (700 MHz, Chloroform-d) δ 7.42-7.39 (m, 2H), 7.31 (t, J=7.8 Hz, 2H), 7.25-7.22 (m, 1H), 7.18 (dd, J=7.5, 1.7 Hz, 1H), 7.12 (td, J=7.7, 1.7 Hz, 1H), 6.89 (td, J=7.5, 1.2 Hz, 1H), 6.80 (dd, J=7.9, 1.2 Hz, 1H), 5.95 (tt, J=5.8, 1.4 Hz, 1H), 4.88 (s, 1H), 3.57 (d, J=7.3 Hz, 2H), 2.19 (d, J=1.3 Hz, 3H); $^{13}$C NMR (176 MHz, Chloroform-d) δ 154.07, 143.45, 137.09, 130.18, 128.37, 127.72, 127.08, 126.77, 125.89, 125.53, 121.08, 115.72, 30.04, 16.16; HRMS: calculated for C16H15O (M-H)$^-$ 223.1123; found 223.1115.

Synthesis of I-37

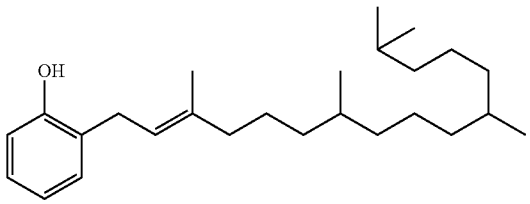 [SMILES: C/C(=C\Cc1ccccc1O)CCCC(C)CCCC(C)CCCC(C)C]

The general procedure was used with phytol (148.3 mg, 0.5 mmol, 174.4 uL), phenol (70.6 mg, 0.75 mmol), acidic aluminum oxide (1 g), and dichloroethane (5 mL). TLC analysis at 19 hours indicated complete consumption of phytol. Compound I-37 was isolated as a colorless oil (121.2 mg, 0.325 mmol, 65% yield); $R_f$=0.43 (Hexane/EtOAc=9:1); $^1$H NMR (700 MHz, Chloroform-d) δ 7.14-7.06 (m, 2H), 6.87 (t, J=7.4 Hz, 1H), 6.81 (d, J=7.6 Hz, 1H), 5.33 (t, J=7.2 Hz, 1H), 5.10 (s, 1H), 3.38 (d, J=7.0 Hz, 2H), 2.03 (h, J=7.4 Hz, 2H), 1.77 (s, 3H), 1.53 (dt, J=13.3, 6.7 Hz, 1H), 1.49-1.42 (m, 1H), 1.42-1.35 (m, 2H), 1.34-1.29 (m, 2H), 1.29-1.23 (m, 7H), 1.21-1.17 (m, 1H), 1.16-1.13 (m, 2H), 1.08-1.05 (m, 4H), 0.87 (d, J=6.6 Hz, 7H), 0.85 (d, J=3.0 Hz, 4H), 0.84 (d, J=3.0 Hz, 3H); $^{13}$C NMR (176 MHz, Chloroform-d) δ 154.45, 139.14, 129.96, 127.55, 126.77, 121.27, 120.72, 115.76, 40.03, 39.39, 37.45, 37.40, 37.31, 36.69, 32.81, 32.69, 29.80, 27.99, 25.35, 24.81, 24.48, 22.74, 22.64, 19.77, 19.73, 16.21;

Synthesis of I-38

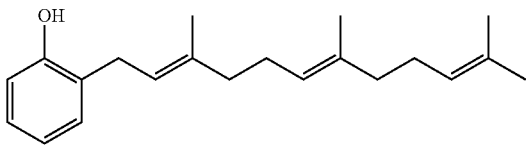 [SMILES: CC(C)=CCC/C(C)=C/CC/C(C)=C/Cc1ccccc1O]

The general procedure was used farnesol (222.4 mg, 1 mmol), phenol (140.1 mg, 1.5 mmol), acidic aluminum oxide (2 g), and dichloroethane (10 mL). TLC analysis at 40 hours indicated complete consumption of farnesol. Compound I-38 was isolated as a colorless oil (238.4 mg, 0.799 mmol, 80% yield); $R_f$=0.67 (Hexane/EtOAc=8:2); $^1$H NMR (700 MHz, Chloroform-d) δ 7.11 (d, J=7.4 Hz, 2H), 6.87 (td, J=7.4, 1.3 Hz, 1H), 6.83-6.79 (m, 1H), 5.35 (ddt, J=7.2, 5.8, 1.3 Hz, 1H), 5.13-5.07 (m, 3H), 3.38 (d, J=7.3 Hz, 2H), 2.15 (q, J=7.3 Hz, 2H), 2.08 (dt, J=23.4, 7.5 Hz, 4H), 1.99 (dd, J=9.2, 6.4 Hz, 2H), 1.79 (s, 3H), 1.69 (d, J=1.5 Hz, 3H), 1.61 (d, J=2.1 Hz, 6H); $^{13}$C NMR (176 MHz, Chloroform-d) δ 154.56, 138.71, 135.68, 131.43, 130.06, 127.66, 126.92, 124.51, 123.82, 121.76, 120.86, 115.92, 39.83, 39.82, 29.90, 26.83, 26.83, 26.52, 25.84, 17.84, 16.36, 16.19; HRMS: calculated for C21H29O (M-H)$^-$ 297.2218; found 297.2221.

Synthesis of I-39

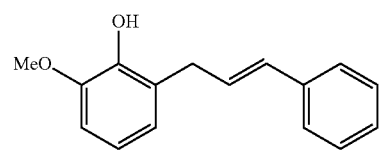 [SMILES: COc1cccc(C/C=C/c2ccccc2)c1O]

The general procedure was used with cinnamyl alcohol (67.1 mg, 0.5 mmol), 2-methoxyphenol (93.1 mg, 0.75 mmol, 83.7 uL), acidic aluminum oxide (1 g), and dichloroethane (5 mL). TLC analysis at 48 hours indicated cinnamyl alcohol was still existed. Compound I-39 was isolated as a yellow oil (17.5 mg, 0.073 mmol, 15% yield); $R_f$=0.68 (Hexane/EtOAc=7:3); $^1$H NMR (700 MHz, Chloroform-d) δ 7.35 (d, J=7.5 Hz, 2H), 7.27 (t, J=7.8 Hz, 2H), 7.18 (t, J=7.3 Hz, 1H), 6.82-6.75 (m, 3H), 6.46 (d, J=15.9 Hz, 1H), 6.40 (dt, J=15.9, 6.7 Hz, 1H), 5.73 (s, 1H), 3.90 (s, 3H), 3.57 (d, J=6.6 Hz, 2H); $^{13}$C NMR (176 MHz, Chloroform-d) δ 146.56, 143.59, 137.83, 130.88, 128.66, 128.56, 127.05, 126.25, 126.14, 122.44, 119.59, 108.87, 56.18, 33.13;

Synthesis of I-40

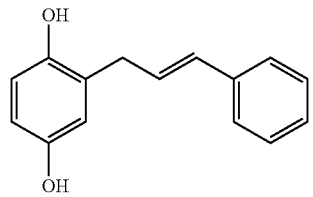 [SMILES: Oc1ccc(O)c(C/C=C/c2ccccc2)c1]

The general procedure was used with cinnamyl alcohol (67.1 mg, 0.5 mmol), hydroquinone (82.6 mg, 0.75 mmol), acidic aluminum oxide (1 g), and dichloroethane (5 mL). TLC analysis at 48 hours indicated complete consumption of cinnamyl alcohol. Compound I-40 was isolated as a yellow oil (58.6 mg, 0.259 mmol, 52% yield); $R_f$=0.26 (DCM/MeOH=98:2). $^1$H NMR (700 MHz, Chloroform-d) δ 7.35 (d, J=7.5 Hz, 2H), 7.30 (t, J=7.7 Hz, 2H), 7.22 (t, J=7.3 Hz, 1H), 6.70 (d, J=8.5 Hz, 1H), 6.67 (d, J=3.0 Hz, 1H), 6.62 (dd, J=8.5, 3.0 Hz, 1H), 6.50 (d, J=15.9 Hz, 1H), 6.36 (dt, J=15.9, 6.7 Hz, 1H), 4.56 (s, 1H), 4.39 (s, 1H), 3.51 (d, J=6.6 Hz, 2H); $^{13}$C NMR (176 MHz, Chloroform-d) δ 149.63, 148.01, 137.16, 131.86, 128.69, 127.67, 127.53, 127.22, 126.35, 117.18, 116.80, 114.32, 34.18; HRMS: calculated for C15H13O2 (M-H)$^-$ 225.0916; found 225.0919.

Synthesis of I-41

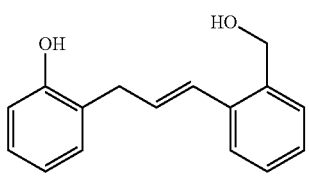 [SMILES: OCc1ccccc1/C=C/Cc1ccccc1O]

The general procedure was used with (E)-3-(2-(hydroxymethyl)phenyl)prop-2-en-1-ol (89.1 mg, 0.543 mmol), phenol (76.7 mg, 0.815 mmol,), acidic aluminum oxide (1.1 g), and dichloroethane (5.5 mL). TLC analysis at 72 hours indicated complete consumption of (E)-3-(2-(hydroxymethyl)phenyl)prop-2-en-1-ol. Compound I-41 was isolated a white solid (56.6 mg, 0.236 mmol, 47% yield); $R_f$=0.68 (Hexane/EtOAc=5:5); $^1$H NMR (600 MHz, Chloroform-d) δ 7.45 (dd, J=7.6, 1.5 Hz, 1H), 7.30 (dd, J=7.4, 1.6 Hz, 1H), 7.28-7.25 (m, 1H), 7.22 (td, J=7.4, 1.4 Hz, 1H), 7.17 (dd, J=7.4, 1.7 Hz, 1H), 7.13 (td, J=7.7, 1.7 Hz, 1H), 6.90 (td, J=7.5, 1.3 Hz, 1H), 6.83-6.79 (m, 2H), 6.27 (dt, J=15.5, 6.6 Hz, 1H), 5.53 (s, 1H), 4.73 (s, 2H), 3.59 (dd, J=6.6, 1.7 Hz, 2H), 1.96 (s, 1H); $^{13}$C NMR (151 MHz, Chloroform-d) δ 154.31, 137.35, 136.74, 131.27, 130.64, 128.65, 128.45, 128.09, 127.54, 126.55, 125.94, 121.14, 116.07, 63.91, 34.87;

Synthesis of I-42 and I-43

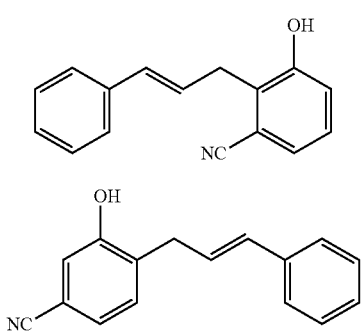

The general procedure was used with cinnamyl alcohol (268.4 mg, 2.0 mmol), 3-nitrilphenol (357.4 mg, 0.75 mmol), acidic aluminum oxide (4 g), and dichloroethane (20 mL). TLC analysis at 72 hours indicated complete consumption of cinnamyl alcohol. Compound I-42 was isolated by column chromatography on C$_{18}$ as a white solid (47.2 mg, 0.201 mmol, 10% yield). Compound I-43 was isolated by column chromatography on silica gel as a colorless oil (68.9 mg, 0.293 mmol, 15% yield);

Compound I-42, $R_f$=0.78 (Hexane/EtOAc=6:4); $^1$H NMR (700 MHz, DMSO-d6) δ 10.30 (s, 1H), 7.35 (d, J=7.5 Hz, 2H), 7.31-7.22 (m, 4H), 7.20 (t, J=7.3 Hz, 1H), 7.16 (dd, J=7.6, 1.6 Hz, 1H), 6.40-6.32 (m, 2H), 3.63 (d, J=5.4 Hz, 2H); $^{13}$C NMR (176 MHz, DMSO-d6) δ 155.74, 136.71, 130.53, 129.29, 128.58, 128.48, 127.25, 126.65, 125.96, 123.40, 120.11, 118.05, 112.61, 31.46;

Compound I-43, $R_f$=0.41 (Hexane/EtOAc=8:2); $^1$H NMR (700 MHz, Chloroform-d) δ 7.34 (d, J=7.7 Hz, 2H), 7.28 (t, J=7.7 Hz, 2H), 7.20 (t, J=7.3 Hz, 1H), 7.06 (t, J=8.0 Hz, 1H), 7.01 (d, J=8.0 Hz, 1H), 6.73 (d, J=8.0 Hz, 1H), 6.48 (d, J=15.9 Hz, 1H), 6.33 (dt, J=15.7, 6.4 Hz, 1H), 5.03 (s, 1H), 3.74 (d, J=6.4 Hz, 2H); $^{13}$C NMR (176 MHz, Chloroform-d) δ 155.01, 137.10, 135.15, 131.36, 128.50, 127.92, 127.31, 126.21, 126.19, 124.26, 122.11, 116.85, 114.31;

Synthesis of I-44

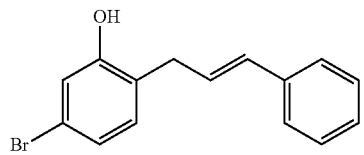

The general procedure was used with cinnamyl alcohol (134.2 mg, 1 mmol), 3-bromophenol (259.5 mg, 1.5 mmol), acidic aluminum oxide (2 g), and dichloroethane (10 mL). TLC analysis at 24 hours indicated complete consumption of cinnamyl alcohol. Compound I-44 was isolated as a colorless oil (214.9 mg, 0.75 mmol, 75% yield); $R_f$=0.64 (Hexane/EtOAc=8:2); $^1$H NMR (600 MHz, Chloroform-d) δ 7.35 (d, J=7.2 Hz, 2H), 7.30 (t, J=7.6 Hz, 2H), 7.22 (t, J=7.2 Hz, 1H), 7.03 (s, 2H), 6.99 (s, 1H), 6.49 (d, J=15.8 Hz, 1H), 6.34 (dt, J=15.9, 6.6 Hz, 1H), 3.51 (dd, J=6.6, 1.3 Hz, 2H); $^{13}$C NMR (151 MHz, Chloroform-d) δ 154.94, 137.03, 132.00, 131.74, 128.71, 127.60, 127.29, 126.34, 125.07, 124.13, 120.62, 119.08, 33.71;

Synthesis of I-45

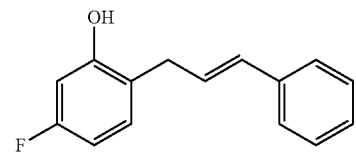 [SMILES: Oc1cc(F)ccc1C/C=C/c1ccccc1]

The general procedure was used with cinnamyl alcohol (134.2 mg, 1 mmol), 3-fluorophenol (168.2 mg, 1.5 mmol), acidic aluminum oxide (2 g), and dichloroethane (10 mL). TLC analysis at 24 hours indicated complete consumption of cinnamyl alcohol. Compound I-45 was isolated as a colorless oil (181.2 mg, 0.79 mmol, 79% yield); $R_f$=0.64 (Hexane/EtOAc=8:2)

$^1$H NMR (700 MHz, Chloroform-d) δ 7.36 (d, J=7.3 Hz, 2H), 7.30 (t, J=7.7 Hz, 2H), 7.23 (t, J=7.3 Hz, 1H), 7.10 (dd, J=8.2, 6.7 Hz, 1H), 6.63 (td, J=8.4, 2.5 Hz, 1H), 6.58 (dd, J=9.9, 2.5 Hz, 1H), 6.50 (d, J=15.9 Hz, 1H), 6.35 (dt, J=15.8, 6.6 Hz, 1H), 5.14 (s, 1H), 3.53 (d, J=6.5 Hz, 2H); $^{13}$C NMR (176 MHz, Chloroform-d) δ 163.17, 161.79, 155.18, 155.12, 137.00, 131.91, 131.26, 131.21, 128.72, 127.69, 127.63, 126.36, 121.40, 121.38, 107.81, 107.69, 103.72, 103.59, 33.71;

Synthesis of I-46

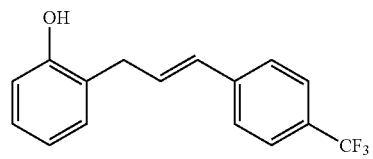 [SMILES: Oc1ccccc1C/C=C/c1ccc(C(F)(F)F)cc1]

The general procedure was used with (E)-3-(4-(trifluoromethyl)phenyl)prop-2-en-1-ol (101.2 mg, 0.5 mmol), phenol (70.6 mg, 0.75 mmol), acidic aluminum oxide (1 g), and dichloroethane (5 mL). TLC analysis at 67 hours indicated complete consumption of (E)-3-(4-(trifluoromethyl)phenyl)prop-2-en-1-ol. Compound I-46 was isolated as a colorless oil (104.1 mg, 0.374 mmol, 75% yield); $R_f$=0.83 (DCM/MeOH=98:2); $^1$H NMR (700 MHz, Chloroform-d) δ 7.56 (d, J=8.1 Hz, 2H), 7.46 (d, J=8.2 Hz, 2H), 7.21-7.16 (m, 2H), 6.94 (t, J=7.4 Hz, 1H), 6.83 (d, J=8.0 Hz, 1H), 6.56-6.52 (m, 2H), 4.84 (s, 1H), 3.61 (d, J=4.7 Hz, 2H); $^{13}$C NMR (176 MHz, Chloroform-d) δ 153.87, 140.87, 131.14, 130.69, 130.08, 129.43, 129.25, 129.06, 128.88, 128.15, 126.43, 125.63, 125.61, 125.59, 125.57, 125.52, 121.28, 115.79, 34.01;

Synthesis of I-47

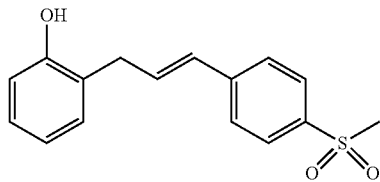 [SMILES: CS(=O)(=O)c1ccc(/C=C/Cc2ccccc2O)cc1]

The general procedure was used with (E)-3-(4-(methylsulfonyl)phenyl)prop-2-en-1-ol (106.2 mg, 0.5 mmol), phenol (70.6 mg, 0.75 mmol), acidic aluminum oxide (1 g), and dichloroethane (5 mL). TLC analysis at 72 hours indicated complete consumption of (E)-3-(4-(methylsulfonyl)phenyl)prop-2-en-1-ol. Compound I-47 was isolated as a colorless oil (74.3 mg, 0.258 mmol, 52% yield); $R_f$=0.67 (Hexanez/EtOAc=5:5); $^1$H NMR (700 MHz, Chloroform-d) δ 7.87-7.84 (m, 2H), 7.51 (dd, J=8.4, 1.3 Hz, 2H), 7.17 (ddd, J=13.9, 7.6, 1.6 Hz, 2H), 6.93 (tt, J=7.5, 1.3 Hz, 1H), 6.84 (dd, J=8.0, 1.2 Hz, 1H), 6.60 (dtd, J=15.9, 6.6, 1.1 Hz, 1H), 6.50 (dd, J=15.8, 1.5 Hz, 1H), 5.21 (s, 1H), 3.62 (dd, J=6.6, 1.5 Hz, 2H), 3.06 (d, J=1.0 Hz, 3H); $^{13}$C NMR (176 MHz, Chloroform-d) δ 153.87, 143.13, 138.51, 133.20, 130.66, 129.36, 128.15, 127.79, 126.92, 125.37, 121.15, 115.73, 44.73, 33.97;

Synthesis of I-48

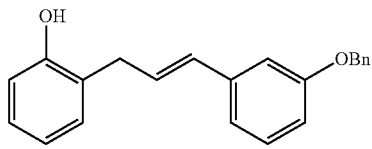 [SMILES: Oc1ccccc1C/C=C/c1cccc(OCc2ccccc2)c1]

The general procedure was used with (E)-3-(3-(benzyloxy)phenyl)prop-2-en-1-ol (120.2 mg, 0.5 mmol), phenol (70.6 mg, 0.75 mmol), acidic aluminum oxide (1 g), and dichloroethane (5 mL). TLC analysis at 6 hours indicated complete consumption of (E)-3-(3-(benzyloxy)phenyl)prop-2-en-1-ol. Compound I-48 was isolated as a colorless oil (99.7 mg, 0.315 mmol, 63% yield); $R_f$=0.66 (Hexanez/EtOAc=7:3); $^1$H NMR (700 MHz, Chloroform-d) δ 7.44 (d, J=8.1 Hz, 2H), 7.39 (t, J=7.5 Hz, 2H), 7.35-7.31 (m, 1H), 7.21 (t, J=7.9 Hz, 1H), 7.19-7.14 (m, 2H), 7.00 (s, 1H), 6.97 (dd, J=7.6, 1.5 Hz, 1H), 6.91 (td, J=7.4, 1.3 Hz, 1H), 6.85 (dd, J=8.3, 2.5 Hz, 1H), 6.82 (d, J=7.8 Hz, 1H), 6.48 (dd, J=15.8, 1.5 Hz, 1H), 6.39 (dt, J=15.6, 6.5 Hz, 1H), 5.06 (s, 2H), 4.91 (s, 1H), 3.57 (d, J=6.6 Hz, 2H); $^{13}$C NMR (176 MHz, Chloroform-d) δ 159.17, 154.11, 138.77, 137.15, 131.47, 130.61, 129.67, 128.72, 128.49, 128.09, 127.63, 125.77, 121.16, 119.31, 115.88, 113.99, 112.66, 70.11, 34.16;

Synthesis of I-49

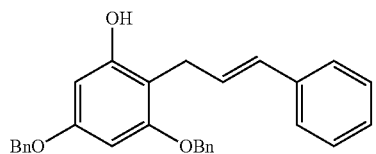 [SMILES: Oc1cc(OCc2ccccc2)cc(OCc2ccccc2)c1C/C=C/c1ccccc1]

The general procedure was used with cinnamyl alcohol (67.1 mg, 0.5 mmol), 3,5-bis(benzyloxy)phenol (229.8 mg, 0.75 mmol), acidic aluminum oxide (1 g), and dichloroethane (5 mL). TLC analysis at 22 hours indicated complete consumption of cinnamyl alcohol. Compound I-49 was isolated as an off white solid (143.5 mg, 0.340 mmol, 68% yield); $R_f$=0.63 (Hexanez/EtOAc=7:3); $^1$H NMR (700 MHz, Chloroform-d) δ 7.44-7.36 (m, 8H), 7.34-7.30 (m, 4H), 7.28 (t, J=7.6 Hz, 2H), 7.19 (t, J=7.3 Hz, 1H), 6.47 (d, J=15.8 Hz, 1H), 6.33 (dt, J=15.8, 6.4 Hz, 1H), 6.29 (d, J=2.3 Hz, 1H), 6.18 (d, J=2.2 Hz, 1H), 5.04 (d, J=3.2 Hz, 3H), 5.01 (s, 2H), 3.59 (dd, J=6.4, 1.8 Hz, 2H); $^{13}$C NMR (176 MHz, Chloroform-d) δ 158.96, 158.07, 155.81, 137.43, 137.21, 137.02, 130.68, 128.75, 128.67, 128.59, 128.47, 128.16, 128.00, 127.69, 127.44, 127.23, 126.28, 107.01, 95.27, 93.89, 70.51, 70.29, 26.60;

Synthesis of I-51

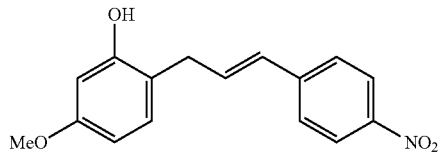 [SMILES: COc1ccc(C/C=C/c2ccc([N+](=O)[O-])cc2)c(O)c1]

The general procedure was used with (E)-3-(4-nitrophenyl)prop-2-en-1-ol (89.6 mg, 0.5 mmol), 3,5-dimethylphenol (93.1 mg, 0.75 mmol), acidic aluminum oxide (1 g), and dichloroethane (5 mL). TLC analysis at 42 hours indicated complete consumption of (E)-3-(4-nitrophenyl)prop-2-en-1-ol. Compound I-51 was isolated as a yellow solid (109.2 mg, 0.38 mmol, 77% yield); $R_f$=0.69 (Hexanez/EtOAc=5:5); $^1$H NMR (700 MHz, Chloroform-d) δ 8.14 (d, J=8.7 Hz, 2H), 7.45 (d, J=8.7 Hz, 2H), 7.05 (d, J=8.3 Hz, 1H), 6.58 (dt, J=15.7, 6.4 Hz, 1H), 6.53-6.44 (m, 2H), 6.41 (d, J=2.2 Hz, 1H), 4.99 (s, 1H), 3.78 (s, 3H), 3.54 (d, J=6.4 Hz, 2H); $^{13}$C NMR (176 MHz, Chloroform-d) δ 159.82, 154.64, 146.72, 144.08, 134.23, 131.18, 128.99, 126.72, 124.09, 117.35, 106.41, 102.23, 55.51, 33.41;

Synthesis of I-52

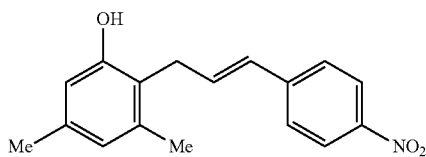

The general procedure was used with (E)-3-(4-nitrophenyl)prop-2-en-1-ol (89.6 mg, 0.5 mmol), 3,5-dimethylphenol (91.6 mg, 0.75 mmol), acidic aluminum oxide (1 g), and dichloroethane (5 mL). TLC analysis at 48 hours indicated complete consumption of (E)-3-(4-nitrophenyl)prop-2-en-1-ol. Compound I-52 was isolated as a yellow oil (88.1 mg, 0.31 mmol, 62% yield); $R_f$=0.52 (Hexanez/EtOAc=7:3); $^1$H NMR (700 MHz, Chloroform-d) δ 8.12 (d, J=8.8 Hz, 2H), 7.42 (d, J=8.8 Hz, 2H), 6.64 (s, 1H), 6.54 (dt, J=15.9, 6.1 Hz, 1H), 6.50 (s, 1H), 6.38 (d, J=15.9 Hz, 1H), 4.72 (s, 1H), 3.59 (d, J=5.1 Hz, 2H), 2.29 (s, 3H), 2.26 (s, 3H); $^{13}$C NMR (176 MHz, Chloroform-d) δ 153.68, 146.59, 144.30, 138.26, 137.41, 133.61, 128.27, 126.64, 124.03, 124.01, 120.43, 114.04, 29.72, 21.09, 19.64;

Synthesis of I-53

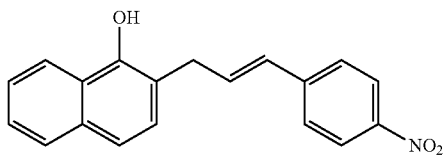 [SMILES: O=[N+]([O-])c1ccc(/C=C/Cc2ccc3ccccc3c2O)cc1]

The general procedure was used with (E)-3-(4-nitrophenyl)prop-2-en-1-ol (89.6 mg, 0.5 mmol), naphthalen-1-ol (108.1 mg, 0.75 mmol), acidic aluminum oxide (1 g), and dichloroethane (5 mL). TLC analysis at 24 hours indicated complete consumption of (E)-3-(4-nitrophenyl)prop-2-en-1-ol. Compound I-53 was isolated as a yellow oil (120.1 mg, 0.39 mmol, 79% yield); $R_f$=0.46 (Hexanez/EtOAc=7:3); $^1$H NMR (700 MHz, Chloroform-d) δ 8.14 (d, J=8.7 Hz, 2H), 8.11 (d, J=8.2 Hz, 1H), 7.82 (d, J=7.9 Hz, 1H), 7.52-7.43 (m, 5H), 7.28 (d, J=8.4 Hz, 1H), 6.64 (dt, J=15.9, 6.3 Hz, 1H), 6.54 (d, J=15.9 Hz, 1H), 5.35 (s, 1H), 3.78 (d, J=6.1 Hz, 2H); $^{13}$C NMR (176 MHz, Chloroform-d) δ 149.12, 146.89, 143.58, 133.97, 133.13, 129.63, 128.43, 128.00, 126.83, 126.12, 125.77, 124.73, 124.12, 121.03, 120.85, 118.04, 34.40;

Synthesis of I-54

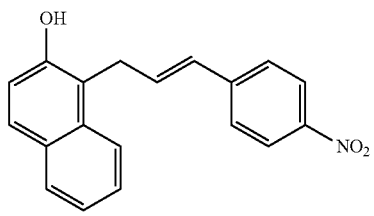 [SMILES: O=[N+]([O-])c1ccc(/C=C/Cc2c(O)ccc3ccccc23)cc1]

The general procedure was used with (E)-3-(4-nitrophenyl)prop-2-en-1-ol (89.6 mg, 0.5 mmol), naphthalen-2-ol (108.1 mg, 0.75 mmol), acidic aluminum oxide (1 g), and dichloroethane (5 mL). TLC analysis at 24 hours indicated complete consumption of (E)-3-(4-nitrophenyl)prop-2-en-1-ol. Compound I-54 was isolated as a yellow oil (135.0 mg, 0.44 mmol, 88% yield); $R_f$=0.37 (Hexanez/EtOAc=7:3); $^1$H NMR (700 MHz, Chloroform-d) δ 8.08 (d, J=8.8 Hz, 2H), 7.92 (d, J=8.5 Hz, 1H), 7.81 (d, J=8.1 Hz, 1H), 7.71 (d, J=8.8 Hz, 1H), 7.53-7.49 (m, 1H), 7.38 (d, J=8.8 Hz, 3H), 7.11 (d, J=8.7 Hz, 1H), 6.66 (dt, J=15.9, 6.1 Hz, 1H), 6.44 (d, J=15.9 Hz, 1H), 5.17 (s, 1H), 4.04 (dd, J=6.1, 1.4 Hz, 2H); $^{13}$C NMR (176 MHz, Chloroform-d) δ 151.07, 146.62, 144.12, 133.58, 133.40, 129.59, 128.88, 128.85, 128.78, 126.97, 126.67, 124.00, 123.51, 123.02, 117.89, 116.64, 28.63;

Synthesis of I-55 and I-56

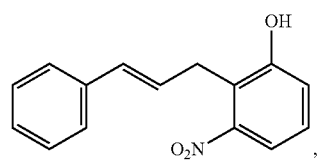

I-55

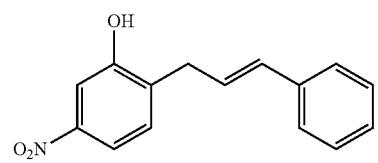

I-56

The general procedure was used with cinnamyl alcohol (268.4 mg, 2.0 mmol), 3-nitrophenol (417.3 mg, 3.0 mmol), acidic aluminum oxide (4 g), and dichloroethane (20 mL). TLC analysis at 48 hours indicated complete consumption of cinnamyl alcohol. Compound I-55 was isolated by column chromatography on C18 as a brown solid (38.9 mg, 0.17 mmol, 9% yield); Compound I-56 was isolated by column chromatography on $C_{18}$ as a yellow solid (62.7 mg, 0.28 mmol, 14% yield); Compound I-55, $R_f$=0.61 (Hexanez/EtOAc=7:3); $^1$H NMR (700 MHz, Chloroform-d) δ 7.78 (d, J=8.3 Hz, 1H), 7.69 (s, 1H), 7.36 (d, J=7.8 Hz, 2H), 7.33-7.30 (m, 4H), 7.24 (t, J=7.3 Hz, 1H), 6.53 (d, J=15.9 Hz, 1H), 6.38-6.31 (m, 1H), 5.54 (s, 1H), 3.64 (d, J=6.7 Hz, 2H); 13C NMR (176 MHz, Chloroform-d) δ 154.42, 147.70, 136.77, 134.06, 132.94, 130.91, 128.79, 127.87, 126.39, 125.95, 116.27, 110.79, 34.06;

Compound I-56, Rf=0.37 (Hexanez/EtOAc=7:3); 1H NMR (700 MHz, Chloroform-d) δ 7.45 (d, J=8.1 Hz, 1H), 7.34 (d, J=7.7 Hz, 2H), 7.28 (t, J=7.4 Hz, 2H), 7.27-7.23 (m, 2H), 7.21 (t, J=7.3 Hz, 1H), 7.06 (d, J=8.0 Hz, 1H), 6.55 (d, J=15.8 Hz, 1H), 6.41-6.35 (m, 1H), 5.46 (s, 1H), 3.75 (d, J=6.5 Hz, 2H); 13C NMR (176 MHz, Chloroform-d) δ 155.45, 151.12, 136.93, 132.35, 128.68, 127.89, 127.68, 126.43, 125.88, 120.98, 120.23, 117.03, 29.52;

Synthesis of I-57

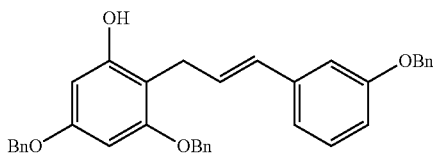 [SMILES: Oc1cc(OCc2ccccc2)cc(OCc2ccccc2)c1C/C=C/c1cccc(OCc2ccccc2)c1]

The general procedure was used with (E)-3-(3-(benzyloxy)phenyl)prop-2-en-1-ol (120.2 mg, 0.5 mmol), 3,5-bis(benzyloxy)phenol (229.8 mg, 0.75 mmol), acidic aluminum oxide (1 g), and dichloroethane (5 mL). TLC analysis at 22 hours indicated complete consumption of (E)-3-(3-(benzyloxy)phenyl)prop-2-en-1-ol. Compound I-57 was isolated as a yellow oil (210.1 mg, 0.355 mmol, 71% yield); $R_f$=0.45 (Hexanez/EtOAc=7:3); $^1$H NMR (700 MHz, Chloroform-d) δ 7.44-7.30 (m, 16H), 7.19 (t, J=7.9 Hz, 1H), 6.96 (t, J=2.0 Hz, 1H), 6.93 (d, J=7.6 Hz, 1H), 6.82 (dd, J=8.2, 2.5 Hz, 1H), 6.43 (d, J=15.8 Hz, 1H), 6.32 (dt, J=15.9, 6.4 Hz, 1H), 6.29 (d, J=2.3 Hz, 1H), 6.17 (d, J=2.3 Hz, 1H), 5.05 (s, 2H), 5.03 (s, 2H), 5.01 (s, 2H), 3.60-3.56 (m, 2H); $^{13}$C NMR (176 MHz, Chloroform-d) 159.13, 158.96, 158.08, 155.77, 138.99, 137.20, 137.01, 130.50, 129.57, 128.90, 128.75, 128.70, 128.67, 128.16, 128.06, 128.00, 127.68, 127.62, 127.44, 119.28, 113.83, 112.53, 106.97, 95.26, 93.87, 70.50, 70.29, 70.08, 26.56;

Synthesis of I-58

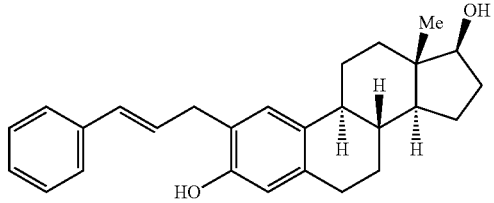

The general procedure was used with cinnamyl alcohol (67.1 mg, 0.5 mmol), beta-estradiol (204.3 mg, 0.75 mmol), acidic aluminum oxide (1 g), and dichloroethane (5 mL). TLC analysis at 18 hours indicated complete consumption of cinnamyl alcohol. Compound I-58 was isolated as a white solid (159.4 mg, 0.410 mmol, 82% yield); $R_f$=0.36 (DCM/MeOH=98:2); $^1$H NMR (700 MHz, Chloroform-d) δ 7.35 (dt, J=8.1, 1.8 Hz, 2H), 7.29 (dd, J=8.5, 6.9 Hz, 2H), 7.23-7.18 (m, 1H), 7.08 (s, 1H), 6.56 (s, 1H), 6.51 (dt, J=15.9, 1.7 Hz, 1H), 6.38 (dt, J=15.9, 6.7 Hz, 1H), 4.86 (s, 1H), 3.73 (t, J=8.6 Hz, 1H), 3.58-3.48 (m, 2H), 2.87-2.76 (m, 2H), 2.32 (dtd, J=13.5, 4.2, 2.6 Hz, 1H), 2.20-2.15 (m, 1H), 2.12 (dtd, J=13.4, 9.3, 5.8 Hz, 1H), 1.94 (ddd, J=12.7, 4.0, 2.8 Hz, 1H), 1.89-1.85 (m, 1H), 1.73-1.67 (m, 1H), 1.59 (s, 1H), 1.53-1.26 (m, 5H), 1.19 (ddd, J=12.4, 11.0, 7.3 Hz, 1H), 0.78 (s, 3H); $^{13}$C NMR (176 MHz, Chloroform-d) δ 152.00, 137.34, 136.61, 132.96, 131.31, 128.64, 128.57, 127.54, 127.37, 126.33, 123.03, 115.94, 82.09, 50.17, 44.10, 43.39, 39.01, 36.85, 34.40, 30.73, 29.40, 27.38, 26.54, 23.27, 11.22;

Synthesis of I-59

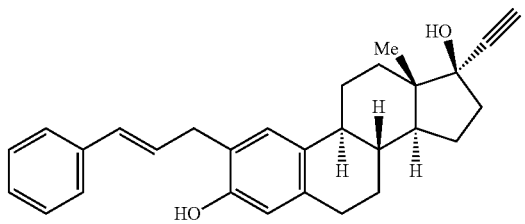

The general procedure was used with cinnamyl alcohol (67.1 mg, 0.5 mmol), 17-alpha-ethynylestradiol (222.3 mg, 0.75 mmol), acidic aluminum oxide (1 g), and dichloroethane (5 mL). TLC analysis at 21 hours indicated complete consumption of cinnamyl alcohol. Compound I-59 was isolated as a white solid (143.2 mg, 0.347 mmol, 69% yield); $R_f$=0.80 (Hexane/EtOAc=6:4); $^1$H NMR (700 MHz, Chloroform-d) δ 7.35 (d, J=7.3 Hz, 2H), 7.29 (t, J=7.7 Hz, 2H), 7.21 (t, J=7.3 Hz, 1H), 7.08 (s, 1H), 6.56 (s, 1H), 6.51 (d, J=15.9 Hz, 1H), 6.38 (dt, J=15.9, 6.7 Hz, 1H), 4.85 (s, 1H), 3.53 (m, 2H), 2.84-2.78 (m, 2H), 2.60 (s, 1H), 2.40-2.31 (m, 2H), 2.25-2.19 (m, 1H), 2.05-2.00 (m, 1H), 1.95 (s, 1H), 1.92-1.85 (m, 2H), 1.81-1.78 (m, 1H), 1.73-1.68 (m, 2H), 1.53-1.32 (m, 4H); $^{13}$C NMR (176 MHz, Chloroform-d) δ 152.00, 137.31, 136.61, 132.89, 131.34, 128.64, 128.54, 127.58, 127.38, 126.33, 123.03, 115.95, 87.63, 80.06, 74.20, 49.60, 43.67, 39.58, 39.10, 34.41, 32.87, 29.41, 27.37, 26.61, 22.94, 12.84;

Synthesis of I-60

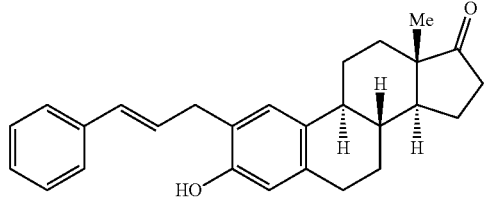

The general procedure was used with cinnamyl alcohol (67.1 mg, 0.5 mmol), estrone (202.8 mg, 0.75 mmol), acidic aluminum oxide (1 g), and dichloroethane (5 mL). TLC analysis at 21 hours indicated complete consumption of cinnamyl alcohol. Compound I-60 was isolated as a colorless oil (119.9 mg, 0.310 mmol, 62% yield); $R_f$=0.84 (Hexane/EtOAc=6:4); $^1$H NMR (700 MHz, Chloroform-d) δ 7.35 (d, J=7.3 Hz, 2H), 7.29 (t, J=7.6 Hz, 2H), 7.21 (t, J=7.3 Hz, 1H), 7.08 (s, 1H), 6.58 (s, 1H), 6.51 (d, J=15.9 Hz, 1H), 6.37 (dt, J=15.7, 6.6 Hz, 1H), 4.98 (s, 1H), 3.58-3.49 (m, 2H), 2.91-2.81 (m, 2H), 2.51 (dd, J=19.2, 8.6 Hz, 1H), 2.43-2.38 (m, 1H), 2.24 (dt, J=11.1, 5.8 Hz, 1H), 2.19-2.11 (m, 1H), 2.05 (ddd, J=13.3, 8.7, 5.8 Hz, 2H), 2.02-1.92 (m, 2H), 1.64-1.40 (m, 6H), 0.91 (s, 3H); $^{13}$C NMR (176 MHz, Chloroform-d) δ 221.35, 152.18, 137.29, 136.36, 132.33, 131.36, 128.64, 128.44, 127.54, 127.40, 126.32, 123.24, 115.97, 50.54, 48.18, 44.12, 38.53, 36.03, 34.

Example 6: Synthesis of an Exemplary Anti-Inflammatory Drug Candidate (L-651896)

To further illustrate the utility of the method of the application, synthetic target L-651896 (I-125), an anti-inflammatory drug candidate developed at Merck, was selected.[63] The reported synthesis of I-125 was accomplished in seven steps from phenol II-4 wherein and allylic alcohol III-4 (Scheme 8).[64] When the same two substrates were subjected to the alumina-templated allylation reaction of the application=, the final product (I-125) was obtained in one step with an isolated yield of 49%.

Scheme 8

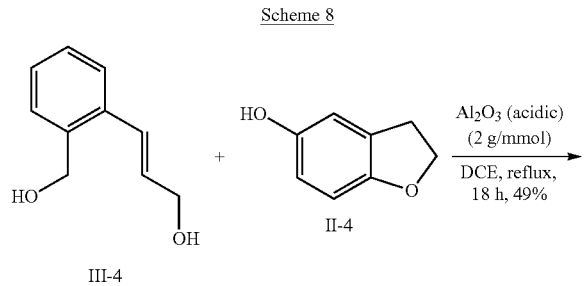

Synthesis of I-125

Step 1

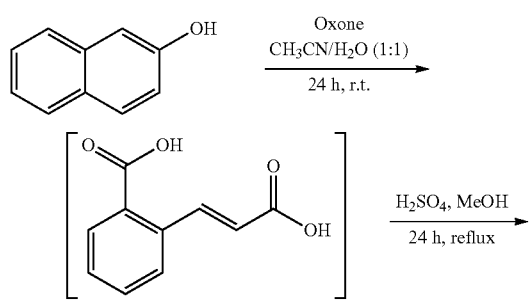

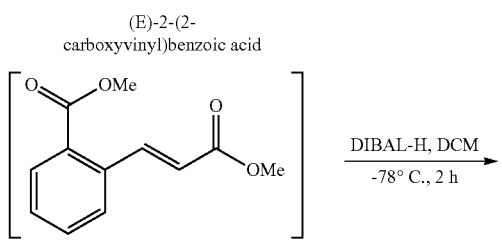

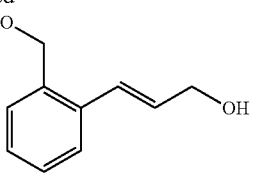

III-4
(E)-3-(2-(hydroxymethyl)phenyl)prop-2-en-1-ol

To a solution of 2-naphthol (2 g, 13.9 mmol) in an acetonitrile-water (100 mL, 1:1, v/v) mixture was incrementally added Oxone (6.346 g, 41.7 mmol). After completion of the reaction, based on TLC analysis, the reaction mixture was extracted with ethyl acetate multiple times. The combined organic extract was dried over anhydrous $Na_2SO_4$ and concentrated in vacuum to give a crude yellow solid product (E)-2-(2-carboxyvinyl)benzoic acid. The crude product was directly used without purification for the next step. A catalytic amount of concentrated $H_2SO_4$ was slowly added to the solution of (E)-2-(2-carboxyvinyl)benzoic acid in MeOH, the mixture was stirred at reflux for 24 hours and then concentrated in vacuo, the residue was diluted with DCM and washed with saturated $NaHCO_3$, brine and dried over $Na_2SO_4$ to give a crude yellow oil methyl (E)-2-(3-methoxy-3-oxoprop-1-en-1-yl)benzoate. Crude oil was used without purification for the next step. The crude oil from last step (379 mg, 1.72 mmol, 1 equiv.) was dissolved in anhydrous DCM (18 mL) and cooled to −78° C. under Argon. DIBAL-H (6.145 mL, 7.6 mmol) was dropwise added to the solution, the reaction mixture was kept at −78° C. under Argon with stirring for 2 hours and then quenched by 10% NaOH (18 mL) at −78° C. The reaction mixture was warmed to room temperature with stirring for another 1 hour, and then was extracted by DCM (3×50 mL). Organic layers were combined, washed with brine, dried over $Na_2SO_4$, concentrated under reduced pressure and the residue purified by C18 column chromatography, eluted with $CH_3CN/H_2O$ to afford compound III-4 (E)-3-(2-(hydroxymethyl)phenyl)prop-2-en-1-ol as a yellow oil.

$^1$H NMR (700 MHz, Chloroform-d) δ 7.40 (d, J=7.6 Hz, 1H), 7.22 (t, J=7.7 Hz, 2H), 7.20-7.16 (m, 1H), 6.82 (d, J=15.8 Hz, 1H), 6.15 (dt, J=1.8, 5.2 Hz, 1H), 4.58 (s, 2H), 4.16 (dt, J=5.2, 1.4 Hz, 2H), 3.92 (s, 2H);

$^{13}$C NMR (176 MHz, Chloroform-d) δ 137.5, 136.1, 131.0, 129.0, 128.2, 127.6, 127.2, 126.2, 63.1, 63.0. This spectral data is consistent with a previous literature report.[64]

Step 2

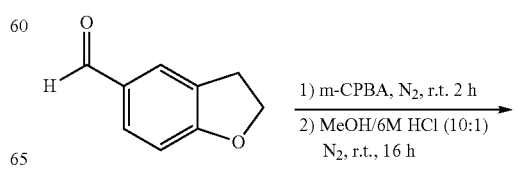

-continued

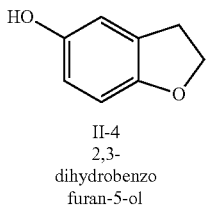

II-4
2,3-dihydrobenzofuran-5-ol 2,3-dihydro-1-benzofuran-5-carbaldehyde (500 mg, 3.37 mmol) was dissolved in 5 mL anhydrous DCM in a 50 mL round bottom flask charged with a magnetic stir bar. The flask was flushed with nitrogen and cooled to 0° C. in an ice bath. m-CPBA (1.187 g, 5.16 mmol) was added to the solution and the reaction mixture was stirred at 0° C. for 5 minutes, then warmed to room temperature with stirring for another 2 hours. The reaction mixture was washed with saturated $Na_2SO_3$ solution and extracted by DCM (3×50 mL), organic layers were combined, dried over $Na_2SO_4$, and concentrated in vacuo. The crude residue was dissolved in a MeOH-6M HCl (11 mL, 10:1, v/v) mixture and stirred under nitrogen for 16 hours. The mixture was washed by saturated $NaHCO_3$, brine, dried over $Na_2SO_4$ and concentrated in vacuo. The residue was purified by flash column chromatography on silica gel, eluted with EtOAc/Hexane to yield compound 84 2,3-dihydrobenzofuran-5-ol as a white solid.

$^1$H NMR (700 MHz, Chloroform-d) δ 6.72 (dt, J=2.5, 1.1 Hz, 1H), 6.63 (d, J=8.5 Hz, 1H), 6.56 (dd, J=8.5, 2.6 Hz, 1H), 4.55 (s, 1H), 4.53 (t, J=8.6 Hz, 2H), 3.16 (t, J=8.6 Hz, 2H);

$^{13}$C NMR (176 MHz, Chloroform-d) δ 154.2, 149.7, 128.3, 114.3, 112.5, 109.4, 71.4, 30.3 This spectral data is consistent with a previous literature report.[64]

Step 3: Synthesis of Compound 85 (L-651896, I-125)

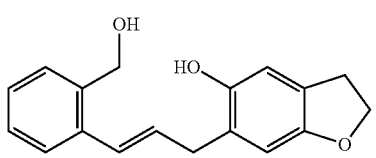 [SMILES: OCc1ccccc1/C=C/Cc1cc2c(cc1O)CCO2]

General Procedure as described in Example 4 was used with (E)-3-(2-(hydroxymethyl)phenyl)prop-2-en-1-ol (130.0 mg, 0.79 mmol), 2,3-dihydrobenzofuran-5-ol (161.7 mg, 1.19 mmol), acidic aluminum oxide (1.6 g), and dichloroethane (8 mL). TLC analysis at 16 hours indicated complete consumption of (E)-3-(2-(hydroxymethyl)phenyl)prop-2-en-1-ol. Compound I-125 (L-651896) was isolated a white solid (110.2 mg, 0.39 mmol, 49% yield); $R_f$=0.50 (Hexane/EtOAc=5:5); $^1$H NMR (700 MHz, Acetone-d6) δ 7.70 (s, 1H), 7.47-7.44 (m, 1H), 7.42-7.39 (m, 1H), 7.22-7.16 (m, 2H), 6.81 (d, J=15.6 Hz, 1H), 6.75 (s, 1H), 6.56 (s, 1H), 6.29 (dt, J=15.6, 7.0 Hz, 1H), 4.70 (d, J=5.4 Hz, 2H), 4.42 (t, J=8.6 Hz, 2H), 4.08 (t, J=5.5 Hz, 1H), 3.52-3.47 (m, 2H), 3.13-3.06 (m, 2H); $^{13}$C NMR (176 MHz, Acetone-d6) δ 154.5, 149.4, 139.6, 137.0, 131.8, 128.4, 128.4, 128.0, 127.6, 126.5, 126.3, 126.3, 112.8, 110.6, 71.5, 62.7, 34.6, 30.7; This spectral data is consistent with a previous literature report.[64]

Example 7

The effect of various commercially available reagents instead of or in addition to alumina on an exemplary process of the application was investigated.

General Reaction Procedure: Geraniol (III-1, 1.0 equiv.) was charged to a microwave reaction vial in 1,2-dichloroethane (10 mL/mmol of geraniol) followed by 1-naphthol (II-5, 1.5 equiv.) and additive. The suspension was stirred in a Microwave Synthesis Reactor at 150° C. for 10 minutes. The reaction mixture was cooled and filtered through Celite®. The solids were washed with EtOAc (3×10 mL) and the filtrates combined and concentrated in vacuo. The yield of product (I-129) was determined by $^1$H NMR analysis of the crude reaction mixture using 1,2-dibromomethane as an internal standard.

TABLE 7

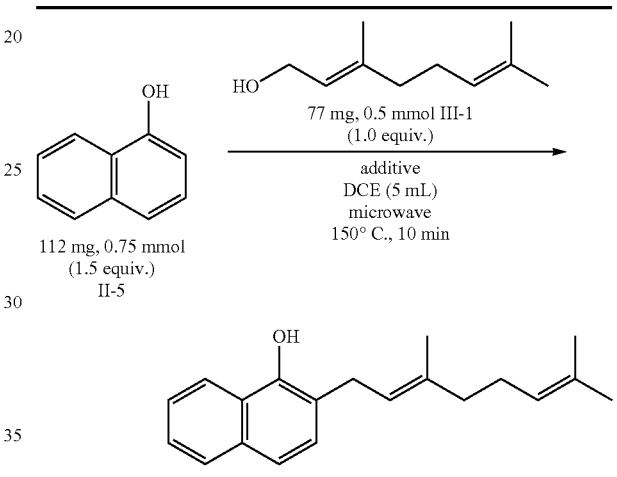

| Additive | Yield of Product[a] (%) | Recovered Naphthol (%) |
|---|---|---|
| none | 0 | >95 |
| $Al_2O_3$, Acidic (1 g, 2 g/mmol) | 74 | 33 |
| $Al_2O_3$, Acidic (0.5 g, 1 g/mmol) | 36 | 73 |
| $Al(OiPr)_3$ (0.16 g, 1.5 equiv.) | 63 | 20 |
| $MgSO_4$ (0.19 g, 3 equiv.) + $Al_2O_3$ (1 g, 2 g/mmol) | 52 | 33 |
| $MgSO_4$ (0.5 g, 1 g/mmol) + $Al_2O_3$ (0.5 g, 1 g/mmol) | 51 | 61 |
| $MgSO_4$ (0.58 g, 1 g/mmol) + $Al_2O_3$ (0.58 g, 1 g/mmol)[b] | 62 | 25 |
| $MgSO_4$ (1 g, 2 g/mmol) | 18 | 88 |
| Montmorillonite K10 (1 g, 2 g/mmol) | 12 | 83 |
| Kaolinite (1 g, 2 g/mmol) | 12 | 72 |
| MsOH (0.057 g, 1 mmol) | <5 | 40 |
| $V_2O_5$ (0.16 g, 1.6 equiv.) | <5 | 80 |
| NaOTf (0.13 g, 1.5 equiv.) | <5 | 81 |
| 3Å Molecular Sieves (1 g, 2 g/mmol) | <5 | >95 |
| $Al(OTf)_3$ (0.39 g, 1.5 equiv.) | 0 | 40 |
| LiOTf (0.12 g, 1.5 equiv.) | 0 | 57 |
| $SnCl_4$ (0.16 g, 1.0 equiv.) | 0 | 58 |
| $ZnCl_2$ (1 g, 2 g/mmol) | 0 | 84 |
| $AlCl_3$ (0.093 g, 1.3 equiv) | 0 | 87 |
| $AlCl_3$ (0.099 g, 1.5 equiv.) + $Al_2O_3$ (1 g, 2 g/mmol) | 0 | 92 |
| $AlCl_3$ (0.11 g, 1.7 equiv.) + geranyl bromide[c] | 0 | 95 |
| AcOH (0.034 g, 1 equiv.) | 0 | >95 |
| $CoCl_2 \cdot 6H_2O$ (0.23 g, 1.5 equiv.) | 0 | >95 |
| $Cs_2CO_3$ (1 g, 2 g/mmol) | 0 | >95 |
| KCl (1 g, 2 g/mmol) | 0 | >95 |
| LiCl (1 g, 2 g/mmol) | 0 | >95 |
| MgO (0.52 g, 1 g/mmol) | 0 | >95 |

TABLE 7-continued

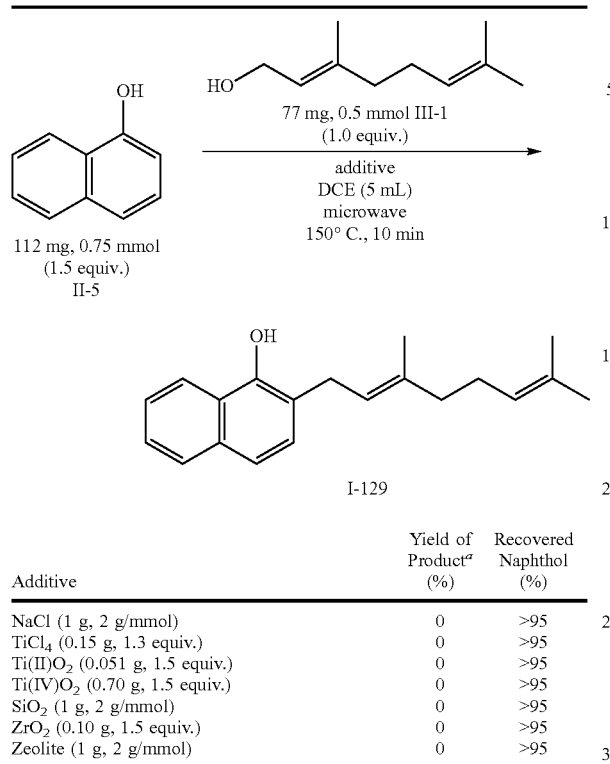

| Additive | Yield of Product[a] (%) | Recovered Naphthol (%) |
|---|---|---|
| NaCl (1 g, 2 g/mmol) | 0 | >95 |
| TiCl₄ (0.15 g, 1.3 equiv.) | 0 | >95 |
| Ti(II)O₂ (0.051 g, 1.5 equiv.) | 0 | >95 |
| Ti(IV)O₂ (0.70 g, 1.5 equiv.) | 0 | >95 |
| SiO₂ (1 g, 2 g/mmol) | 0 | >95 |
| ZrO₂ (0.10 g, 1.5 equiv.) | 0 | >95 |
| Zeolite (1 g, 2 g/mmol) | 0 | >95 |

[a] Yields determined using 1H NMR with an internal standard
[b] Reaction was completed in flask refluxing in 1,2-dichloroethane using an oil bath (see procedure below).
[c] Reaction used geranyl bromide in substitution of geraniol.

Example 8 Synthesis of Exemplary Compounds of Formula (I)

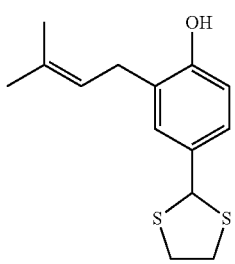 [SMILES: CC(C)=CCc1cc(C2SCCS2)ccc1O]

Synthesis of I-126

To a stirring solution of 150 mg (1.74 mmol) of prenol (1 equiv.) and 517.7 mg (2.61 mmol) of 4-(1,3-dithiolan-2-yl) phenol (1.5 equiv.) was added 1742.8 mg of acidic alumina (1 g/mmol of prenol) in 9 mL of 1,2-dichloroethane (0.2 M). The crude mixture was heated to 80° C. and stirred for 24 hours. The reaction was cooled down to room temperature, filtered through a Celite® pad and rinsed with EtOAc. The filtrate was concentrated under reduced pressure and purified by normal phase chromatography onto a 24 g SiO₂ column, eluted from 2 to 20% EtOAc/hexanes over 20 CVs. 165.4 mg (36% yield) of the desired product was recovered as a yellow oil; $^1$H NMR (400 MHz, Chloroform-c) δ 7.29 (dd, J=8.3, 2.4 Hz, 1H), 7.25 (d, J=2.3 Hz, 1H), 6.74 (d, J=8.2 Hz, 1H), 5.61 (s, 1H), 5.31 (dddt, J=7.2, 5.8, 2.9, 1.4 Hz, 1H), 5.12 (s, 1H), 3.55-3.46 (m, 2H), 3.34 (ddd, J=7.6, 6.0, 3.9 Hz, 4H), 1.78 (dd, J=3.2, 1.4 Hz, 6H).

Synthesis of I-127

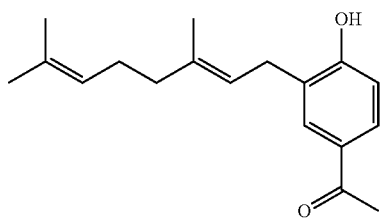

To a stirring solution of 226 mg (1.46 mmol) of geraniol (2 equiv.) and 100 mg (0.73 mmol) of 4-hydroxy actetophenone (1 equiv.) was added 2.94 g of acidic alumina (2 g/mmol of geraniol) in 5 mL of 1,2 dichloroethane. The mixture was heated to 80° C. and stirred for 24 hours. The reaction was cooled down to room temperature, filtered through a Celite® pad and rinsed with EtOAc and MeOH. The filtrate was concentrated under reduced pressure and purified by normal phase chromatography with a gradient up to 30% EtOAc/Hex. 21.0 mg (10% yield) of the desired product was recovered as a white solid; 1H NMR (400 MHz, Chloroform-d) δ 7.78 (t, J=2.1 Hz, 1H), 7.75 (d, J=2.3 Hz, 1H), 6.87 (d, J=8.2 Hz, 1H), 6.44 (s, 1H), 5.37-5.28 (m, 1H), 5.07 (tdd, J=5.3, 2.8, 1.4 Hz, 1H), 3.41 (d, J=7.2 Hz, 2H), 2.55 (s, 3H), 2.15-2.05 (m, 4H), 1.77 (d, J=1.3 Hz, 3H), 1.68 (s, 3H), 1.59 (d, J=1.3 Hz, 3H).

Synthesis of I-128

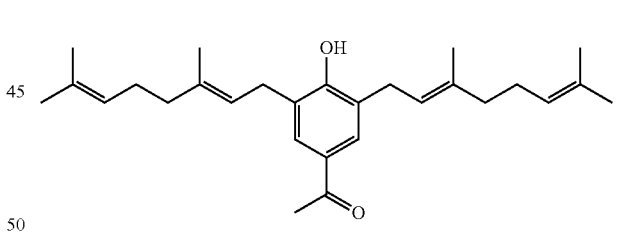

To a stirring solution of 226 mg (1.46 mmol) of geraniol (2 equiv.) and 100 mg (0.73 mmol) of 4-hydroxyactetophenone (1 equiv.) was added 2.94 g of acidic alumina (2 g/mmol of geraniol) in 5 mL of 1,2 dichloroethane. The mixture was heated to 80° C. and stirred for 24 hours. The reaction was cooled down to room temperature, filtered through a Celite® pad and rinsed with EtOAc and MeOH. The filtrate was concentrated under reduced pressure and purified by normal phase chromatography with a gradient up to 25% EtOAc/Hex. 51.4 mg (17% yield) of the desired product was recovered as a white solid; 1H NMR (400 MHz, Chloroform-d) δ 7.26 (s, 2H), 4.97-4.92 (m, 2H), 4.70 (tq, J=5.0, 1.6 Hz, 2H), 3.01 (d, J=7.2 Hz, 4H), 2.15 (s, 3H), 1.78-1.68 (m, 12H), 1.39 (d, J=1.4 Hz, 6H), 1.30 (d, J=1.4 Hz, 6H), 1.22 (d, J=1.5 Hz, 6H).

Synthesis of I-129: Microwave Reaction

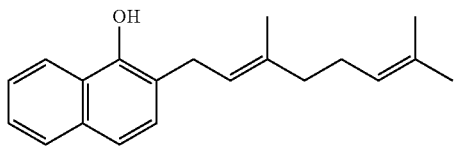 [SMILES: CC(C)=CCC/C(C)=C/Cc1ccc2ccccc2c1O]

Geraniol (87.1 mg, 0.565 mmol) was charged to a vial in 1,2-dichloroethane (5 mL) followed by 1-naphthol (122 mg, 0.846 mmol) and acidic aluminum oxide (1.02 g). The suspension was stirred in a Microwave Synthesis Reactor at 150° C. for 10 minutes. The reaction mixture was cooled and filtered through Celite®. The solids were washed with EtOAc (3×10 mL) and the filtrates combined and concentrated in vacuo. The yield of product was determined by 1H NMR analysis of the crude reaction mixture using 1,2-dibromomethane (118 mg, 0.679 mmol) as an internal standard; NMR Yield=74% (0.417 mmol); 1H NMR (700 MHz, Chloroform-d)=δ 8.07-8.04 (m, 1H), 7.65-7.63 (m, 1H), 7.35-7.29 (m, 2H), 7.25 (d, J=8.1 Hz, 1H), 7.09 (d, J=8.3, 1H), 5.29 (m, 1H), 4.96 (m, 1H), 3.40 (d, J=7.2 Hz, 2H), 2.03 (m, 4H), 1.72 (s, 3H), 1.59 (s, 3H), 1.50 (s, 3H).

Synthesis of I-129: Microwave Reaction with Aluminum Isopropoxide

Geraniol (84.4 mg, 0.547 mmol) was charged to a reaction vial in 1,2-dichloroethane (5 mL) followed by 1-naphthol (124 mg, 0.861 mmol) and aluminum isopropoxide (165 mg, 0.810 mmol). The suspension was stirred in a Microwave Synthesis Reactor at 150° C. for 10 minutes. The reaction mixture was cooled and filtered through Celite®. The solids were washed with EtOAc (3×10 mL) and the filtrates combined and concentrated in vacuo. The yield of product was determined by 1H NMR analysis of the crude reaction mixture using 1,2-dibromomethane (69.8 mg, 0.402 mmol) as an internal standard; NMR Yield=63% (0.347 mmol); 1H NMR (700 MHz, Chloroform-d)=δ 8.07-8.04 (m, 1H), 7.65-7.63 (m, 1H), 7.35-7.29 (m, 2H), 7.25 (d, J=8.1 Hz, 1H), 7.09 (d, J=8.3 Hz, 1H), 5.29 (m, 1H), 4.96 (m, 1H), 3.40 (d, J=7.2 Hz, 2H), 2.03 (m, 4H), 1.72 (s, 3H), 1.59 (s, 3H), 1.50 (s, 3H).

Synthesis of I-129: Alumina and Magnesium Sulfate

Geraniol (85.7 mg, 0.556 mmol) was charged to a 50 mL RBF in 1,2-dichloroethane (5 mL) followed by 1-naphthol (125 mg, 0.867 mmol), acidic aluminum oxide (0.583 mg, 1 g/mmol) and magnesium sulfate (0.586 g, 1 g/mmol). The suspension was stirred in an oil bath at refluxing temperature (84° C.). TLC analysis at 24 hours indicated complete consumption of geraniol. The reaction mixture was cooled and filtered through Celite®. The solids were washed with EtOAc (3×10 mL) and the filtrates combined and concentrated in vacuo. The yield of product was determined by 1H NMR analysis of the crude reaction mixture using 1,2-dibromomethane (73.0 mg, 0.420 mmol) as an internal standard; NMR Yield=63% (0.347 mmol); 1H NMR (700 MHz, Chloroform-d)=δ 8.07-8.04 (m, 1H), 7.65-7.63 (m, 1H), 7.35-7.29 (m, 2H), 7.25 (d, J=8.1 Hz, 1H), 7.09 (d, J=8.3, 1H), 5.29 (m, 1H), 4.96 (m, 1H), 3.40 (d, J=7.2 Hz, 2H), 2.03 (m, 4H), 1.72 (s, 3H), 1.59 (s, 3H), 1.50 (s, 3H).

Synthesis of I-1: No Chromatography

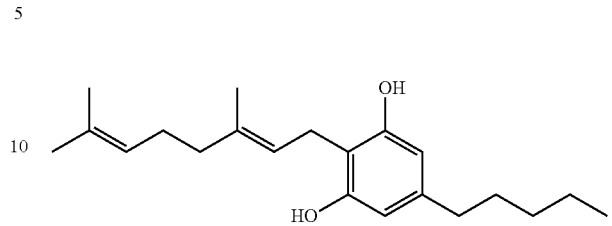

To a round bottom flask containing DCE (0.2M; pre-dried over 4A MS) was added acidic alumina (2 g/mmol of alcohol) which was pre-dried under vacuum at 200° C. and stored in desiccator. To the reaction mixture was added olivetol (3.0 equiv.) followed by geraniol (1.0 equiv.) and the mixture was heated to reflux for one hour. The reaction mixture was filtered through a frit funnel under vacuum eluting with DCE. The solution was concentrated and the crude oil was filtered through a silica pad eluting with 5% ethyl acetate/hexanes providing CBG as a yellow-orange solid (70%). The solid can be recrystallized using hot heptane, allowed to cool to room temperature and placed in freezer overnight. The white solids were filtered under vacuum and washed with cold heptane providing pure CBG (88% based of crude yield).

Synthesis of I-1: Aluminum Isopropoxide

Geraniol (80.8 mg, 0.524 mmol) was charged to a reaction vial in 1,2-dichloroethane (5 mL) followed by olivetol (146 mg, 0.808 mmol) and aluminum isopropoxide (158 mg, 0.775 mmol). The suspension was stirred in a Microwave Synthesis Reactor at 150° C. for 10 minutes. The reaction mixture was cooled and filtered through Celite®. The solids were washed with EtOAc (3×10 mL) and the filtrates combined and concentrated in vacuo. The yields of Cannabigerol and (55854-24-5) were determined by 1H NMR analysis of the crude reaction mixture using 1,2-dibromomethane (70.6 mg, 0.406 mmol) as an internal standard; NMR Yield=CBG: 21% (0.108 mmol)

Synthesis of I-110: Arachidin 2

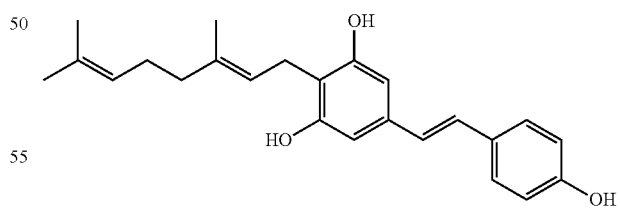

To a round bottom flask containing MeCN (0.08M, pre-dried over 4A MS) was added acidic alumina (2 g/mmol of alcohol) which was pre-dried under vacuum at 200° C. and stored in desiccator. To the stirring mixture was added resveratrol (5.0 equiv.) followed by geraniol (1.0 equiv.) and the reaction was heated to reflux for 24 hrs. The reaction mixture was filtered through a Celite® pad eluting with ethyl acetate, concentrated and purified by column chromatography providing Arachidin 2 as an off-white solid (42%); 1H NMR (700 MHz, DMSO) δ 9.51 (s, 1H), 9.07 (s, 2H), 7.38 (d, J=8.6 Hz, 2H), 6.78 (d, J=1.9 Hz, 2H), 6.75 (d, J=8.4 Hz, 2H), 6.44 (s, 2H), 5.18 (t, J=7.0 Hz, 1H), 5.05 (tdd, J=5.7, 2.9, 1.5 Hz, 1H), 3.17 (d, J=7.1 Hz, 2H), 2.01-1.98 (m, 2H), 1.91-1.89 (m, 2H), 1.71 (s, 3H), 1.61 (s, 3H), 1.54 (s, 3H).

Synthesis of I-111: Amorphastilbol

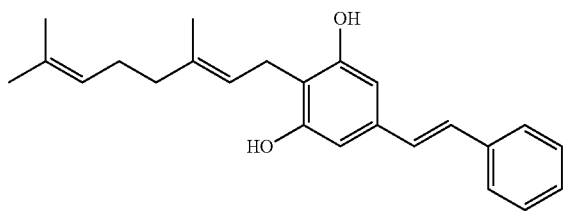 [SMILES: CC(C)=CCC/C(C)=C/Cc1c(O)cc(/C=C/c2ccccc2)cc1O]

To a round bottom flask containing DCE (0.08M; pre-dried over 4A MS) was added acidic alumina (2 g/mmol of phenol) which was pre-dried under vacuum at 200° C. and stored in desiccator. To the reaction mixture was added pinosylvin (3.0 equiv.) followed by geraniol (1.0 equiv.) and the reaction mixture was heated to reflux overnight. The reaction mixture was cooled to room temperature and filtered through a Celite® pad eluting with ethylacetate. The solution was concentrated and purified by column chromatography providing Amorphastilbol as a beige solid (70%); 1H NMR (400 MHz, CDCl$_3$) δ 7.49-7.47 (m, 2H), 7.35 (t, J=7.5 Hz, 2H), 7.27-7.23 (m, 1H), 7.02, 6.93 (ABq, J=16.3 Hz, 2H), 6.59 (s, 2H), 5.30-5.26 (m, 1H), 5.08-5.04 (m, 3H), 3.44 (d, J=7.0 Hz, 2H), 2.13-2.06 (m, 4H), 1.83 (s, 3H), 1.68 (s, 3H), 1.60 (s, 3H).

Synthesis of I-114

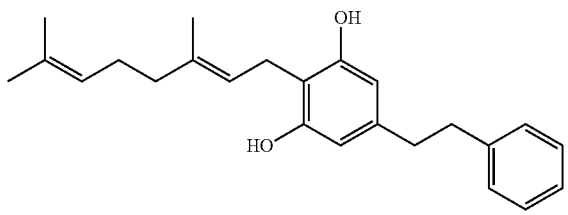 [SMILES: CC(C)=CCC/C(C)=C/Cc1c(O)cc(CCc2ccccc2)cc1O]

To a round bottom flask containing DCE (0.08M; pre-dried over 4A MS) was added acidic alumina (2 g/mmol of alcohol) which was pre-dried under vacuum at 200° C. and stored in desiccator. To the reaction mixture was added dihydropinosylvin (1.0 equiv.) followed by geraniol (1.0 equiv.) and the mixture was heated to reflux overnight. The reaction mixture was cooled to room temperature and filtered through a Celite® pad eluting with ethyl acetate. The solution was concentrated and purified by column chromatography providing the desired compound as a white solid (30%); 1H NMR (700 MHz, CDCl$_3$) δ 7.32-7.27 (m, 2H), 7.23-7.19 (m, 3H), 6.28 (s, 2H), 5.31-5.27 (m, 1H), 5.10-5.05 (m, 3H), 3.42 (d, J=7.1 Hz, 2H), 2.91-2.85 (m, 2H), 2.82-2.76 (m, 2H), 2.16-2.05 (m, 4H), 1.83 (s, 3H), 1.70 (s, 3H), 1.61 (s, 3H).

Synthesis of I-115: Chiricanin A

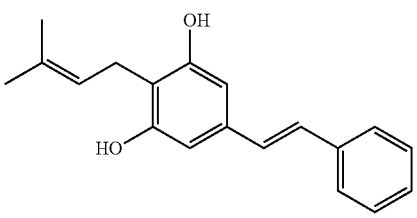 [SMILES: CC(C)=CCc1c(O)cc(/C=C/c2ccccc2)cc1O]

To a round bottom flask containing DCE (0.08M; pre-dried over 4A MS) was added acidic alumina (2 g/mmol of phenol) which was pre-dried under vacuum at 200° C. and stored in desiccator. To the stirring mixture was added pinosylvin (3 equiv.) followed by prenol (1.0 equiv.) and the reaction mixture was stirred at reflux overnight. Once complete, based on TLC analysis, the reaction mixture was filtered through a Celite® pad eluting with ethyl acetate, concentrated and purified by column chromatography providing Chiricanin A as a beige solid (62%); 1H NMR (700 MHz, CDCl$_3$) δ 7.48 (br d, J=7.3 Hz, 2H), 7.35 (t, J=7.7 Hz, 2H), 7.27-7.24 (m, 1H), 7.00, 6.93 (ABq, J=16.3 Hz, 2H), 6.59 (s, 2H), 5.28 (ddt, J=7.1, 5.7, 1.4 Hz, 1H), 5.14 (br s, 2H), 3.43 (d, J=7.1 Hz, 2H), 1.84 (s, 3H), 1.77 (s, 3H).

Synthesis of I-131

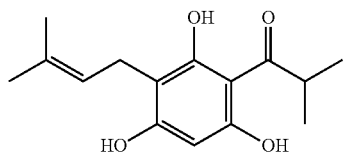 [SMILES: CC(C)=CCc1c(O)cc(O)c(C(=O)C(C)C)c1O]

Prenol (1 equiv.) and the isobutyrylphloroglucinol (1.5 equiv.) were dissolved in EtOAc (0.2 M). Acidic alumina (2 g/mmol) was added to the reaction mixture and was allowed to stir at reflux for 24 h. The crude mixture was filtered over a Celite® pad, rinsed with EtOAc and concentrated to dryness under vacuum. The crude reaction mixture was purified by reverse phase chromatography on C18 column with gradient elution using CH$_3$CN and H$_2$O. Purification afforded 22.4 mg (36% yield) of the desired product as a yellow solid; 1H NMR (700 MHz, Chloroform-d) δ 5.82 (s, 1H), 5.78 (s, 1H), 5.25 (tp, J=7.2, 1.4 Hz, 1H), 3.86 (hept, J=6.7 Hz, 1H), 3.37 (d, J=7.1 Hz, 2H), 1.83 (s, 3H), 1.78 (d, J=1.4 Hz, 3H), 1.18 (d, J=6.8 Hz, 6H); 13C NMR (176 MHz, Chloroform-d) δ 210.52, 160.50, 136.47, 121.49, 105.65, 104.20, 95.42, 60.43, 39.34, 25.85, 21.71, 21.07, 19.30, 17.92, 14.21.

Synthesis of I-132

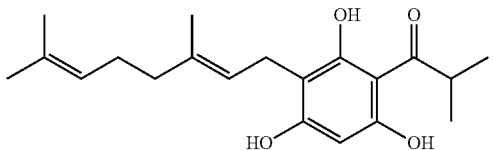 [SMILES: CC(C)=CCC/C(C)=C/Cc1c(O)cc(O)c(C(=O)C(C)C)c1O]

Prenol (1 equiv.) and the isobutyrylphloroglucinol (1.5 equiv.) were dissolved in EtOAc (0.2 M). Acidic alumina (2 g/mmol) was added to the reaction mixture and was allowed to stir at reflux for 24 h. The crude mixture was filtered over a Celite® pad, rinsed with EtOAc and concentrated to dryness under vacuum. The crude reaction mixture was purified by reverse phase chromatography on C18 column with gradient elution using CH$_3$CN and H$_2$O. Purification afforded 238.9 mg (37% yield) of the desired product as a yellow oil; 1H NMR (700 MHz, Chloroform-d): δ 11.54 (br. s, 1H), 8.35 (br. s, 1H), 5.95 (s, 1H), 5.84 (s, 1H), 5.25 (t, J=7.2 Hz, 1H), 5.05 (t, J=6.2 Hz, 1H), 3.88 (hept, J=6.8 Hz, 1H), 3.38 (d, J=7.2 Hz, 2H), 2.11 (t, J=6.8 Hz, 2H), 2.09 (m, 2H), 1.81 (s, 3H), 1.67 (s, 3H), 1.60 (s, 3H), 1.17 (d, J=6.8 Hz, 6H); 13C NMR (176 MHz, Chloroform-d): δ 210.76, 160.86, 140.35, 132.35, 121.58, 105.77, 104.34, 95.64, 39.83, 39.45, 21.78, 19.44, 17.86, 16.38.

Synthesis of I-133

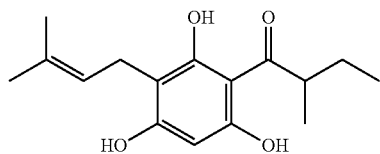 [SMILES: CCC(C)C(=O)c1c(O)cc(O)c(CC=C(C)C)c1O]

Prenol (1 equiv.) and the acylphloroglucinol substrate (1.5 equiv.) were dissolved in EtOAc (0.2 M). Acidic alumina (2 g/mmol) was added to the reaction mixture and was allowed to stir at reflux for 24 h. The crude mixture was filtered over a Celite® pad, rinsed with EtOAc and concentrated to dryness under vacuum. The crude reaction mixture was purified by reverse phase chromatography on C18 column with gradient elution using CH$_3$CN and H$_2$O. Purification afforded 109.1 mg (27% yield) of the desired product as a yellow solid; 1H NMR (700 MHz, Chloroform-d) δ 5.86-5.79 (m, 2H), 5.28-5.23 (m, 1H), 3.76-3.69 (m, 1H), 3.40-3.34 (m, 2H), 1.86-1.81 (m, 3H), 1.78 (s, 3H), 1.45-1.37 (m, 1H), 1.19-1.14 (m, 3H), 0.95-0.88 (m, 3H); 13C NMR (176 MHz, Chloroform-d) δ 210.33, 160.51, 136.43, 121.50, 105.66, 104.71, 95.41, 46.01, 26.93, 25.85, 21.70, 17.92, 16.71, 11.97.

Synthesis of I-134

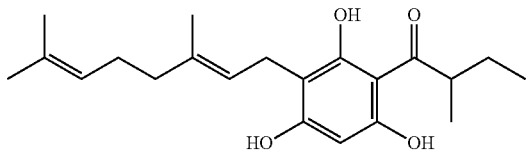 [SMILES: CCC(C)C(=O)c1c(O)cc(O)c(C/C=C(\C)CCC=C(C)C)c1O]

Geraniol (300 mg, 1.95 mmol, 1 equiv.) and the acylphloroglucinol substrate (1.5 equiv.) were dissolved in EtOAc (0.2 M). Acidic alumina (2 g/mmol) was added to the reaction mixture and was allowed to stir at reflux for 24 h. The crude mixture was filtered over a Celite® pad, rinsed with EtOAc and concentrated to dryness under vacuum. The crude reaction mixture was purified by reverse phase chromatography on C18 column with gradient elution using CH$_3$CN and H$_2$O. Purification afforded 222.2 mg (33% yield) of the desired product as a yellow oil; 1H NMR (700 MHz, Chloroform-d) δ 6.22 (s, 1H), 5.85 (s, 1H), 5.26 (t, J=7.2 Hz, 1H), 5.05 (t, J=6.8 Hz, 1H), 3.81-3.71 (m, 1H), 3.37 (d, J=7.1 Hz, 2H), 2.15-2.03 (m, 4H), 1.88-1.79 (m, 4H), 1.67 (s, 3H), 1.59 (s, 3H), 1.41 (dp, J=14.5, 7.3 Hz, 1H), 1.16 (d, J=6.7 Hz, 3H), 0.91 (t, J=7.4 Hz, 3H); 13C NMR (176 MHz, Chloroform-d) δ 210.80, 162.74, 161.00, 160.10, 140.13, 132.30, 123.75, 121.62, 105.86, 104.86, 95.64, 46.07, 39.83, 27.09, 26.44, 25.81, 21.76, 17.84, 16.82, 16.36, 12.09.

Synthesis of I-135

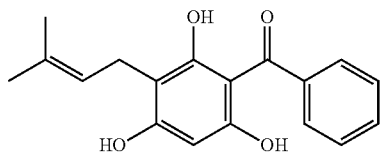 [SMILES: CC(C)=CCc1c(O)cc(O)c(C(=O)c2ccccc2)c1O]

Prenol (100 mg, 1.16 mmol, 1 equiv.) and the acylphloroglucinol substrate (1.5 equiv.) were dissolved in EtOAc (0.2 M). Acidic alumina (2 g/mmol) was added to the reaction mixture and was allowed to stir at reflux for 24 h. The crude mixture was filtered over a Celite® pad, rinsed with EtOAc and concentrated to dryness under vacuum. The crude reaction mixture was purified by reverse phase chromatography on C18 column with gradient elution using CH$_3$CN and H$_2$O. Purification afforded 119.6 mg (35% yield) of the desired product as a yellow oil; 1H NMR (700 MHz, Chloroform-d) δ 10.35 (s, 1H), 7.66-7.63 (m, 2H), 7.61-7.58 (m, 1H), 7.52 (dd, J=8.4, 7.0 Hz, 2H), 7.37 (s, 1H), 6.02 (s, 1H), 5.94 (s, 1H), 5.26 (tp, J=7.2, 1.4 Hz, 1H), 3.39-3.34 (m, 2H), 1.81 (d, J=1.4 Hz, 3H), 1.76 (q, J=1.4 Hz, 3H); 13C NMR (176 MHz, Chloroform-d) δ 197.64, 162.63, 160.83, 159.39, 139.90, 135.72, 132.33, 129.27, 127.85, 121.54, 106.46, 104.58, 96.30, 25.84, 21.69, 17.91.

Synthesis of I-136

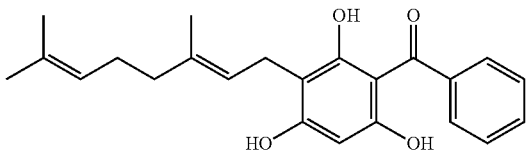 [SMILES: CC(C)=CCC/C(C)=C/Cc1c(O)cc(O)c(C(=O)c2ccccc2)c1O]

Geraniol (200 mg, 1.3 mmol, 1 equiv.) and the acylphloroglucinol substrate (1.5 equiv.) were dissolved in EtOAc (0.2 M). Acidic alumina (2 g/mmol) was added to the reaction mixture and was allowed to stir at reflux for 24 h. The crude mixture was filtered over a Celite® pad, rinsed with EtOAc and concentrated to dryness under vacuum. The crude reaction mixture was purified by reverse phase chromatography on C18 column with gradient elution using CH$_3$CN and H$_2$O. Purification afforded 148 mg (31% yield) of the desired product as a yellow oil; 1H NMR (700 MHz, Chloroform-d) δ 10.37 (s, 1H), 7.65 (d, J=d, 8.1 Hz, 2H), 7.59 (t, J=7.4 Hz, 1H), 7.52 (dd, J=7.4, 8.1 Hz, 2H), 7.37 (br. s, 1H), 6.08 (br. s, 1H), 5.94 (s, 1H), 5.27 (t, J=7.2 Hz, 1H), 5.05 (t, J=7.0 Hz, 1H), 3.38 (d, J=7.0 Hz, 2H), 2.10 (t, J=7.4 Hz, 2H), 2.07 (m, 2H), 1.80 (s, 3H), 1.67 (s, 3H), 1.59 (s, 3H); 13C NMR (176 MHz, Chloroform-d) δ 197.79, 163.00, 160.96, 159.53, 140.09, 139.76, 132.43, 129.37, 128.01, 123.80, 121.56, 106.49, 96.52, 41.00, 39.85, 26.47, 25.82, 21.78, 17.86, 16.37.

Synthesis of I-137

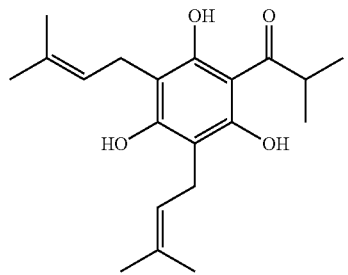 [SMILES: CC(C)=CCc1c(O)c(CC=C(C)C)c(O)c(C(=O)C(C)C)c1O]

Isobutyrylphloroglucinol (200 mg, 1.02 mmol, 1 equiv.) and prenol (5 equiv.) were dissolved in cyclohexane (0.2 M). Acidic alumina (2 g/mmol) was added to the reaction mixture and was allowed to stir at reflux for 24 h. The crude mixture was filtered over a Celite® pad, rinsed with EtOAc and concentrated to dryness under vacuum. The crude reaction mixture was purified by reverse phase chromatography on C18 column with gradient elution using CH$_3$CN and H$_2$O. Purification afforded 159 mg (47% yield) of the desired product as a yellow oil; 1H NMR (700 MHz, Chloroform-d) δ 6.26 (s, 1H), 5.25-5.21 (m, 2H), 3.90 (h, J=6.7 Hz, 1H), 3.38 (dd, J=7.5, 1.9 Hz, 4H), 1.84 (d, J=1.5 Hz, 6H), 1.79 (d, J=1.6 Hz, 6H), 1.17 (d, J=6.7 Hz, 6H); 13C NMR (176 MHz, Chloroform-d) δ 210.97, 159.12, 136.58, 121.69, 104.79, 104.39, 39.32, 25.87, 21.87, 19.41, 17.92.

Synthesis of I-138: 4-Deoxyadhumulone

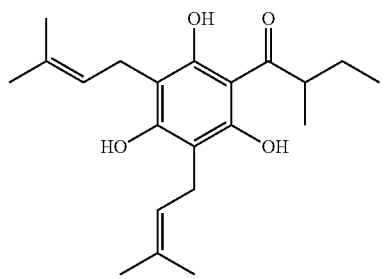 [SMILES: CCC(C)C(=O)c1c(O)c(CC=C(C)C)c(O)c(CC=C(C)C)c1O]

2'-methylisobutyrylphloroglucinol (200 mg, 0.95 mmol, 1 equiv.) and prenol (5 equiv.) were dissolved in cyclohexane (0.2 M). Acidic alumina (2 g/mmol) was added to the reaction mixture and was allowed to stir at reflux for 24 h. The crude mixture was filtered over a Celite® pad, rinsed with EtOAc and concentrated to dryness under vacuum. The crude reaction mixture was purified by reverse phase chromatography on C18 column with gradient elution using CH$_3$CN and H$_2$O. Purification afforded 102.8 mg (31% yield) of the desired product as a yellow oil; 1H NMR (700 MHz, Chloroform-d) δ 6.26 (s, 1H), 5.23 (tp, J=7.2, 1.4 Hz, 2H), 3.76 (h, J=6.7 Hz, 1H), 3.38 (d, J=7.2 Hz, 4H), 1.84 (d, J=1.4 Hz, 6H), 1.79 (d, J=1.6 Hz, 6H), 1.47-1.33 (m, 2H), 1.15 (d, J=6.7 Hz, 3H), 0.90 (t, J=7.4 Hz, 3H).

Synthesis of I-139: Clusiaphenone B

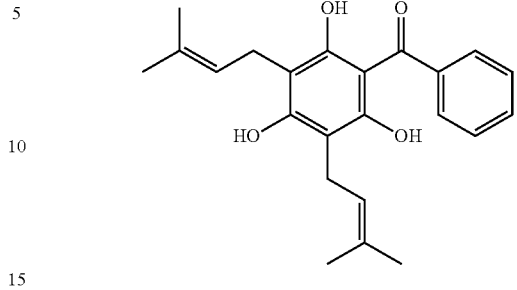

Benzoylphloroglucinol (200 mg, 0.87 mmol, 1 equiv.) and prenol (5 equiv.) were dissolved in cyclohexane (0.2 M). Acidic alumina (2 g/mmol) was added to the reaction mixture and was allowed to stir at reflux for 24 h. The crude mixture was filtered over a Celite® pad, rinsed with EtOAc and concentrated to dryness under vacuum. The crude reaction mixture was purified by reverse phase chromatography on C18 column with gradient elution using CH$_3$CN and H$_2$O. Purification afforded 39.5 mg (12% yield) of the desired product as a yellow oil; 1H NMR (700 MHz, Chloroform-d) δ 8.91 (s, 2H), 7.64 (d, J=7.3 Hz, 2H), 7.57 (t, J=7.3 Hz, 1H), 7.50 (t, J=7.7 Hz, 2H), 6.35 (s, 1H), 5.22 (t, J=7.1 Hz, 2H), 3.34 (d, J=7.0 Hz, 4H), 1.79 (s, 6H), 1.74 (s, 6H); 13C NMR (176 MHz, Chloroform-d) δ 198.06, 161.10, 157.66, 140.30, 135.12, 132.07, 129.06, 127.96, 121.85, 106.32, 104.56, 25.83, 21.85, 17.90.

Synthesis of I-140: Hyperbeanol Q

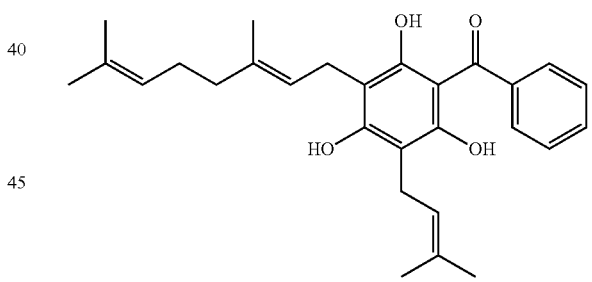

3-geranyl-1-benzoylphloroglucinol (150 mg, 0.41 mmol, 1 equiv.) and prenol (5 equiv.) were dissolved in cyclohexane (0.2 M). Acidic alumina (2 g/mmol) was added to the reaction mixture and was allowed to stir at reflux for 24 h. The crude mixture was filtered over a Celite® pad, rinsed with EtOAc and concentrated to dryness under vacuum. The crude reaction mixture was purified by reverse phase chromatography on C18 column with gradient elution using CH$_3$CN and H2O. Purification afforded 63.2 mg (36% yield) of the desired product as a yellow solid; 1H NMR (700 MHz, Chloroform-d) δ 8.97 (s, 1H), 8.86 (s, 1H), 7.64 (d, J=7.4 Hz, 2H), 7.58-7.55 (m, 1H), 7.49 (t, J=7.8 Hz, 2H), 6.36 (s, 1H), 5.22 (q, J=6.8, 6.3 Hz, 2H), 5.07-5.03 (m, 1H), 3.35 (dd, J=16.2, 7.1 Hz, 4H), 2.10 (q, J=7.4 Hz, 2H), 2.07-2.03 (m, 2H), 1.78 (s, 6H), 1.73 (s, 3H), 1.66 (s, 3H), 1.59 (s, 3H); 13C NMR (176 MHz, Chloroform-d) δ 198.14, 161.11, 157.70, 157.67, 140.39, 139.12, 134.89, 132.03, 132.02, 128.97, 127.99, 123.75, 121.90, 121.71, 106.45, 106.14, 104.58, 39.72, 26.36, 25.83, 25.68, 21.84, 21.80, 17.89, 17.70, 16.22.

Synthesis of I-141

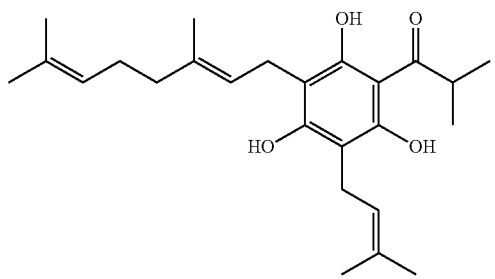 [SMILES: CC(C)=CCC/C(C)=C/Cc1c(O)c(CC=C(C)C)c(O)c(C(=O)C(C)C)c1O]

3-geranyl-1-isobutyrylphloroglucinol (150 mg, 0.45 mmol, 1 equiv.) and prenol (5 equiv.) were dissolved in cyclohexane (0.2 M). Acidic alumina (2 g/mmol) was added to the reaction mixture and was allowed to stir at reflux for 24 h. The crude mixture was filtered over a Celite® pad, rinsed with EtOAc and concentrated to dryness under vacuum. The crude reaction mixture was purified by reverse phase chromatography on C18 column with gradient elution using $CH_3CN$ and $H_2O$. Purification afforded 47.8 mg (26% yield) of the desired product as a yellow oil; 1H NMR (700 MHz, Chloroform-d) δ 6.29 (s, 1H), 5.26-5.21 (m, 2H), 5.07-5.03 (m, 1H), 3.90 (hept, J=6.7 Hz, 1H), 3.39 (t, J=7.6 Hz, 4H), 2.15-2.07 (m, 4H), 1.84 (d, J=1.3 Hz, 3H), 1.83 (d, J=1.1 Hz, 3H), 1.79 (d, J=1.2 Hz, 3H), 1.68 (d, J=1.4 Hz, 3H), 1.60 (d, J=1.6 Hz, 3H), 1.16 (d, J=6.7 Hz, 6H); 13C NMR (176 MHz, Chloroform-d) δ 210.98, 159.22, 140.35, 136.53, 132.24, 123.53, 121.73, 121.69, 104.84, 104.39, 39.69, 39.32, 26.22, 25.87, 25.69, 21.86, 21.80, 19.41, 17.91, 17.72, 16.21.

Synthesis of I-142

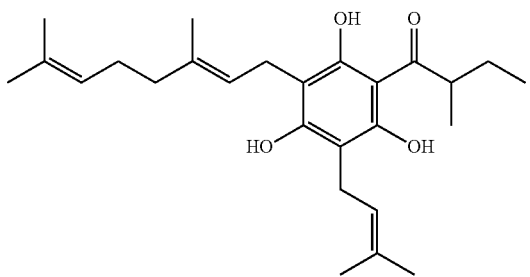 [SMILES: CCC(C)C(=O)c1c(O)c(CC=C(C)C)c(O)c(C/C=C(\C)CCC=C(C)C)c1O]

3-geranyl-1-(2'-methylisobutyryl)phloroglucinol (200 mg, 0.60 mmol, 1 equiv.) and prenol (5 equiv.) were dissolved in cyclohexane (0.2 M). Acidic alumina (2 g/mmol) was added to the reaction mixture and was allowed to stir at reflux for 24 h. The crude mixture was filtered over a Celite® pad, rinsed with EtOAc and concentrated to dryness under vacuum. The crude reaction mixture was purified by reverse phase chromatography on C18 column with gradient elution using $CH_3CN$ and $H_2O$. Purification afforded 113.7 mg (43% yield) of the desired product as a yellow oil; 1H NMR (700 MHz, Chloroform-d) δ 6.29 (s, 1H), 5.27-5.20 (m, 2H), 5.07-5.04 (m, 1H), 3.77 (h, J=6.7 Hz, 1H), 3.43-3.36 (m, 4H), 2.16-2.07 (m, 4H), 1.86-1.82 (m, 6H), 1.80-1.78 (m, 3H), 1.70-1.66 (m, 4H), 1.61-1.59 (m, 3H), 1.44-1.38 (m, 1H), 1.15 (d, J=6.8 Hz, 3H), 0.90 (t, J=7.4 Hz, 3H).

Synthesis of I-143: 3-C-Prenylresacetophenone

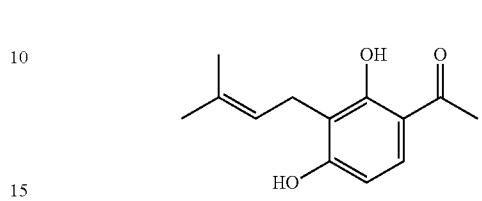

To a stirring solution of 50 mg (0.58 mmol) of prenol (1 equiv.) and 132.5 mg (0.87 mmol) of 2,4-dihydroxyacetophenone (1.5 equiv.) was added 1161.8 mg of acidic alumina (2 g/mmol of prenol) in 3 mL of 1,2-dichloroethane (0.2 M). The crude mixture was heated to 80° C. and stirred for 24 hours. The reaction was cooled down to room temperature, filtered through a Celite® pad and rinsed with EtOAc. The filtrate was concentrated under reduced pressure and purified by normal phase chromatography onto a 12 g $SiO_2$ column, eluted from 2 to 20% EtOAc/hexanes over 20 CVs. 27.1 mg (21% yield) of the desired product was recovered as a white solid; 1H NMR (400 MHz, Chloroform-d) δ 12.51 (s, 1H), 7.44 (d, J=0.9 Hz, 1H), 6.36 (s, 1H), 5.71 (s, 1H), 5.29 (ddq, J=8.6, 5.8, 1.4 Hz, 1H), 3.31 (d, J=7.2 Hz, 2H), 2.55 (s, 3H), 1.79 (dt, J=2.7, 1.3 Hz, 6H).

Synthesis of I-144: Hispaglabridin A

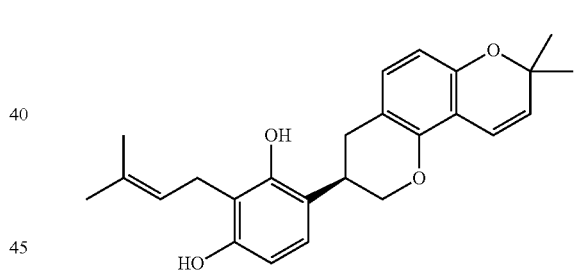

To a stirring solution of 15 mg (0.17 mmol) of prenol (1 equiv.) and 226 mg (0.70 mmol) of glabridin (4 equiv.) was added 348.6 mg of acidic alumina (2 g/mmol of prenol) in 1 mL of 1,2-dichloroethane (0.2 M). The crude mixture was heated to 80° C. and stirred for 24 hours. The reaction was cooled down to room temperature, filtered through a Celite® pad and rinsed with EtOAc. The filtrate was concentrated under reduced pressure and purified by normal phase chromatography onto a 12 g $SiO_2$ column, eluted in $CH_2Cl_2$ for 10 CVs, then gradient up to 10% EtOAc/$CH_2Cl_2$ over 10 CVs. 8.2 mg (12% yield) of the desired product was recovered as a yellow semi-solid; 1H NMR (400 MHz, Chloroform-d) δ 6.82 (d, J=8.2 Hz, 1H), 6.79 (s, 1H), 6.65 (dd, J=9.8, 0.7 Hz, 1H), 6.37 (dd, J=8.2, 0.7 Hz, 1H), 6.29 (s, 1H), 5.56 (d, J=9.9 Hz, 1H), 5.28 (dddd, J=8.7, 5.8, 3.0, 1.5 Hz, 1H), 5.15 (s, 1H), 4.78 (s, 1H), 4.37 (ddd, J=10.4, 3.5, 2.1 Hz, 1H), 4.02 (t, J=10.3 Hz, 1H), 3.53-3.41 (m, 1H), 3.26 (d, J=7.2 Hz, 2H), 2.99 (ddd, J=15.7, 11.1, 1.1 Hz, 1H), 2.85 (ddd, J=15.8, 5.2, 2.1 Hz, 1H), 1.76 (d, J=1.4 Hz, 6H), 1.42 (d, J=6.8 Hz, 6H).

Synthesis of I-145: Dihydrochalcone M2

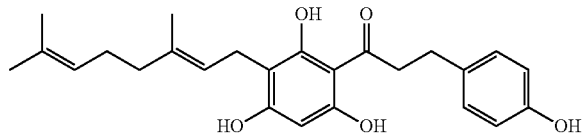 [SMILES: CC(C)=CCC/C(C)=C/Cc1c(O)cc(O)c(C(=O)CCc2ccc(O)cc2)c1O]

To a stirring solution of 175 mg (1.12 mmol) of geraniol (2 equiv.) and 154 mg (0.56 mmol) of phloretin (1 equiv.) was added 2.19 g of acidic alumina (2 g/mmol of geraniol) in 3 mL of ethyl acetate. The mixture was heated to 77° C. and stirred for 24 hours. The reaction was cooled down to room temperature, filtered through a Celite® pad and rinsed with EtOAc and MeOH. The filtrate was concentrated under reduced pressure and purified by normal phase chromatography with a gradient up to 60% EtOAc/Hex. 27.2 mg (12% yield) of the desired product was recovered as a yellow solid. 1H NMR (400 MHz, DMSO-d6) δ 14.03 (s, 1H), 10.54 (s, 1H), 10.26 (s, 1H), 9.12 (br s, 1H), 7.01 (d, J=8.5 Hz, 2H), 6.66 (d, J=8.5 Hz, 2H), 5.99 (s, 1H), 5.11 (5.11 (tt, J=5.8, 3.2 Hz, 1H), 5.03 (ddq, J=7.1, 5.4, 1.5 Hz, 1H), 3.21 (dd, J=8.6, 6.9 Hz, 2H), 3.08 (d, J=7.1 Hz, 2H), 2.76 (dd, J=8.7, 6.8 Hz, 2H), 1.98 (dd, J=9.1, 5.6 Hz, 2H), 1.88 (dd, J=9.0, 6.1 Hz, 2H), 1.68 (s, 3H), 1.59 (s, 3H), 1.52 (s, 3H).

Synthesis of I-146

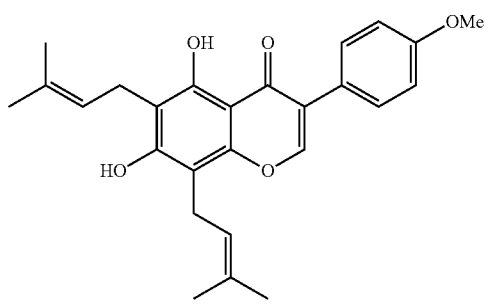 [SMILES: COc1ccc(-c2coc3c(CC=C(C)C)c(O)c(CC=C(C)C)c(O)c3c2=O)cc1]

To a stirring solution of 34 mg (0.35 mmol) of prenol (2 equiv.) and 52 mg (0.18 mmol) of biochanin (1 equiv.) was added 704 mg of acidic alumina (2 g/mmol of prenol) in 3 mL of 1,2 dichloroethane. The mixture was heated to 80° C. and stirred for 24 hours. The reaction was cooled down to room temperature, filtered through a Celite® pad and rinsed with EtOAc and MeOH. The filtrate was concentrated under reduced pressure and purified by normal phase chromatography with a gradient up to 30% EtOAc/Hex. 17.3 mg (23% yield) of the desired product was recovered as a white solid. 1H NMR (400 MHz, Chloroform-d) δ 13.18 (s, 1H), 7.91 (s, 1H), 7.46 (d, J=8.8 Hz, 2H), 6.98 (d, J=8.8 Hz, 2H), 6.34 (s, 1H), 5.39-5.08 (m, 2H), 3.84 (s, 3H), 3.49-3.45 (m, 4H), 1.84 (dd, J=4.6, 1.3 Hz, 6H), 1.76 (dd, J=11.4, 1.5 Hz, 6H).

Synthesis of I-147: Demethylsuberosin

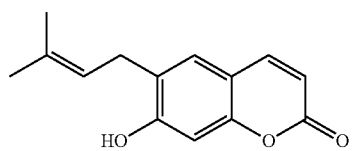 [SMILES: CC(C)=CCc1cc2ccc(=O)oc2cc1O]

50 mg (2 equiv.) of umbelliferone (7-hydroxycoumarin) and 13.3 mg (1 equiv.) of prenol (3-methyl-2-buten-1-ol) were suspended in dry dichloroethane (DCE). 1.5 g/mmol of dry acidic alumina (Al₂O₃) relative to the scaffold was added to the reaction mixture, which was subsequently heated overnight at reflux. The mixture was then poured over diatomaceous earth and washed with hexane, ethyl acetate, and acetone. The collected solvents were combined and concentrated under reduced pressure. Demethylsuberosin was eluted through column chromatography using hexanes/ethyl acetate (13.3 mg, 37% yield). 1H NMR (400 MHz, Chloroform-d) δ 7.61 (d, J=8.9 Hz, 1H), 7.19 (s, 1H), 6.81 (s, 1H), 6.23 (d, J=9.5 Hz, 1H), 6.08 (s, 1H), 5.34-5.27 (m, 1H), 3.38 (d, J=7.2 Hz, 2H), 1.87-1.70 (m, 6H).

Synthesis of I-148

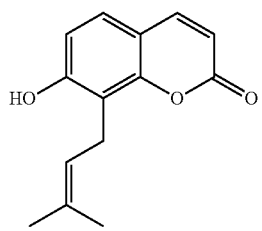 [SMILES: CC(C)=CCc1c(O)ccc2ccc(=O)oc12]

4 equivalents of umbelliferone (7-hydroxycoumarin) and 1 equivalent of prenol (3-methyl-2-buten-1-ol) were suspended in dry dichloroethane (DCE). 1.5 g/mmol of dry acidic alumina (Al₂O₃) relative to the scaffold was added to the reaction mixture, which was subsequently heated overnight at reflux. The mixture was then poured over diatomaceous earth and washed with hexane, ethyl acetate, and acetone. The collected solvents were combined and concentrated under reduced pressure. 7-hydroxy-8-(3-methylbut-2-en-1-yl)-2H-chromen-2-one was eluted through column chromatography using hexanes/ethyl acetate (14.2 mg, 40% yield). 1H NMR (400 MHz, Chloroform-d) δ 7.63 (d, J=9.5 Hz, 1H), 7.36 (d, J=8.5 Hz, 1H), 6.82 (d, J=2.4 Hz, 1H), 6.24 (d, J=9.5 Hz, 1H), 5.47 (ddq, J=8.1, 5.6, 1.4 Hz, 1H), 4.58 (dt, J=6.7, 0.9 Hz, 2H), 1.79 (dt, J=16.0, 1.0 Hz, 6H).

Synthesis of I-149: Ostruthin

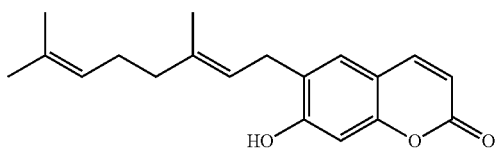 [SMILES: CC(C)=CCC/C(C)=C/Cc1cc2ccc(=O)oc2cc1O]

100 mg (2.1 equiv.) of umbelliferone (7-hydroxycoumarin) and 45 mg (1 equiv.) of geraniol (3,7-dimethylocta-trans-2,6-dien-1-ol) were suspended in xylenes. 1.5 g/mmol of dry acidic alumina (Al₂O₃) relative to the scaffold was added to the reaction mixture, which was subsequently heated at 160° C. for 2 hours in a monowave reactor. The mixture was then poured over diatomaceous earth and washed with hexane, ethyl acetate, and acetone. The collected solvents were combined and concentrated under reduced pressure. Ostruthin was eluted through column chromatography using hexanes/ethyl acetate (31.2 mg, 36% yield). 1H NMR (400 MHz, Chloroform-d) δ 7.61 (d, J=9.5 Hz, 1H), 7.19 (s, 1H), 6.84 (s, 1H), 6.24 (d, J=9.4 Hz, 1H), 5.97 (s, 1H), 5.35-5.27 (m, 1H), 5.08 (dddd, J=6.9, 5.5, 3.5, 1.7 Hz, 1H), 3.40 (d, J=7.2 Hz, 2H), 2.13 (q, J=5.3, 4.8 Hz, 4H), 1.77 (d, J=1.4 Hz, 3H), 1.69 (d, J=1.3 Hz, 3H), 1.61 (d, J=1.3 Hz, 3H).

Synthesis of I-150: 8-geranylumbelliferone

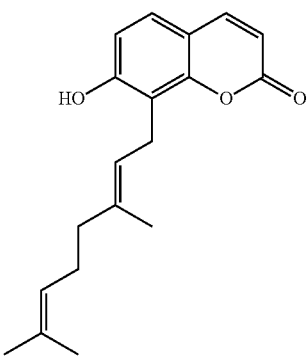 [SMILES: CC(C)=CCC/C(C)=C/Cc1c(O)ccc2ccc(=O)oc12]

100 mg (2.1 equiv.) of umbelliferone (7-hydroxycoumarin) and 45 mg (1 equiv.) of geraniol (3,7-dimethylocta-trans-2,6-dien-1-ol) were suspended in xylenes. 1.5 g/mmol of dry acidic alumina (Al$_2$O$_3$) relative to the scaffold was added to the reaction mixture, which was subsequently heated at 160° C. for 2 hours in a monowave reactor. The mixture was then poured over diatomaceous earth and washed with hexane, ethyl acetate, and acetone. The collected solvents were combined and concentrated under reduced pressure. 8-geranylumbelliferone was eluted through column chromatography using hexanes/ethyl acetate (9.7 mg, 11% yield). 1H NMR (400 MHz, Chloroform-d) δ 7.63 (d, J=9.5 Hz, 1H), 7.24 (d, J=8.4 Hz, 1H), 6.80 (d, J=8.5 Hz, 1H), 6.24 (d, J=9.4 Hz, 1H), 6.20 (s, 1H), 5.27 (tq, J=7.2, 1.3 Hz, 1H), 5.03 (dddt, J=6.8, 5.4, 2.8, 1.4 Hz, 1H), 3.64 (d, J=7.3 Hz, 2H), 2.14-2.02 (m, 4H), 1.85 (q, J=1.0 Hz, 3H), 1.66 (d, J=1.3 Hz, 3H), 1.58 (d, J=1.3 Hz, 3H).

Synthesis of I-151: 6-prenyl naringenin

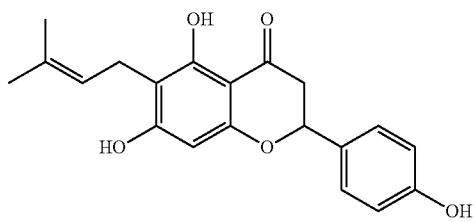 [SMILES: CC(C)=CCc1c(O)cc2c(c1O)C(=O)CC(c1ccc(O)cc1)O2]

48 mg (1.0 equiv.) of naringenin and 15 mg (1.0 equiv.) of prenol (3-methyl-2-buten-1-ol) were suspended in dichloroethane. 2.0 g/mmol of dry acidic alumina (Al$_2$O$_3$) relative to the scaffold was added to the reaction mixture, which was subsequently heated at 120° C. for 2 hours monowave reactor. The mixture was then poured over diatomaceous earth and washed with ethyl acetate. The collected solvents were combined and concentrated under reduced pressure. 6-prenylnaringenin was eluted through column chromatography on a C18 column using water/acetonitrile (0.1% trifluoroacetic acid) (3.6 mg, 6% yield). 1H NMR (400 MHz, Chloroform-d) δ 11.99 (s, 1H), 7.33 (d, J=8.1 Hz, 2H), 6.88 (d, J=8.6 Hz, 2H), 6.02 (s, 1H), 5.99 (s, 1H), 5.35 (dd, J=12.9, 3.0 Hz, 1H), 5.20 (ddq, J=8.7, 5.7, 1.4 Hz, 1H), 3.31 (d, J=7.3 Hz, 2H), 3.05 (dd, J=17.1, 13.0 Hz, 2H), 2.80 (dd, J=17.1, 3.0 Hz, 1H), 1.73 (s, J=1.3 Hz, 6H).

Synthesis of I-152: macarangin (6-geranyl kaempferol)

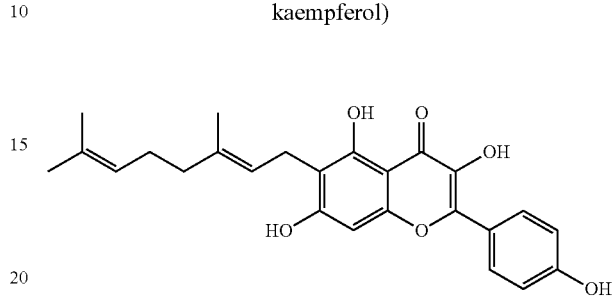

52 mg (1.0 equiv.) of kaempferol and 30 mg (1.0 equiv.) of geraniol (3,7-dimethylocta-trans-2,6-dien-1-ol) were suspended in dichloroethane. 2.0 g/mmol of dry acidic alumina (Al$_2$O$_3$) relative to the scaffold was added to the reaction mixture, which was subsequently heated at 140° C. for 2 hours in a monowave reactor. The mixture was then poured over diatomaceous earth and washed with ethyl acetate. The collected solvents were combined and concentrated under reduced pressure. Macarangin (6-geranylkaempferol was eluted through column chromatography on a C18 column using water/acetonitrile (0.1% trifluoroacetic acid) (3.6 mg, 6% yield). 1H NMR (400 MHz, Chloroform-d) δ 11.73 (s, 1H), 8.13 (d, J=8.9 Hz, 2H), 6.98 (d, J=8.9 Hz, 2H), 6.59 (s, 1H), 6.33 (s, 1H), 6.04 (s, 1H), 5.31 (td, J=7.1, 1.3 Hz, 1H), 5.09 (s, 1H), 5.04 (dddd, J=8.1, 6.6, 2.9, 1.4 Hz, 1H), 3.71 (s, 1H), 3.63 (d, J=7.1 Hz, 2H), 2.10 (m, 4H), 1.86 (s, 3H), 1.66 (s, 3H), 1.58 (s, 3H).

Synthesis of I-153

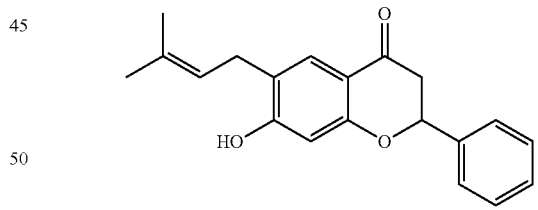

25 mg (0.10 mmol, 1 equiv.) of 7-Hydroxyflavanone and 18 mg (0.21 mmol, 2 equiv.) of (3-methyl-2-buten-1-ol) were suspended in dichloroethane. 416 mg (2.0 g/mmol of prenol) of dry acidic alumina (Al$_2$O$_3$) was added to the reaction mixture, which was subsequently heated at 150° C. for 20 minutes in a monowave reactor. The mixture was cooled to room temperature and then poured over diatomaceous earth and washed with ethyl acetate and methanol. The collected solvents were combined and concentrated under reduced pressure. 6-prenyl-7-hydroxyflavanone was eluted through column chromatography using ethyl acetate/hexanes (1.7 mg, 5% yield). 1H NMR (400 MHz, Chloroform-d) δ 7.69 (d, J=1.2 Hz, 1H), 7.59 (s, 1H), 7.51-7.34 (m, 5H), 5.51-5.39 (m, 1H), 5.36-5.27 (m, 1H), 3.33 (dd, J=11.2, 6.6 Hz, 3H), 3.01 (dd, J=16.9, 13.0 Hz, 1H), 2.82 (dd, J=16.9, 3.0 Hz, 1H), 1.35 (d, J=2.2 Hz, 6H).

Synthesis of I-153

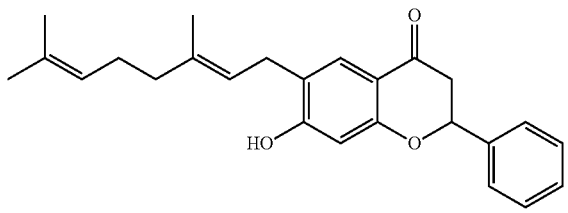 [SMILES: CC(C)=CCC/C(C)=C/Cc1cc2c(cc1O)OC(c1ccccc1)CC2=O]

To a stirring solution of 39 mg (0.25 mmol) of geraniol (2 equiv.) and 30 mg (0.13 mmol) of 7-Hydroxyflavanone (1 equiv.) was added 499.4 mg of acidic alumina (2 g/mmol of geraniol) in 1.5 mL of 1,2 dichloroethane. The mixture was heated to 150° C. and stirred for 20 minutes. The reaction was cooled down to room temperature, filtered through a Celite pad and rinsed with EtOAc and MeOH. The filtrate was concentrated under reduced pressure and purified by normal phase chromatography with a gradient up to 25% EtOAc/Hex. 5.4 mg (11% yield) of the desired product was recovered as a white solid. $^1$H NMR (700 MHz, DMSO-d6) δ 9.40 (s, 1H), 7.50 (s, 1H), 7.45-7.30 (m, 5H), 5.53 (dd, J=12.5, 3.1 Hz, 1H), 5.11 (tt, J=7.0, 1.5 Hz, 1H), 5.02 (dddd, J=7.0, 5.6, 2.9, 1.5 Hz, 1H), 3.24 (d, J=7.3 Hz, 2H), 3.01 (dd, J=16.7, 12.6 Hz, 1H), 2.75 (dd, J=16.7, 3.1 Hz, 1H), 1.98 (q, J=7.4 Hz, 2H), 1.89 (dd, J=9.0, 6.3 Hz, 2H), 1.63 (s, 3H), 1.56 (s, 6H)

Synthesis of I-154

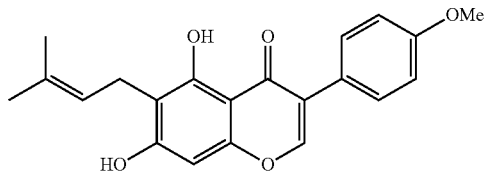 [SMILES: COc1ccc(-c2coc3cc(O)c(CC=C(C)C)c(O)c3c2=O)cc1]

To a stirring solution of 25 mg (0.35 mmol) of prenol (1 equiv.) and 124 mg (mmol) of biochanin (1.5 equiv.) was added 509 mg of acidic alumina (2 g/mmol of prenol) in 3 mL of 1,2 dichloroethane. The mixture was heated to 80° C. and stirred for 24 hours. The reaction was cooled down to room temperature, filtered through a Celite pad and rinsed with EtOAc and MeOH. The filtrate was concentrated under reduced pressure and purified by normal phase chromatography with a gradient up to 25% EtOAc/Hex. 8.5 mg (8% yield) of the desired product was recovered as a white solid. $^1$H NM R (400 MHz, Chloroform-d) δ 12.85 (s, 1H), 7.92 (s, 1H), 7.46 (d, J=8.9 Hz, 2H), 6.98 (d, J=8.9 Hz, 2H), 6.30 (s,z 1H), 5.24 (mf, 1H), 3.84 (s, 3H), 3.51-3.44 (d, J=6.9 Hz, 2H), 1.83 (d, J=1.4 Hz, 3H), 1.75 (d, J=1.6 Hz, 3H).

A person skilled in the art would appreciate that further manipulation of the substituent groups using known chemistry can be performed on the intermediates and final compounds in the Schemes above to provide alternative compounds of the application.

Salts of compounds of the application may be formed by methods known to those of ordinary skill in the art, for example, by reacting a compound of the application with an amount of acid or base, such as an equivalent amount, in a medium such as one in which the salt precipitates or in aqueous medium followed by lyophilization.

The formation of solvates will vary depending on the compound and the solvate. In general, solvates are formed by dissolving the compound in the appropriate solvent and isolating the solvate by cooling or using an antisolvent. The solvate is typically dried or azeotroped under ambient conditions. The selection of suitable conditions to form a particular solvate can be made by a person skilled in the art. Examples of suitable solvents are ethanol, water and the like. When water is the solvent, the molecule is referred to as a "hydrate". The formation of solvates of the compounds of the application will vary depending on the compound and the solvate. In general, solvates are formed by dissolving the compound in the appropriate solvent and isolating the solvate by cooling or using an antisolvent. The solvate is typically dried or azeotroped under ambient conditions. The selection of suitable conditions to form a particular solvate can be made by a person skilled in the art.

Throughout the processes described herein it is to be understood that, where appropriate, suitable protecting groups will be added to and subsequently removed from, the various reactants and intermediates in a manner that will be readily understood by one skilled in the art. Conventional procedures for using such protecting groups as well as examples of suitable protecting groups are described, for example, in "Protective Groups in Organic Synthesis", T. W. Green, P. G. M. Wuts, Wiley-Interscience, New York, (1999). It is also to be understood that a transformation of a group or substituent into another group or substituent by chemical manipulation can be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities and ways to circumvent them by carrying out appropriate transformations and synthetic steps in a suitable order, will be readily understood to one skilled in the art. Examples of transformations are given herein and it is to be understood that the described transformations are not limited only to the generic groups or substituents for which the transformations are exemplified. References and descriptions of other suitable transformations are given in "Comprehensive Organic Transformations—A Guide to Functional Group Preparations" R. C. Larock, VHC Publishers, Inc. (1989). References and descriptions of other suitable reactions are described in textbooks of organic chemistry, for example, "Advanced Organic Chemistry", March, 4th ed. McGraw Hill (1992) or, "Organic Synthesis", Smith, McGraw Hill, (1994). Techniques for purification of intermediates and final products include, for example, straight and reversed phase chromatography on column or rotating plate, recrystallisation, distillation and liquid-liquid or solid-liquid extraction, which will be readily understood by one skilled in the art.

While the present application has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

FULL CITATIONS FOR DOCUMENTS REFERRED TO IN THE SPECIFICATION

A number of publications are cited herein. Full citations for these references are provided below. Each of these references is incorporated herein by reference in its entirety into the present disclosure, to the same extent as if each individual reference was specifically and individually indicated to be incorporated by reference.

1. Tyman, J. H. P.; Editor, Synthetic and Natural Phenols. Elsevier1996; p 718 pp.
2. Rappoport, Z., The Chemistry of Phenols, Part 2. John Wiley & Sons Ltd. 2003; p 819 pp.
3. Huang, Z.; Lumb, J.-P., Phenol-Directed C—H Functionalization. ACS Catal. 2019, 9, 521-555.
4. Anderson, J. C.; Headley, C.; Stapleton, P. D.; Taylor, P. W., Asymmetric total synthesis of B-ring modified (-)-epicatechin gallate analogues and their modulation of β-lactam resistance in Staphylococcus aureus. Tetrahedron 2005, 61, 7703-7711.
5. Wan, S. B.; Landis-Piwowar, K. R.; Kuhn, D. J.; Chen, D.; Dou, Q. P.; Chan, T. H., Structure-activity study of epi-gallocatechin gallate (EGCG) analogs as proteasome inhibitors. Bioorg. Med. Chem. 2005, 13, 2177-2185.
6. Anderson, J. C.; McCarthy, R. A.; Paulin, S.; Taylor, P. W., Anti-staphylococcal activity and β-lactam resistance attenuating capacity of structural analogs of (-)-epicatechin gallate. Bioorg. Med. Chem. Lett. 2011, 21, 6996-7000.
7. Barluenga, J.; Sanz, R.; Fananas, F. J., Regio- and stereoselective copper-induced isomerization of 2-alkenyl 2-lithiophenyl ethers to 2-(2-alkenyl)phenols. [Erratum to document cited in CA127:262485]. Tetrahedron Lett. 1997, 38, 7129.
8. Simas, A. B. C.; Coelho, A.; Costa, P. R. R., Regioselective lithiation of resorcinol derivatives. Synthesis of mono-O-MOM- and O-benzylresorcinols prenylated at C(2) or C(4) positions. Synthesis 1999, 1017-1021.
9. Paz, J. L.; Rodrigues, J. A. R., Preparation of aromatic geraniol analogues via a Cu(I)-mediated grignard coupling. J. Braz. Chem. Soc. 2003, 14, 975-981.
10. Mino, T.; Kogure, T.; Abe, T.; Koizumi, T.; Fujita, T.; Sakamoto, M., Palladium-Catalyzed Allylic Arylation of Allylic Ethers with Arylboronic Acids Using Hydrazone Ligands. Eur. J. Org. Chem. 2013, 2013, 1501-1505.
11. Gardner, K. D.; Wiemer, D. F., Selective Prenylation of Protected Phenols for Synthesis of Pawhuskin A Analogues. J. Org. Chem. 2016, 81, 1585-1592.
12. Bedford, R. B.; Limmert, M. E., Catalytic Intermolecular Ortho-Arylation of Phenols. J. Org. Chem. 2003, 68, 8669-8682.
13. Boebel, T. A.; Hartwig, J. F., Silyl-directed, iridium-catalyzed ortho-borylation of arenes. a one-pot ortho-borylation of phenols, arylamines, and alkylarenes. J. Am. Chem. Soc. 2008, 130, 7534-7535.
14. Chattopadhyay, B.; Dannatt, J. E.; Andujar-De Sanctis, I. L.; Gore, K. A.; Maleczka, R. E.; Singleton, D. A.; Smith, M. R., Ir-Catalyzed ortho-Borylation of Phenols Directed by Substrate-Ligand Electrostatic Interactions: A Combined Experimental/in Silico Strategy for Optimizing Weak Interactions. J. Am. Chem. Soc. 2017, 139, 7864-7871.
15. Xiao, B.; Fu, Y.; Xu, J.; Gong, T.-J.; Dai, J.-J.; Yi, J.; Liu, L., Pd(II)—Catalyzed C—H Activation/Aryl-Aryl Coupling of Phenol Esters. J. Am. Chem. Soc. 2010, 132, 468-469.
16. Ackermann, L.; Diers, E.; Manvar, A., Ruthenium-catalyzed C—H bond arylations of arenes bearing removable directing groups via six-membered ruthenacycles. Org. Lett. 2012, 14, 1154-1157.
17. Reed, J.; Snieckus, V. J. T. L., Ortho-amination of lithiated tertiary benzamides. Short route to polysubstituted anthranilamides. 1983, 24, 3795-3798.
18. Baek, S.-H.; Yook, C. N.; Han, D. S., Boron trifluoride etherate on alumina—a modified Lewis acid reagent(V) a convenient single-step synthesis of cannabinoids. Bull. Korean Chem. Soc. 1995, 16, (3), 293-6.
19. Taura, F.; Morimoto, S.; Shoyama, Y., Purification and characterization of cannabidiolic-acid synthase from Cannabis sativa L. Biochemical analysis of a novel enzyme that catalyzes the oxidocyclization of cannabigerolic acid to cannabidiolic acid. J. Biol. Chem. 1996, 271, (29), 17411-17416.
20. Mechoulam, R.; Yagen, B., Stereoselective cyclizations of cannabinoid 1,5-dienes. Tetrahedron Lett. 1969, (60), 5349-52.
21. Zhang, X.; Jones-Mensah, E.; Deobald, J.; Magolan, J., Alkylation of Indoles with α,β-Unsaturated Ketones using Alumina in Hexane. Adv. Synth. Catal. 2019, 361, (24), 5548-5551.
22. Kavarana, M. J.; Peet, R. C. Chemoenzymatic synthesis of tetrahydrocannabivarin, carnnabivarin, and cannabinol. US20170283837A1, 2017.
23. Hirata, Y., Grifolin, an antibiotic substance from a mushroom, Grifola confluens. Chem. Research, Biochem. and Org. Chem. 1950, 7, 119-43; English summary, 144.
24. Misasa, H.; Matsui, Y.; Uehara, H.; Tanaka, H.; Ishihara, M.; Shibata, H., Studies on chemical components of mushroom. Part II. Tyrosinase inhibitors from Albatrellus confluens. Biosci., Biotechnol., Biochem. 1992, 56, (10), 1660-1.
25. Nukata, M.; Hashimoto, T.; Yamamoto, I.; Iwasaki, N.; Tanaka, M.; Asakawa, Y., Neogrifolin derivatives possessing anti-oxidative activity from the mushroom Albatrellus ovinus. Phytochemistry 2002, 59, (7), 731-737.
26. Iwata, N.; Wang, N.; Yao, X.; Kitanaka, S., Structures and Histamine Release Inhibitory Effects of Prenylated Orcinol Derivatives from Rhododendron dauricum. J. Nat. Prod. 2004, 67, (7), 1106-1109.
27. Ye, M.; Liu, J.-k.; Lu, Z.-x.; Zhao, Y.; Liu, S.-f.; Li, L.-I.; Tan, M.; Weng, X.-x.; Li, W.; Cao, Y., Grifolin, a potential antitumor natural product from the mushroom Albatrellus confluens, inhibits tumor cell growth by inducing apoptosis in vitro. FEBS Lett. 2005, 579, (16), 3437-3443.
28. Jin, S.; Pang, R.-P.; Shen, J.-N.; Huang, G.; Wang, J.; Zhou, J.-G., Grifolin induces apoptosis via inhibition of PI3K/AKT signalling pathway in human osteosarcoma cells. Apoptosis 2007, 12, (7), 1317-1326.
29. Ye, M.; Luo, X.; Li, L.; Shi, Y.; Tan, M.; Weng, X.; Li, W.; Liu, J.; Cao, Y., Grifolin, a potential antitumor natural product from the mushroom Albatrellus confluens, induces cell-cycle arrest in G1 phase via the ERK1/2 pathway. Cancer Lett. (Amsterdam, Neth.) 2007, 258, (2), 199-207.
30. Che, X.; Yan, H.; Sun, H.; Dongol, S.; Wang, Y.; Lv, Q.; Jiang, J., Grifolin induces autophagic cell death by inhibiting the Akt/mTOR/S6K pathway in human ovarian cancer cells. Oncol. Rep. 2016, 36, (2), 1041-1047.

31. Sugiyama, K.; Tanaka, A.; Kawagishi, H.; Ojima, F.; Sakamoto, H.; Ishiguro, Y., Hypocholesterolemic action of dietary grifolin on rats fed a high-cholesterol diet. *Biosci., Biotechnol., Biochem.* 1994, 58, (1), 211-12.

32. Huang, H. Q.; Pan, X. L.; Ji, C. J.; Zeng, G. Z.; Jiang, L. H.; Fu, X.; Liu, J. K.; Hao, X. J.; Zhang, Y. J.; Tan, N. H., Screening and docking studies of natural phenolic inhibitors of carbonic anhydrase II. *Sci. China, Ser. B: Chem.* 2009, 52, (3), 332-337.

33. Quang, D. N.; Hashimoto, T.; Arakawa, Y.; Kohchi, C.; Nishizawa, T.; Soma, G.-I.; Asakawa, Y., Grifolin derivatives from *Albatrellus caeruleoporus*, new inhibitors of nitric oxide production in RAW 264.7 cells. *Bioorg. Med. Chem.* 2006, 14, (1), 164-168.

34. Isobe, M.; Goto, T., Synthesis of grifolin, an antibiotic from a basidiomycete. *Tetrahedron* 1968, 24, (2), 945-8.

35. Ohta, S.; Nozaki, A.; Ohashi, N.; Matsukawa, M.; Okamoto, M., A total synthesis of grifolin. *Chem. Pharm. Bull.* 1988, 36, (6), 2239-43.

36. Grabovyi, G. A.; Mohr, J. T., Total Synthesis of Grifolin, Grifolic Acid, LL-Z1272α, LL-Z1272β, and Ilicicolinic Acid A. *Org. Lett.* 2016, 18, (19), 5010-5013.

37. Ma, T.-K.; White, A. J. P.; Barrett, A. G. M., Meroterpenoid total synthesis: Conversion of geraniol and farnesol into amorphastilbol, grifolin and grifolic acid by dioxinone-p-keto-acylation, palladium catalyzed decarboxylative allylic rearrangement and aromatization. *Tetrahedron Lett.* 2017, 58, (28), 2765-2767.

38. Mahiou, V.; Roblot, F.; Hocquemiller, R.; Cave, A.; Barrios, A. A.; Founet, A.; Ducrot, P.-H., Piperogalin, a new prenylated diphenol from *Peperomia galioides*. *J. Nat. Prod.* 1995, 58, (2), 324-8.

39. Tanaka, T.; Asai, F.; Iinuma, M., Phenolic compounds from *Peperomia Obtusifolia*. *Phytochemistry* 1998, 49, (1), 229-232.

40. Fournet, A.; Ferreira, M. E.; Rojas de Arias, A.; Fuentes, S.; Torres, S.; Inchausti, A.; Yaluff, G.; Nakayama, H.; Mahiou, V.; et, a., In vitro and in vivo leishmanicidal studies of *Peperomia galioides*. *Phytomedicine* 1996, 3, (3), 271-275.

41. Kumano, T.; Richard, S. B.; Noel, J. P.; Nishiyama, M.; Kuzuyama, T., Chemoenzymatic syntheses of prenylated aromatic small molecules using *Streptomyces* prenyltransferases with relaxed substrate specificities. *Bioorg. Med. Chem.* 2008, 16, (17), 8117-8126.

42. Goto, T.; Kakisawa, H.; Hirata, Y., The structure of grifolin, an antibiotic from a basidiomycete. *Tetrahedron* 1963, 19, (12), 2079-83.

43. Manners, G.; Jurd, L.; Stevens, K., Biogenetic-type synthesis of isoprenoid and diisoprenoid derivatives of orcinol. *Tetrahedron* 1972, 28, (11), 2949-59.

44. Eisohly, H. N.; Turner, C. E.; Clark, A. M.; Eisohly, M. A., Synthesis and antimicrobial activities of certain cannabichromene and cannabigerol related compounds. *J. Pharm. Sci.* 1982, 71, (12), 1319-23.

(45) Fujisaki, S.; Eguchi, H.; Omura, A.; Okamoto, A.; Nishida, A., Halogenation using N-halo compounds. I. Effect of amines on ortho-bromination of phenols with NBS. *Bull. Chem. Soc. Jpn.* 1993, 66 (5), 1576-9.

(46) Gnaim, J. M.; Sheldon, R. A., Highly regioselective ortho-chlorination of phenol with sulfuryl chloride in the presence of amines. *Tetrahedron Lett.* 1995, 36 (22), 3893-6.

(47) Saper, N. I.; Snider, B. B., 2,2,6,6-Tetramethylpiperidine-Catalyzed, Ortho-selective Chlorination of Phenols by Sulfuryl Chloride. *J. Org. Chem.* 2014, 79 (2), 809-813.

(48) Xiong, X.; Yeung, Y.-Y., Ammonium Salt-Catalyzed Highly Practical Ortho-Selective Monohalogenation and Phenylselenation of Phenols: Scope and Applications. *ACS Catal.* 2018, 8 (5), 4033-4043.

(49) Maddox, S. M.; Dinh, A. N.; Armenta, F.; Um, J.; Gustafson, J. L., The Catalyst-Controlled Regiodivergent Chlorination of Phenols. *Org. Lett.* 2016, 18 (21), 5476-5479.

(50) Vila, C.; Quintero, L.; Blay, G.; Munoz, M. C.; Pedro, J. R., Organocatalytic Enantioselective Synthesis of α-Hydroxyketones through a Friedel-Crafts Reaction of Naphthols and Activated Phenols with Aryl- and Alkylglyoxal Hydrates. *Org. Lett.* 2016, 18 (21), 5652-5655.

(51) Han, X.; Ye, C.; Chen, F.; Chen, Q.; Wang, Y.; Zeng, X., A highly enantioselective Friedel-Crafts reaction of 3,5-dimethoxyphenol with nitroolefins mediated by a bifunctional quinine derived thiourea catalyst. *Org. Biomol. Chem.* 2017, 15 (16), 3401-3407.

(52) Casiraghi, G.; Casnati, G.; Puglia, G.; Sartori, G.; Terenghi, G., Selective reactions between phenols and formaldehyde. A novel route to salicylaldehydes. *J. Chem. Soc., Perkin Trans.* 1 1980, (9), 1862-5.

(53) Sartori, G.; Casnati, G.; Bigi, F.; Predieri, G., Ortho-coordinated acylation of phenol systems. *J. Org. Chem.* 1990, 55 (14), 4371-7.

(54) Sartori, G.; Bigi, F.; Maggi, R.; Arienti, A., Acidity effect in the regiochemical control of the alkylation of phenol with alkenes. *J. Chem. Soc., Perkin Trans.* 1 1997, (3), 257-260.

(55) Bigi, F.; Casiraghi, G.; Casnati, G.; Sartori, G., Unusual Friedel-Crafts reactions; I. Exclusive ortho allylation of phenols. *Synthesis* 1981, (4), 310-12.

(56) Shalit, H.; Dyadyuk, A.; Pappo, D., Selective Oxidative Phenol Coupling by Iron Catalysis. *J. Org. Chem.* 2019, 84 (4), 1677-1686.

(57) Kshirsagar, U. A.; Regev, C.; Parnes, R.; Pappo, D., Iron-Catalyzed Oxidative Cross-Coupling of Phenols and Alkenes. *Org. Lett.* 2013, 15 (12), 3174-3177.

(58) Sun, W.; Lin, H.; Zhou, W.; Li, Z., Oxidative ortho-amino-methylation of phenols via C—H and C—C bond cleavage. *RSC Advances* 2014, 4 (15), 7491-7494.

(59) Dai, J.-L.; Shao, N.-Q.; Zhang, J.; Jia, R.-P.; Wang, D.-H., Cu(II)-Catalyzed ortho-Selective Aminomethylation of Phenols. *J. Am. Chem. Soc.* 2017, 139 (36), 12390-12393.

(60) Yu, C.; Patureau, F. W., Cu-Catalyzed Cross-Dehydrogenative ortho-Aminomethylation of Phenols. *Angew. Chem., Int. Ed.* 2018, 57 (36), 11807-11811.

(61) Yu, Z.; Li, Y.; Shi, J.; Ma, B.; Liu, L.; Zhang, J., (C6F5)3B Catalyzed Chemoselective and ortho-Selective Substitution of Phenols with α-Aryl α-Diazoesters. *Angew. Chem., Int. Ed.* 2016, 55 (47), 14807-14811.

(62) Jurrat, M.; Maggi, L.; Lewis, W.; Ball, L. T., Modular bismacycles for the selective C—H arylation of phenols and naphthols. *Nat. Chem.* 2020, 12 (3), 260-269.

(63) Chang, M. N.; Hammond, M. L.; Jensen, N. P.; McDonald, J.; Zambias, R. A. Substituted cinnamyl-2,3-dihydrobenzofuran and analogs useful as antiinflammatory agents. EP143952A1, 1985.

(64) Alabaster, R. J.; Cottrell, I. F.; Hands, D.; Humphrey, G. R.; Kennedy, D. J.; Wright, S. H. B., Synthesis of 6-(3-aryl-2-propenyl)-2,3-dihydro-5-hydroxybenzofuran derivatives by cross coupling reactions. *Synthesis* 1989, (8), 598-603.

The invention claimed is:

1. A process for preparing a compound of Formula (I) comprising:

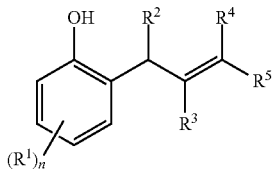

reacting a compound of Formula (II)

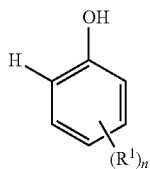

with a compound of Formula (III)

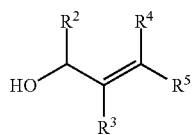

in the presence of an aluminum compound selected from alumina and aluminum alkoxides and in a non-protic solvent to form the compound of Formula (I), wherein:

n is 2, 3 or 4;

two $R^1$ groups are linked together to form a polycyclic ring system having 8 or more atoms together with the phenyl ring to which said groups are bonded, and in which one or more carbon atoms in said polycyclic ring system is optionally replaced with a heteromoiety selected from $NR^6$, O and S, wherein the polycyclic ring system is optionally substituted with one or more substituents selected from =O, OH, halo, $C_{1-16}$alkyl, $C_{2-16}$alkenyl, $C_{2-16}$alkynyl, $OC_{1-16}$alkyl, $OC_{2-16}$alkenyl, $OC_{2-16}$alkynyl; $C_{1-16}$alkyleneOR$^8$, $C_{2-16}$alkenyleneOR$^8$, $C_{2-16}$alkynyleneOR$^8$, $C_{6-18}$ aryl, $C_{3-18}$ cycloalkyl, $C_{3-18}$heterocycloalkyl, and $C_{5-18}$heteroaryl, the latter 4 groups being optionally substituted with one or more substituents selected from OH, halo, $C_{1-16}$alkyl, $OC_{1-16}$alkyl, and $C_{2-16}$alkenyl;

when n is 3 or 4, further $R^1$ groups are independently selected from OH, halo, CN, $NO_2$, COOH, $C_{2-16}$alkenyl, $C_{2-16}$alkynyl, $C_{3-18}$cycloalkyl, $C_{1-16}$alkylene $C_{3-18}$cycloalkyl, $C_{2-16}$alkenylene$C_{3-18}$ cycloalkyl, $C_{2-16}$alkynylene$C_{3-18}$cycloalkyl, $C_{3-18}$heterocycloalkyl, $C_{1-16}$alkylene$C_{3-18}$heterocycloalkyl, $C_{1-16}$alkenylene$C_{3-18}$heterocycloalkyl, $C_{2-16}$alkynylene$C_{3-18}$ heterocycloalkyl, $C_{6-18}$ aryl, $C_{1-16}$alkylene$C_{6-18}$ aryl, $C_{2-16}$alkenylene$C_{6-18}$ aryl, $C_{2-16}$alkynylene$C_{6-18}$aryl, $C_{5-18}$heteroaryl, $C_{2-16}$alkylene$C_{5-18}$heteroaryl, $C_{2-16}$alkenylene$C_{5-18}$heteroaryl, $C_{2-16}$alkynylene$C_{5-18}$ heteroaryl, $Z$—$C_{2-16}$alkenyl, $Z$—$C_{2-16}$alkynyl, $Z$—$C_{3-18}$ cycloalkyl, $Z$—$C_{1-16}$alkylene$C_{3-18}$cycloalkyl, $Z$—$C_{2-16}$alkenylene$C_{3-18}$cycloalkyl, $Z$—$C_{2-16}$alkynylene$C_{3-18}$ cycloalkyl, $Z$—$C_{3-18}$heterocycloalkyl, $Z$—$C_{1-16}$alkylene$C_{3-18}$ heterocycloalkyl, $Z$—$C_{2-16}$alkenylene$C_{3-18}$heterocycloalkyl, $Z$—$C_{2-16}$alkynylene$C_{3-18}$heterocycloalkyl, $Z$—$C_{6-18}$aryl, $Z$—$C_{1-16}$alkylene$C_{6-18}$aryl, $Z$—$C_{2-16}$alkenylene$C_{6-18}$aryl, $Z$—$C_{2-16}$alkynylene$C_{6-18}$aryl, $Z$—$C_{5-18}$heteroaryl, $Z$—$C_{1-16}$alkylene$C_{5-18}$ heteroaryl, $Z$—$C_{2-16}$alkenylene$C_{5-18}$ heteroaryl, and $Z$—$C_{2-16}$alkynylene$C_{5-18}$ heteroaryl, wherein all alkyl, alkenyl, alkynyl, alkylene, alkenylene, alkynylene, cycloalkyl heterocycloalkyl, aryl, and heteroaryl groups are optionally substituted with one or more substituents selected from OH, halo, $C_{1-16}$alkyl, $C_{2-16}$alkenyl, $C_{2-6}$alkynyl, $OC_{1-16}$alkyl, $OC_{2-16}$alkenyl, and $OC_{2-16}$alkynyl;

Z is selected from O, C(O), $CO_2$, S, $SO_2$, SO, and $NR^7$;

$R^2$ is H, $R^3$ is selected from H and $C_{1-6}$alkyl, $R^4$ is selected from H, $C_{1-6}$alkyl, $C_{6-18}$aryl, $C_{1-16}$alkylene$C_{6-18}$aryl, $C_{5-18}$ heteroaryl, and $C_{2-16}$alkylene$C_{5-18}$ heteroaryl;

$R^5$ is selected from H, $C_{2-26}$alkenyl, $C_{2-26}$alkynyl, $C_{3-18}$ cycloalkyl, $C_{1-16}$alkylene$C_{3-18}$cycloalkyl, $C_{2-16}$alkenylene$C_{3-18}$ cycloalkyl, $C_{2-16}$alkynylene$C_{3-18}$ cycloalkyl, $C_{3-18}$heterocycloalkyl, $C_{1-16}$alkylene$C_{3-18}$ heterocycloalkyl, $C_{1-16}$alkenylene$C_{3-18}$heterocycloalkyl, $C_{2-16}$alkynylene$C_{3-18}$ heterocycloalkyl, $C_{6-18}$aryl, $C_{1-16}$alkylene$C_{6-18}$aryl, $C_{2-16}$alkenylene$C_{6-18}$aryl, $C_{2-16}$alkynylene$C_{6-18}$aryl, $C_{5-18}$heteroaryl, $C_{2-16}$alkylene$C_{5-18}$heteroaryl, $C_{2-16}$alkenylene$C_{5-18}$ heteroaryl, $C_{2-16}$alkynylene$C_{5-18}$ heteroaryl, wherein all cycloalkyl, heterocycloalkyl, aryl and heteroaryl are optionally substituted with one or more substituents selected from OH, $NO_2$, CN, halo, $C_{1-16}$alkyl, $C_{2-16}$alkenyl, $C_{2-16}$alkynyl, $OC_{1-16}$alkyl, $OC_{2-16}$alkenyl, $OC_{2-16}$alkynyl, $C_{1-16}$alkyleneOR$^9$ $C_{2-16}$alkenyleneOR$^9$, $C_{2-16}$alkynyleneOR$^9$, $SO_3C_{1-16}$alkyl, $SO_3C_{6-16}$aryl, and $SO_3C_{5-18}$heteroaryl substituted with $C_{1-16}$alkyl; or any two of $R^2$, $R^3$, $R^4$ and $R^5$ are linked together to form an unsubstituted or substituted monocyclic or polycyclic ring system having 4 or more atoms together with the carbon atoms to which said any two of $R^2$, $R^3$, $R^4$ and $R^5$ are bonded, wherein the monocyclic or polycyclic ring system is optionally substituted with one or more substituents selected =O, OH, halo, $C_{1-16}$alkyl, $C_{2-16}$alkenyl, $C_{2-16}$alkynyl, $OC_{1-16}$alkyl, $OC_{2-16}$alkenyl, $OC_{2-16}$alkynyl; $C_{1-16}$alkyleneOR$^8$, $C_{2-16}$alkenyleneOR$^8$, $C_{2-16}$alkynyleneOR$^8$, $C_{6-18}$aryl, $C_{3-18}$ cycloalkyl, $C_{3-18}$heterocycloalkyl, and $C_{5-18}$heteroaryl, the latter 4 groups being optionally substituted with one or more substituents selected from OH, halo, $C_{1-16}$alkyl, $OC_{1-16}$alkyl, and $C_{2-16}$alkenyl;

$R^6$, $R^7$, $R^8$ and $R^9$ are independently selected from H and $C_{1-6}$alkyl; and all alkyl, alkenyl, alkynyl, alkylene, alkenylene, alkynylene, cycloalkyl, and heterocycloalkyl groups are optionally fluoro-substituted.

2. The process of claim 1, wherein the non-protic solvent is a non-polar solvent or a polar aprotic solvent.

3. The process of claim 1, wherein the aluminum compound is acidic alumina.

4. The process of claim 3, wherein the process further comprises a dehydrating agent and/or an acid.

5. The process of claim 1, wherein the polycyclic ring system is a gonanyl (steroid nucleus) which is optionally substituted with one or more substituents selected from OH, =O, halo, $C_{1-16}$alkyl, $C_{2-16}$alkenyl, $C_{2-16}$alkynyl, $OC_{1-16}$alkyl, $OC_{2-16}$alkenyl, $OC_{2-16}$alkynyl, $C_{1-16}$alkyleneOR$^8$, C(O)$C_{1-16}$alkyl, C(O)$C_{2-16}$alkenyl, C(O)$C_{2-16}$alkynyl, $C_{2-16}$alkenyleneOR$^8$, $C_{2-16}$alkynyleneOR$^8$, $C_{6-18}$ aryl, $C_{3-18}$ cycloalkyl, $C_{3-18}$heterocycloalkyl, and $C_{5-18}$heteroaryl, the latter 4 groups being optionally substituted with one or more substituents selected from OH, halo, $C_{1-16}$alkyl, $OC_{1-16}$alkyl, and $C_{2-16}$alkenyl.

6. The process of claim 1, wherein the polycyclic ring system is selected from benzofuranyl, isobenzofuranyl, indolyl, isoindolyl, quinolinyl, isoquinolinyl, benzepinyl, carbazolyl, and acridinyl which are optionally substituted with one or more substituents selected from OH, =O, halo, $C_{1-16}$alkyl, $C_{2-16}$alkenyl, $C_{2-16}$alkynyl, $OC_{1-16}$alkyl, $OC_{2-16}$alkenyl, $OC_{2-16}$alkynyl, C(O)$C_{1-16}$alkyl, C(O)$C_{2-16}$alkenyl, C(O)$C_{2-16}$alkynyl, $C_{1-16}$alkyleneOR$^8$, $C_{2-16}$alkenyleneOR$^8$, $C_{2-16}$alkynyleneOR$^8$, $C_{6-18}$ aryl, $C_{3-18}$ cycloalkyl, $C_{3-18}$heterocycloalkyl, and $C_{5-18}$heteroaryl, the latter 4 groups being optionally substituted with one or more substituents selected from OH, halo, $C_{1-16}$alkyl, $OC_{1-16}$alkyl, and $C_{2-16}$alkenyl.

7. The process of claim 1, wherein the polycyclic ring system is a benzofused ring system selected from benzofurochromenone, benzodiozinyl, benzodiozolyl, indenyl, indolinyl, chromenyl, dihydrochromenonyl, chromenonyl, chromanonyl, benzoxazinyl, quinolinonyl, isoquinolinonyl and coumarinyl which are optionally substituted with one or more substituents selected from OH, =O, halo, $C_{1-16}$alkyl, $C_{2-16}$alkenyl, $C_{2-16}$alkynyl, $OC_{1-16}$alkyl, $OC_{2-16}$alkenyl, $OC_{2-16}$alkynyl, $C_{1-16}$alkyleneOR$^8$, $C_{2-16}$alkenyleneOR$^8$, $C_{2-16}$alkynyleneOR$^8$, $C_{6-18}$aryl, $C_{3-18}$cycloalkyl, $C_{3-18}$heterocycloalkyl, and $C_{5-18}$heteroaryl, the latter 4 groups being optionally substituted with one or more substituents selected from OH, halo, $C_{1-16}$alkyl, $OC_{1-16}$alkyl, and $C_{2-16}$alkenyl.

8. The process of claim 1, wherein the polycyclic ring system is selected from chromenyl, chromenonyl (chromonyl) and chromanonyl (dihydrochromenonyl) which are optionally substituted with one or more substituents selected from OH, =O, halo, $C_{1-16}$alkyl, $C_{2-16}$alkenyl, $C_{2-16}$alkynyl, $OC_{1-16}$alkyl, $OC_{2-16}$alkenyl, $OC_{2-16}$alkynyl, $C_{1-16}$alkyleneOR$^8$, C(O)$C_{1-16}$alkyl, C(O)$C_{2-16}$alkenyl, C(O)$C_{2-16}$alkynyl, $C_{2-16}$alkenyleneOR$^8$, $C_{2-16}$alkynyleneOR$^8$, $C_{6-18}$aryl, $C_{3-18}$ cycloalkyl, $C_{3-18}$ heterocycloalkyl, and $C_{5-18}$heteroaryl, the latter 4 groups being optionally substituted with one or more substituents selected from OH, halo, $C_{1-16}$alkyl, $OC_{1-16}$alkyl, and $C_{2-16}$alkenyl.

9. The process of claim 1, wherein the polycyclic ring system is a flavonyl, isoflavonyl, flavavonyl or isoflavavonyl, which are optionally substituted with one or more substituents selected from OH, halo, $C_{1-16}$alkyl, $OC_{1-16}$alkyl, and $C_{2-16}$alkenyl.

10. The process of claim 1, wherein polycyclic ring system is coumarinyl which is optionally substituted with one or more substituents selected from OH, =O, halo, $C_{1-16}$alkyl, $C_{2-16}$alkenyl, $C_{2-16}$alkynyl, $OC_{1-16}$alkyl, $OC_{2-16}$alkenyl, $OC_{2-16}$alkynyl, $C_{1-16}$alkyleneOR$^8$, $C_{2-16}$alkenyleneOR$^8$, $C_{2-16}$alkynyleneOR$^8$, $C_{6-18}$aryl, $C_{3-18}$cycloalkyl, $C_{3-18}$heterocycloalkyl, and $C_{5-18}$heteroaryl, the latter 4 groups being optionally substituted with one or more substituents selected from OH, halo, $C_{1-16}$alkyl, $OC_{1-16}$alkyl, and $C_{2-16}$alkenyl.

11. The process of claim 1, wherein the polycyclic ring system is selected from flourenyl, carbazolyl, dibenzofuranyl, phenoxazinyl, and xanthonyl which are optionally substituted with one or more substituents selected from OH, =O, halo, $C_{1-16}$alkyl, $C_{2-16}$alkenyl, $C_{2-16}$alkynyl, $OC_{1-16}$alkyl, $OC_{2-16}$alkenyl, $OC_{2-16}$alkynyl, $C_{1-16}$alkyleneOR$^8$, C(O)$C_{1-16}$alkyl, C(O)$C_{2-16}$alkenyl, C(O)$C_{2-16}$alkynyl, $C_{2-16}$alkenyleneOR$^8$, $C_{2-16}$alkynyleneOR$^8$, $C_{6-18}$aryl, $C_{3-18}$cycloalkyl, $C_{3-18}$heterocycloalkyl, and $C_{3-18}$heterocycloalkyl, the latter 4 groups being optionally substituted with one or more substituents selected from OH, halo, $C_{1-16}$alkyl, $OC_{1-16}$alkyl, and $C_{2-16}$alkenyl.

12. The process of claim 1, wherein the polycyclic ring system is a benzofurochromenone which is optionally substituted with one or more substituents selected from OH, $C_{1-16}$alkyl, $C_{2-16}$alkenyl, and $OC_{1-16}$alkyl.

13. The process of claim 1, wherein the polycyclic ring system is selected from naphthalenyl, anthracenyl, phenanthrenyl, tetracenyl, chrysenyl, triphenylenyl, pyrenyl, pentacenyl, benzo[a]pyrenyl, corannulenyl, benzo[ghi]perylenyl, coronenyl, ovalenyl and benzo[c]fluorinyl which are optionally substituted with one or more substituents selected from OH, =O, halo, $C_{1-16}$alkyl, $C_{2-16}$alkenyl, $C_{2-16}$alkynyl, $OC_{1-16}$alkyl, $OC_{2-16}$alkenyl, $OC_{2-16}$alkynyl, $C_{1-16}$alkyleneOR$^8$, C(O)$C_{1-16}$alkyl, C(O)$C_{2-16}$alkenyl, C(O)$C_{2-16}$alkynyl, $C_{2-16}$alkenyleneOR$^8$, $C_{2-16}$alkynyleneOR$^8$, $C_{6-18}$ aryl, $C_{3-18}$ cycloalkyl, $C_{3-18}$heterocycloalkyl, and $C_{3-18}$heterocycloalkyl, the latter 4 groups being optionally substituted with one or more substituents selected from OH, halo, $C_{1-16}$alkyl, $OC_{1-16}$alkyl, and $C_{2-16}$alkenyl.

14. The process of claim 1, when n is 3 or 4, further $R^1$ groups are independently selected from OH, Br, Cl, F, $C_{1-12}$alkyl, $C_{2-16}$alkenyl, $C_{2-16}$alkynyl, 0-$C_{1-12}$alkyl, $C_{1-16}$alkyleneOH, C(O)$C_{1-12}$alkylene$C_{6-18}$ heterocycloalkyl, C(O)$C_{1-12}$alkylene$C_{3-18}$heterocycloalkyl, C(O)$C_{1-12}$alkyl, C(O)$C_{1-12}$alkylene$C_{6-18}$ aryl, C(O)$C_{2-16}$alkylene$C_{6-18}$aryl, and C(O)$C_{6-18}$aryl wherein all alkyl, alkenyl, alkylene, alkenylene, alkynyl, heterocycloalkyl, and aryl groups are optionally substituted with one or more substituents selected from OH, halo, $C_{1-16}$alkyl, $C_{2-16}$alkenyl and $OC_{1-16}$alkyl.

15. The process of claim 1, wherein $R^3$ is selected from H, $CH_3$ and $CH_2CH_3$.

16. The process of claim 1, wherein $R^4$ is selected from H, $CH_3$, $CH_2CH_3$, $C_{6-10}$aryl, $C_{1-6}$alkylene$C_{6-18}$ aryl, $C_{5-10}$heteroaryl, and $C_{2-6}$alkylene$C_{5-10}$heteroaryl.

17. The process of claim 1, wherein $R^5$ is selected from H, $C_{1-10}$alkyl, $C_{2-20}$alkenyl, and $C_{6-10}$aryl, wherein aryl is optionally substituted with one or more substituents selected from OH, $NO_2$, CN, F, Cl, Br, $C_{1-6}$alkyl, $C_{2-6}$alkenyl, $C_{2-6}$alkynyl, $OC_{1-16}$alkyl and $SO_3C_{1-6}$alkyl.

18. The process of claim 1, wherein $R^5$ is selected from

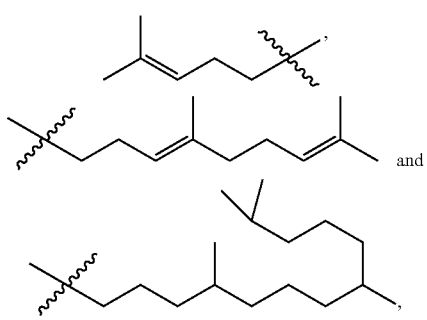
and wherein

represents a point of covalent attachment.

19. The process of claim 1, wherein $R^2$ and $R^5$ are linked together to form an unsubstituted or substituted monocyclic ring system having 6 or more atoms together with the carbon atoms to which said $R^2$ and $R^5$ are bonded, wherein the monocyclic ring system is optionally substituted with one or more substituents selected OH, $C_{1-16}$alkyl, and $C_{2-16}$alkenyl.

20. The process of claim 1, wherein the compound of Formula (I) is a compound selected from the compounds listed below:

| Compound I.D | Structure |
|---|---|
| I-10 | 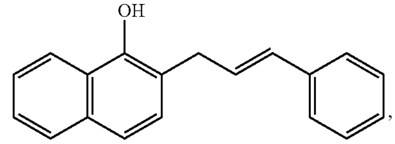 [SMILES: Oc1c(C/C=C/c2ccccc2)ccc2ccccc12] |
| I-11 | 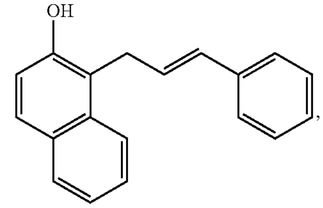 [SMILES: Oc1ccc2ccccc2c1C/C=C/c1ccccc1] |
| I-23 | 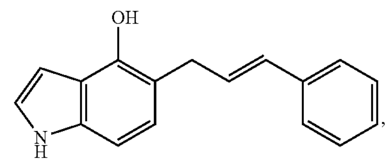 [SMILES: Oc1c(C/C=C/c2ccccc2)ccc2[nH]ccc12] |
| I-24 | 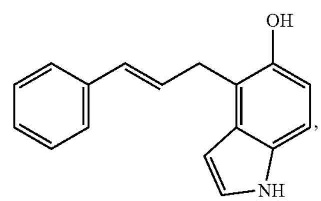 [SMILES: Oc1ccc2[nH]ccc2c1C/C=C/c1ccccc1] |
| I-25 | 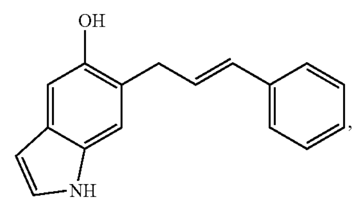 [SMILES: Oc1cc2cc[nH]c2cc1C/C=C/c1ccccc1] |
| I-53 | 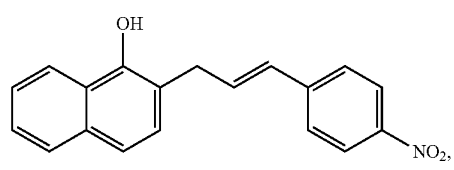 [SMILES: O=[N+]([O-])c1ccc(/C=C/Cc2ccc3ccccc3c2O)cc1] |
| I-54 | 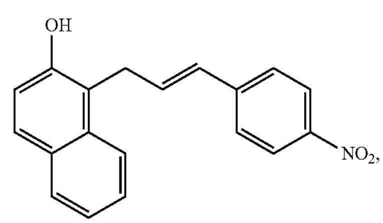 [SMILES: O=[N+]([O-])c1ccc(/C=C/Cc2c(O)ccc3ccccc23)cc1] |

| Compound I.D | Structure |
|---|---|
| I-58 | 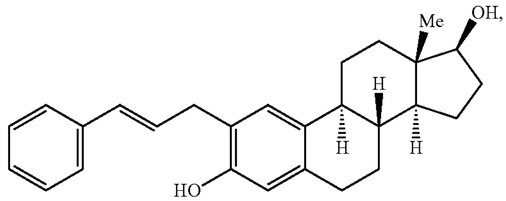 |
| I-59 | 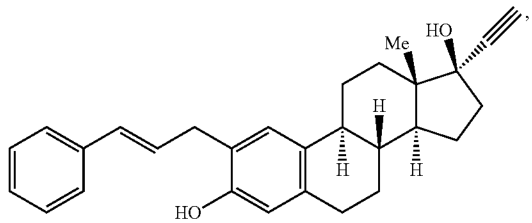 |
| I-60 | 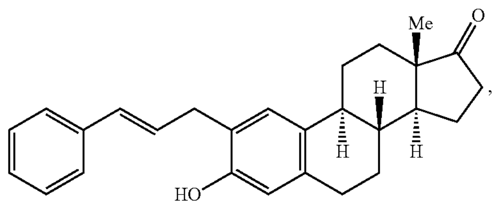 |
| I-61 | 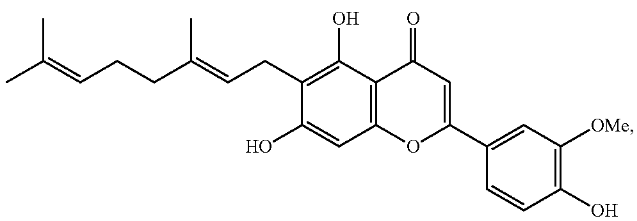 [SMILES: COc1cc(-c2cc(=O)c3c(O)c(C/C=C(\C)CCC=C(C)C)c(O)cc3o2)ccc1O] |
| I-62 | 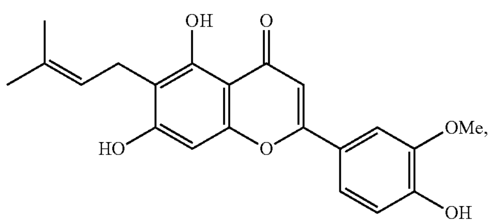 [SMILES: COc1cc(-c2cc(=O)c3c(O)c(CC=C(C)C)c(O)cc3o2)ccc1O] |
| I-63 | 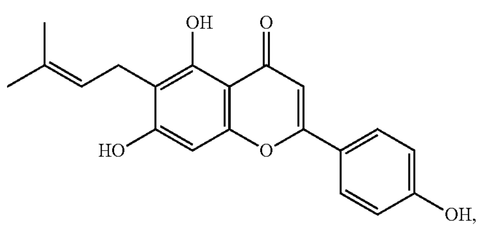 [SMILES: CC(C)=CCc1c(O)cc2oc(-c3ccc(O)cc3)cc(=O)c2c1O] |
| I-64 | 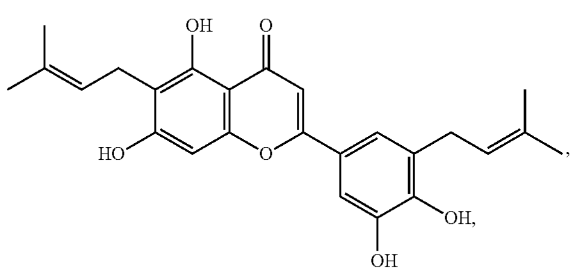 [SMILES: CC(C)=CCc1cc(-c2cc(=O)c3c(O)c(CC=C(C)C)c(O)cc3o2)cc(O)c1O] |

| Compound I.D | Structure |
|---|---|
| I-65 | 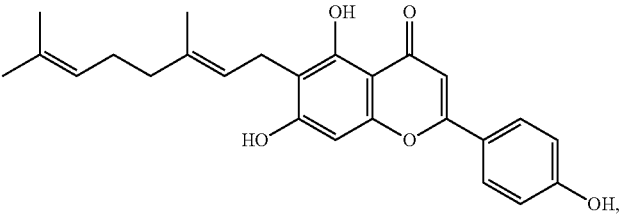 |
| I-66 | 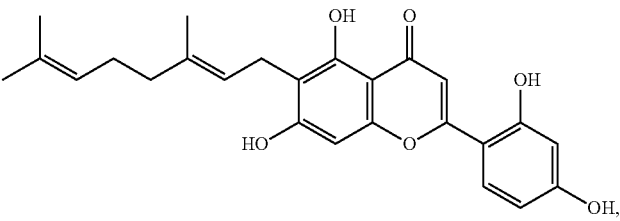 |
| I-67 | 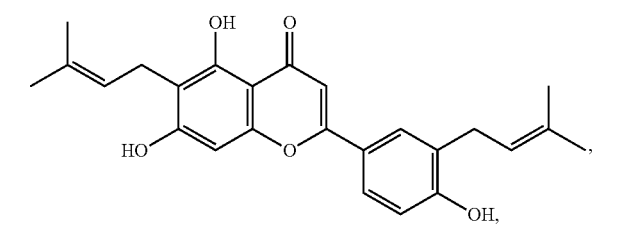 [SMILES: CC(C)=CCc1cc(-c2cc(=O)c3c(O)c(CC=C(C)C)c(O)cc3o2)ccc1O] |
| I-68 | 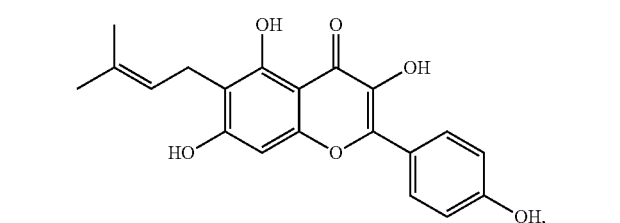 |
| I-69 | 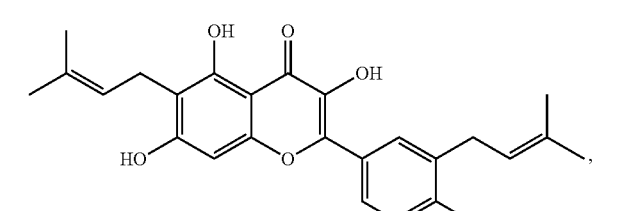 |
| I-70 | 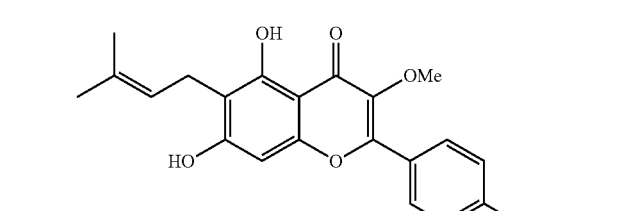 |
| I-71 | 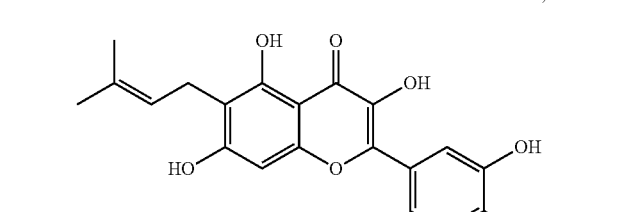 |

-continued

| Compound I.D | Structure |
|---|---|
| I-72 | (structure) |
| I-73 | (structure) |
| I-74 | (structure) |
| I-75 | (structure) |
| I-76 | (structure) |
| I-77 | (structure) |
| I-78 | (structure) |
| I-79 | (structure) |

-continued

| Compound I.D | Structure |
|---|---|
| I-80 | 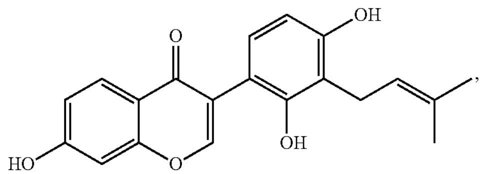 [SMILES: CC(C)=CCc1c(O)ccc(-c2coc3cc(O)ccc3c2=O)c1O] |
| I-81 | 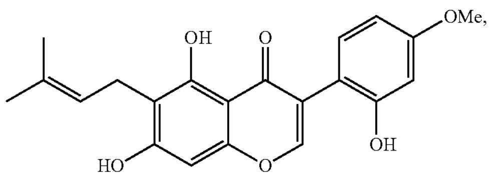 [SMILES: COc1ccc(-c2coc3cc(O)c(CC=C(C)C)c(O)c3c2=O)c(O)c1] |
| I-82 | 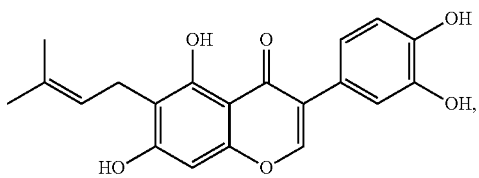 [SMILES: CC(C)=CCc1c(O)cc2occ(-c3ccc(O)c(O)c3)c(=O)c2c1O] |
| I-83 | 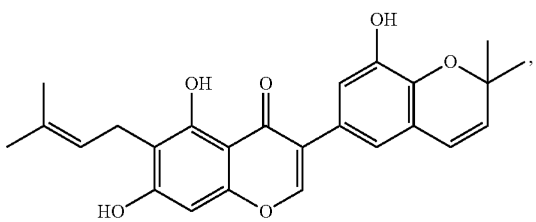 [SMILES: CC(C)=CCc1c(O)cc2occ(-c3cc(O)c4c(c3)C=CC(C)(C)O4)c(=O)c2c1O] |
| I-84 | 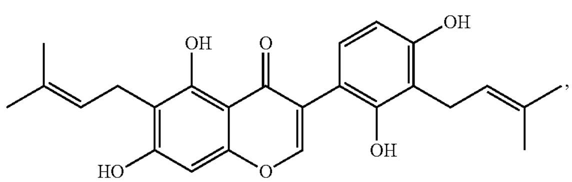 [SMILES: CC(C)=CCc1c(O)ccc(-c2coc3cc(O)c(CC=C(C)C)c(O)c3c2=O)c1O] |
| I-85 | 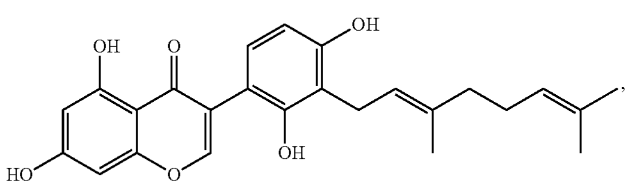 |
| I-93 | 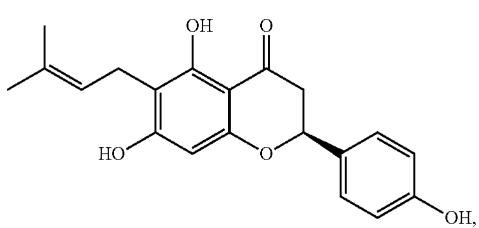 [SMILES: CC(C)=CCc1c(O)cc2c(c1O)C(=O)C[C@@H](c1ccc(O)cc1)O2] |
| I-94 | 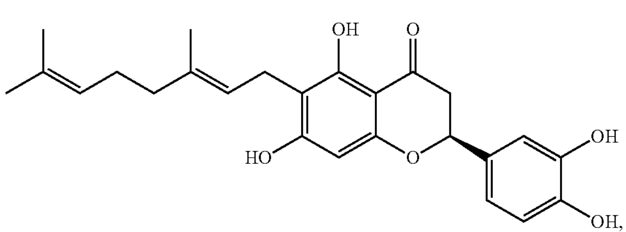 [SMILES: CC(C)=CCC/C(C)=C/Cc1c(O)cc2c(c1O)C(=O)C[C@@H](c1ccc(O)c(O)c1)O2] |

| Compound I.D | Structure |
|---|---|
| I-95 | 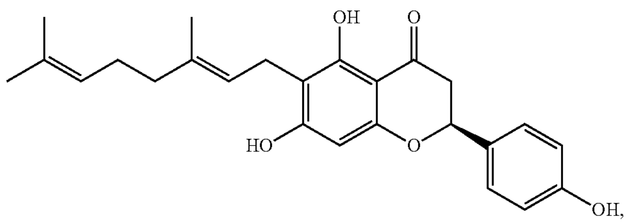 [SMILES: CC(C)=CCC/C(C)=C/Cc1c(O)cc2c(c1O)C(=O)C[C@@H](c1ccc(O)cc1)O2] |
| I-96 | 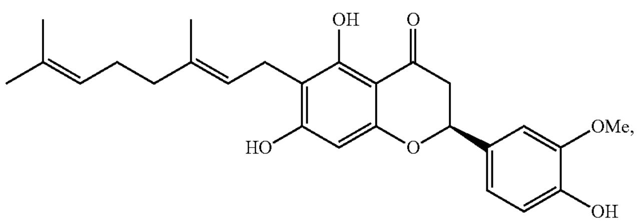 [SMILES: COc1cc([C@@H]2CC(=O)c3c(cc(O)c(C/C=C(\C)CCC=C(C)C)c3O)O2)ccc1O] |
| I-97 | 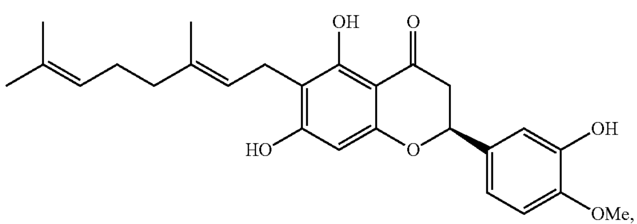 [SMILES: COc1ccc([C@@H]2CC(=O)c3c(cc(O)c(C/C=C(\C)CCC=C(C)C)c3O)O2)cc1O] |
| I-98 | 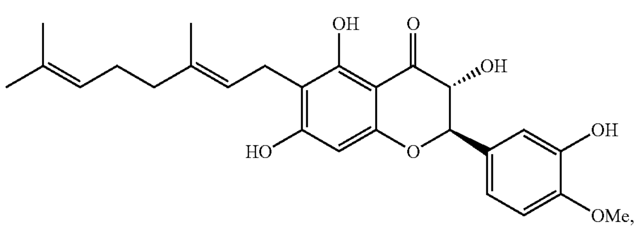 [SMILES: COc1ccc([C@H]2Oc3cc(O)c(C/C=C(\C)CCC=C(C)C)c(O)c3C(=O)[C@@H]2O)cc1O] |
| I-99 | 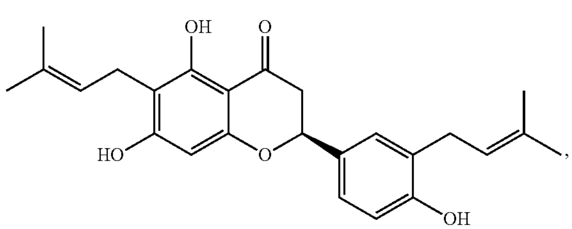 [SMILES: CC(C)=CCc1cc([C@@H]2CC(=O)c3c(cc(O)c(CC=C(C)C)c3O)O2)ccc1O] |
| I-100 | 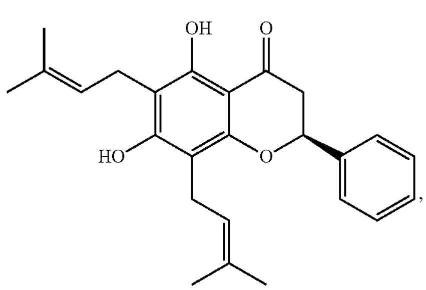 [SMILES: CC(C)=CCc1c(O)c(CC=C(C)C)c2c(c1O)C(=O)C[C@@H](c1ccccc1)O2] |

-continued

| Compound I.D | Structure |
|---|---|
| I-101 | 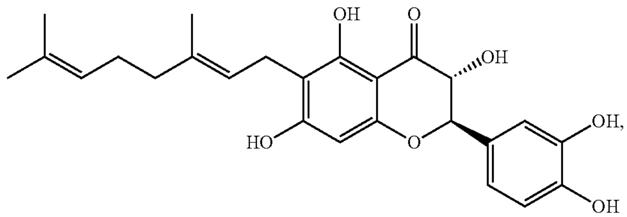 [SMILES: CC(C)=CCC/C(C)=C/Cc1c(O)cc2c(c1O)C(=O)[C@H](O)[C@@H](c1ccc(O)c(O)c1)O2] |
| I-102 | 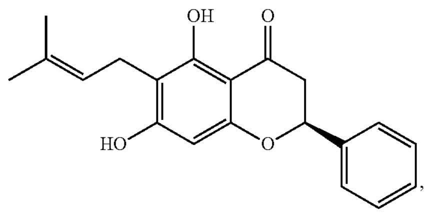 [SMILES: CC(C)=CCc1c(O)cc2c(c1O)C(=O)C[C@@H](c1ccccc1)O2] |
| I-117 | 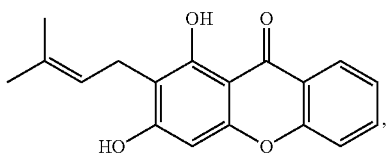 [SMILES: CC(C)=CCc1c(O)cc2oc3ccccc3c(=O)c2c1O] |
| I-118 | 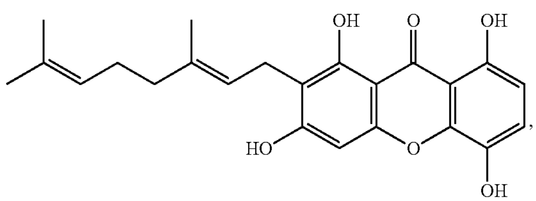 [SMILES: CC(C)=CCC/C(C)=C/Cc1c(O)cc2oc3c(O)ccc(O)c3c(=O)c2c1O] |
| I-119 | 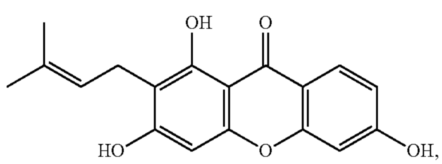 [SMILES: CC(C)=CCc1c(O)cc2oc3cc(O)ccc3c(=O)c2c1O] |
| I-120 | 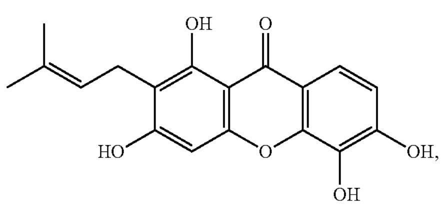 [SMILES: CC(C)=CCc1c(O)cc2oc3c(O)c(O)ccc3c(=O)c2c1O] |
| I-121 | 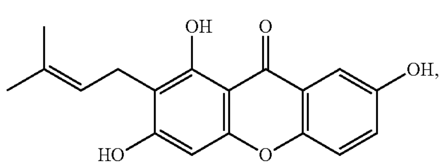 [SMILES: CC(C)=CCc1c(O)cc2oc3ccc(O)cc3c(=O)c2c1O] |
| I-122 | 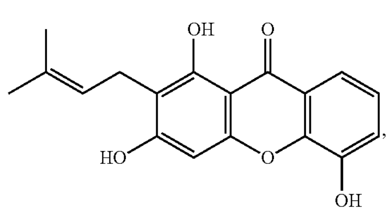 [SMILES: CC(C)=CCc1c(O)cc2oc3c(O)cccc3c(=O)c2c1O] |

-continued

| Compound I.D | Structure |
|---|---|
| I-129 | 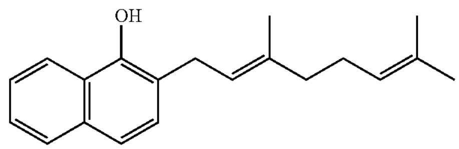 [SMILES: CC(C)=CCC/C(C)=C/Cc1ccc2ccccc2c1O] |
| I-146 | 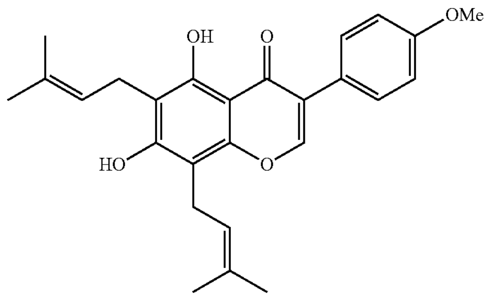 [SMILES: COc1ccc(-c2coc3c(CC=C(C)C)c(O)c(CC=C(C)C)c(O)c3c2=O)cc1] |
| I-147 | 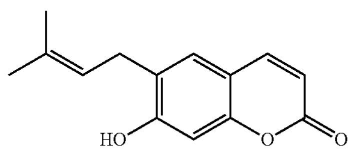 [SMILES: CC(C)=CCc1cc2ccc(=O)oc2cc1O] |
| I-148 | 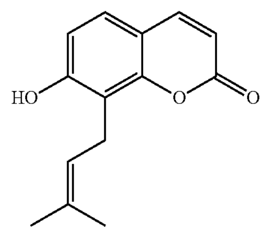 [SMILES: CC(C)=CCc1c(O)ccc2ccc(=O)oc12] |
| I-149 | 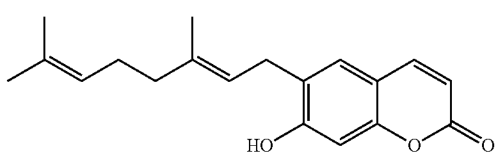 [SMILES: CC(C)=CCC/C(C)=C/Cc1cc2ccc(=O)oc2cc1O] |
| I-150 | 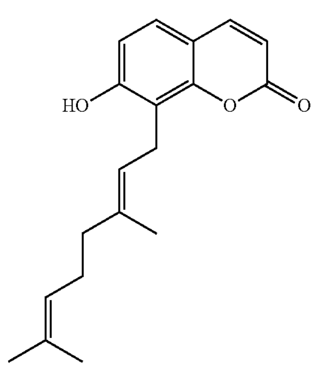 [SMILES: CC(C)=CCC/C(C)=C/Cc1c(O)ccc2ccc(=O)oc12] |
| I-151 | 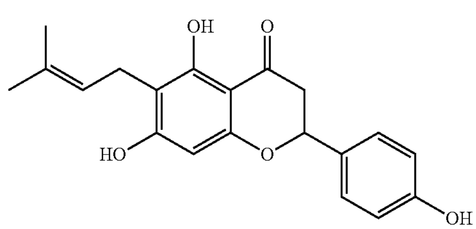 [SMILES: CC(C)=CCc1c(O)cc2c(c1O)C(=O)CC(c1ccc(O)cc1)O2] |

-continued

| Compound I.D | Structure |
|---|---|
| I-152 | 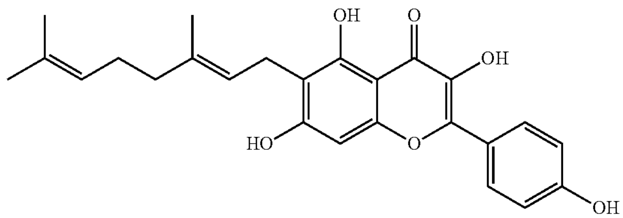 [SMILES: CC(C)=CCC/C(C)=C/Cc1c(O)cc2oc(-c3ccc(O)cc3)c(O)c(=O)c2c1O] |
| I-153 | 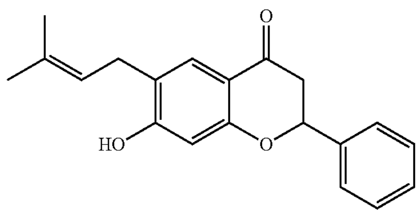 [SMILES: CC(C)=CCc1cc2c(cc1O)OC(c1ccccc1)CC2=O] |
| I-154 | 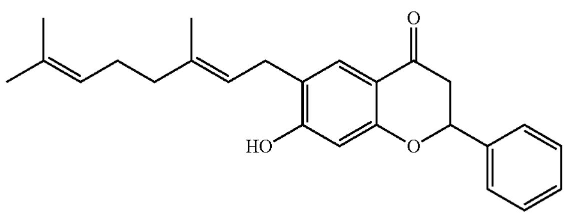 [SMILES: CC(C)=CCC/C(C)=C/Cc1cc2c(cc1O)OC(c1ccccc1)CC2=O] |
| I-155 | 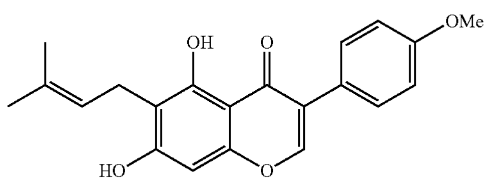 [SMILES: COc1ccc(-c2coc3cc(O)c(CC=C(C)C)c(O)c3c2=O)cc1] |
| I-159 | 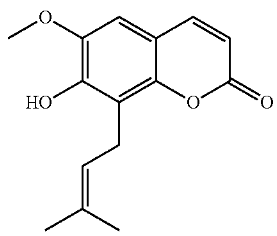 [SMILES: COc1cc2ccc(=O)oc2c(CC=C(C)C)c1O] |
| I-162 | , and |
| I-164 | . |

* * * * *

UNITED STATES PATENT AND TRADEMARK OFFICE
CERTIFICATE OF CORRECTION

PATENT NO. : 11,795,127 B2
APPLICATION NO. : 17/964347
DATED : October 24, 2023
INVENTOR(S) : Jakob Magolan et al.

It is certified that error appears in the above-identified patent and that said Letters Patent is hereby corrected as shown below:

In the Claims

Claim 1, Column 191, Line 58: "selected from OH, halo, CN, $NO_2$, COOH, $C_{2-16}$alkenyl" should read
-- selected from OH, halo, CN, $NO_2$, COOH, $C_{1-16}$alkyl, $C_{2-16}$alkenyl --.

Claim 1, Column 191, Line 60: "$C_{3-18}$cycloalkyl, $C_{2-16}$alkenylene$C_{3-18}$ cycloalkyl," should read
-- $C_{3-18}$cycloalkyl, $C_{2-16}$alkenylene$C_{3-18}$cycloalkyl, --.

Claim 1, Column 192, Line 1: "heteroaryl, Z-$C_{2-16}$alkenyl, Z-$C_{2-16}$alkynyl, Z-" should read
-- heteroaryl, Z-$C_{1-16}$alkyl, Z-$C_{2-16}$alkenyl, Z-$C_{2-16}$alkynyl, Z- --.

Claim 1, Column 192, Line 13: "alkenylene, alkynylene, cycloalkyl heterocycloalkyl," should read
-- alkenylene, alkynylene, cycloalkyl, heterocycloalkyl, --.

Claim 1, Column 192, Line 24: "$R^5$ is selected from H, $C_{2-26}$alkenyl, $C_{2-26}$alkynyl, $C_{3-18}$" should read
-- $R^5$ is selected from H, $C_{1-26}$alkyl, $C_{2-26}$alkenyl, $C_{2-26}$alkynyl, $C_{3-18}$ --.

Claim 1, Column 192, Line 29: "$C_{2-16}$alkynylene$C_{3-18}$ heterocycloalkyl, $C_{6-18}$aryl," should read
-- $C_{2-16}$alkynylene$C_{3-1}$heterocycloalkyl, $C_{6-18}$aryl, --.

Claim 1, Column 192, Line 32: "kylene$C_{5-18}$heteroaryl, $C_{2-16}$alkenylene$C_{5-18}$ het-" should read
-- kylene$C_{5-18}$heteroaryl, $C_{2-16}$alkenylene$C_{5-18}$het- --.

Claim 1, Column 192, Line 33: "eroaryl, $C_{2-16}$alkynylene$C_{5-18}$ heteroaryl, wherein all" should read
-- eroaryl, $C_{2-16}$alkynylene$C_{5-18}$heteroaryl, wherein all --.

Claim 14, Column 194, Line 28: "$C_{1-12}$alkyl, $C_{2-16}$alkenyl, $C_{2-16}$alkynyl, 0-$C_{1-12}$alkyl," should read
-- $C_{1-12}$alkyl, $C_{2-16}$alkenyl, $C_{2-16}$alkynyl, O-$C_{1-12}$alkyl, --.

Signed and Sealed this
Thirty-first Day of December, 2024

Derrick Brent
*Acting Director of the United States Patent and Trademark Office*

CERTIFICATE OF CORRECTION (continued)
U.S. Pat. No. 11,795,127 B2

Claim 14, Column 194, Line 31: "C(O)$C_{1-12}$alkyl, C(O)$C_{1-12}$alkylene$C_{6-18}$ aryl, C(O)$C_{2-16}$" should read -- C(O)$C_{1-12}$alkyl, C(O)$C_{1-12}$alkylene$C_{6-18}$aryl, C(O)$C_{2-16}$ --.